US010513717B2

(12) United States Patent
Damcevski et al.

(10) Patent No.: US 10,513,717 B2
(45) Date of Patent: *Dec. 24, 2019

(54) SYNTHESIS OF FATTY ACIDS

(71) Applicant: Commonwealth Scientific and Industrial Research Organisation, Acton (AU)

(72) Inventors: Katherine Damcevski, Calwell (AU); Karen Glover, Moss Vale (AU); Allan Green, Cremorne Point (AU); Victoria S. Haritos, Kingsville (AU); Irene Horne, Yass (AU); Surinder Pal Singh, Downer (AU); Craig C. Wood, Dickson (AU); Xue-Rong Zhou, Harrison (AU)

(73) Assignees: COMMONWEALTH SCIENTIFIC AND INDUSTRIAL RESEARCH ORGANISATION, Acton (AU); GRAINS RESEARCH AND DEVELOPMENT CORPORATION, Barton (AU)

( * ) Notice: Subject to any disclaimer, the term of this patent is extended or adjusted under 35 U.S.C. 154(b) by 705 days.

This patent is subject to a terminal disclaimer.

(21) Appl. No.: 14/467,942

(22) Filed: Aug. 25, 2014

(65) Prior Publication Data
US 2015/0045567 A1    Feb. 12, 2015

Related U.S. Application Data

(63) Continuation of application No. 12/310,645, filed as application No. PCT/AU2007/001242 on Aug. 29, 2007, now Pat. No. 8,816,106.

(60) Provisional application No. 60/841,285, filed on Aug. 29, 2006.

(51) Int. Cl.
| C12P 7/64 | (2006.01) |
| C12N 9/02 | (2006.01) |
| C12N 9/48 | (2006.01) |
| C12N 15/82 | (2006.01) |
| C11B 1/10 | (2006.01) |

(52) U.S. Cl.
CPC .............. *C12P 7/6427* (2013.01); *C11B 1/10* (2013.01); *C12N 9/0004* (2013.01); *C12N 9/0071* (2013.01); *C12N 9/48* (2013.01); *C12N 15/8247* (2013.01)

(58) Field of Classification Search
None
See application file for complete search history.

(56) References Cited

U.S. PATENT DOCUMENTS

| 5,552,306 A | 9/1996 | Thomas et al. |
| 5,614,393 A | 3/1997 | Thomas et al. |
| 5,663,068 A | 9/1997 | Thomas et al. |
| 5,668,299 A | 9/1997 | Debonte et al. |
| 5,683,898 A | 11/1997 | Yazawa et al. |
| 5,689,050 A | 11/1997 | Thomas et al. |
| 5,789,220 A | 8/1998 | Thomas et al. |
| 5,798,259 A | 8/1998 | Yazawa et al. |
| 5,952,544 A | 9/1999 | Browse et al. |
| 5,968,809 A | 10/1999 | Knutzon et al. |
| 5,972,664 A | 10/1999 | Knutzon et al. |
| 6,051,754 A | 4/2000 | Knutzon et al. |
| 6,075,183 A | 6/2000 | Knutzon et al. |
| 6,136,574 A | 10/2000 | Knutzon et al. |
| 6,140,486 A | 10/2000 | Facciotti et al. |
| 6,194,167 B1 | 2/2001 | Browse et al. |
| 6,342,658 B1 | 1/2002 | DeBonte et al. |
| 6,355,861 B1 | 3/2002 | Thomas et al. |
| 6,372,965 B1 | 4/2002 | Lightner et al. |
| 6,403,349 B1 | 6/2002 | Mukerji et al. |
| 6,410,288 B1 | 6/2002 | Knutzon et al. |
| 2,002,178 A1 | 8/2002 | Meyers et al. |
| 6,428,990 B1 | 8/2002 | Mukerji et al. |
| 6,432,684 B1 | 8/2002 | Mukerji et al. |
| 6,459,018 B1 | 10/2002 | Knutzon et al. |
| 6,492,108 B1 | 12/2002 | Hillman et al. |
| 6,566,583 B1 | 5/2003 | Facciotti et al. |
| 6,589,767 B1 | 7/2003 | Knutzon et al. |
| 6,635,451 B2 | 10/2003 | Mukerji et al. |
| 6,677,145 B2 | 1/2004 | Mukerji et al. |
| 6,683,232 B1 | 1/2004 | Thomas et al. |
| 6,686,185 B1 | 2/2004 | Logan et al. |
| 6,825,017 B1 | 11/2004 | Browse et al. |
| 6,825,335 B1 | 11/2004 | Marin et al. |

(Continued)

FOREIGN PATENT DOCUMENTS

| AU | 775417 | 9/2004 |
| AU | 776447 | 9/2004 |

(Continued)

OTHER PUBLICATIONS

Peyou-Ndi et al., Identification and Characterization of an Animal Δ 12 Fatty Acid Desaturase Gene by Heterologous Expression in Saccharomyces cerevisae, Archives of Biochemistry and Biophysics vol. 376, No. 2, Apr. 15, pp. 399-408, 2000.*
Brenda—Information on EC 1.14.19.6.*
Brenda—Information on EC 1.14.19.47.*
Expasy Enzyme entry 1.14.19.6.*
Expasy Enzyme entry 1.14.19.47.*
International Preliminary Report on Patentability, dated May 24, 2011 in connection with PCT International Application Publication No. PCT/AU2009/001488.

(Continued)

*Primary Examiner* — Sharmila G Landau
*Assistant Examiner* — Stephen M Chong
(74) *Attorney, Agent, or Firm* — John P. White; Gary J. Gershik; Cooper & Dunham LLP

(57) ABSTRACT

The present invention relates to enzymes which possess desaturase, conjugase, epoxidase and/or hydroxylase activity that can be used in methods of synthesizing fatty acids.

17 Claims, 11 Drawing Sheets

Figure 6:
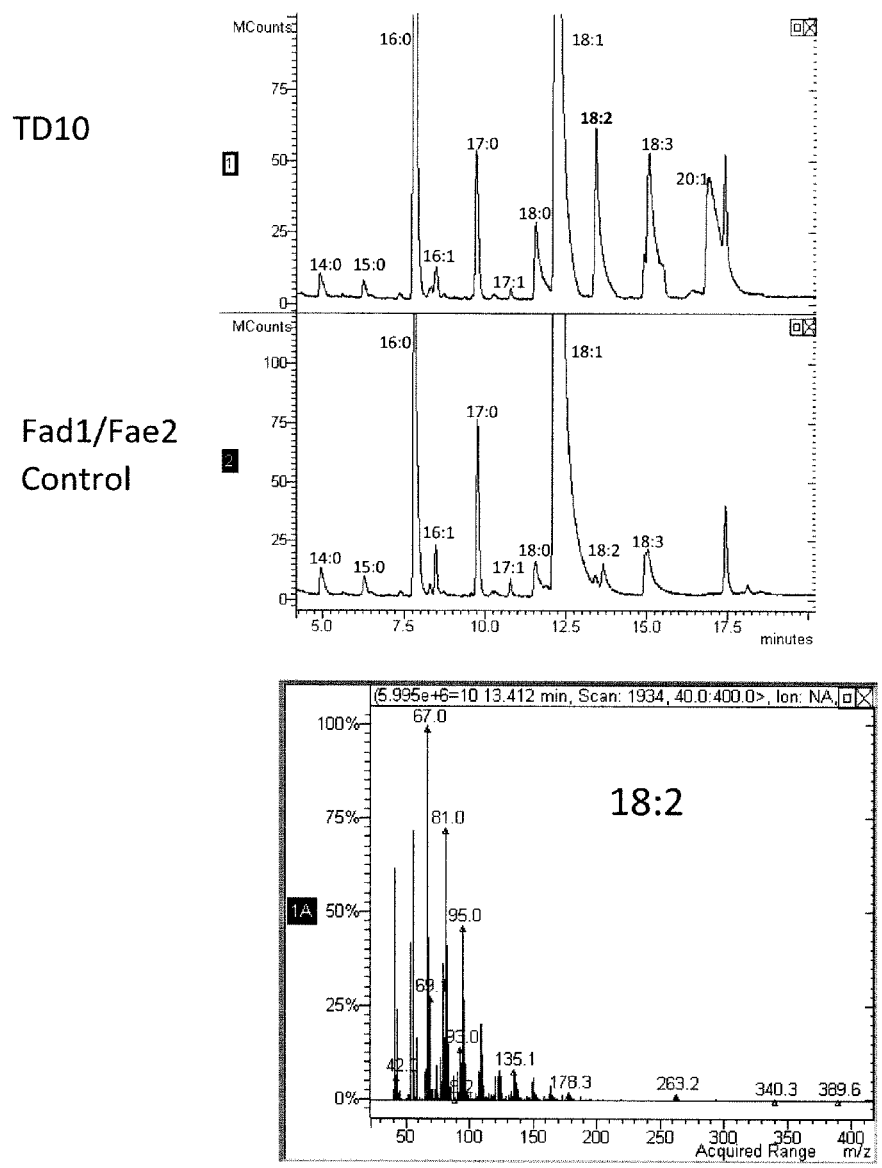

Specification includes a Sequence Listing.

(56) References Cited

U.S. PATENT DOCUMENTS

| | | |
|---|---|---|
| 6,838,594 B1 | 1/2005 | Kinney et al. |
| 6,967,243 B2 | 1/2005 | Debonte et al. |
| 6,858,416 B2 | 2/2005 | Mukerji et al. |
| 6,864,077 B1 | 3/2005 | Cahoon et al. |
| 6,875,595 B2 | 4/2005 | Kloek et al. |
| 6,884,921 B2 | 4/2005 | Browse et al. |
| 6,897,050 B1 | 5/2005 | Napier et al. |
| 6,913,916 B1 | 7/2005 | Mukerji et al. |
| 6,958,229 B2 | 10/2005 | Suzuki et al. |
| 7,001,772 B2 | 2/2006 | Roessler et al. |
| 7,045,683 B2 | 5/2006 | Mukerji et al. |
| 7,067,285 B2 | 6/2006 | Mukerji et al. |
| 7,067,722 B2 | 6/2006 | Fillatti et al. |
| 7,070,970 B2 | 7/2006 | Mukerji et al. |
| 7,081,356 B2 | 7/2006 | Putten et al. |
| 7,087,432 B2 | 8/2006 | Qiu et al. |
| 7,091,005 B2 | 8/2006 | Petrushkin et al. |
| 7,109,392 B1 | 9/2006 | Broglie et al. |
| 7,135,614 B1 | 11/2006 | DeBonte et al. |
| 7,135,623 B1 | 11/2006 | Rusing et al. |
| 7,148,336 B2 | 12/2006 | Fillatti et al. |
| 7,179,620 B2 | 2/2007 | Petrukhin et al. |
| 7,179,647 B2 | 2/2007 | Lerchl et al. |
| 7,189,559 B2 | 3/2007 | Damude et al. |
| 7,192,762 B2 | 3/2007 | Macool et al. |
| 7,198,937 B2 | 4/2007 | Xue et al. |
| 7,211,418 B2 | 5/2007 | Metz et al. |
| 7,217,856 B2 | 5/2007 | Weaver et al. |
| 7,244,563 B2 | 7/2007 | Cahoon et al. |
| 7,256,033 B2 | 8/2007 | Damude et al. |
| 7,262,343 B1 | 8/2007 | DeBonte et al. |
| 7,270,315 B2 | 9/2007 | Metz et al. |
| 7,271,315 B2 | 9/2007 | Metz et al. |
| 7,273,746 B2 | 9/2007 | Yadav et al. |
| 7,402,735 B2 | 7/2008 | Browse et al. |
| 7,411,054 B2 | 8/2008 | Meyers et al. |
| 7,504,259 B2 | 3/2009 | Yadav et al. |
| 7,537,920 B2 | 5/2009 | Renz et al. |
| 7,550,651 B2 | 6/2009 | Damude et al. |
| 7,589,253 B2 | 9/2009 | Green et al. |
| 7,615,679 B2 | 11/2009 | Lerchl et al. |
| 7,659,120 B2 | 2/2010 | Yadav et al. |
| 7,709,239 B2 | 5/2010 | Damude et al. |
| 7,714,185 B2 | 5/2010 | Napier et al. |
| 7,736,884 B2 | 6/2010 | Gunnarsson et al. |
| 7,777,098 B2 | 8/2010 | Cirpus et al. |
| 7,807,849 B2 | 10/2010 | Singh et al. |
| 7,834,248 B2 | 11/2010 | Green et al. |
| 7,834,250 B2 | 11/2010 | Singh et al. |
| 7,838,651 B2 | 11/2010 | Picataggio et al. |
| 7,842,852 B2 | 11/2010 | Cirpus et al. |
| 7,855,321 B2 | 12/2010 | Renz et al. |
| 7,871,804 B2 | 1/2011 | Cirpus et al. |
| 7,901,928 B2 | 3/2011 | Yadav et al. |
| 7,932,438 B2 | 4/2011 | Singh et al. |
| 8,071,341 B2 | 12/2011 | Singh et al. |
| 8,084,074 B2 | 12/2011 | Kinney et al. |
| 8,106,226 B2 | 1/2012 | Singh et al. |
| 8,158,392 B1 | 4/2012 | Singh et al. |
| 8,288,572 B2 | 10/2012 | Singh et al. |
| 8,535,917 B2 | 9/2013 | Singh et al. |
| 8,575,377 B2 | 11/2013 | Singh et al. |
| 8,716,555 B2 | 5/2014 | Liu et al. |
| 8,778,644 B2 | 7/2014 | Singh et al. |
| 8,809,559 B2 | 8/2014 | Petrie et al. |
| 8,816,106 B2 | 8/2014 | Damcevski et al. |
| 8,816,111 B2 | 8/2014 | Petrie et al. |
| 8,853,432 B2 | 10/2014 | Singh et al. |
| 8,921,652 B2 | 12/2014 | Liu et al. |
| 2001/0023259 A1 | 9/2001 | Slabas et al. |
| 2002/0009779 A1 | 1/2002 | Meyers et al. |
| 2002/0042933 A1 | 4/2002 | Browse et al. |
| 2002/0065406 A1 | 5/2002 | Meyers et al. |
| 2002/0076786 A1 | 6/2002 | Curtis et al. |
| 2002/0107373 A1 | 8/2002 | Curtis et al. |
| 2002/0108147 A1 | 8/2002 | Thomas et al. |
| 2002/0111307 A1 | 8/2002 | Glucksmann et al. |
| 2002/0138874 A1 | 9/2002 | Mukerji et al. |
| 2002/0146784 A1 | 10/2002 | Suzuki et al. |
| 2002/0156254 A1 | 10/2002 | Qiu et al. |
| 2002/0170090 A1 | 11/2002 | Browse et al. |
| 2002/0194641 A1 | 12/2002 | Metz et al. |
| 2003/0033622 A1 | 2/2003 | Lightner et al. |
| 2003/0033633 A1 | 2/2003 | Lightner et al. |
| 2003/0077747 A1 | 4/2003 | Hillman et al. |
| 2003/0079250 A1 | 4/2003 | Fillatti et al. |
| 2003/0082754 A1 | 5/2003 | Mukerji et al. |
| 2003/0084480 A1 | 5/2003 | Fillatti et al. |
| 2003/0101486 A1 | 5/2003 | Facciotti et al. |
| 2003/0104596 A1 | 6/2003 | Mukerji et al. |
| 2003/0131379 A1 | 7/2003 | Debonte et al. |
| 2003/0134400 A1 | 7/2003 | Mukerji et al. |
| 2003/0152983 A1 | 8/2003 | Napier et al. |
| 2003/0157144 A1 | 8/2003 | Mukerji et al. |
| 2003/0159164 A1 | 8/2003 | Kopchick et al. |
| 2003/0163844 A1 | 8/2003 | Lightner et al. |
| 2003/0163845 A1 | 8/2003 | Mukerji et al. |
| 2003/0166207 A1 | 9/2003 | Roessler et al. |
| 2003/0167525 A1 | 9/2003 | Mukerji et al. |
| 2003/0172398 A1* | 9/2003 | Browse .................. 800/281 |
| 2003/0172399 A1 | 9/2003 | Fillatti et al. |
| 2003/0177508 A1 | 9/2003 | Mukerji et al. |
| 2003/0190733 A1 | 10/2003 | Mukerji et al. |
| 2003/0196217 A1 | 10/2003 | Mukerji et al. |
| 2004/0009501 A1 | 1/2004 | Curtis et al. |
| 2004/0049805 A1 | 3/2004 | Lerchl et al. |
| 2004/0053234 A1 | 3/2004 | Winther et al. |
| 2004/0053379 A1 | 3/2004 | Lerchl et al. |
| 2004/0067226 A1 | 4/2004 | Petrukhin et al. |
| 2004/0078845 A1 | 4/2004 | Thomas et al. |
| 2004/0086899 A1 | 5/2004 | Winther et al. |
| 2004/0098762 A1 | 5/2004 | Fillatti et al. |
| 2004/0111763 A1 | 6/2004 | Heinz et al. |
| 2004/0157221 A9 | 8/2004 | Curtis et al. |
| 2004/0172682 A1 | 9/2004 | Kinney et al. |
| 2004/0180414 A1 | 9/2004 | Putten et al. |
| 2004/0195512 A1 | 10/2004 | Crosetto et al. |
| 2004/0224413 A1 | 11/2004 | Cahoon et al. |
| 2004/0235127 A1 | 11/2004 | Metz et al. |
| 2005/0003442 A1 | 1/2005 | Mukerji et al. |
| 2005/0005328 A1 | 1/2005 | Mukerji et al. |
| 2005/0005329 A1 | 1/2005 | Mukerji et al. |
| 2005/0009140 A1 | 1/2005 | Mukerji et al. |
| 2005/0089865 A1 | 4/2005 | Napier et al. |
| 2005/0089879 A1 | 4/2005 | Feussner et al. |
| 2005/0089981 A1 | 4/2005 | Napier et al. |
| 2005/0100995 A1 | 5/2005 | Weaver et al. |
| 2005/0112719 A1 | 5/2005 | Roessler et al. |
| 2005/0164192 A1 | 7/2005 | Graham et al. |
| 2005/0166271 A1 | 7/2005 | Feubner et al. |
| 2005/0214761 A1 | 9/2005 | Lerchl et al. |
| 2005/0262589 A1 | 11/2005 | Fillatti et al. |
| 2005/0262591 A1 | 12/2005 | Debonte et al. |
| 2005/0266440 A1 | 12/2005 | Metz et al. |
| 2005/0273883 A1 | 12/2005 | Metz et al. |
| 2005/0273884 A1 | 12/2005 | Metz et al. |
| 2005/0273885 A1 | 12/2005 | Singh et al. |
| 2006/0014268 A1 | 1/2006 | Suzuki et al. |
| 2006/0078973 A1 | 4/2006 | Renz et al. |
| 2006/0094088 A1 | 5/2006 | Picataggio et al. |
| 2006/0094092 A1 | 5/2006 | Damude et al. |
| 2006/0094102 A1 | 5/2006 | Xue et al. |
| 2006/0110806 A1 | 5/2006 | Damude et al. |
| 2006/0115881 A1 | 6/2006 | Damude et al. |
| 2006/0117414 A1 | 6/2006 | Qiu et al. |
| 2006/0156435 A1 | 7/2006 | Ursin et al. |
| 2006/0168687 A1 | 7/2006 | Renz et al. |
| 2006/0174376 A1 | 8/2006 | Renz et al. |
| 2006/0191042 A1 | 8/2006 | Fillatti et al. |
| 2006/0195939 A1 | 8/2006 | Damude et al. |
| 2006/0205047 A1 | 9/2006 | Putten et al. |
| 2006/0206961 A1 | 9/2006 | Cirpus et al. |
| 2006/0218668 A1 | 9/2006 | Cirpus et al. |
| 2006/0246556 A1 | 11/2006 | Napier et al. |

(56) References Cited

U.S. PATENT DOCUMENTS

| | | |
|---|---|---|
| 2007/0028326 A1 | 2/2007 | Cirpus et al. |
| 2007/0059730 A1 | 3/2007 | Curtis et al. |
| 2007/0061921 A1 | 3/2007 | Graham et al. |
| 2007/0118929 A1 | 5/2007 | Damude et al. |
| 2007/0163002 A1 | 7/2007 | DeBonte et al. |
| 2007/0220634 A1 | 9/2007 | Metz et al. |
| 2007/0224661 A1 | 9/2007 | Cirpus et al. |
| 2007/0238648 A1 | 10/2007 | Brownlie |
| 2007/0244192 A1 | 10/2007 | Metz |
| 2007/0245431 A1 | 10/2007 | Metz et al. |
| 2007/0259355 A1 | 11/2007 | Luy et al. |
| 2007/0261138 A1 | 11/2007 | Graham et al. |
| 2007/0270494 A1 | 11/2007 | Metz et al. |
| 2007/0294790 A1 | 12/2007 | Graham et al. |
| 2008/0005811 A1 | 1/2008 | Metz et al. |
| 2008/0022422 A1 | 1/2008 | Weaver et al. |
| 2008/0057495 A1 | 3/2008 | Ohyama et al. |
| 2008/0063691 A1 | 3/2008 | Ursin et al. |
| 2008/0076166 A1 | 3/2008 | Cirpus et al. |
| 2008/0155705 A1 | 6/2008 | Zank et al. |
| 2008/0160054 A1 | 7/2008 | Heinz et al. |
| 2008/0214667 A1 | 9/2008 | Das et al. |
| 2008/0220143 A1 | 9/2008 | Kinney et al. |
| 2008/0220500 A1 | 9/2008 | Winther et al. |
| 2008/0241133 A1 | 10/2008 | Curtis et al. |
| 2008/0254191 A1 | 10/2008 | Damude et al. |
| 2008/0254195 A1 | 10/2008 | Damude et al. |
| 2008/0260929 A1 | 10/2008 | Ursin et al. |
| 2008/0268539 A1 | 10/2008 | Singh et al. |
| 2009/0093033 A1 | 4/2009 | Luy et al. |
| 2009/0158462 A1 | 6/2009 | Cirpus et al. |
| 2009/0222951 A1 | 9/2009 | Cirpus et al. |
| 2009/0253188 A1 | 10/2009 | Zhu et al. |
| 2009/0320161 A1 | 12/2009 | McGonigle et al. |
| 2010/0088776 A1 | 4/2010 | Bauer et al. |
| 2010/0092640 A1 | 4/2010 | Ursin et al. |
| 2010/0189868 A1 | 6/2010 | Damude et al. |
| 2010/0222951 A1 | 9/2010 | Tanaka et al. |
| 2010/0227924 A1 | 9/2010 | Singh et al. |
| 2011/0015415 A1 | 1/2011 | Singh et al. |
| 2011/0016585 A1 | 1/2011 | Periera et al. |
| 2011/0054198 A1 | 3/2011 | Singh et al. |
| 2011/0059204 A1 | 3/2011 | Jackson et al. |
| 2011/0059496 A1 | 3/2011 | Zhu et al. |
| 2011/0190521 A1 | 8/2011 | Damcevski et al. |
| 2011/0201065 A1 | 8/2011 | Singh et al. |
| 2011/0218348 A1 | 9/2011 | Zhou et al. |
| 2011/0223311 A1 | 9/2011 | Liu et al. |
| 2011/0229623 A1 | 9/2011 | Liu et al. |
| 2011/0269983 A1 | 11/2011 | Kinney et al. |
| 2011/0314725 A1 | 12/2011 | Petrie et al. |
| 2012/0041218 A1 | 2/2012 | Singh et al. |
| 2012/0083615 A1 | 4/2012 | Singh et al. |
| 2012/0215018 A1 | 8/2012 | Singh et al. |
| 2013/0060053 A1 | 3/2013 | Singh et al. |
| 2013/0296589 A1 | 11/2013 | Singh et al. |
| 2014/0314727 A1 | 10/2014 | Singh et al. |
| 2015/0018571 A1 | 1/2015 | Petrie et al. |
| 2015/0045569 A1 | 2/2015 | Petrie et al. |

FOREIGN PATENT DOCUMENTS

| | | | |
|---|---|---|---|
| AU | 2007/276257 | 1/2008 | |
| JP | 2000217582 | 8/2000 | |
| JP | 2001095588 | 4/2001 | |
| JP | 2001145490 | 5/2001 | |
| JP | 2001169780 | 6/2001 | |
| JP | 2003116566 | 4/2003 | |
| WO | WO 1993/006712 | 4/1993 | |
| WO | WO 1993/023545 | 11/1993 | |
| WO | WO 1996/021022 | 7/1996 | |
| WO | WO 1997/21340 | 6/1997 | |
| WO | WO 1998/001565 | 1/1998 | |
| WO | WO 1998/018952 | 5/1998 | |
| WO | WO 1998/046763 | 10/1998 | |
| WO | WO 1998/046764 | 10/1998 | |
| WO | WO 1998/046765 | 10/1998 | |
| WO | WO 1998/039468 | 11/1998 | |
| WO | WO 1998/055625 | 12/1998 | |
| WO | WO 1998/056239 | 12/1998 | |
| WO | WO 1999/033958 | 7/1999 | |
| WO | WO 1999/049050 | 9/1999 | |
| WO | WO 1999/061602 | 12/1999 | |
| WO | WO 1999/064614 | 12/1999 | |
| WO | WO 1999/064616 | 12/1999 | |
| WO | WO 2000/012720 | 3/2000 | |
| WO | WO 2000/020602 | 4/2000 | |
| WO | WO 2000/020603 | 4/2000 | |
| WO | WO 2000/021557 | 4/2000 | |
| WO | WO 2000/040705 | 7/2000 | |
| WO | WO 2000/042195 | 7/2000 | |
| WO | WO 2000/052183 | 9/2000 | |
| WO | WO 2000/053770 | 9/2000 | |
| WO | WO 2000/055330 | 9/2000 | |
| WO | WO 2000/075341 | 12/2000 | |
| WO | WO 2001/002591 | 1/2001 | |
| WO | WO 2001/004636 | 1/2001 | |
| WO | WO 2001/014538 | 3/2001 | |
| WO | WO 2001/020001 | 3/2001 | |
| WO | WO 2001/038484 | 5/2001 | |
| WO | WO 2001/038512 | 5/2001 | |
| WO | WO 2001/044485 | 6/2001 | |
| WO | WO 2001/066758 | 9/2001 | |
| WO | WO 2001/075069 | 10/2001 | |
| WO | WO 2001/092489 | 12/2001 | |
| WO | WO 2001/96363 | 12/2001 | |
| WO | WO 2002/008401 | 1/2002 | |
| WO | WO 2002/026946 | 4/2002 | |
| WO | WO 2002/081668 | 10/2002 | |
| WO | WO 2002/081702 | 10/2002 | |
| WO | WO 2002/083869 | 10/2002 | |
| WO | WO 2002/083870 | 10/2002 | |
| WO | WO 2002/090493 | 11/2002 | |
| WO | WO 2002/092540 | 11/2002 | |
| WO | WO 2003/064596 | 8/2003 | |
| WO | WO 2003/093482 | 11/2003 | |
| WO | WO 2003/102138 | 12/2003 | |
| WO | WO 2004/005442 | 1/2004 | |
| WO | WO 2004/057001 | 7/2004 | |
| WO | WO 2004/071467 | 8/2004 | |
| WO | WO 2004/087180 | 10/2004 | |
| WO | WO 2005/007845 | 1/2005 | |
| WO | WO 2004/071467 | 2/2005 | |
| WO | WO 2005/012316 | 2/2005 | |
| WO | WO 2005/083053 | 9/2005 | |
| WO | WO 2005/083093 | 9/2005 | |
| WO | WO 2005/097982 | 10/2005 | |
| WO | WO 2005/098033 | 10/2005 | |
| WO | WO 2005/118814 | 12/2005 | |
| WO | WO 2006/064317 | 6/2006 | |
| WO | WO 2006/069936 | 7/2006 | |
| WO | WO 2006/069936 * | 7/2006 | ........... C12N 9/1029 |
| WO | WO 2005/080578 | 9/2006 | |
| WO | WO 2007/005882 | 1/2007 | |
| WO | WO 2007/092460 | 8/2007 | |
| WO | WO 2007/127381 | 11/2007 | |
| WO | WO 2008/009600 | 1/2008 | |
| WO | WO 2008/025068 | 3/2008 | |
| WO | WO 2003/078639 | 9/2009 | |
| WO | WO 2009/129582 | 10/2009 | |
| WO | WO 2010/009500 | 1/2010 | |
| WO | WO 2010/023202 | 3/2010 | |

OTHER PUBLICATIONS

Written Opinion of the International Search Authority, dated Apr. 1, 2010 in connection with PCT International Application Publication No. PCT/AU2009/001488.

International Search Report, dated Apr. 1, 2010 in connection with PCT International Application Publication No. PCT/AU2009/001488.

(56) References Cited

OTHER PUBLICATIONS

International Preliminary Report on Patentability dated Oct. 25, 2006 for PCT International Application Publication No. WO 2005/103253.

Abbadi et al., "Transgenic Oilseeds As Sustainable Source of Nutritionally Relevant C20 and C22 Polyunsaturated Fatty Acids?" European Journal of Lipid Science and. Technology, 103(2):106-113 (2001).

Abbadi et al., "Biosynthesis of Very-Long-Chain Polyunsaturated Fatty Acids in Transgenic Oilseeds: Constraints on Their Accumulation," The Plant Cell, 16(10):2734-3748 (2004).

Abdullah, R., Cocking, E. C., & Thompson, J. A. (Dec. 1986). Efficient plant regeneration from rice protoplasts through somatic embryogenesis. Biotechnology, 4, 1087-1090.

The C. Elegans Sequencing Consortium, "Genome Sequence of the Nematode C. elegans: A Platform for Investigating Biology," Science, 282(5396):2012-2018 (1998).

Agaba et al., "Zebrafish cDNA Encoding Multifunctional Fatty Acid Elongase Involved in Production of Eicosapentaenoic (20:5n-3) and Docosahexaenoic (22:6n-3) Acids," Marine Biotechnology, 6(3):251-261 (2004).

Akiyama et al., "A Novel Plasmid Recombination Mechanism of the Marine *Cyanobacterium synechococcus* sp. PCC7002," DNA Research, 5(6):327-334 (1998).

Akiyama et al., "Nucleotide Sequence of Plasmid pAQ1 of Marine *Cyanobacterium synechococcus* sp. PCC7002," DNA Research, 5(2):127-129 (1998).

Altschul, S. F., Madden, T. L., Schaffer, A. A., Zhang, J., Zhang, Z., Miller, W., & Lipman, D. J. (1997). Gapped BLAST and PSI-BLAST: a new generation of protein database search programs. Nucleic Acids Research, 25(17), 3389-3402.

Badami, R. C., & Patil, K. B. (1980). Structure and occurrence of unusual fatty acids in minor seed oils. Prog. Lipid Res., 19, 119-153.

Bäumlein et al., "Cis-Analysis of a Seed Protein Gene Promoter: The Conservative RY Repeat CATGCATC Within the Legumin Box Is Essential for Tissue-Specific Expression of a Legumin Gene," The Plant Journal, 2(2):233-239 (1992).

Bäumlein et al., "A Novel Seed Protein Gene From *Vicia faba* Is Developmentally Regulated in Transgenic Tobacco and *Arabidopsis* Plants," Molecular and General Genetics, 225(3):459-467 (1991).

Bäumlein, H., Nagy, I., Villarroel, R., Inzé, D., & Wobus, U. (1992). Cis-analysis of a seed protein gene promoter: the conservative RY repeat CATGCATG within the legumin box is essential for tissue-specific expression of a legumin gene. The Plant Journal. 2(2), 233-239.

Beaudoin et al., "Heterologous Reconstitution in Yeast of the Polyunsaturated Fatty Acid Biosynthetic Pathway," Proceedings of the National Academy of Sciences of the United States of America, 97(12):6421-6426 (2000).

Berberich et al., "Two Maize Genes Encoding Omega-3 Fatty Acid Desaturase and Their Differential Expression to Temperature," Plant Molecular Biology, 36(2):297-306 (1998).

Bolch et al., "Genetic, Morphological, and Toxicological Variation Among Globally Distributed Strains of Nodularia (Cyanobacteria)," Journal of Phycology, 35(2):339-355 (1999).

Bolch et al., "Genetic Variation Among Strains of the Toxic Dinoflagellate Gymnodinium Catenatum (Dinophyceae)," Journal of Phycology, 35:356-367 (1999).

Brown et al., "A Bifunctional oleate 12-Hydroxylase: Desaturase From Lesquerella fendleri," The Plant Journal, 13(2):201-210.

Brown et al., "Nutritional Properties of Microalgae for Mariculture," Aquaculture, 151(1):315-331 (1997).

Browse and Slack, "Catalase Stimulates Linoleate Desaturase Activity in Microsomes From Developing Linseed Cotyledons," Federation of European Biochemical Societies Letters, 131(1):111-114 (1981).

Cahoon, E. B., Ripp, K. G., Hail, S. E., & Kinney, A. J. (2001). Formation of conjugated Δ8,Δ10-double bonds by Δ12-oleic-acid desaturase-related enzymes. The Journal of Biological Chemistry, 276(4), 2637-2643.

Cahoon, E. B., Marillia, E., Stecca, K. L., Hall, S. E., Taylor, D. C., & Kinney, A. J. (2000). Production of fatty acid components of meadowfoam oil in somatic soybean embryos. Plant Physiology, 124, 243-251.

Cahoon, E. B., Shanklin, J., & Ohlrogge, J. B. (1992). Expression of a coriander desaturase results in petroselinic acid production in transgenic tobacco. Proc. Natl. Acad. Sci. USA, 89, 11164-11188.

Certik and Shimizu, "Biosynthesis and regulation of microbial polyunsaturated fatty acid production," J. Biosci Bioeng, 87(1):1-14 (1999).

Cheng, M., Jarret, R. L., Li, Z., Xing, A., & Oemski, J. W. (1996). Production of fertile transgenic peanut (*Arachis hypogaea* L.) plants using Agrobacterium tumefaciens. Plant Cell Reports, 15, 653-657.

Chinain et al., "Intraspecific Variation in the Dinoflagellate Gambierdiscus Toxicus (Dinophyceae). I. Isozyme Analysis," Journal of Phycology, 33:36-43 (1997).

Cho et al., "Cloning, Expression, and Nutritional Regulation of the Mammalian Δ-6 Desaturase," The Journal of Biological Chemistry, 274(1):471-477 (1999).

Cho et al., "Cloning, Expression, and Fatty Acid Regulation of the Human Δ-5 Desaturase," The Journal of Biological Chemistry, 274(52):37335-37339 (1999).

Clough and Bent, "Floral Dip: A Simplified Method for Agrobacterium-Mediated Transformation of *Arabidopsis thaliana*," 16(6):735-743 (1998).

Coleman, "Sexual and Genetic Isolation in the Cosmopolitan Algal Species Pandorina Morum," American Journal of Botany, 64(3):361-368 (1977).

Cripps, C., Borgeson, C., Blomquist, G. J., & de Renobales, M. (1990). The Δ12-desaturase from the house cricket, *Acheta domesticus* (orthoptera: gryllidae): characterization and form of the substrate. Archives of Biochemistry and Biophysics, 278(1), 46-51.

Crombie, L., & Holloway, S. J. (1984). Origins of conjugated triene fatty acids. The biosynthesis of calendic acid by Calendula Officinalis. J. Chem. Soc., Chem. Commun., 15, 953-955.

Crombie, L., & Holloway, S. J. (1985). The biosynthesis of calendic acid, octadeca-(8E,10E,12Z)-trienoic acid, by developing marigold seeds: origins of (E,E,Z) and (Z,E,Z) conjugated triene acids in higher plants. J. Chem. Soc. Perkin Trans. 1, 2425-2434.

Cuperus, F. P., & Derksen, J. T. P. (1996). High value-added applications from vernolic acid. In J. Janick (Ed.), Progress in new crops (pp. 354-356). Alexandria, VA: ASHS Press.

Domergue et al., "Cloning and Functional Characterization of Phaeodactylum Tricornutum Front-End Desaturases Involved in Eicosapentaenoic Acid Biosynthesis," European Journal of Biochemistry, 269(16):4105-4113 (2002).

Domergue et al., "In vivo characterization of the first acyl-CoA Δ6-desaturase from a member of the plant kingdom, the microalga Ostreococcus tauri," Biochem J. 389, 483-490 (2005).

Domergue et al., "New Insight Into Phaeodactylum tricornutum Fatty Acid Metabolism. Cloning and Functional Characterization of Plastidial and Microsomal Δ12-Fatty Acid Desaturases," Plant Physiology, 131(4):1648-1660 (2003).

De Renobales, M., Cripps, C., Stanley-Samuelson, D. W., Jurenka, R. A., & Blomquist, G. J. (1987). Biosynthesis of linoleic acid in insects. Trends in Biochemical Sciences, 12, 364-366.

Dobson, G., & Christie, W. W. (2002). Mass spectrometry of fatty acid derivatives. Eur. J. Lipid Sci. Technol., 104, 36-43.

Drexler et al., "Metabolic Engineering of Fatty Acids for Breeding of New Oilseed Crops: Strategies, Problems and First Results," Journal of Plant Physiology, 160(7):779-802 (2003).

Dunstan et al., "Essential Polyunsaturated Fatty Acids From 14 Species of Diatom (Bacillariophyceae)," Phytochemistry, 35(1):155-161 (1994).

Fay, L., & Richli, U. (1991). Location of double bonds in polyunsaturated fatty acids by gas chromatography-mass spectrometry after 4,4-dimethyloxazoline derivatization. Journal of Chromatography, 541, 89-98.

Fritsche, K., Hornung, E., Peitzsch, N., Renz, A., & Feussner, I. (1999). Isolation and characterization of a calendic acid producing (8,11)-linoleoyl desaturase. FEBS Letters, 462, 249-253.

(56) References Cited

OTHER PUBLICATIONS

Gallagher, "Population Genetics of Skeletonema Costatum (Bacillariophyceae) in Narragansett Bay," Journal of Phycology, (16)3:464-474 (1980).
Garcia-Maroto et al., "Cloning and Molecular Characterization of the Δ6-Desaturase From Two Echium Plant Species: Production of GLA by Heterologous Expression in Yeast and Tobacco," Lipids, 37(4):417-426 (2002).
Girke et al., "Identification of a Novel Δ6-Acyl-Group Desaturase by Targeted Gene Disruption in Physcomitrella patens," The Plant Journal, 15(1):39-48 (1998).
Grant, J. E., Cooper, P. A., McAra, A. F., & Frew, T. J. (1995). Transformation of peas (*Pisum sativum* L.) using immature cotyledons. Plant Cell Reports, 15, 254-258.
Guil-Guerrero et al., "Occurrence and Characterization of Oils Rich in γ-Linolenic Acid Part I: Echium Seeds From Macaronesia," Phytochemistry, 53(4):451-456 (2000).
Haseloff and Gerlach, "Simple RNA Enzymes With New and Highly Specific Endoribonuclease Activities," Nature, 334:585-591.
Hastings et al., "A Vertebrate Fatty Acid Desaturase With Δ5 and Δ6 Activities," Proceedings of the National Academy of Sciences of the United States of America, 98(25):14304-14309 (2001).
Hao, G., Liu, W., O'Conner, M., & Roelofs, W. L. (2002). Acyl-CoA Z9- and Z10-desaturase genes from a New Zealand leafroller moth species, Planotortrix octo. Insect Biochemistry and Molecular Biology, 32, 961-966.
Harayama, S. (1998). Artificial evolution by DNA shuffling. Trends in Biotechnology, 16(2), 76-82.
Hong et al., "Isolation and Characterization of a Δ5 FA Desaturase From Pythium irregulars by Heterologous Expression in *Saccaromyces cerevisiae* and Oilseed Crops," Lipids, 37(9):863-868 (2002).
Horiguchi et al., "Developmental Regulation of Genes for Microsome and Plastid Omega-3 Patty Acid Desaturases in Wheat (*Triticum aestivum* L.)," Plant and Cell Physiology, 39(5):540-544 (1998).
Huang et al., "Cloning of Δ12-And Δ6-Desaturases From Mortierella alpina and Recombinant Production of γ-Linolenic Acid in *Saccharomyces cerevisiae*," Lipids, 34(7):649-659 (1999).
Ikeda et al., "Transformation of the Fresh Water Cyanobacterium Synechococcus PCC7942 With the Shuttle-Vector pAQ-EX1 Developed for the Marine Cyanobacterium Synechococcus PCC7002," World Journal of Microbiology & Biotechnology, 18(1):55-56 (2002).
Inagaki et al., "Identification and Expression of a Rat Fatty Acid Elongase Involved in the Biosynthesis of C18 Fatty Acids," Bioscience, Biotechnology, and Biochemistry, 66(3):613-621 (2002).
Jones and Harwood, "Desaturation of Linoleic Acid From Exogenous Lipids by Isolated Chloroplasts," The Biochemical Journal, 190(3):851-854 (1980).
Kajikawa et al., "Isolation and Characterization of Δ6-Desaturase, an ELO-Like Enzyme and Δ5-Desaturase From the Liverwort Marchantia polymorpha and Production of Arachidonic and Eicosapentaenoic Acids in the Methylotrophic Yeast Pichia pastoris," Plant Molecular Biology, 54:335-352 (2004).
Kleiman, R., & Spencer, G. F. (Jan. 1982). Search for new industrial oils: XVI. umbelliflorae-seed oils rich in petroselinic acid. Journal of the American Oil Chemists' Society, 59(1), 29-38.
Knipple, D. C., Rosenfield, C., Nielsen, R., You, K. M., & Jeong, S. E. (2002). Evolution of the integral membrane desaturase gene family in moths and flies. Genetics, 162, 1737-1752.
Knutzon et al., "Identification of Δ5-Desaturase From Mortierella alpine by Heterologous Expression in Bakers' Yeast and Canola," The Journal of Biological Chemistry, 273(45):29360-29366 (1998).
Koziel, M. G., Carozzi, N. B., & Decal, N. (1996). Optimizing expression of transgenes with an emphasis on post- transcriptional events. Plant Molecular Biology, 32, 393-405.
Lee et al., "Identification of Non-Heme Diiron Proteins That Catalyze Triple Bond and Epoxy Group Formation," Science, 280(5365):915-918 (1998).

Leonard et al., "cDNA Cloning and Characterization of Human Δ5-Desaturase Involved in the Biosynthesis of Arachidonic Acid," The Biochemical Journal, 347(Pt 3):719-724 (2000).
Leonard et al., "Cloning of a Human cDNA Encoding a Novel Enzyme Involved in the Elongation of Long-Chain Polyunsaturated Fatty Acids," The Biochemical Journal, 350(Pt 3):765-770 (2000).
Leonard et al., "Identification and Expression of Mammalian Long-Chain PUPA Elongation Enzymes," Lipids, 37(8):733-740.
Lewis, T., Nichols, P. D., & McMeekin, T. A. (2000). Evaluation of extraction methods for recovery of fatty acids from lipid-producing microheterotrophs. Journal of Microbiological Methods, 43, 107-116.
Lo et al., "15,000 Unique Zebrafish EST Clusters and Their Future Use in Microarray for Profiling Gene Expression Patterns During Embryogenesis," Genome Research Letter, 13(3):455-466.
Lu, L., Xiao, M., Clapp, D. W., Li, Z., & Broxmeyer, H. E. (Dec. 1993). High efficiency retrovirel mediated gene transduction into single isolated immature and replatable CD343+ hematopoietic stem/progenitor cells from human umbilical cord blood. J. Exp. Med., 178, 2089-2096.
Mansour et al., "The Fatty Acid and Sterol Composition of Five Marine Dinoflagellates," Journal of Phycology, 35(4):710-720 (1999).
Medlin et al., "Genetic Characterization of Emiliania huxleyi (Haptophyta)," Journal of Marine Systems, 9:13-31 (1996).
Metz et al., "Production of Polyunsaturated Fatty Acids by Polyketide Syntheses in Both Prokaryotes and Eukaryotes," Science, 293(5528):290-293 (2001).
Meyer et al., "Biosynthesis of Docosahexaenoic Acid in Euglena gracilis: Biochemical and Molecular Evidence for the Involvement of a Δ4-Fatty Acyl Group Desaturase," Biochemistry, 42(32):9779-9788 (2003).
Stukey, J. E., McDonough, V. M., & Martin, C. E. (1990). The OLE1 gene of *Saccharomyces cerevisiae* encodes the Δ9 fatty acid desaturase and can be functionally replaced by the rat stearoyl-CoA desaturase gene. The Journal of Biological Chemistry, 265(33), 20144-20149.
Tsevegsuren et al., (2003) "Isomers of hexadecenoic and hexadecadienoic acids in Androspace septentrionalis (Primulaceae) seed oil" Lipids 38(11):1173-1178.
File History of U.S. Pat. No. 7,807,849, Singh et al., issued Oct. 5, 2010 (U.S. Appl. No. 11/112,882, filed Apr. 22, 2005).
File History of U.S. Patent Application Publication No. 2011/0015415, Singh, et al., published Jan. 20, 2011 (U.S. Appl. No. 12/661,978, filed Mar. 26, 2010).
File History of U.S. Patent Application Publication No. 2012-0041218, Singh et al., published Feb. 16, 2012, (U.S. Appl. No. 13/243,747, filed Sep. 23, 2011).
File History of U.S. Pat. No. 7,834,250, Singh et al., issued Nov. 16, 2010 (U.S. Appl. No. 11/587,092, filed Oct. 20, 2006).
File History of U.S. Pat. No. 7,932,438, Singh et al., issued (U.S. Appl. No. 12/945,708, filed Nov. 12, 2010).
File History of U.S. Patent Application Publication No. 2011/0201065, Singh et al., published Aug. 18, 2011 (U.S. Appl. No. 13/093,252, filed Apr. 25, 2011).
File History of U.S. Pat. No. 8,158,392, Singh et al., issued Apr. 17, 2012 (U.S. Appl. No. 13/311,240, filed Sep. 23, 2011).
File History of U.S. Patent Application Publication No. 2011/0190521, Damcevski et al., published Aug. 4, 2011 (U.S. Appl. No. 12/310,645, filed Feb. 16, 2011).
File History of U.S. Appl. No. 12/989,405, Zhou et al., filed May 16, 2011.
File History of U.S. Pat. No. 7,589,253, Green et al., issued Sep. 15, 2009 (U.S. Appl. No. 09/981,124, filed Oct. 17, 2011).
File History of U.S. Pat. No. 7,834,248, Green et al., issued Nov. 16, 2010 (U.S. Appl. No. 11/699,817, filed Jan. 30, 2007).
File History of U.S. Patent Application No. 2012-0016144, Singh et al., Jan. 19, 2012 (U.S. Appl. No. 13/129,940, filed Sep. 30, 2011).
File History of U.S. Pat. No. 8,809,559, Petrie et al., issued Aug. 19, 2014.
File History of U.S. Pat. No. 8,816,106, issued Aug. 26, 2014 (Damcevski et al.).
Mar. 12, 2013 Office Action, issued in connection with U.S. Appl. No. 12/310,645.

(56) References Cited

OTHER PUBLICATIONS

Aug. 12, 2013 Response, filed in connection with U.S. Appl. No. 12/310,645.
Oct. 22, 2013 Office Action, issued in connection with U.S. Appl. No. 12/310,645.
Jan. 22, 2014 Response, filed in connection with U.S. Appl. No. 12/310,645.
Jan. 24, 2014 Examiner Interview Summary, issued in connection with U.S. Appl. No. 12/310,645.
Feb. 6, 2014 Notice of Allowance, issued in connection with U.S. Appl. No. 12/310,645.
Mar. 7, 2014 Request for Continued Examination, including Information Disclosure Statement, filed in connection with U.S. Appl. No. 12/310,645.
Apr. 7, 2014 Notice of Allowance, issued in connection with U.S. Appl. No. 12/310,645.
International Search Report issued by the International Searching Authority (ISA/AU) dated Nov. 21, 2007 in connection with International Patent Application No. PCT/AU2007/001242.
Written Opinion of the International Searching Authority issued by the International Searching Authority (ISA/AU) dated Nov. 21, 2007 in connection with International Patent Application No. PCT/AU2007/001242.
Australian Examination Report dated Jul. 25, 2012 in connection with Australian Patent Application No. 2007291937.
Apr. 2, 2014 Office Action, issued in connection with Australian Patent Application No. 2007291937.
Mar. 21, 2014 Response, filed in connection with Australian Patent Application No. 2007291937.
Aug. 1, 2014 Response to First Canadian Office Action, filed in connection with Canadian Patent Application No. 2,661,697.
Feb. 4, 2014 Office Action, issued in connection with Canadian Patent Application No. 2,661,697.
Aug. 22, 2014 Office Action, issued in connection with Canadian Patent Application No. 2,661,697.
Supplemental European Search Report and Search Opinion dated Jun. 24, 2010 in connection with European Patent Application No. 07784864.6.
Response filed to European Search Opinion dated Jan. 19, 2011 in connection with European Patent Application No. 07784864.6.
European Examination Report dated Jul. 18, 2011 in connection with European. Patent Application No. 07784864.6.
Mar. 17, 2014 Response, filed in connection with European Patent Application No. 07784864.6.
Sep. 13, 2013 Office Action, issued in connection with European Patent Application No. 07784864.6.
Response filed to European Examination Report dated May 15, 2012 in connection with European Patent Application No. 07784864.6.
Zealand Examination Report dated Jul. 29, 2010 in connection with New Zealand Patent Application No. 575809.
Response filed to New Zealand Examination Report filed Dec. 23, 2011 in connection with New Zealand Patent Application No. 575809.
Zealand Examination Report dated Jan. 24, 2012 in connection with New Zealand Patent Application No. 575809.
Chinese Office Action dated May 17, 2011 in connection with Chinese Patent Application No. 200720040245.5, including English Language translation.
Response filed to Chinese Office Action dated Nov. 30, 2011 in connection with Chinese Patent Application No. 200780040245.5, including English Language translation of claims.
Second Chinese Office Action dated Jun. 6, 2012 in connection with Chinese Patent Application No. 200780040245.5, including English Language translation.
Response filed to Second Chinese Office Action dated Oct. 22, 2012 in connection with Chinese Patent Application No. 200780040245.5.
Third Chinese Office Action dated Feb. 17, 2013 in connection with Chinese Patent Application No. 200780040245.5, including English Language translation.
Response filed to Chinese Office Action dated Jul. 4, 2013 in connection with Chinese Patent Application No. 200780040245.5.
Aug. 21, 2013 Office Action, issued in connection with Chinese Patent Application No. 200780040245.5, including English Language Translation.
PCT International Patent Application Publication No. WO 97/21340, published Jun. 19, 1997 (DeBonte et al.).
PCT International Patent Application Publication No. WO 99/49050, published Sep. 20, 1999 (E.I. Du Pont De Nemours and Company).
PCT International Patent Application Publication No. WO 01/96363, published Dec. 20, 2001 (Boyce Thompson Institute for Plant Research).
PCT International Patent Application Publication No. WO 2006/069936, published Jul. 6, 2006 (Cirpus et al.).
Eigenheer et al (2002) Isolation and molecular characterization of *Musca domestica* delta-9 desaturase sequences. Insect Molecular Biology 11(6):533-542.
Morimoto et al. (2005) Hot Topic: Endogenous Production of n-3 and n-6 Fatty Acids in Mammalian Cells. J. Dairy Sci., 88:1142-1146.
Park and Jeong (2005) Cloning and Functional Expression of eDNA Encoding Pheromone $\Delta 9$ Acyl-CoA Desaturase of the Tobacco Cutworm, Spodoptera litura (Lepidoptera: Noctuidae). Entomological Research, 35(4):253-263.
Passorn et al (1999) Heterologous Expression of *Mucor rouxii* $\Delta^{12}$-Desaturase Gene in *Saccharomyces cerevisiae*. Biochemical and Biophysical Research Communications 263, 47-51.
Pereira et al (2004) A novel ω3-fatty acid desaturase involved in the biosynthesis of eicosapentaenoic acid. Biochem J. 378, 665-671.
Peyou-Ndi et al. (2000) Identification and Characterization of an Animal $\Delta 12$ Fatty Acid Desaturase Gene by Heterologous Expression in *Saccharomyces cerevisiae*. Archives of Biochemistry and Biophysics, vol. 376, No. 2, pp. 399-408.
Riddervold et al (2002) Biochemical and molecular characterizaton of house cricket (*Acheta domesticus*, Orthoptera: Gryllidae) $\Delta 9$ desaturase. Insect Biochemistry and Molecular Biology 32, 1731-1740.
Stanley-Samuelson et al (1998) Fatty Acids in Insects: Composition, Metabolism, and Biological Significance. Archives of Insect Biochemistry and Physiology 9:1-33.
Stymne and Appelgvist (1978) The Biosynthesis of Linoleate from Oleoyl-CoA via Oleoyl-Phosphatidylcholine in Microsomes of Developing Safflower Seeds. Eur. J. Biochem. 90, 223-229.
Wada et al (1993) The desA Gene of the *Cyanobacterium syliechocvstis* sp. Strain PCC6803 Is the Structural Gene for $\Delta 12$ Desaturase. Journal of Bacteriology 175(18):6056-6058.
Wang and Hildebrand (1988) Biosynthesis and Regulation of Linolenic Acid in Higher Plants. Plant Physiol. Biochem. 26(6), 777-792.
Zhou et al. (2008) Isolation and Functional Characterization of two independently-evolved fatty acid $\Delta 12$-desaturase genes from insects. Insect Molecular Biology 17(6), 667-676.
Sayanova et al., GenBank Accession No. U79010, NCBI, pp. 1-2 (1996).
Maroto et al., GenBank Accession No. AY055117, NCBI, pp. 1-2 (2001).
Maroto et al., GenBank Accession No. AY055118, NCBI, pp. 1-2 (2001).
Sayanova et al., GenBank Accession No. AY234127, NCBI, pp. 1-2 (2003).
Sayanova et al., GenBank Accession No. AF536525, NCBI, pp. 1-2 (2003).
Sperling et al., GenBank Accession No. A3250735, NCBI, pp. 1-2 (1999).
Kajikawa et al., GenBank Accession No. AY583463, NCBI, pp. 1-2 (2004).
Knutzon et al., GenBank Accession No. AF110510, NCBI, pp. 1-2 (1998).
Kobayashi et al., GenBank Accession No. AB020032, NCBI, pp. 1-2 (1998).

(56) References Cited

OTHER PUBLICATIONS

Qiu et al., GenBank Accession No. AF419296, NCBI, pp. 1-2 (2001).
Aki et al., GenBank Accession No. AB052086, NCBI, pp. 1-2 (2000).
Zhang et al., GenBank Accession No. AY320288, NCBI, pp. 1-2 (2003).
Domergue et al., GenBank Accession No. AY082393, NCBI, pp. 1-2 (2002).
Reddy et al., GenBank Accession No. L11421, NCBI, pp. 1-2 (1993).
Hastings et al., GenBank Accession No. AF309556, NCBI, pp. 1-2 (2000).
Wallis et al., GenBank Accession No. AF139720, NCBI, pp. 1-2 (1991).
Libisch et al., GenBank Accession No. A5133728, NCBI, pp. 1-2 (1999).
GenBank Accession No. NM_069288, NCBI, pp. 1-3 (2003).
Zank et al., GenBank Accession No. AF428243, NCBI, pp. 1-2 (2002).
Kajikawa et al., GenBank Accession No. A1583464, NCBI, pp. 1-2 (2004).
Chaung et al., GenBank Accession No. AF206662, NCBI, pp. 1-2 (1999).
Cirpus et al., GenBank Accession No. AX951565, NCBI, p. 1 (2003).
Heinz et al., GenBank Accession No. AX214454, NCBI, p. 1 (2001).
Leonard et al., GenBank Accession No. AF231981, NCBI, pp. 1-2 (2000).
Aki et al., GenBank. Accession No. AB071985, NCBI, pp. 1-2 (2001).
Aki et al., GenBank Accession No. AB071986, NCBI, pp. 1-2 (2001).
Tvrdik et al., GenBank Accession No. AF170907, NCBI, pp. 1-2 (1999).
Tvrdik et al., GenBank Accession No. AF170908, NCBI, pp. 1-2 (1999).
Agaba et al., GenBank Accession. No. AF532782, NCBI, pp. 1-2 (2004).
Lo et al., GenBank Accession No. NM_199532, NCBI, pp. 1-2 (2003).
Wilkinson et al., GenBank Accession No. 268749, NCBI, pp. 1-8 (1996).
Mukerji et al., GenBank Accession No. AX464802, NCBI, p. 1 (2002).
Qi et al., GenBank Accession No. AF390174, NCBI, pp. 1-2 (2001).
Dafny-Yelin et al., "Delivery of Multiple Transgenes to Plant Cells," Plant Physiology, vol. 145, pp. 1118-11128 (Dec. 2007).
Damude et al., "Engineering Oilseed Plants for a Sustainable, Land-Based Source of Long Chain Polyunsaturated Fatty Acids," Lipids, 42:179-185 (2007).
Domergue et al., "Acyl Carriers Used as Substrates by the Desaturases and Blongases Involved in Very Long-Chain Polyunsaturated Fatty Acids Biosynthesis Reconstituted in Yeast," J. Biol. Chem., 278:35115-35126 (2003).
Halpin, "Gene stacking in transgenic plants—the challenge for 21st century plant biotechnology," Plant Biotechnology Journal, 3:141-155 (2005).
Hoffman et al., "Metabolic Engineering of ω3-Very Long Chain Polyunsaturated Fatty Acid Production by an Exclusively Acyl-CoA-dependent Pathway," The Journal of Biological Chemistry, 283:22352-22362 (2008).
Parker-Barnes et al., "Identification and Characterization of an Enzyme Involved in the Elongation of n-6 and n-3 Polyunsaturated Fatty Acids," Proceedings of The National Academy of Sciences of The United States of America, 97(15):8284-8289 (2000).
Qi et al., "Production of Very Long Chain Polyunsaturated Omega-3 and Omega-6 Fatty Acids in Plants," Nature Biotechnology 22:739-745 (2004).

Robert et al., "Metabolic engineering of Arabidopsis to produce nutritionally important DHA in seed oil," Functional Plant Biology, 32:473-479 (2005) (Abstract Only).
Slater et al., "Metabolic engineering of Arabidopsis and Brassica for poly(3-hydroxybutyrate-co-3-hydroxyvalerate) copolymer production," Nature Biotechnology, 12:1011-1016 (Oct. 1999).
Truksa et al., "Metabolic Engineering of Plants to Produce Very Long-Chain Polyunsaturated Fatty Acids," Transgenic Research, 15:131-137 (2006).
Meyer et al., GenBank Accession No. AY278558, NCBI, pp. 1-2 (2003).
Tenon et al., GenBank Accession No. AY332747, NCBI, pp. 1-2 (2003).
Qiu et al., GenBank Accession No. AF489589, NCBI, pp. 1-2 (2001).
Thurmond et al., GenBank Accession No. AF391543, NCBI, pp. 1-2 (2001).
Cho et al., GenBank Accession No. AF199596, NCBI, pp. 1-2 (1999).
Requirement for Restriction/Election dated Mar. 5, 2007 in connection with U.S. Appl. No. 11/112,882.
Response to Requirement for Restriction/Election filed May 7, 2007 in connection with U.S. Appl. No. 11/112,882.
Non Final Office Action dated Oct. 11, 2007 in connection with U.S. Appl. No. 11/112,882.
Response to Non Final Office Action filed Oct. 31, 2007 in connection with U.S. Appl. No. 11/112,882.
Notice of Informal or Non-Responsive Amendment dated Feb. 26, 2008 in connection with U.S. Appl. No. 11/112,882.
Response to Office Action filed Mar. 11, 2008 in connection with U.S. Appl. No. 11/112,882.
Non-Final Office Action dated Jun. 17, 2008 in connection with U.S. Appl. No. 11/112,882.
Response to Non-Final Office Action filed Oct. 17, 2008 in connection with U.S. Appl. No. 11/112,882.
liFinal Office Action dated Apr. 1, 2009 in connection with U.S. Appl. No. 11/112,882.
Response to Final Office Action filed Jul. 1, 2009 in connection with U.S. Appl. No. 11/112,882.
Notice of Allowance dated Aug. 21, 2009 in connection with U.S. Appl. No. 11/112,882.
Restriction Requirement dated Apr. 30, 2009 in connection with U.S. Appl. No. 11/587,092.
Response to Restriction Requirement filed Jun. 30, 2009 in connection with U.S. Appl. No. 11/587,092.
Non-Final Office Action dated Nov. 17, 2009 in connection with U.S. Appl. No. 11/587,092.
Examiner Interview Summary Record dated Feb. 22, 2010 in connection with U.S. Appl. No. 11/587,092.
Response to Non-Final Office Action, filed Mar. 17, 2010 in connection with U.S. Appl. No. 11/587,092.
Jul. 2, 2010 Notice of Allowance in connection with U.S. Appl. No. 11/587,092.
Office Action issued by the U.S. Patent Office dated Dec. 28, 2010 in connection with U.S. Appl. No. 12/661,978.
Response to Office Action, filed Jan. 25, 2011 in connection with U.S. Appl. No. 12/661,978.
Final Office Action, dated Apr. 18, 2011 in connection with U.S. Appl. No. 12/661,978.
Interview Summary Record, dated May 24, 2011 in connection with U.S. Appl. No. 12/661,978.
Response to Final Office Action, filed Jun. 16, 2011 in connection with U.S. Appl. No. 12/661,978.
Notice of Allowance, dated Sep. 1, 2011 in connection with U.S. Appl. No. 12/661,978.
Non-Final Office Action dated Jan. 5, 2011 in connection with U.S. Appl. No. 12/945,708.
Response to Non-Final Office Action filed Jan. 10, 2011 in connection with U.S. Appl. No. 12/945,708.
Notice of Allowance, dated Feb. 11, 2011 in connection with U.S. Appl. No. 12/945,708.
Accelerated Examination Support Document, filed Apr. 25, 2011 in connection with U.S. Appl. No. 13/093,252.

(56) References Cited

OTHER PUBLICATIONS

Pre-Examination Search Document, filed Apr. 25, 2011 in connection with U.S. Appl. No. 13/093,252.
Non-Final Office Action, dated Aug. 30, 2011 in connection with U.S. Appl. No. 13/093,252.
Examiner Interview Summary, dated Sep. 13, 2011 in connection with U.S. Appl. No. 13/093,252.
Amendment in Response to Office Action and Summary of Examiner Interview, filed Sep. 16, 2011 in connection with U.S. Appl. No. 13/093,252.
Notice of Allowance, dated Oct. 7, 2011 in connection with U.S. Appl. No. 13/093,252.
Dec. 5, 2011 Accelerated Examination Support Document, filed in connection with U.S. Appl. No. 13/311,240.
Dec. 5, 2011 Pre-Examination Search Document, filed in connection with U.S. Appl. No. 13/311,240.
Feb. 6, 2012 Communication, filed in connection with U.S. Appl. No. 13/311,240.
Feb. 17, 2012 Notice of Allowance, issued in connection with U.S. Appl. No. 13/311,240.
Feb. 1, 2012 Non-Final Office Action, issued in connection with U.S. Appl. No. 13/243,747.
May 1, 2012 Amendment, filed in connection with U.S. Appl. No. 13/243,747.
Jul. 6, 2012 Notice of Allowance, issued in connection with U.S. Appl. No. 13/243,747.
Dec. 7, 2012 Office Action, issued in connection with U.S. Appl. No. 13/448,107.
Jan. 7, 2013 Response, filed in connection with U.S. Appl. No. 13/448,107.
Jan. 15, 2013 Office Action, issued in connection with U.S. Appl. No. 13/448,107.
Apr. 15, 2013 Response, filed in connection with U.S. Appl. No. 13/448,107.
May 9, 2013 Notice of Allowance, filed in connection with U.S. Appl. No. 13/448,107.
Mar. 11, 2013 Office Action, issued in connection with U.S. Appl. No. 13/651,275.
Jun. 11, 2013 Response, filed in connection with U.S. Appl. No. 13/651,275.
Aug. 16, 2013 Notice of Allowance, issued in connection with U.S. Appl. No. 13/651,275.
Certik M. and Shimizu S., (1999) Biosynthesis and regulation of microbial polyunsaturated fatty acid production. J. Biosci Bioeng, 87(1):1-14.
Damude et al., (2007) Engineering Oilseed Plants for a Sustainable, Land-Based Source of Long Chain Polyunsaturated Fatty Acids. Lipids, 42:179-185.
Domergue et al., (2003) Acyl Carriers Used as Substrates by the Desaturases and Elongases Involved in Very Long-chian Polyunsaturated Patty Acids Biosynthesis Reconstituted in Yeast. J. Biol. Chem. 278; 35115-35126.
Hoffmann et al., (2008) Metabolic Engineering of ω3-Very Long Chain Polyunsaturated Fatty Acid Production by an Exclusively Acyl-CoA-dependent Pathway. The Journal of Biological Chemistry, 283:22352-22362.
Kajikawa M. et al., (2004) Isolation and characterization of delta(6)-desaturase, an ELO-like enzyme and delta(5)-desaturase from liverword Marchantia polymorpha and production of arachidonic and eicosapentaenoic acids in the methylotrophic yeast Pichia pastoris. Plant Mol Biol, 54(3) :335-52.
Marquardt et al., (2000) "cDNA cloning, genomic structure, and chromosomal localization of three members of the human fatty acid desaturase family" Genomics, 66(2):175-83.
Parker-Barnes, J.M., et al., (2000) "Identification and Characterization of an Enzyme Involved in the Elongation of n-6 and n-3 Polyunsaturated Fatty Acids," Proceedings of the National Academy of Sciences of the United States of America, 97(15): 8284-8289.

Qi et al., (2004) "Production of very long chain polyunsatured omega-3 and omega-6 fatty acids in plants" Nature Biotechnology 22:739-745 (published online May 16, 2004).
Qiu et al. (2001) GenBank Accession No. AF489589, NCBI p. 1.
Qiu, X., et al., (2001) "Identification of a Δ4 Fatty Acid Desaturase from Thraustochytrium sp. Involved in the Biosynthesis of Decosahexanoic Acid by Heterologous Expression in Saccharomyces cerevisiae and Brassica juncea," The Journal of Biological Chemistry, 276(34): 31561-31566.
Savanova O.V. and Napier J.A., Eicosapentaenoic acid: biosynthetic routes and the potential for synthesis in transgenic plants. Phytochemistry, 2004; 65(2):147-58.
Truksa et al., (2006) "Metabolic Engineering of Plants to Produce Very Long-Chain Polyunsaturated Fatty Acids", Transgenic Research, 15:131-137.
Notification of European publication number issued Jan. 31, 2007 in connection with European Patent Application No. 05733657.0.
Supplementary European Search Report dated Apr. 1, 2008 in connection with European Patent Application No. 05733657.0.
Communication Pursuant to Article 94(3) EPC dated Feb. 12, 2009 in connection with European Patent Application No. 05733657.0.
Response to Communication from the Examining Division, filed Oct. 22, 2009 in connection with European Application No. EP 05733657.0.
Communication from the Examining Division issued by the European Patent Office dated Aug. 18, 2010 in connection with European Application No. EP 05733657.0.
Response to Communication from the Examining Division, filed Feb. 3, 2011 in connection with European Application No. EP 05733657.0.
Communication from the Examining Division issued by the European Patent Office dated Apr. 6, 2011 in connection with European Application No. EP 05733657.0.
Examination Report dated Mar. 14, 2012 in connection with corresponding European Patent Application No. 05733657.0.
Oct. 17, 2011 Response to Apr. 6, 2011 Communication from the Examining Division, filed in connection with European Application No. EP05733657.0.
Sep. 24, 2012 Response to Mar. 14, 2012 Communication from the Examining Division, filed in connection with European Application No. EP05733657.0.
Communication from the Examining Division issued by the European Patent Office dated Nov. 9, 2012 in connection with European Patent Application No. 05733657.0.
Apr. 5, 2013 Response filed in connection with European Patent Application No. 10184533.7.
European Search Report, issued by the European Patent Office dated Jul. 15, 2011 in connection with European Patent Application No. 11155282.4.
Extended European Search Report, issued by the European Patent Office dated Oct. 25, 2011 in connection with European Patent Application No. 11155282.4.
Sep. 7, 2012 Amendment after receipt of European Search Report, tiled in connection with European Patent Application No. 11155282.4.
Mar. 11, 2013 Office Action, issued in connection with European Patent Application No. 11155282.4.
European Search Report, issued by the European Patent Office dated Jul. 15, 2011 in connection with European Patent Application No. 11155364.0.
Extended European Search Report, issued by the European Patent Office dated Oct. 25, 2011 in connection with European Patent Application No. 11155364.0.
Sep. 10, 2012 Amendment after receipt of European Search Report, filed in connection with European Patent Application No. 11155364.0.
Feb. 13, 2013 Office Action issued in connection with European Patent Application No. 11155364.0.
European Search Report, issued by the European Patent Office dated Oct. 25, 2011 in connection with European Patent Application No. 11155266.7.

(56) References Cited

OTHER PUBLICATIONS

Extended European Search Report and Opinion dated Feb. 10, 2012 in connection with corresponding European Divisional Patent Application No. 11155266.7.
Rule 69 EPC Communication dated Mar. 19, 2012 in connection with European Divisional Patent Application No. 11155266.7.
Jan. 3, 2013 Response filed in connection with European Patent Application No. 11155266.7.
Examination Report, issued by the Australian Patent Office dated Sep. 6, 2012 in connection with Australian Patent Application No. 2011232757.
Australian Examination Report dated Nov. 16, 2009 in connection with Australian Patent Application No. 2005235627.
Australian Examination Report dated Mar. 14, 2011 in connection with Australian Patent Application No. 2005235627.
Response to Australian Examination Report filed Feb. 25, 2011 in connection with Australian Patent Application No. 2005235627.
Response to Australian Examination Report filed Apr. 19, 2011 in connection with Australian Patent Application No. 2005235627.
Australian Examination Report dated May 16, 2011 in connection with Australian Patent Application No. 2005235627.
Response to Australian Examination Report filed Jun. 14, 2011 in connection with Australian Patent Application No. 2005235627.
Chinese Examination Report dated Apr. 10, 2009 in connection with Chinese Patent Application No. 200580020696.3.
Response to Chinese Examination Report filed Jul. 21, 2009 in connection with Chinese Patent Application No. 200580020696.3.
Chinese Examination Report dated Apr. 30, 2010 in connection with Chinese Patent Application No. 200580020696.3.
Response to Chinese Examination Report filed Sep. 15, 2010 in connection with Chinese Patent Application No. 200580020696.3.
Nov. 30, 2011 Request for Re-Examination filed in connection with Chinese Patent Application No. 200580020696.3, including English language translation of submitted claims.
Aug. 18, 2011 Decision of Rejection issued by the Chinese Patent Office in connection with Chinese Patent Application No. 200580020696.3.
Response to Notification of Re-Examination filed on Oct. 18, 2012 in connection with Chinese Patent Application No. 200580020696.3, including English language copy of the filed claims.
Oct. 18, 2012 Request for Reexamination filed in connection with Chinese Patent Application No. 200580020696.3.
Jan. 29, 2013 Office Action issued in connection with Chinese Patent Application No. 201210006139.8.
Brazilian Technical Opinion issued Mar. 1, 2012 in connection with corresponding Brazilian Patent Application No. PI 0510132-8.
Response filed to Brazilian Technical Opinion filed Mar. 29, 2012 in connection with corresponding Brazilian Patent Application No. PI 0510132-8.
Nov. 21, 2011 Examination report issued in connection with Canadian Patent Application No. 2,563,875.
May 22, 2012 Response to Examination Report, filed in connection with Canadian Patent Application No. 2,563,875.
Meyer et al., "Novel Fatty Acid Elongases and Their Use for the Reconstitution of Docosahexanoic Acid Biosynthesis," Journal of Lipid Research, 45(10):1899-1909 (2004).
Michaelson et al., "Isolation of a Δ5-Fatty Acid Desaturase Gene From Mortirella alpina," The Journal of Biological Chemistry, 273(30):19055-19059 (1998).
Michaelson et al., "Functional Identification of a Fatty Acid Δ5 Desaturase Gene From Caenorhabditis elegans," Federation of European Biochemical Societies Letters, 439(3):215-218 (1998).
Mitchell and Martin, "A Novel Cytochrome b5-Like Domain Is Linked to the Carboxyl Terminus of the *Saccharomyces cerevisiae* Δ-9 Patty Acid Desaturase," The Journal of Biological Chemistry, 270(50):29766-29772 (1995).
Morita et al., "Biosynthesis of Fatty Acids in the Docosahexaenoic Acid-Producing Bacterium Moritella marina Strain MP-1" Biochemical Society Transactions, 28(6):943-945 (2000).
Mortimer, R. K., & Johnston, J. R. (1986). Genealogy of principal strains of the yeast genetic stock center. Genetics, 113, 35-43.
Moto, K., Suzuki, M. G., Hull, J. J., Kurata, R., Takahashi, S., Yamamoto, M., . . . Matsumoto, S. (2004). Involvement of a bifunctional fatty-acyl desaturase in the biosynthesis of the silkmoth, *Bombyx mori*, sex pheremone. PNAS, 101(23), 8631-8636.
Murata, N., & Wada, H. (1995). Acyl-lipid desaturases and their importance in the tolerance and acclimatization to cold of cyanobacteria. Biochem. J., 308, 1-8.
Napier et al., "Identification of a Caenorhabditis elegans Δ6-Fatty-Acid-Desaturase by Heterologous Expression in *Saccharomyces cerevisiae*," The Biochemical Journal, 330(Pt 2):611-614 (1998).
Napier et al., "A Growing Family of Cytochrome b5-Domain Fusion Proteins," Trends in Plant Science, 4(1):2-4 (1999).
Napier et al., "Plant Desaturases: Harvesting the Fat of the Land," Current Opinion in Plant Biology, 2(2):123-127 (1999).
Needleman and Wunsch, "A general method applicable to the search for similarities in the amino acid sequence of two proteins," J. Mol. Biol., 48:443-453 (1970).
Pereira et al., "A Novel omega3-Fatty Acid Desaturase Involved in the Biosynthesis of Eicosapentaenoic Acid," The Biochemical Journal, 378(Pt 2):665-671 (2004).
Perriman et al., "Extended Target-Site Specificity for a Hammerhead Ribozyme," Gene, 113(2):157-163 (1992).
Qi et al., "Identification of a cDNA Encoding a Novel C18-Δ9 Polyunsaturated Fatty Acid-Specific Elongating Activity From the Docosahexaenoic Acid(DHA)-Producing Microalga, Isochrysis galbana," Federation of European Biochemical Societies Letters, 510(3):159-155 (2002).
Qiu et al., "Identification of a Δ4 Fatty Acid Desaturase From *Thraustochytrium* sp. Involved in the Biosynthesis of Docosahexanoic Acid by Heterologous Expression in *Saccharomyces cerveisiae* and Brassica juncea," The Journal of Biological Chemistry, 276(34):31561-31566 (2001).
Qiu, X., Reed, D. W., Hong, H., MacKenzie, S. L., & Covello, P. S. (2001). Identification and analysis of a gene from Calendula officinalis encoding a fatty acid conjugase. Plant Physiology, 125, 847-855.
Reddy et al., "Isolation of a Δ6-Desaturase Gene From the *Cyanobacteriurn synechocystis* sp. Strain PCC6803 by Gain-Of-Function Expression in *Anabaena* sp. Strain PCC7120," Plant Molecular Biology, 27: 293-300 (1993).
Rodriguez, S., Mao, G., Liu, W., Pifta, B., Rooney, a. P., Camps, F., . . . Fabrics, G. (2004). Expression and evolution of 89 and Δ11 desaturase genes in the moth Spodoptera littoralis. Insect Biochemistry and Molecular Biology, 34, 1315-1328.
Saito et al., "A Second Functional Δ5 Fatty Acid Desaturase in the Cellular Slime Mould Dictyostelium discoideurn," European Journal of Biochemistry, 267(6):1813-1818 (2000).
Sakuradani et al., "Δ6-Fatty Acid Desaturase From an Arachidonic Acid-Producing Mortierella Fungus. Gene Cloning and Its Heterologous Expression in a Fungus, Aspergillus," Gene, 238(2):445-453 (1999).
Sayanova et al., "Expression of a Borage Desaturase cDNA Containing an N-Terminal Cytochrome b5 Domain Results in the Accumulation of High Levels of Δ6-Desaturated Patty Acids in Transgenic Tobacco," Proceedings of The National Academy of Sciences of The United States of America, 94(8):4211-4216 (1997).
Sayanova et al., "Histidine-41 of the Cytochrome b5 Domain of the Borage Δ6 Fatty Acid Desaturase Is Essential for Enzyme Activity," Plant Physiology, 121(2):641-646 (1999).
Sayanova et al., "Identification of Primula Fatty Acid Δ6-Desaturases with n-3 Substrate Preferences," Federation of European Biochemical Societies, 542:100-110 (2003).
Sayanova and Napier, "Eicosapentaenoic Acid: Biosynthetic Routes and the Potential for Synthesis in Transgenic Plants," Phytochemistry, 65(2):147-158 (2004).
Sayanova, O., Haslam, R., Caleron, M. V., & Napier, J. A. (May 2007), Cloning and characterization of unusual fatty acid desaturases from Anemone leveillei: identification of an acyl-coenzyme A C20 Δ5-desaturase responsible for the synthesis of sciadonic acid. Plant Physiology, 144, 455-467.

(56) References Cited

OTHER PUBLICATIONS

Serra, N., Gauthier, L. T., Fabrias, C., & Buist, P. H. (2006). Δ11 desaturases of Trichoplusia ni and Spodoptera littoralis exhibit dual catalytic behaviour. Insect Biochemistry and Molecular Biology, 36, 822-825.

Shanklin, J., & Cahoon, E. B. (1998). Desaturation and related modifications of fatty acids. Annu. Rev. Plant Physiol. Plant Mol. Biol., 49, 611-641.

Shippy et al., "The Hairpin Ribozyme—Discovery, Mechanism, and Development for Gene Therapy," Molecular Biotechnology, 12(1):117-129 (1999).

Simopoulos, "Symposium: Role of Poultry Products in Enriching the Human Diet With N-3 PUFA," Poultry Science, 79:961-970 (2000).

Simopoulus, A. P. (2000). Human requirement for N-3 polyunsaturated fatty acids. Poultry Science, 79(7), 961-970.

Singh et al., "Transgenic Expression of a Δ12-Epoxygenase Gene in Arabidopsis Seeds Inhibits Accumulation of Linoleic Acid," Planta, 212:872-879 (2001).

Smith, C. R., Jr. (1971). Occurrence of unusual fatty acids in plants. Progress in the Chemistry of Fats and Other Lipids, 11, 137, 139-177.

Smith, M. A., Moon, H., Chowrira, G., & Kunst, L. (2003). Heterologous expression of a fatty acid hydroxylase gene in developing seeds of Arabidopsis thaliana. Planta, 217, 507-516.

Sperling et al., "A Bifunctional Δ6-Fatty Acyl Acetylenase/Desaturase From the Moss Ceratodon purpureus," European Journal of Biochemistry, 267(12):3801-3811 (2000).

Sperling and Heinz, "Desaturases Fused to Their Electron Donor," European Journal of Lipid Science and Technology, 103(3):158-180 (2001).

Sprecher et al., "Reevaluation of the Pathways for the Biosynthesis of Polyunsaturated Fatty Acids," Journal of Lipid Research, 36(12):2471-2477 (1995).

Spychalla et al., "Identification of an animal omega-3 Fatty Acid Desaturase by Heterologous Expression in Arabidopsis," Proceedings of the National Academy of Sciences of the United States of America, 94(4):1142-1147 (1997).

Stålberg et al., "Deletion Analysis of a 2S Seed Storage Protein Promoter of Brassica napus in Transgenic Tobacco," Plant Molecular Biology, 23(4):671-683 (1993).

Stymne, S., & Appelqvist, L. (1978). The biosynthesis of linoleate from oleoyl-CoA via oleoyl-phosphatidylcholine in microsomes of developing safflower seeds. Fur. J. Biochem, 90, 223-229.

Takeyama et al., "Expression of the Eicosapentaenoic Acid Synthesis Gene Cluster From Shewaneila sp. in a Transgenic Marine Cyanobacterium, Synechococcus sp.," Microbiology, 143(Pt 8):2725-2731 (1997).

Tanaka et al., "Isolation of Clustered Genes That Are Notably Homologous to the Eicosapentaenoic Acid Biosynthesis Gene Cluster From the Docosaehexaenoic Acid-Producing Bacterium Vibrio marinus Strain MP-1," Biotechnology Letters, 21(11):939-945 (1999).

Thompson, J. D., Gibson, T. J., Plewniak, F., Jeanmougin, F., & Higgins, D. G. (1997). The CLUSTAL_K windows interface: flexible strategies for multiple sequence alignment aided by quality analysis tools. Nucleic Acids Research, 25(24), 4876-4882.

Tonon et al., "Identification of a very Long Chain Polyunsaturated Fatty Acid Δ4-Desaturase From the Microalga Pavlova lutheri," Federation of European Biochemical Societies, 553(3):440-444 (2003).

Trautwein, "n-3 Fatty Acids—Physiological and Technical Aspects for Their Use in Food," European Journal of Lipid Science and Technology, 103(1):45-55 (2001).

Valvekens et al., "Agrobacterium tumefaciens-Mediated Transformation of Arabidopsis thaliana Root Explants by Using Kanamycin Selection," Proceedings of the National Academy of Sciences of the United States of America, 85(15):5536-5540.

Van de Loo et al., "An oleate 12-hydroxylase from Ricinus communis L. is a fatty acyl desaturase homolog," Proc. Natl. Acad. Sci. USA, 92:6743-6747 (Jul. 1995).

Volkman et al., "Fatty Acid and Lipid Composition of 10 Species of Microalgae Used in Mariculture," Journal of Experimental Marine Biology and Ecology, 128(3):219-240 (1989).

Wagner, E., Zatloukal, K., Cotten, M., Kirlappos, H., Mechtler, K., Curiel, D. T., & Birnstiel, M. L. (Jul. 1992). Coupling of adenovirus to transferrin-polylysine/DNA complexes greatly enhances receptor-mediated gene delivery and expression of transfected genes. Proc. Natl. Acad. Sci. USA, 89, 6099-6103.

Wallis and Browse, "The Δ8-Desaturase of Euglena gracilis: An Alternate Pathway for Synthesis of 20-Carbon Polyunsaturated Fatty Acids," Archives of Biochemistry and Biophysics, 365(2):307-316 (1999).

Wang et al., "Intron-Mediated Improvement of a Selectable Marker Gene for Plant Transformation Using Agrobacterium Tumefaciens," Journal of Genetics & Breeding, 51:325-334 (1997).

Waterbury and Willey, "Isolation and Growth of Marine Planktonic Cyanobacteria," Methods of Enzymology, 167:100-105 (1988).

Waterhouse et al., "Virus Resistance and Gene Silencing in Plants Can Be Induced by Simultaneous Expression of Sense and Antisense RNA," Proceedings of the National Academy of Sciences of the United States of America, 95(23):13959-13964 (1998).

Watts and Browse, "Isolation and Characterization of a Δ5-Fatty Acid Desaturase From Caenorhabditis elegans," Archives of Biochemistry and Biophysics, 362(1):175-182 (1999).

Williams and Szalay, "Stable Integration of Foreign DNA Into the Chromosome of the Cyanobacterium Synechococcus R2," Gene, 24(1):37-51 (1983).

Whitney et al., "Functional Characterization of Two Cytochrome b5-Fusion Desaturases From Anemone leveillei: The Unexpected Identification of a Fatty Acid Δ6-Desaturase," Planta, 217(6):983-992 (2003).

Whittle, E., Cahoon, E. B., Subrahmanyam, S., & Shanklin, J. (2005). A multifunctional acyl-acyl carrier protein desaturase from Hedera helix L. (English ivy) can synthesize 16- and 18- carbon monoene and diene products. The journal of Biological Chemistry, 280(31), 28169-28176.

Wolff et al., "Arachidonic, Eicosapentaenoic, and Biosynthetically Related Fatty Acids in the Seed Lipids from a Primitive Gymnosperm, Agathis Robusta" Lipids, 34(10):1083-1097 (1999).

Yazawa, "Production of Eicosapentaenoic Acid From Marine Bacteria," Lipids, 31:S297-300 (1996).

Yu et al., "Production of Eicosapentaenoic Acid by a Recombinant Marine Cyanobacterium, Synechococcus sp.," Lipids, 35(10):1061-1064 (2000).

Zank et al., "Cloning and Functional Characterization of an Enzyme Involved in the Elongation of Δ6-Polyunsaturated Fatty Acids From the Moss Physcomitrella patens," The Plant Journal, 31(3):255-268 (2002).

Zhang et al., "Identification and Characterization of a Novel Δ6-Fatty Acid Desaturase Gene From Rhizopus arrhizus," Federation of European Biochemical Societies Letters, 556(1-3):81-85 (2004).

Zhou and Christie, "Suppression of Mutant Phenotypes of the Agrobacterium tumefaciens VirB11 ATPase by Overproduction of VirB Proteins," Journal of Bacteriology, 179(18):5835-5842 (1997).

Zhou, X., Robert, S., Singh, S., & Green, A. (2005). Heterologous production of GLA and SDA by expression of an Echium plantagineum Δ6-desaturase gene. Plant Science, 170, 665-673.

Sanger Institute, GenBank Accession No. NM_069350, NCBI, pp. 1-4 (2003).

Knutzon et al., GenBank Accession No. AF067654, NCBI, pp. 1-2 (1998).

Hong et al., GenBank Accession No. AF419297, NCBI, pp. 1-2 (2001).

Saito et al., GenBank Accession No. AB022097, NCBI, pp. 1-2 (1999).

Domergue et al., GenBank Accession No. AY082392, NCBI, pp. 1-2 (2002).

Qiu et al., GenBank Accession No. AF489588, NCBI, pp. 1-2 (2003).

Kajikawa et al., GenBank Accession No. AY583465, NCBI, pp. 1-2 (2004).

Stohr et al., GenBank Accession No. NM_013402, NCBI, pp. 1-6 (1998).

(56) References Cited

OTHER PUBLICATIONS

Cho et al., GenBank Accession No. NM_019699, NCBI, pp. 1-3 (2009).
Swinburne et al., GenBank Accession No. 270271, NCBI, pp. 1-11 (1998).
Summons to Oral Proceedings which issued in relation to corresponding European patent application 07784864.6.
Third Examination Report dated Sep. 8, 2015 in relation to corresponding Canadian patent application 2,661,697.
Written submissions filed Sep. 4, 2014 in relation to corresponding European patent application 07784864.6.
Amended description pages filed Sep. 4, 2014 in relation to corresponding European patent application 07784864.6.
Main and AR1 claims filed Sep. 4, 2014 in relation to corresponding European patent application 07784864.6.
Result of Consultation from EPO dated Sep. 15, 2014 in relation to corresponding European patent application 07784864.6.
Revised written submissions filed Sep. 16, 2014 in relation to corresponding European patent application 07784864.6.
Amended claims filed Sep. 16, 2014 in relation to corresponding European patent application 07784864.6.

\* cited by examiner

```
                          10        20        30        40        50        60
                    ....|....|....|....|....|....|....|....|....|....|....|....|
Tbdes2bprediction   ATGTCTAGCGAGCTAGCGCCCCTTAACATCCGACCAGTTTGGTTAAAAATAGTATATTTT
Tbdes2b             ............................................................

70        80        90       100       110       120
                    ....|....|....|....|....|....|....|....|....|....|....|....|
Tbdes2bprediction   GCGTACCTACATTACGGTACCATTTTGG--------------------------------
Tbdes2b             ............................GTACTTACTACTTGTTAACAGCGGCGCAATGG 130       140       150       160       170       180
                    ....|....|....|....|....|....|....|....|....|....|....|....|
Tbdes2bprediction   --------------------CCTATTTATTACTCCTTTCGGCCACTCATGGTATTGCAGTGGGT
Tbdes2b             AAAACAATTCTATGGA............................................

190       200       210       220       230       240
                    ....|....|....|....|....|....|....|....|....|....|....|....|
Tbdes2bprediction   GCCCATAGATTATGGGCCCATAGGGCTTACAAAGCCAAACTACCATTGCGCCTCCTTCTG
Tbdes2b             ............................................................

250       260       270       280       290       300
                    ....|....|....|....|....|....|....|....|....|....|....|....|
Tbdes2bprediction   GCCTTTGACCAGACTTTAACATTCCAGAAAGATATATATGATTGGGTTCGAGACCATCGA
Tbdes2b             ............................................................

310       320       330       340       350       360
                    ....|....|....|....|....|....|....|....|....|....|....|....|
Tbdes2bprediction   ATCCATCACAAGTACTCTGACACAGAGTACGACCCCCATAACGCAACCAGAGGGTTCTTT
Tbdes2b             ............................................................

370       380       390       400       410       420
                    ....|....|....|....|....|....|....|....|....|....|....|....|
Tbdes2bprediction   TACAGCCACATTGGTTGGCTGATGATTAAAAAATCGGATAAAGTTATCGCAAAAGGGAAA
Tbdes2b             ............................................................

430       440       450       460       470       480
                    ....|....|....|....|....|....|....|....|....|....|....|....|
Tbdes2bprediction   GAACTAGACTTGAGTGATTTGGAGCAAGACCCAGTGTATGGTACCAAAGAAAGTACTAC
Tbdes2b             ............................................................

490       500       510       520       530       540
                    ....|....|....|....|....|....|....|....|....|....|....|....|
Tbdes2bprediction   TGGTATATGGCACCGTTTCTCGCCTTTATTTTCCCAGCTATGGTACCATGGTACTTTTGG
Tbdes2b             ............................................................

550       560       570       580       590       600
                    ....|....|....|....|....|....|....|....|....|....|....|....|
Tbdes2bprediction   TCGGAACAGTTCAAAGTCTCATGGTACCTTTGCAGTATTTTTCGCTTATGTGTTACTCTA
Tbdes2b             ............................................................

610       620       630       640       650       660
                    ....|....|....|....|....|....|....|....|....|....|....|....|
Tbdes2bprediction   CATGGTACTTGTTTGGTAAACAGTGCGGCCCACATTTGGGGCTCCAAACCATACGATAAG
Tbdes2b             ...........................................................-

670       680       690       700       710       720
                    ....|....|....|....|....|....|....|....|....|....|....|....|
Tbdes2bprediction   TATGACGGCACTAAATCTATTAAGTG----------------------------------
Tbdes2b             --------------------------AAATATTAAACCAGTGGAAACGTCATGGGTGGCT 730       740       750       760       770       780
                    ....|....|....|....|....|....|....|....|....|....|....|....|
Tbdes2bprediction   --------TCATGGTGAGGGTTGGCATAACTACCATCATGTCTTCCCATGGGATTATAAA
Tbdes2b             CATATTAG....................................................

790       800       810       820       830       840
                    ....|....|....|....|....|....|....|....|....|....|....|....|
Tbdes2bprediction   GCTGCAGAATTGGGGTCATATTATGGCAATTGGAATACGGCCTTTATTGATTTATGGCC
Tbdes2b             ............................................................

850       860       870       880       890       900
                    ....|....|....|....|....|....|....|....|....|....|....|....|
Tbdes2bprediction   AAAATTGGGTGGGCCTATGACCTTAAAAGCGCCCCATTGGACATGGTCAAAAAAAGGGGG
Tbdes2b             ............................................................
```

Figure 1

```
                         10         20         30         40         50         60
                ....|....|....|....|....|....|....|....|....|....|....|....|
Tbdes3predicted ATGTTTTTACGTACAATAACATCCAAATTTTATTCAGACCAAATTGTGTGGCGTAATGTT
Tbdes3          ............................................................

70         80         90        100        110        120
                ....|....|....|....|....|....|....|....|....|....|....|....|
Tbdes3predicted TTTCTTTTGCTCATTCTCCACATTATTTCTCTGCAGGG----------------------
Tbdes3          ......................................TTGGTATTTTGTTCTGACAACA 130        140        150        160        170        180
                ....|....|....|....|....|....|....|....|....|....|....|....|
Tbdes3predicted ------------------------GTTTATTTTCGGGGCCTTGACTGGCCAAGGAATC
Tbdes3          ACGAATTGGCCCACATTAATTTACGG..................................

190        200        210        220        230        240
                ....|....|....|....|....|....|....|....|....|....|....|....|
Tbdes3predicted ACAGTGGGGGCCCATCGCCTGTGGGCCCATCGTTGCTACAAAGCGAAGCTTCCTCTAAGA
Tbdes3          .A.T....................C.................A................

250        260        270        280        290        300
                ....|....|....|....|....|....|....|....|....|....|....|....|
Tbdes3predicted ATATTTTTGTGTTTTTTGCAAACTGTTACTTTACAAAATCCCCTGTATGAATGGGTGAGG
Tbdes3          ............................................................

310        320        330        340        350        360
                ....|....|....|....|....|....|....|....|....|....|....|....|
Tbdes3predicted GACCATCGAGTCCATCACAAATATACCGATACCAACGCAGACCCACATAATGCAACCAGG
Tbdes3          .......A.................................T.................

370        380        390        400        410        420
                ....|....|....|....|....|....|....|....|....|....|....|....|
Tbdes3predicted GGATTTTTTTCTCACACATGGGTTGGTTGTTGGTACGTAAACACCCAGATGTCATTGCG
Tbdes3          .........................................A.................

430        440        450        460        470        480
                ....|....|....|....|....|....|....|....|....|....|....|....|
Tbdes3predicted AAAGGAAAAACATTGGATTTGAGTGATCTCCAAGAAGATCCTGTCGTTATGTTTCAAAAA
Tbdes3          ..................................G..........G.............

490        500        510        520        530        540
                ....|....|....|....|....|....|....|....|....|....|....|....|
Tbdes3predicted AAGTACTACAAAATTATAGCCCCGGTCTTGAGCCTTGTCATACCAGCCCTAATCCCATGG
Tbdes3          .............................C.....C.......................

550        560        570        580        590        600
                ....|....|....|....|....|....|....|....|....|....|....|....|
Tbdes3predicted TACTTTTTTGGAGAAGATTTATACGTATCATGGGTTACGACATGTGTGCTTCGCTACGTC
Tbdes3          ..........G.........T.........................C....T..

610        620        630        640        650        660
                ....|....|....|....|....|....|....|....|....|....|....|....|
Tbdes3predicted ATTACCCTGCATTCCACATGGGCTGTGAACAGTGTGGCCCATATCTGGGGCACAAAACCA
Tbdes3          .............G..........C...................................

670        680        690        700        710        720
                ....|....|....|....|....|....|....|....|....|....|....|....|
Tbdes3predicted TACGATAAAAACATTAAACCTACAGAAAATATCGCAGTGGCAATTGTTGCCTATGGAGAA
Tbdes3          ...A..........CTC..C....................A...................

730        740        750        760        770        780
                ....|....|....|....|....|....|....|....|....|....|....|....|
Tbdes3predicted GGTTGGCATAATTACCATCACGTTTTTCCATGGGATTATAAAGCGGCTGAGTTGGGAAAC
Tbdes3          ..........................................A................

790        800        810        820        830        840
                ....|....|....|....|....|....|....|....|....|....|....|....|
Tbdes3predicted TACAGAACAAATCTTAGTACTGCTTTTATTGACTTTATGGCAAAAATTGGATGGGCCTAT
Tbdes3          ......C..............................................C......G...

850        860        870        880        890        900
                ....|....|....|....|....|....|....|....|....|....|....|....|
Tbdes3predicted GATTTGAAAAGTGTCTCGCCTGAAATGTTGAGAAAACGGAAAATGCGGACCGGGGATTGT
Tbdes3          ................T...........................................
```

Figure 2

```
                         10        20        30        40        50        60
                    ....|....|....|....|....|....|....|....|....|....|....|....|
Tbdes6bpredicted    ATGCTAATCTTACTTTCCACAATTGGAGTAACAGCCGGAGCACATCGATTATGGGCACAC
Tbdes6b             ............................................................

70        80        90       100       110       120
                    ....|....|....|....|....|....|....|....|....|....|....|....|
Tbdes6bpredicted    AATTCCTACCAAGCAACAACTTCACTAAAAATATTTCTTATGCTTTGTCAAACATTGGCT
Tbdes6b             ............................................................

130       140       150       160       170       180
                    ....|....|....|....|....|....|....|....|....|....|....|....|
Tbdes6bpredicted    GGACAAAGACCTCCATATACAACTGGGTTCGTCTTCATCGGCTTCATCACAAATATTTCC
Tbdes6b             .......---......T.......................C..................

190       200       210       220       230       240
                    ....|....|....|....|....|....|....|....|....|....|....|....|
Tbdes6bpredicted    AAACAGAAATGGATCCATTTAATCCTCAAAAAGGTTTCATTTATTCTCATTTTATAGCAA
Tbdes6b             ..................C.........................................

250       260       270       280       290       300
                    ....|....|....|....|....|....|....|....|....|....|....|....|
Tbdes6bpredicted    ATAATTTGAAACTGAGTCCAGCGCAAGAAAAATTGTTGGAAGAAATCGACATGTCTGATT
Tbdes6b             ............................................................

310       320       330       340       350       360
                    ....|....|....|....|....|....|....|....|....|....|....|....|
Tbdes6bpredicted    TAGAGCAAGACAAAATTGTCATGTTTCAGAAAAAGTATTATTGGTTCCTTTTTGTAATTG
Tbdes6b             ............................................................

370       380       390       400       410       420
                    ....|....|....|....|....|....|....|....|....|....|....|....|
Tbdes6bpredicted    TAACTTTACTTTTGCCAATAAATGCTCCTGTGGAATATTGGGACGAAACTATTTTGAATT
Tbdes6b             ............................................................

430       440       450       460       470       480
                    ....|....|....|....|....|....|....|....|....|....|....|....|
Tbdes6bpredicted    CATTCTTCATACTTGGGTGGTTACGTTTGGGAATTAGTTACCATTTAACTTTACTAATTC
Tbdes6b             ............................................................

490       500       510       520       530       540
                    ....|....|....|....|....|....|....|....|....|....|....|....|
Tbdes6bpredicted    ACAGCGCTATAAATGTTTTTGATTTAAAACAAATGGACAGGAATTCTTATGACAGCAATG
Tbdes6b             ............................................................

550       560       570       580       590       600
                    ....|....|....|....|....|....|....|....|....|....|....|....|
Tbdes6bpredicted    CAGTTTTCTTCATAAACAAGTCTTATTGGATTTCTTATCACTACATGTCTCCTTGGGATT
Tbdes6b             ............................................................

610       620       630       640       650       660
                    ....|....|....|....|....|....|....|....|....|....|....|....|
Tbdes6bpredicted    ACCAAACGGGTGAATATGGCAAATATGGAAGTGATTGTACTTCAAAATTTATTCGAGTGT
Tbdes6b             ............................................................

670       680       690       700       710       720
                    ....|....|....|....|....|....|....|....|....|....|....|....|
Tbdes6bpredicted    GCGCTGCTTTGGAACTTGCAACAGATTTGAAAACAGTTGATAGTGAAATGATTCGAGAAG
Tbdes6b             ............................................................

730       740       750       760       770       780
                    ....|....|....|....|....|....|....|....|....|....|....|....|
Tbdes6bpredicted    CTTTGACTCTGTGTGTTGATGAGAAGAAACCAATAGAAGAATGTTTGACACGGCTAGGAA
Tbdes6b             ............................................................

790       800       810       820       830
                    ....|....|....|....|....|....|....|....|....|....|....|.
Tbdes6bpredicted    AAAAATCCCATGATAAATTGTTAAAGCATTATCTAACACCTTCAAAATTTCATTAG
Tbdes6b             .........................................................
```

Figure 3

```
                          10         20         30         40         50         60
                    ....|....|....|....|....|....|....|....|....|....|....|....|
Tbdes10predicted    ATGTCGGCCCAGACCATTACCACGACCGAGACCACACAAAATGCCCAGAAACCGCAGCAG
Tbdes10             .............................G..............................

70         80         90        100        110        120
                    ....|....|....|....|....|....|....|....|....|....|....|....|
Tbdes10predicted    TACCATTGGAGGATGGTCTGGAGGAACATCATCCTGTACATTATCATGCACCTCACCGGC
Tbdes10             ............................................................

130        140        150        160        170        180
                    ....|....|....|....|....|....|....|....|....|....|....|....|
Tbdes10predicted    TTCTATGGACTGTACCTGGCCATGTTCTACGCCCAGTGGAAAACAGTCTTTTACAGTTGG
Tbdes10             ............................................................

190        200        210        220        230        240
                    ....|....|....|....|....|....|....|....|....|....|....|....|
Tbdes10predicted    TTCCTTCTGGTCATAGCCCTCCAAGGAGTGACAGCTGGTAGTCACCGCCTCTGGGCCCAC
Tbdes10             ................T...........................................

250        260        270        280        290        300
                    ....|....|....|....|....|....|....|....|....|....|....|....|
Tbdes10predicted    AAGGCCTACAAGGCGCGACTCCCCCTCCGAATGCTTCTTTGTATTTTCCAAACCCTGTCC
Tbdes10             ............................................................

310        320        330        340        350        360
                    ....|....|....|....|....|....|....|....|....|....|....|....|
Tbdes10predicted    CTCCAGAACCACATCTACGACTGGGCCACGTACCACCGCGTCCACCACAAGTTCGTCGAT
Tbdes10             ............................................................

370        380        390        400        410        420
                    ....|....|....|....|....|....|....|....|....|....|....|....|
Tbdes10predicted    ACCAACGCCGACCCACACAACTCGCGCCGCGGCTTCTTCTTCTCCCATATGGGTTGGTTG
Tbdes10             ...........................................C................

430        440        450        460        470        480
                    ....|....|....|....|....|....|....|....|....|....|....|....|
Tbdes10predicted    TTCATCGAGCCCCACAAAGACGTGGAGGATAAATACAAGTCGATCGACTTCAGCGACTTG
Tbdes10             ............................................................

490        500        510        520        530        540
                    ....|....|....|....|....|....|....|....|....|....|....|....|
Tbdes10predicted    CATGCCGATTCCGTGGTCATGATCCAGAAAAAGTACTACCACACGTTCTTTGCCCCAGTC
Tbdes10             ......................................................G.....

550        560        570        580        590        600
                    ....|....|....|....|....|....|....|....|....|....|....|....|
Tbdes10predicted    ATTGGGTTCTACCTCCCGGCGGCGATCCCATGGTACTTCTGGGGCGAGAACTTCTGGACC
Tbdes10             ............................................................

610        620        630        640        650        660
                    ....|....|....|....|....|....|....|....|....|....|....|....|
Tbdes10predicted    GCGTTTTTCGTTGCGACCATGCTGCGGTACTGCGCCTGCACCAACATTACGTTCCTTGTG
Tbdes10             .............................T..............................

670        680        690        700        710        720
                    ....|....|....|....|....|....|....|....|....|....|....|....|
Tbdes10predicted    AACAGTTGGGCCCATATCTATGGGTCCCGCCCATACGACAAGTACGGAACCGCGTCCAGT
Tbdes10             ........T...........................................--------

730        740        750        760        770        780
                    ....|....|....|....|....|....|....|....|....|....|....|....|
Tbdes10predicted    GGTACCATCATGGTTAAATTAATTTT--------------------TGCCACGATTGCGG
Tbdes10             --------------------------AACATTTATCCCACCGAAAG...A..........

790        800        810        820        830        840
                    ....|....|....|....|....|....|....|....|....|....|....|....|
Tbdes10predicted    TTTTGACCGGTGGGGAGGGTTGGCACAACTACCATCACACTTTCCCGTGGGATTATAAGA
Tbdes10             ..............................................C.............

850        860        870        880        890        900
                    ....|....|....|....|....|....|....|....|....|....|....|....|
Tbdes10predicted    CCCGGGGAGTTTGGGAAGTACCGAAGTAACCTTACCACGGGCTTTTTGGACTTTATGGCGG
Tbdes10             ....................G........................................
```

Figure 4

```
                       10         20         30         40         50         60
                ....|....|....|....|....|....|....|....|....|....|....|....|
Tbdes11predict  ATGGGAGCGCTCAAACAAACCGAGGAGGAAAAAACTCTACTACCACAAGACATCGGAACC
Tbdes11         ............................................................

70         80         90        100        110        120
                ....|....|....|....|....|....|....|....|....|....|....|....|
Tbdes11predict  GATTACACATTCAAGCGGAAAATCGTCTGGTTCAATGCTATTGGGTTCTTCATCTTGCAC
Tbdes11         ........C...................................A...............

130        140        150        160        170        180
                ....|....|....|....|....|....|....|....|....|....|....|....|
Tbdes11predict  CTCTTGGCCCTTTATGGCGGCTACCGGCTGCTGCATTGCCACATCCTGACGCCGCTTTTC
Tbdes11         ............................................................

190        200        210        220        230        240
                ....|....|....|....|....|....|....|....|....|....|....|....|
Tbdes11predict  GCCCTAGCACTGATGTTCGTCTCTGGCGAAGGCATCACCCTCGGGGCCCACCGCCTGTAC
Tbdes11         ............................................................

250        260        270        280        290        300
                ....|....|....|....|....|....|....|....|....|....|....|....|
Tbdes11predict  TCCCACAAGGCCTTCAAAGCGTCTTTCGTCGTGCGATTAGCTGTGATAATTTTGCACACC
Tbdes11         ............................................................

310        320        330        340        350        360
                ....|....|....|....|....|....|....|....|....|....|....|....|
Tbdes11predict  ATCGCCGGTCAG---------------------------------CATCACAAATAC
Tbdes11         ...........AATTGTCTCTACATCTGGGTTCGCGACCACCGCCAG...C.........

370        380        390        400        410        420
                ....|....|....|....|....|....|....|....|....|....|....|....|
Tbdes11predict  AGCGACACCGACGCCGACCCCCACAACTCCAACAGGGGCTTCTTCTTCTCGCACATCGGC
Tbdes11         ............................................................

430        440        450        460        470        480
                ....|....|....|....|....|....|....|....|....|....|....|....|
Tbdes11predict  TGGCTGATGAGCAGGAAGCACCCCGCTGTCATCGCCAAGGGCAAGACCATCGACATGAGC
Tbdes11         ........................T...................................

490        500        510        520        530        540
                ....|....|....|....|....|....|....|....|....|....|....|....|
Tbdes11predict  GACCTGGAGAACGACTCGCTCGTGATGTTGCAGAAAGAACATTACAAGTTTCTGTACATC
Tbdes11         ............................C.A.............................

550        560        570        580        590        600
                ....|....|....|....|....|....|....|....|....|....|....|....|
Tbdes11predict  ATTTTCGCCATCGGGATCCCGATCGCAATCCCGATTTACGGCTGGAACGAGTCTTTCACC
Tbdes11         ..................A.........................................

610        620        630        640        650        660
                ....|....|....|....|....|....|....|....|....|....|....|....|
Tbdes11predict  AACTCGCTCTTTATCAGCTATTTTGGAAGATACATTCTTCAGTTACACGCCACTTGGCTG
Tbdes11         ....................C.......................................

670        680        690        700        710        720
                ....|....|....|....|....|....|....|....|....|....|....|....|
Tbdes11predict  ATCAACAGCGCTACGCACTTGTACGGGACCAAGCCCTACGACAAGTTCATGAATCCGGTG
Tbdes11         ............................................................

730        740        750        760        770        780
                ....|....|....|....|....|....|....|....|....|....|....|....|
Tbdes11predict  GAGAATTATTTTATTTCGATGATTGCTCTTGGCGAAGGCTGGCATAACTACCACCACGCC
Tbdes11         ..........................C.................................

790        800        810        820        830        840
                ....|....|....|....|....|....|....|....|....|....|....|....|
Tbdes11predict  TTTCCTTCGGATTATCGGGCGGCGGAGTATGGCGTTAGATACTCGATAACGACTTTTCTG
Tbdes11         .....C..A....................................................

850        860        870        880        890        900
                ....|....|....|....|....|....|....|....|....|....|....|....|
Tbdes11predict  ATAGACGCTCTTGCCTTTTTTGGCCTGGTTTATGACTTGAAAGAGGCCAACTCGGAGCAA
Tbdes11         ............................C...............................
```

Figure 5

Figure 7C:
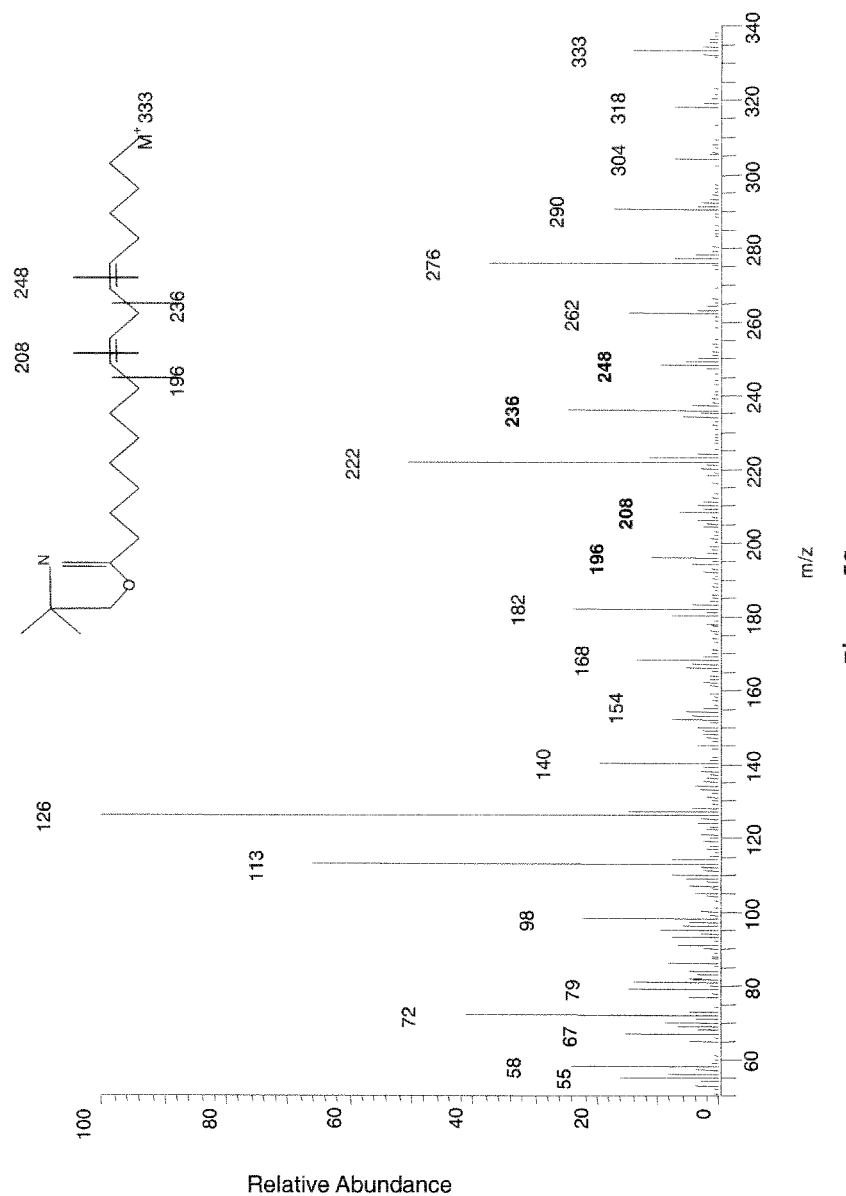

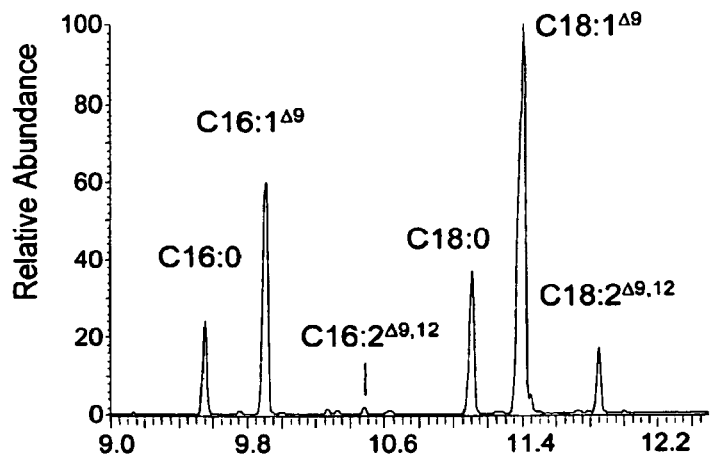
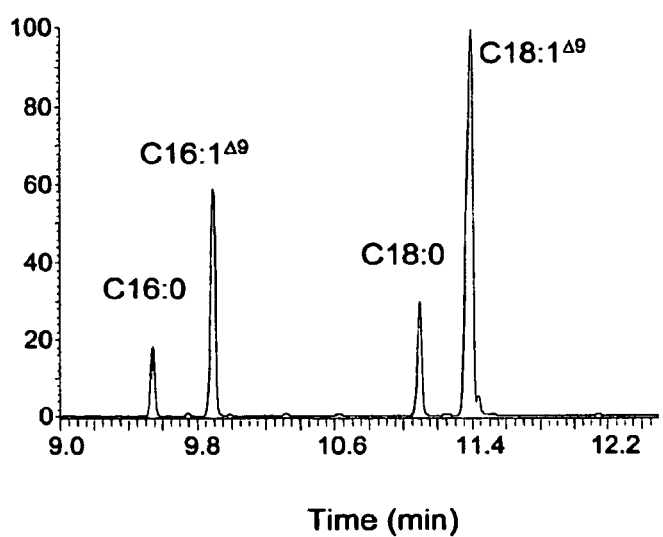
Figure. 7

SYNTHESIS OF FATTY ACIDS

This application is a continuation of U.S. Ser. No. 12/310,645, filed Feb. 16, 2011, now allowed, which is a § 371 national stage of PCT International Application No. PCT/AO2007/001242, filed Aug. 29, 2007, which claims the benefit of U.S. Provisional Application No. 60/841,285, filed Aug. 29, 2006, the contents of all of which are hereby incorporated by reference into this application.

FIELD OF THE INVENTION

The present invention relates to enzymes which possess desaturase, conjugase, epoxidase, and/or hydroxylase activity that can be used in methods of synthesizing fatty acids.

This application incorporates-by-reference nucleotide and/or amino acid sequences which are present in the file named "140825_2251_76813-AA-PCT-US_Substitute_Sequence_Listing_AHC.txt," which is 107 kilobytes in size, and which was created Aug. 25, 2014 in the IBM-PC machine format, having an operating system compatibility with MS-Windows, which is contained in the text file filed Aug. 25, 2014 as part of this application.

BACKGROUND OF THE INVENTION

The primary products of fatty acid biosynthesis in most organisms are 16- and 18-carbon compounds. However, the relative ratio of chain lengths and degree of unsaturation of these fatty acids vary widely among species. Mammals and insects, for example, produce primarily saturated and monosaturated fatty acids, while most higher plants produce fatty acids with one, two, or three double bonds, the latter two comprising polyunsaturated fatty acids (PUFA's).

Two main families of PUFAs are the omega-3 fatty acids (also represented as "n-3" fatty acids), exemplified by eicosapentaenoic acid (EPA, 20:5, n-3), and the omega-6 fatty acids (also represented as "n-6" fatty acids), exemplified by arachidonic acid (ARA, 20:4, n-6). PUFAs are important components of the plasma membranes of cells, predominantly esterified in the form of phospholipids, and adipose tissue in triglycerides.

The ability of cells to modulate the degree of unsaturation in their membranes is mainly determined by the action of fatty acid desaturases. Desaturase enzymes introduce unsaturated bonds at specific positions in their fatty acyl chain substrates. Desaturase enzymes generally show considerable selectivity both for the chain length of the substrate and for the location of existing double bonds in the fatty acyl chain (Shanklin and Cahoon, 1998) and may be classified on this basis. Another classification of fatty acid desaturases is based on the moiety to which the hydrocarbon chains of their substrates are acylated. Desaturases recognize substrates that are bound either to acyl carrier protein, to coenzyme A, or to lipid molecules such as phospholipids (Murata and Wada, 1995; Shanklin and Cahoon, 1998).

The desaturation of fatty acids in glycerolipids is essential for the proper function of biological membranes. Introduction of unsaturation in the Δ9 position of palmitic or stearic acid provides fluidity to membrane lipids and thus Δ9 desaturases are found universally in living systems.

Linoleic acid (LA; 18:2, Δ9, 12) is produced from oleic acid (18:1, Δ9) by a Δ2-desaturase while α-linolenic acid (ALA; 18:3) is produced from LA acid by a Δ15-desaturase. Stearidonic acid (18:4, Δ6, 9, 12, 15) and γ-linolenic acid (18:3, Δ6, 9, 12) are produced from ALA and LA, respectively, by a Δ6-desaturase. However, mammals cannot desaturate beyond the Δ9 position and therefore cannot convert oleic acid into LA. Fourteen insect species (de Renobales, 1987) have been shown to produce linoleic acid de novo from $^{14}$C-acetate, suggesting the presence of native Δ12-desaturase activity. The house cricket *Acheta domesticus* Δ12-desaturase activity was the first of this type reported to utilise oleoyl-CoA (Cripps, 1990). However, no gene responsible for the conversion of oleic acid to LA has been identified from an insect despite extensive effort. Likewise, ALA cannot be synthesized by mammals. The major polyunsaturated fatty acids of animals therefore are derived from diet via the subsequent desaturation and elongation of dietary LA and ALA. Other eukaryotes, including fungi, nematodes and plants, have enzymes which desaturate at the carbon 12 and carbon 15 positions. The membrane-associated Δ12 desaturases of *Arabidopsis* sp. and soybean use acyl lipid substrates Less commonly, saturated fatty acids can be unsaturated initially at positions other than the 9-position by desaturases with unusual specificities. Petroselinic acid (cis-6-octadecenoic acid) is concentrated in the seed oils of the Umbelliferae (Apiaceae), Araliaceae and Garryaceae plant families, where it can reach 85% of the total lipid fatty acid (Kleiman and Spencer, 1982). The desaturase from coriander (*Coriandrum sativum*) has been characterised that makes the unusual lipid. A plastid-located acyl-acyl carrier protein (ACP) Δ4 desaturase acts on ACP-palmitic acid to produce cis-4-hexadecenoic acid which is transferred from the plastid to the developing seed where it is elongated to cis-6-octadecenoic acid (Cahoon et al. 1992). A related desaturase with 83% sequence identity has been obtained from English Ivy (*Hedra helix* L.) which produces cis-4-hexadecenoic acid and cis-6-octadecenoic acid when expressed in *Arabidopsis* (Whittle et al 2005). cis-5-Eicosenoic acid (C20:1 Δ5) is a major component of the seed oil of meadowfoam (*Limnanthes alba*) and related *Limnathes* species. The enzyme responsible for the production of the unusual oil in *L. douglasii* was identified as an acyl coenzyme A-Δ5 desaturase whose substrate preference is eicosanoic acid (Cahoon et al., 2000). Expression of *L. douglasii* Δ5 desaturase and fatty acid elongase genes in soybean embryos resulted in the production of cis-5-eicosenoic acid (C20:1 Δ5) and cis-5-docosenoic acid (C22:1Δ5). Sayanova et al (2007) have identified an acyl CoA-Δ5 desaturase which is related to the *Limnathes* sp. desaturase but it utilizes saturated fatty acids (C16:0, C18:0) and unsaturated fatty acids (LA, ALA) to make Δ5 monoenoic acids and polyunsaturated fatty acids. Genes encoding similar enzymes have not been cloned from animals such as insects.

Some Lepidopteran insects carry out Δ11 desaturation of saturated fatty acids (C16:0, C18:0) esterified to acylCoA as a step in the production of a diversity of moth sex pheromones (Rodriguez et al 2004). Desaturases from the moth *Spodoptera littoralis* were expressed in *Saccharomyces cerevisiae* to produce cis-Δ11 mono-unsaturated products of C14:0, C16:0 and C18:0 when the yeast cells were fed additional saturated fatty acids (Rodriguez et al 2004). In addition, trans-Δ11 tetradecenoic acid was formed from myristic acid (C14:0) fed to the yeast. A minor byproduct of the Δ11 desaturation was the formation of 11-hydroxy hexadecanoic or octadecanoic acid (up to 0.1% of total fatty acids) (Serra et al., 2006). Moto et al. (2004) identified a bi-functional acyl-CoA desaturase from the pheromone gland of the silkmoth which was responsible for the biosynthesis of the pheromone precursor. The desaturase first utilised palmitic acid to make cis-11-hexadecenoic acid and then acted on this to remove allylic 2H and form a conjugated diene fatty acid (trans-Δ10,cis-Δ12-hexadecendienoic acid and some trans-Δ10,trans-Δ12-hexadecendienoic acid) and therefore it possessed both cis-Δ11 and conjugase desaturase activities. In the New Zealand leaf roller, *Planotortrix octo*, a desaturase has been identified from pheromone gland that desaturates palmitic acid at the Δ10 position to form cis-Δ10-hexadecenoic acid (Hao et al. 2002).

Omega-3 LC-PUFA are now widely recognized as important compounds for human and animal health and the inclusion of omega-3 LC-PUFA such as EPA and DHA in the human diet has been linked with numerous health-related benefits. These include prevention or reduction of coronary heart disease, hypertension, type-2 diabetes, renal disease, rheumatoid arthritis, ulcerative colitis, chronic obstructive pulmonary disease, various mental disorders such as schizophrenia, attention deficit hyperactive disorder and Alzheimer's disease, and aiding brain development and growth (Simopoulos, 2000). These fatty acids may be obtained from dietary sources or by conversion of linoleic (LA, omega-6) or α-linolenic (ALA, omega-3) fatty acids, both of which are regarded as essential fatty acids in the human diet. While humans and many other vertebrate animals are able to convert LA or ALA, obtained from plant sources, to LC-PUFA, they carry out this conversion at a very low rate. Moreover, most modern societies have imbalanced diets in which at least 90% of polyunsaturated fatty acid(s) consist of omega-6 fatty acids, instead of the 4:1 ratio or less for omega-6:omega-3 fatty acids that is regarded as ideal (Trautwein, 2001). The immediate dietary source of LC-PUFA such as eicosapentaenoic acid (EPA, 20:5) and docosahexaenoic acid (DHA, 22:6) for humans is mostly from fish or fish oil. Health professionals have therefore recommended the regular inclusion of fish containing significant levels of LC-PUFA into the human diet. Increasingly, fish-derived LC-PUFA oils are being incorporated into food products and in infant formula. However, due to a decline in global and national fisheries, alternative sources of these beneficial health-enhancing oils are needed.

Fatty acids may also be hydroxylated, for example ricinoleic acid (12-hydroxy-octadec-cis-9-enoic acid) which comprises up to 90% of the fatty acid in castor oil from *Ricinus communis* and is an important agricultural commodity oil. Other related hydroxylated fatty acids found in plant oils include 12-hydroxy-octadeca-cis-9,cis-15-dienoic (densipolic) and 14-hydroxy-eicosa-cis-11,cis-17-dienoic (auricolic) acids. The *Ricinus* Δ12 hydroxylase acts on oleic acid lipid substrate to produce ricinoleic acid; the desaturase gene responsible for the transformation is most closely related to but divergent from plant membrane Δ12 acyl lipid desaturases (van de Loo et al 1995). There is a homologous C20 hydroxylated fatty acid produced at high levels in seed oil of *Lesquerella* sp. as 14-hydroxy-eicos-cis-11-enoic (lesquerolic acid) (Gunstone et al., 1994). The *L. fendleri* hydroxylase gene has been cloned and expressed in an *Arabidopsis* FAD2 mutant which accumulated ricinoleic, lesquerolic and densipolic acids in seeds (Broun et al 1998). 2-hydroxy fatty acids occur in appreciable amounts in the sphingolipids of plants and animals but they are also present as minor components of seeds oils such as 2-hydroxy-octadeca-9,12,15-trienoate from *Thymus vulgaris* seeds and 2-hydroxy-oleic and linoleic acids are found in *Salvia nilotica* (Smith, 1971; Badami and Patil, 1981).

Fatty acids may also comprise epoxy groups. The most widely known natural epoxy fatty acid is vernolic acid (12,13-epoxy-octadec-cis-9-enoic acid) from the seed oils of *Vernonia* spp and *Euphorbia lagascae* (Cuperus and Derksen, 1996). The epoxygenase gene of *C. palaestina*, which is related to but divergent from plant membrane Δ12-oleate desaturases, has been functionally characterized and shown to use linoleate as a substrate (Lee et al. 1998).

In some organisms, conjugated fatty acids are produced by the activity of a conjugase (Crombie et al., 1984; Crombie et al., 1985; Fritsche et al., 1999; Cahoon et al., 2001; Qiu et al., 2001). The biosynthesis of conjugated fatty acids such as calendulic acid, eleostearic acid or punicic acid proceeds via the desaturation of oleic acid to linoleic acid by a Δ12-desaturase and a further desaturation in conjunction with a rearrangement of the Z9- or Z12-double bond to the conjutrienic fatty acid by a specific conjutriene-forming desaturase (conjugase).

There is a need for further methods of producing fatty acids in recombinant cells and for more efficient production or production of novel fatty acids.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

The present inventors have identified novel enzymes having desaturase, conjugase, epoxygenase, and/or hydroxylase activity from insects of the Order Coleoptera and Orthoptera.

Accordingly, the present invention provides a eukaryotic cell comprising an exogenous nucleic acid encoding a polypeptide which is:

(i) a polypeptide comprising amino acids having a sequence as set forth in any one of SEQ ID NOs:16 to 30, 73 to 78, 80 and 134, (ii) a polypeptide comprising amino acids having a sequence which is at least 50% identical to any one or more of the sequences set forth in SEQ ID NOs: 16 to 30, 73 to 78, 80 and/or 134, and/or (iii) a biologically active fragment of i) or ii), wherein the polypeptide has one or more activities selected from desaturase, conjugase, epoxidase and hydroxylase activity.

In one embodiment, the polypeptide can be isolated from an insect of the Order Coleoptera or Orthoptera. Examples of insect species from which the polypeptide can be isolated include, but are not limited to, *Tribolium, Chauliognathus* or *Acheta*.

In one embodiment, the polypeptide encoded by the exogenous nucleic acid is:

(i) a polypeptide comprising amino acids having a sequence as set forth in any one of SEQ ID NOs: 28, 73, and/or 134, (ii) a polypeptide comprising amino acids having a sequence which is at least 50% identical to any one or more of the sequences set forth in SEQ ID NOs: 28, 73, and/or 134, and/or (iii) a biologically active fragment of (i) or (ii), wherein the polypeptide has acyl-CoA Δ12 desaturase activity.

In another embodiment, the polypeptide is:

(i) a polypeptide comprising amino acids having a sequence as set forth in SEQ ID NO: 18 or SEQ ID NO: 19, (ii) a polypeptide comprising amino acids having a sequence which is at least 50% identical to a sequence set forth in SEQ ID NO: 18 or SEQ ID NO: 19, and/or (iii) a biologically active fragment of (i) or (ii), wherein the polypeptide has acyl-CoA D5 desaturase activity.

In yet another embodiment, the polypeptide is:

(i) a polypeptide comprising amino acids having a sequence as set forth in any one of SEQ ID NOs: 17, 22, 23, 27, 29, 74, 75 and/or 76, (ii) a polypeptide comprising amino acids having a sequence which is at least 50% identical to any one or more of the sequences set forth in SEQ ID NOs: 17, 22, 23, 27, 29, 74, 75 and/or 76, and/or (iii) a biologically active fragment of (i) or (ii), wherein the polypeptide has acyl-CoA $\Delta 9$ desaturase activity.

The present inventors are the first to identify a nucleic acid encoding an acyl-CoA $\Delta 12$ desaturase. Thus, the present invention provides a eukaryotic cell comprising an exogenous nucleic acid encoding an acyl-CoA $\Delta 12$ desaturase.

In one embodiment, the acyl-CoA $\Delta 12$ desaturase comprises:

(i) amino acids having a sequence as set forth in any one of SEQ ID NOs: 28, 73, and/or 134, (ii) amino acids having a sequence which is at least 50% identical to any one or more of the sequences set forth in SEQ ID NOs: 28, 73, and/or 134, and/or (iii) a biologically active fragment of (i) or (ii).

In one embodiment, the eukaryotic cell comprises an increased level of $16:2^{\Delta 9,\Delta 12}$ and/or $18:2^{\Delta 9,\Delta 12}$ fatty acids relative to a corresponding eukaryotic cell lacking the exogenous nucleic acid.

In yet another embodiment, the eukaryotic cell comprises an increased level of $16:2^{\Delta 9,\Delta 12}$ and/or $18:2^{\Delta 9,\Delta 12}$ fatty acids which are esterified to CoA.

The present inventors are also the first to identify an acyl-CoA $\Delta 5$ desaturase which has a preference for a 18:0 and/or 16:0 fatty acid substrate when compared to a number of other substrates. Accordingly, in a further aspect the present invention provides a eukaryotic cell comprising an exogenous nucleic acid encoding an acyl-CoA $\Delta 5$ desaturase; wherein the desaturase is more active on a 18:0 and/or 16:0 substrate than on a fatty acid substrate esterified to CoA, wherein the fatty acid is any one, two, three or all of a $18:1^{\Delta 9}$, $16:1^{\Delta 9}$, 20:0 and $20:2^{\Delta 11,\Delta 14}$.

In one embodiment, the acyl-CoA $\Delta 5$ desaturase comprises:

(i) amino acids having a sequence as set forth in SEQ ID NO: 18 or SEQ ID NO:19, (ii) amino acids having a sequence which is at least 50% identical to SEQ ID NO: 18 or SEQ ID NO:19, and/or (iii) a biologically active fragment of (i) or (ii).

In another embodiment, the eukaryotic cell comprises an increased level of $16:1^{\Delta 5}$ and/or $18:1^{\Delta 5}$, fatty acids relative to a corresponding eukaryotic cell lacking the exogenous nucleic acid.

In yet another embodiment, the eukaryotic cell comprises an increased level of $16:1^{\Delta 5}$ and/or $18:1^{\Delta 5}$ fatty acids which are esterified to CoA.

The present inventors are also the first to identify an acyl-CoA $\Delta 9$ desaturase which is more active on a 14:0 substrate than on certain fatty acid substrates esterified to CoA. Thus, in a further aspect the present invention provides a eukaryotic cell comprising an exogenous nucleic acid encoding an acyl-CoA $\Delta 9$ desaturase, wherein the desaturase is more active on a 14:0 substrate than on a fatty acid substrate esterified to CoA, wherein the fatty acid is 16:0 and/or 18:0.

In an embodiment, the acyl-CoA $\Delta 9$ desaturase comprises:

(i) amino acids having a sequence as set forth in SEQ ID NO: 23 or SEQ ID NO: 74, (ii) amino acids having a sequence which is at least 50% identical to SEQ ID NO: 23 or SEQ ID NO:74, and/or (iii) a biologically active fragment of (i) or (ii).

In one particular embodiment, the eukaryotic cell comprises an increased level of $14:1^{\Delta 9}$ relative to a corresponding eukaryotic cell lacking the exogenous nucleic acid.

In yet another embodiment, the eukaryotic cell comprises an increased level of $14:1^{\Delta 9}$ which is esterified to CoA.

Preferably, the eukaryotic cell comprising the exogenous nucleic acid is a plant cell, a mammalian cell, an insect cell, a fungal cell or a yeast cell.

In one embodiment, the eukaryotic cell is in a plant or plant seed.

Preferably, the plant or plant seed is an oilseed plant or an oilseed respectively.

In one aspect of the invention there is provided a process for identifying a nucleic acid molecule involved in fatty acid modification comprising:

(i) obtaining a nucleic acid molecule operably linked to a promoter, the nucleic acid molecule encoding a polypeptide comprising amino acids having a sequence more closely related to SEQ ID NO: 28 than to SEQ ID NO: 135, (ii) introducing the nucleic acid molecule into a cell or cell-free expression system in which the promoter is active, (iii) determining whether the fatty acid composition is modified relative to the cell or cell-free expression system before introduction of the nucleic acid molecule, and (iv) optionally, selecting a nucleic acid molecule which modified the fatty acid composition.

In another aspect the present invention provides a process for identifying a nucleic acid molecule involved in fatty acid modification comprising:

(i) obtaining a nucleic acid molecule operably linked to a promoter, the nucleic acid molecule encoding a polypeptide comprising amino acids having a sequence that is at least 50% identical to any one or more of the sequences set forth in SEQ ID NOs: 28, 73, and/or 134, (ii) introducing the nucleic acid molecule into a cell or cell-free expression system in which the promoter is active, (iii) determining whether the fatty acid composition is modified relative to the cell or cell-free expression system before introduction of the nucleic acid molecule, and (iv) optionally, selecting a nucleic acid molecule which modified the fatty acid composition.

In one embodiment, step (iv) comprises selecting a nucleic acid molecule encoding an acyl-CoA $\Delta 12$ desaturase.

In another embodiment, the modified fatty acid composition comprises an increased level of $16:2^{\Delta 9,\Delta 12}$ and/or $18:2^{\Delta 9,\Delta 12}$.

The present invention further provides a process for identifying a nucleic acid molecule involved in fatty acid modification comprising:

(i) obtaining a nucleic acid molecule operably linked to a promoter, the nucleic acid molecule encoding a polypeptide comprising amino acids having a sequence that is at least 50% identical to any one or more of the sequences set forth in SEQ ID NOs: 18 and/or 19, (ii) introducing the nucleic acid molecule into a cell or cell-free expression system in which the promoter is active, (iii) determining whether the fatty acid composition is modified relative to the cell or cell-free expression system before introduction of the nucleic acid, and (iv) optionally, selecting a nucleic acid molecule which modified the fatty acid composition.

In one embodiment, step (iv) comprises selecting a nucleic acid molecule an acyl-CoA Δ5 desaturase, wherein the desaturase is more active on a 18:0 and/or 16:0 substrate than on a fatty acid substrate esterified to CoA, wherein the fatty acid is any one, two, three or all of a $18:1^{\Delta 9}$, $16:1^{\Delta 9}$, 20:0 and $20:2^{\Delta 11\Delta 14}$.

In another embodiment, the modified fatty acid composition comprises an increased level of $16:1^{\Delta 5}$ and/or $18:1^{\Delta 5}$ fatty acids.

The present invention further provides a process for identifying a nucleic acid molecule involved in fatty acid modification comprising:

(i) obtaining a nucleic acid molecule operably linked to a promoter, the nucleic acid molecule encoding a polypeptide comprising amino acids having a sequence that is at least 50% identical to any one or more of the sequences set forth in SEQ BD NOs: 17, 22, 23, 27, 29, 74, 75 and/or 76, (ii) introducing the nucleic acid molecule into a cell or cell-free expression system in which the promoter is active, (iii) determining whether the fatty acid composition is modified relative to the cell or cell-free expression system before introduction of the nucleic acid, and (iv) optionally, selecting a nucleic acid molecule which modified the fatty acid composition.

In one embodiment, step (iv) comprises selecting a nucleic acid molecule encoding an acyl-CoA Δ9 desaturase, wherein the desaturase is more active on a 14:0 substrate than on a fatty acid substrate esterified to CoA, wherein the fatty acid is 16:0 and/or 18:0.

In another embodiment, the modified fatty acid composition comprises an increased level of $14:1^{\Delta 9}$.

In yet another embodiment, the polypeptide encoded by the nucleic acid molecule is an insect polypeptide or mutant thereof.

The present invention further provides a substantially purified or recombinant polypeptide which is an acyl-CoA Δ12 desaturase.

In one embodiment, the polypeptide is:

(i) a polypeptide comprising amino acids having a sequence as set forth in any one of SEQ ID NOs: 28, 73, and/or 134, (ii) a polypeptide comprising amino acids having a sequence which is at least 50% identical to any one or more of the sequences set forth in SEQ ID NOs: 28, 73, and/or 134, and/or (iii) a biologically active fragment of (i) or (ii).

The present invention further provides a substantially purified or recombinant polypeptide which is an acyl-CoA Δ5 desaturase, wherein the desaturase is more active on a 18:0 and/or 16:0 substrate than on a fatty acid substrate esterified to CoA, wherein the fatty acid is any one, two, three or all of a $18:1^{\Delta 9}$, $16:1^{\Delta 9}$, 20:0 and $20:2^{\Delta 11\Delta 14}$.

In one embodiment, the polypeptide is:

(i) a polypeptide comprising amino acids having a sequence as set forth in SEQ ID NO: 18 or SEQ NO:19, (ii) a polypeptide comprising amino acids having a sequence which is at least 50% identical to SEQ ID NO:18 and/or SEQ ID NO:19, and/or (iii) a biologically active fragment of (i) or (ii).

The present invention further provides a substantially purified or recombinant polypeptide which is an acyl-CoA Δ9 desaturase, wherein the desaturase is more active on a 14:0 substrate than on a fatty acid substrate esterified to CoA, wherein the fatty acid is 16:0 and/or 18:0.

In one embodiment, the polypeptide is:

(i) a polypeptide comprising amino acids having a sequence as set forth in SEQ ID NO: 17 or SEQ ID NO:74, (ii) a polypeptide comprising amino acids having a sequence which is at least 50% identical to one or more of the sequences as set forth in SEQ ID NO: 17 and/or SEQ ID NO: 74, and/or (iii) a biologically active fragment of (i) or (ii).

The present invention further provides a substantially purified or recombinant polypeptide which is:

(i) a polypeptide comprising amino acids having a sequence as set forth in any one of SEQ ID NOs:16 to 30, 73 to 78, 80 and 134, (ii) a polypeptide comprising amino acids having a sequence which is at least 50% identical to any one or more of the sequences set forth in SEQ ID NOs: 16 to 30, 73 to 78, 80 and/or 134, and/or (iii) a biologically active fragment of i) or wherein the polypeptide has one or more an activities selected from desaturase, conjugase, epoxidase and/or hydroxylase activity.

Preferably, the polypeptide comprises amino acids having a sequence which is at least 90% identical to any one or more of the sequences set forth in SEQ ID NOs: 16 to 30, 73 to 78, 80 and/or 134.

In one embodiment, the polypeptide can be isolated from an insect of the Order Coleoptera or Orthoptera.

Preferably, the polypeptide has desaturase activity upon a carbon-carbon bond located at any one of the Δ2 to Δ15 positions of a fatty acid.

In one embodiment, the polypeptide has desaturase activity on a C16 or C18 fatty acid.

In another embodiment, the polypeptide is a fusion protein further comprising at least one other polypeptide sequence.

The present invention further provides an isolated and/or exogenous polynucleotide comprising:

(i) a sequence of nucleotides selected from any one of SEQ ID NOs: 1 to 15, 67 to 72, 79 and 133, (ii) a sequence of nucleotides encoding a polypeptide of the invention, (iii) a sequence of nucleotides which are at least 50% identical to one or more of the sequences set forth in SEQ ID NOs: 1 to 15, 67 to 72, 79 and/or 133, and/or (iv) a sequence which hybridises to any one of (i) to (iii) under stringent conditions.

Also provided is a vector comprising a polynucleotide of the invention.

In one embodiment, the polynucleotide is operably linked to a promoter.

The present invention further provides a cell comprising the recombinant polypeptide according to the invention, the exogenous polynucleotide of the invention and/or the vector of the invention.

Preferably, the cell is a plant, fungal, yeast, bacterial or animal cell. More preferably, the cell is a eukaryote cell.

The present invention further provides a method of producing the polypeptide according to the invention, the method comprising expressing in a cell or cell free expression system the polynucleotide of the invention.

In one embodiment, the method further comprises isolating the polypeptide.

The present invention further provides a transgenic non-human organism comprising a cell according to the invention.

In one embodiment, the organism is a transgenic plant.

The present invention further provides a seed comprising the cell according to the invention.

The present invention further provides oil produced by, or obtained from, the cell according to the invention, the transgenic non-human organism of the invention, or the seed of the invention.

In one embodiment, the oil comprises fatty acids 16:0, 16:1$^{\Delta 5}$, 18:0 and 18:1$^{\Delta 5}$, wherein the ratio of the total amount of 18:1$^{\Delta 5}$ to 18:0 in the oil is between 100:1 and 1:2, and wherein the fatty acid of the oil comprises less than 10%, or less than 5% (w/w) 20:1$^{\Delta 5}$.

In another embodiment, at least 43%, or at least 50%, or at least 60%, of the C18 fatty acid of the oil is 18:1$^{\Delta 5}$.

In yet another embodiment, the fatty acid of the oil comprises at least 3.0% (w/w), or at least 5% (w/w) or at least 10% (w/w), 18:1$^{\Delta 5}$ as a percentage of the total fatty acid of the oil.

In another embodiment, the oil comprises less than 10% (w/w), or less than 5% (w/w), 18:3$^{\Delta 9,\Delta 12,\Delta 15}$ (ALA) as a percentage of the total fatty acid in the oil.

In one embodiment, the oil is obtained by extraction of oil from an oilseed.

The present invention further provides an oil comprising fatty acids 16:0, 16:1$^{\Delta 5}$, 18:0 and 18:1$^{\Delta 5}$, wherein the ratio of the total amount of 18:1$^{\Delta 5}$ to 18:0 in the oil is between 100:1 and 1:2, and wherein the fatty acid of the oil comprises less than 10% (w/w), or less than 5%, 20:1$^{\Delta 5}$.

The present invention further provides an oil comprising fatty acids, wherein at least 43%, or at least 50%, or at least 60%, of the C18 fatty acid of the oil is 18:0$^{\Delta 5}$.

The invention further provides an oil comprising fatty acids comprising at least 3.0% (w/w), or at least 5% (w/w) or at least 10% (w/w), 18:1$^{\Delta 5}$ as a percentage of the total fatty acid of the oil.

In one embodiment, oil comprises less than 10% (w/w), or less than 5% (w/w), 18:3$^{\Delta 9,\Delta 12,\Delta 15}$ (ALA) as a percentage of the total fatty acid in the oil.

The present invention further provides a fatty acid produced by, or obtained from, the cell according to the invention, the transgenic non-human organism of the invention, or the seed of the invention.

The invention also provides a method of producing oil containing unsaturated fatty acids, the method comprising extracting oil from the cell according to the invention, the transgenic non-human organism of the invention, or the seed of the invention.

The present invention further provides a composition comprising a cell according to the invention, the polypeptide according to the invention, a polynucleotide according to the invention, a vector of the invention, an oil according to the invention or a fatty acid of the invention.

The invention also provides feedstuffs, cosmetics or chemicals comprising the oil according to the invention or a fatty acid of the invention.

The present invention also provides a method of performing a desaturase reaction, the method comprising contacting a substrate saturated, monounsaturated or polyunsaturated fatty acid esterified to CoA with the polypeptide of the invention The present invention further provides a substantially purified antibody, or fragment thereof, that specifically binds a polypeptide of the invention The invention further provides a method of treating or preventing a condition which would benefit from a PUFA, the method comprising administering to a subject a cell according to the invention, the polypeptide according to the invention, a polynucleotide according to the invention, a vector of the invention, an oil according to the invention, a fatty acid of the invention and/or a feedstuff of the invention.

In one embodiment, the condition is cardiac arrhythmia's, angioplasty, inflammation, asthma, psoriasis, osteoporosis, kidney stones, AIDS, multiple sclerosis, rheumatoid arthritis, Crohn's disease, schizophrenia, cancer, foetal alcohol syndrome, attention deficient hyperactivity disorder, cystic fibrosis, phenylketonuria, unipolar depression, aggressive hostility, adrenoleukodystophy, coronary heart disease, hypertension, diabetes, obesity, Alzheimer's disease, chronic obstructive pulmonary disease, ulcerative colitis, restenosis after angioplasty, eczema, high blood pressure, platelet aggregation, gastrointestinal bleeding, endometriosis, premenstrual syndrome, myalgic encephalomyelitis, chronic fatigue after viral infections or an ocular disease.

The present invention also provides use of a cell according to the invention, the polypeptide according to the invention, a polynucleotide according to the invention, a vector of the invention, an oil according the invention or a fatty acid of the invention and/or a feedstuff of the invention for the manufacture of a medicament for treating or preventing a condition which would benefit from a PUFA.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. A comparison of the nucleic acid sequence obtained from the gene prediction program and that of the authentic RT-PCR product for Tribdesat 2b. Dots indicate sequence identity, while different nucleotides are indicated.

FIG. 2. A comparison of the nucleic acid sequence obtained from the gene prediction program and that of the authentic RT-PCR product for Tribdesat 3. Dots indicate sequence identity, while different nucleotides are indicated.

FIG. 3. A comparison of the nucleic acid sequence obtained from the gene prediction program and that of the authentic RT-PCR product for Tribdesat 6b. Dots indicate sequence identity, while different nucleotides are indicated.

FIG. 4. A comparison of the nucleic acid sequence obtained from the gene prediction program and that of the authentic RT-PCR product for Tribdesat 10. Dots indicate sequence identity, while different nucleotides are indicated.

FIG. 5. A comparison of the nucleic acid sequence obtained from the gene prediction program and that of the authentic RT-PCR product for Tribdesat 11. Dots indicate sequence identity, while different nucleotides are indicated.

FIG. 6. GC/MS trace and spectrum showing linoleic acid (18:2 Δ9Δ12) production by Tribdesat 10 in *Arabidopsis*, with *Arabidopsis* Fad1/Fae2 control.

FIG. 7. A. Gas chromatography (GC) of yeast fatty acid methyl esters from *S. cerivisiae* expressing AdD12Des. B. Gas chromatography (GC) of yeast fatty acid methyl esters from *S. cerivisiae*, vector only. C. Confirmation of the double bond positions of C16:2 and C18:2 products by GC-mass spectrometry.

Figure 8:
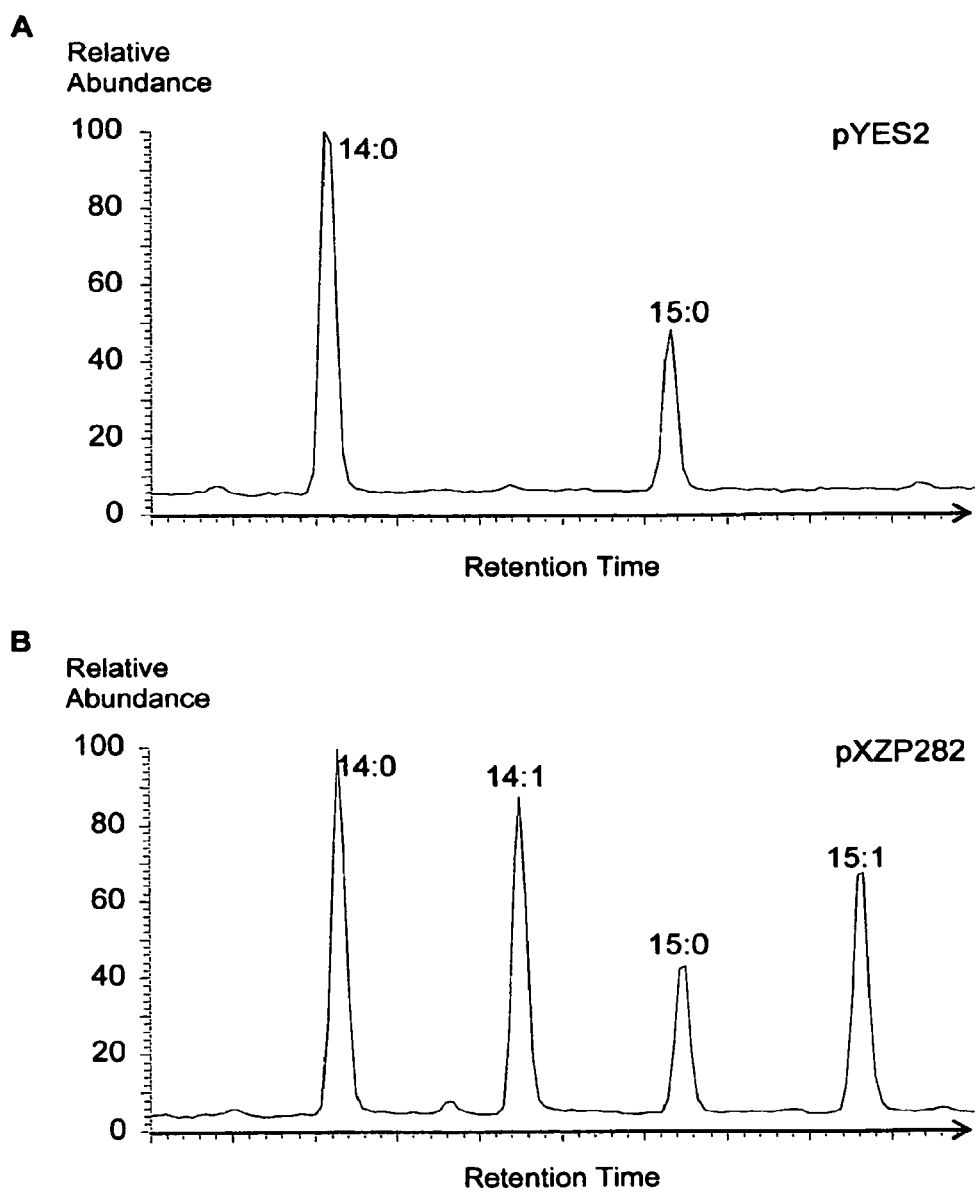

FIG. 8. GC analysis of yeast ole1 cells expressing pYES2 vector only (Panel A) or *A. domesticus* Δ12-desaturase in pXZP282 (Panel B) after fed with mixture of C14:0 and C15:0.

Figure 9:
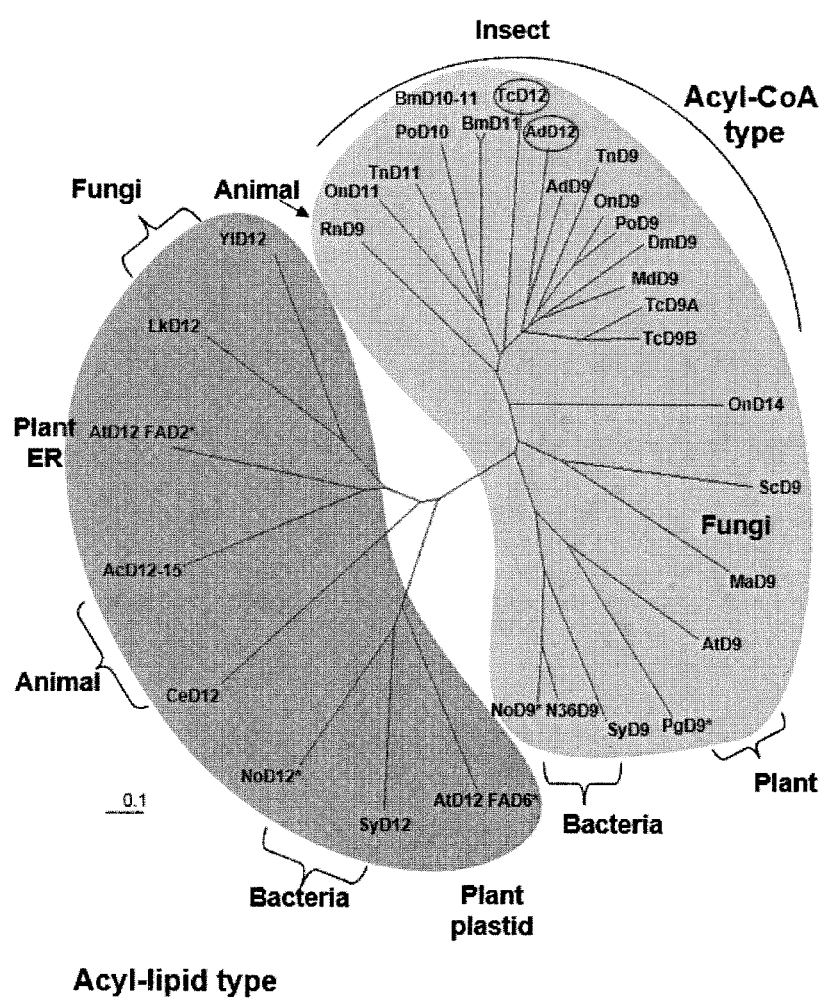

FIG. 9. Phylogenetic analysis of representative acyl-CoA or acyl-lipid desaturase protein sequences.

Figure 10:
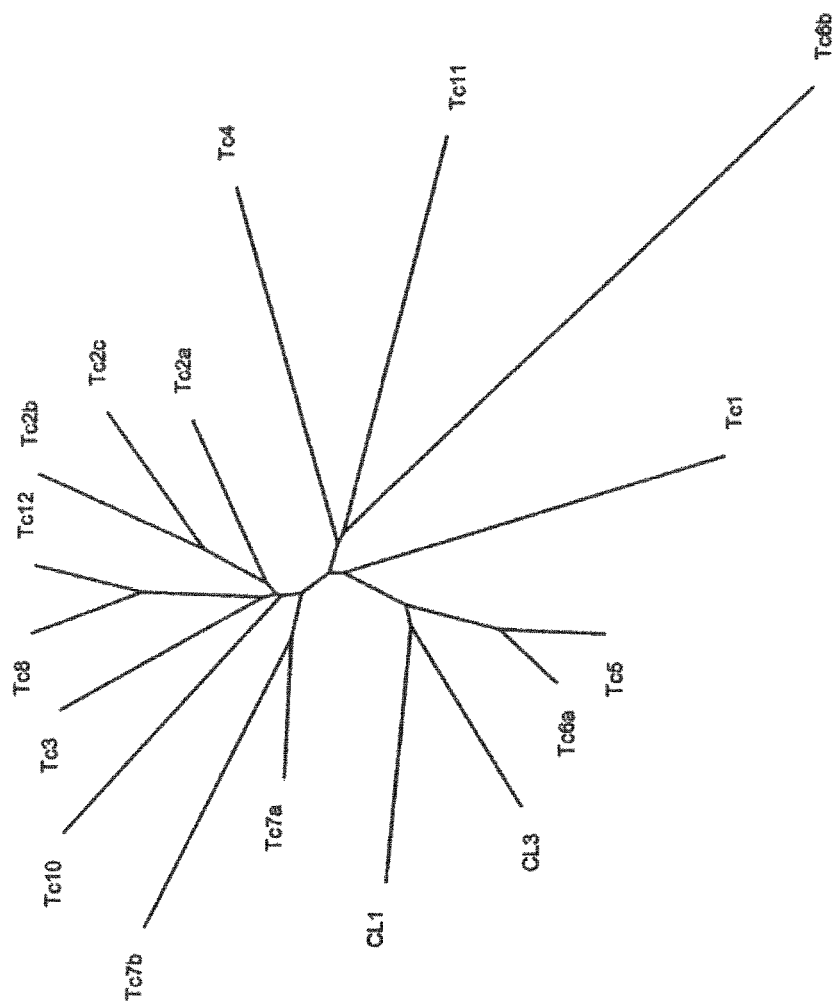

FIG. 10. Phylogenetic analysis of representative acyl-CoA or acyl-lipid desaturase protein sequences.

KEY TO THE SEQUENCE LISTING

SEQ ID NO: 1—coding sequence of *Tribolium* desaturase 1

SEQ ID NO: 2—coding sequence of *Tribolium* desaturase 2a

SEQ ID NO: 3—coding sequence of *Tribolium* desaturase 2b

SEQ ID NO: 4—coding sequence of *Tribolium* desaturase 2c

SEQ ID NO: 5—coding sequence of *Tribolium* desaturase 3

SEQ ID NO: 6—coding sequence of *Tribolium* desaturase 4

SEQ ID NO: 7—coding sequence of *Tribolium* desaturase 5

SEQ ID NO: 8—coding sequence of *Tribolium* desaturase 6a

SEQ ID NO: 9—coding sequence of *Tribolium* desaturase 6b

SEQ ID NO: 10—coding sequence of *Tribolium* desaturase 7a

SEQ ID NO: 11—coding sequence of *Tribolium* desaturase 7b

SEQ ID NO: 12—coding sequence of *Tribolium* desaturase 8

SEQ ID NO: 13—coding sequence of *Tribolium* desaturase 10

SEQ ID NO: 14—coding sequence of *Tribolium* desaturase 11

SEQ ID NO: 15—coding sequence of *Tribolium* desaturase 12

SEQ ID NO: 16—amino acid sequence of *Tribolium* desaturase 1

SEQ ID NO: 17—amino acid sequence of *Tribolium* desaturase 2a

SEQ ID NO: 18—amino acid sequence of *Tribolium* desaturase 2b

SEQ ID NO: 19—amino acid sequence of *Tribolium* desaturase 2c

SEQ ID NO: 20—amino acid sequence of *Tribolium* desaturase 3

SEQ ID NO: 21—amino acid sequence of *Tribolium* desaturase 4

SEQ ID NO: 22—amino acid sequence of *Tribolium* desaturase 5

SEQ ID NO: 23—amino acid sequence of *Tribolium* desaturase 6a

SEQ ID NO: 24—amino acid sequence of *Tribolium* desaturase 6b

SEQ ID NO: 25—amino acid sequence of *Tribolium* desaturase 7a

SEQ ID NO: 26—amino acid sequence of *Tribolium* desaturase 7b

SEQ ID NO: 27—amino acid sequence of *Tribolium* desaturase 8

SEQ ID NO: 28—amino acid sequence of *Tribolium* desaturase 10

SEQ ID NO: 29—amino acid sequence of *Tribolium* desaturase 11

SEQ ID NO: 30—amino acid sequence of *Tribolium* desaturase 12

SEQ ID NO: 31—conserved insect desaturase sequence

SEQ ID NOs: 32 to 66—oligonucleotide primers

SEQ ID NO: 67—coding sequence of *Chauliognathus* desaturase CL1

SEQ ID NO: 68—coding sequence of *Chauliognathus* desaturase CL3

SEQ ID NO: 69—partial coding sequence of *Chauliognathus* desaturase CL6

SEQ ID NO: 70—partial coding sequence of *Chauliognathus* desaturase CL7

SEQ ID NO: 71—partial coding sequence of *Chauliognathus* desaturase CL8

SEQ ID NO: 72—partial coding sequence of *Chauliognathus* desaturase CL9

SEQ ID NO: 73—amino acid sequence of *Chauliognathus* desaturase CL1

SEQ ID NO: 74—amino acid sequence of *Chauliognathus* desaturase CL3

SEQ ID NO: 75—partial amino acid sequence of *Chauliognathus* desaturase CL6

SEQ ID NO: 76—partial amino acid sequence of *Chauliognathus* desaturase CL7

SEQ ID NO: 77—partial amino acid sequence of *Chauliognathus* desaturase CL8

SEQ ID NO: 78—partial amino acid sequence of *Chauliognathus* desaturase CL9

SEQ ID NO: 79—coding sequence of *Chauliognathus* desaturase CN1

SEQ ID NO: 80—amino acid sequence of *Chauliognathus* desaturase CN1

SEQ ID NOs: 81 to 103—oligonucleotide primers

SEQ ID NOs: 104 to 111—conserved desaturase motifs

SEQ ID NOs: 112 to 122—histidine boxes in desaturase sequences

SEQ ID NOs: 123 to 126—signature motifs

SEQ ID NOs: 127 to 130—oligonucleotides

SEQ ID NOs: 131 and 132—conserved regions

SEQ ID NO: 133—coding sequence of *Acheta domesticus* desaturase AdD12Des

SEQ ID NO: 134—amino acid sequence of *Acheta domesticus* desaturase AdD12Des

SEQ ID NO: 135—*Arabidopsis thaliana* FAD2 Δ12 desaturase

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J.

Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

Selected Definitions

As used herein, the term "fatty acid" refers to a carboxylic acid (or organic acid), often with a long aliphatic tail, either saturated or unsaturated. Typically fatty acids have a carbon-carbon bonded chain of at least 8 carbon atoms in length, more preferably at least 12 carbons in length. Most naturally occurring fatty acids have an even number of carbon atoms because their biosynthesis involves acetate which has two carbon atoms. The fatty acids may be in a free state (non-esterified) or in an esterified form such as part of a triglyceride, diacylglyceride, monoacyiglyceride, acyl-CoA (thio-ester) bound or other bound form. The fatty acid may be esterified as a phospholipid such as a phosphatidylcholine, phosphatidylethanolamine, phosphatidylserine, phosphatidylglycerol, phosphatidylinositol or diphosphatidylglycerol forms.

"Saturated fatty acids" do not contain any double bonds or other functional groups along the chain. The term "saturated" refers to hydrogen, in that all carbons (apart from the carboxylic acid [—COOH] group) contain as many hydrogens as possible. In other words, the omega (α) end contains 3 hydrogens (CH3-) and each carbon within the chain contains 2 hydrogens (—CH2-).

"Unsaturated fatty acids" are of similar form to saturated fatty acids, except that one or more alkene functional groups exist along the chain, with each alkene substituting a singly-bonded "—CH2-CH2-" part of the chain with a doubly-bonded "—CH=CH—" portion (that is, a carbon double bonded to another carbon). The two next carbon atoms in the chain that are bound to either side of the double bond can occur in a cis or trans configuration.

As used herein, the terms "monounsaturated fatty acid" refers to a fatty acid which comprises at least 12 carbon atoms in its carbon chain and only one alkene group in the chain. As used herein, the terms "polyunsaturated fatty acid" or "PUFA" refer to a fatty acid which comprises at least 12 carbon atoms in its carbon chain and at least two alkene groups (carbon-carbon double bonds). Ordinarily, the number of carbon atoms in the carbon chain of the fatty acids refers to an unbranched carbon chain. If the carbon chain is branched, the number of carbon atoms excludes those in sidegroups. In one embodiment, the long-chain polyunsaturated fatty acid is an ω3 fatty acid, that is, having a desaturation (carbon-carbon double bond) in the third carbon-carbon bond from the methyl end of the fatty acid. In another embodiment, the long-chain polyunsaturated fatty acid is an ω6 fatty acid, that is, having a desaturation (carbon-carbon double bond) in the sixth carbon-carbon bond from the methyl end of the fatty acid.

As used herein, the terms "long-chain polyunsaturated fatty acid" or "LC-PUFA" refer to a fatty acid which comprises at least 20 carbon atoms in its carbon chain and at least two carbon-carbon double bonds.

As used herein, the term "desaturase" refers to an enzyme which is capable of introducing a carbon-carbon double bond into the acyl group of a fatty acid substrate, which is typically in an esterified form such as, for example, fatty acid CoA esters. The acyl group may be esterified to a phospholipid such as phosphatidyl choline, or to acyl carrier protein (ACP), or in a preferred embodiment to CoA. Desaturases generally may be categorized into three groups accordingly.

As used herein, the term "Δ12 desaturase" refers to a protein which performs a desaturase reaction that introduces a carbon-carbon double bond located at the $12^{th}$ bond from the carboxyl end and has greater activity in desaturation at this position than any other position. In one embodiment, the Δ12 desaturase activity includes oleoyl-CoA Δ12 desaturase activity. In another embodiment, the Δ12 desaturase activity includes palmitoleoyl-CoA Δ12 desaturase activity. These fatty acids may be in an esterified form, such as, for example, as part of a phospholipid. Examples of Δ12 desaturases include proteins comprising an amino acid sequence provided in SEQ ID NOs: 28, 78 and 134.

There are two types of Δ12 desaturases; acyl-CoA Δ12 desaturases and acyl-PC Δ12 desaturases, which are predominantly active on acyl-CoA and acyl-PC linked 18:1 substrates, respectively. However, Δ9 desaturases may also be active on an acyl-ACP (acyl carrier protein).

As used herein, the term "acyl-CoA Δ12 desaturase activity" or "acyl-CoA Δ12 desaturase" refers to the desaturase having greater activity on an acyl-CoA substrate than an acyl-lipid (such as acyl-PC) and/or acyl-ACP substrate. In an embodiment, the activity is at least two-fold greater.

As used herein, a "Δ5 desaturase" refers to a protein which performs a desaturase reaction that introduces a carbon-carbon bond located at the $5^{th}$ bond from the carboxyl end and has greater activity in desaturation at this position than any other position. In one embodiment the Δ5 desaturase has acyl-CoA-stearoyl Δ5 desaturase activity. In another embodiment, the Δ5 desaturase has acyl-CoA-palmitoyl Δ5 desaturase activity. In one embodiment, the enzyme Δ5 desaturase catalyses the desaturation of C20 LC-PUFA, converting dihomo-γ-linoleic acid DGLA to arachidonic acid (ARA, 20:4ω6) and ETA to EPA (20:5ω3).

As used herein, the term "acyl-CoA Δ5 desaturase activity" or "acyl-CoA Δ5 desaturase" refers to the desaturase having greater activity on an acyl-CoA substrate than an acyl-lipid (such as acyl-PC) and/or acyl-ACP substrate. In an embodiment, the activity is at least two-fold greater.

As used herein, a "Δ9 desaturase" refers to a protein which performs a desaturase reaction that introduces a carbon-carbon bond located at the $9^{th}$ bond from the carboxyl end and has greater activity in desaturation at this position than any other position. Examples of Δ9 desaturase activity include myristoyl-CoA Δ9 desaturase activity, stearoyl-CoA Δ9 desaturase activity, palmitoyl-CoA Δ9 desaturase activity, lignoceroyl-CoA Δ9 desaturase activity and behenoyl-CoA Δ9 desaturase activity.

As used herein, the term "acyl-CoA Δ9 desaturase activity" or "acyl-CoA Δ9 desaturase" refers to the desaturase having greater activity on an acyl-CoA substrate than an acyl-lipid (such as acyl-PC) and/or acyl-ACP substrate. In an embodiment, the activity is at least two-fold greater.

As used herein, the term "conjugase" refers to a conjutriene-forming desaturase.

The term "epoxidase" as used herein refers to an enzyme that introduces an epoxy group into a fatty acid resulting in the production of an epoxy fatty acid. In preferred embodiment, the epoxy group is introduced at the 2nd and/or 12th carbon on a fatty acid chain, especially of a C16 or C18 fatty acid chain.

"Hydroxylase", as used herein, refers to an enzyme that introduces a hydroxyl group into a fatty acid resulting in the production of a hydroxylated fatty acid. In a preferred embodiment, the hydroxyl group is introduced at the 2nd, 12th and/or 17th carbon on a C18 fatty acid chain. In another preferred embodiment, the hydroxyl group is introduced at the 15th carbon on a C16 fatty acid chain.

The term "plant" includes whole plants, vegetative structures (for example, leaves, stems), roots, floral organs/structures, seed (including embryo, endosperm, and seed coat), plant tissue (for example, vascular tissue, ground tissue, and the like), cells and progeny of the same.

A "transgenic plant", "genetically modified plant" or variations thereof refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

The terms "seed" and "grain" are used interchangeably herein. "Grain" generally refers to mature, harvested grain but can also refer to grain after imbibition or germination, according to the context. Mature grain commonly has a moisture content of less than about 18-20%.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end and which are involved in expression of the gene. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, the term "can be isolated from" means that the polynucleotide or encoded polypeptide is naturally produced by an organism, particularly an insect.

Polypeptides/Peptides

By "substantially purified polypeptide" or "purified polypeptide" we mean a polypeptide that has generally been separated from the lipids, nucleic acids, other peptides, and other contaminating molecules with which it is associated in its native state. Preferably, the substantially purified polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment the cell is a cell that does not naturally produce the polypeptide. However, the cell may be a cell which comprises a non-endogenous gene that causes an altered amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The terms "polypeptide" and "protein" are generally used interchangeably.

The % identity of a polypeptide is determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns two sequences over their entire length.

As used herein a "biologically active" fragment is a portion of a polypeptide of the invention which maintains a defined activity of the full-length polypeptide, namely possessing desaturase, conjugase, epoxidase, and/or hydroxylase activity. Biologically active fragments can be any size as long as they maintain the defined activity. Preferably, the biologically active fragment maintains at least 10% of the activity of the full length protein.

With regard to a defined polypeptide/enzyme, it will be appreciated that % identity figures higher than those provided above will encompass preferred embodiments. Thus, where applicable, in light of the minimum % identity figures, it is preferred that the polypeptide/enzyme comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

With regard to the acyl-CoA Δ5 desaturases of the invention, this is the first demonstration of an animal desaturase that can produce 5-hexadecenoic and 5-octadecenoic acids and uses an acyl-CoA fatty acid as a substrate.

With regard to the acyl-CoA Δ12 desaturases of the invention, this is the first known demonstration of Δ12 desaturase activity by an enzyme naturally produced by an animal. Furthermore, this is the first demonstration of a desaturase that can produce linoleic acid and uses an acyl-CoA fatty acid as a substrate.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics.

Mutant (altered) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama (1998). Products derived from mutated/altered DNA can readily be screened using techniques described herein to determine if they possess desaturase, conjugase, epoxidase, and/or hydroxylase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In a preferred embodiment a mutant/variant polypeptide has one or two or three or four conservative amino acid changes when compared to a naturally occurring polypeptide. Details of conservative amino acid changes are provided in Table 1. In a preferred embodiment, the changes are not in one or more of the following motifs: AGAHRLW, SETDAD, FFFSHVG, QKKY, NSAAH, GEGWHNYHH, PWDY, and GWAY. In a particularly preferred embodiment, the changes are not in each of the following motifs: AGAHRLW, SETDAD, FFFSHVG, QKKY, NSAAH, GEGWHNYHH, PWDY, and GWAY. As the skilled person would be aware, such minor changes can reasonably be predicted not to alter the activity of the polypeptide when expressed in a recombinant cell.

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides

By "isolated polynucleotide" we mean a polynucleotide which has generally been separated from the polynucleotide sequences with which it is associated or linked in its native state. Preferably, the isolated polynucleotide is at least 60% free, more preferably at least 75% free, and more preferably at least 90% free from other components with which it is naturally associated. Furthermore, the term "polynucleotide" is used interchangeably herein with the terms "nucleic acid molecule", "gene" and "mRNA".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

"Polynucleotide" refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity defined herein.

The % identity of a polynucleotide is determined by GAP (Needleman and Wunsch, 1970) analysis (GCG program) with a gap creation penalty=5, and a gap extension penalty=0.3. The query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. Even more preferably, the query sequence is at least 300 nucleotides in length and the GAP analysis aligns the two sequences over a region of at least 300 nucleotides. Even more preferably, the GAP analysis aligns two sequences over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

A polynucleotide of the present invention may selectively hybridise to a polynucleotide that encodes a polypeptide of the present invention under stringent conditions. As used herein, under stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis or DNA shuffling on the nucleic acid as described above). It is thus apparent that polynucleotides of the invention can be either naturally occurring or recombinant.

Oligonucleotides of the present invention can be RNA, DNA, or derivatives of either. The minimum size of such oligonucleotides is the size required for the formation of a stable hybrid between an oligonucleotide and a complementary sequence on a polynucleotide of the present invention. Preferably, the oligonucleotides are at least 15 nucleotides, more preferably at least 18 nucleotides, more preferably at least 19 nucleotides, more preferably at least 20 nucleotides, even more preferably at least 25 nucleotides in length. The present invention includes oligonucleotides that can be used as, for example, probes to identify nucleic acid molecules, or primers to produce nucleic acid molecules. Oligonucleotides of the present invention used as a probe are typically conjugated with a label such as a radioisotope, an enzyme, biotin, a fluorescent molecule or a chemiluminescent molecule.

Recombinant Vectors One embodiment of the present invention includes a recombinant vector, which comprises at least one isolated polynucleotide molecule of the present invention, inserted into any vector capable of delivering the polynucleotide molecule into a host cell. Such a vector contains heterologous polynucleotide sequences, that is polynucleotide sequences that are not naturally found adjacent to polynucleotide molecules of the present invention and that preferably are derived from a species other than the species from which the polynucleotide molecule(s) are derived. The vector can be either RNA or DNA, either prokaryotic or eukaryotic, and typically is a transposon (such as described in U.S. Pat. No. 5,792,294), a virus or a plasmid.

One type of recombinant vector comprises a polynucleotide molecule of the present invention operatively linked to an expression vector. The phrase "operably linked" refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, animal, and plant cells. Particularly preferred expression vectors of the present invention can direct gene expression in yeast and/or plants cells.

In particular, expression vectors of the present invention contain regulatory sequences such as transcription control sequences, translation control sequences, origins of replication, and other regulatory sequences that are compatible with the recombinant cell and that control the expression of polynucleotide molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Particularly preferred transcription control sequences are promoters active in directing transcription in plants, either constitutively or stage and/or tissue specific, depending on the use of the plant or parts thereof. These plant promoters include, but are not limited to, promoters showing constitutive expression, such as the 35S promoter of Cauliflower Mosaic Virus (CaMV), those for fruit-specific expression, such as the polygalacturonase (PG) promoter from tomato.

Recombinant molecules of the present invention may also (a) contain secretory signals (i.e., signal segment nucleic acid sequences) to enable an expressed polypeptide of the present invention to be secreted from the cell that produces the polypeptide and/or (b) contain fusion sequences which lead to the expression of nucleic acid molecules of the present invention as fusion proteins. Examples of suitable signal segments include any signal segment capable of directing the secretion of a polypeptide of the present invention. Preferred signal segments include, but are not limited to, *Nicotiana nectarin* signal peptide (U.S. Pat. No. 5,939,288), tobacco extensin signal, the soy oleosin oil body binding protein signal. In addition, a nucleic acid molecule of the present invention can be joined to a fusion segment that directs the encoded polypeptide to the proteosome, such as a ubiquitin fusion segment. Recombinant molecules may also include intervening and/or untranslated sequences surrounding and/or within the nucleic acid sequences of nucleic acid molecules of the present invention.

Host Cells

Another embodiment of the present invention includes a recombinant cell comprising a host cell transformed with one or more recombinant molecules of the present invention. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules of the present invention can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide of the present invention. Host cells of the present invention either can be endogenously (i.e., naturally) capable of producing polypeptides of the present invention or can be capable of producing such polypeptides after being transformed with at least one polynucleotide molecule of the present invention. Host cells of the present invention can be any cell capable of producing at least one protein of the present invention, and include plant, bacterial, fungal (including yeast), parasite, and arthropod cells. Preferably, the host cell is a plant, arthropod or yeast cell. Non limiting examples of arthropod cells include insect cells such as *Spodoptera frugiperda* (Sf) cells, e.g. Sf9, Sf21, *Trichoplusia ni* cells, and *Drosophila* S2 cells.

An example of a bacterial cell useful as a host cell of the present invention is *Synechococcus* spp. (also known as *Synechocystis* spp.), for example *Synechococcus elongatus*.

The cells may be of an organism suitable for a fermentation process. As used herein, the term the "fermentation process" refers to any fermentation process or any process comprising a fermentation step. A fermentation process includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, beta-carotene); and hormones. Fermentation processes also include fermentation processes used in the consumable alcohol industry (e.g., beer and wine), dairy industry (e.g., fermented dairy products), leather industry and tobacco industry. Preferred fermentation processes include alcohol fermentation processes, as are well known in the art. Preferred fermentation processes are anaerobic fermentation processes, as are well known in the art.

Suitable fermenting cells, typically microorganisms are able to ferment, i.e., convert, sugars, such as glucose or maltose, directly or indirectly into the desired fermentation product. Examples of fermenting microorganisms include fungal organisms, such as yeast. As used herein, "yeast" includes *Saccharomyces* spp., *Saccharomyces cerevisiae, Saccharomyces carlbergensis, Candida* spp., *Kluveromyces* spp., *Pichia* spp., *Hansenula* spp., *Trichoderma* spp., *Lipomyces starkey*, and *Yarrowia lipolytica*. Preferred yeast include strains of the *Saccharomyces* spp., and in particular, *Saccharomyces cerevisiae*. Commercially available yeast include, e.g., Red Star/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden) and FERMIOL (available from DSM Specialties).

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules of the present invention include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules of the present invention to correspond to the codon usage of the host cell, and the deletion of sequences that destabilize transcripts.

Transgenic Plants

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit. The plants may be vegetables or ornamental plants. The plants of the invention may be: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolour, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Lopmoea batatus*), cassava (*Manihot esculenta*), coffee (*Cofea* spp.), coconut (*Cocos nucifera*), pineapple (*Anana comosus*), citris tree (*Citrus* spp.), cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, or barley.

In a preferred embodiment, the plant is an angiosperm.

In one embodiment, the plant is an oilseed plant, preferably an oilseed crop plant. As used herein, an "oilseed plant" is a plant species used for the commercial production of oils from the seeds of the plant. The oilseed plant may be oil-seed rape (such as canola), maize, sunflower, soybean, sorghum, flax (linseed) or sugar beet. Furthermore, the oilseed plant may be other *Brassicas*, cotton, peanut, poppy, mustard, castor bean, sesame, safflower, or nut producing plants. The plant may produce high levels of oil in its fruit, such as olive, oil palm or coconut. Horticultural plants to which the present invention may be applied are lettuce, endive, or vegetable brassicas including cabbage, broccoli, or cauliflower. The present invention may be applied in tobacco, cucurbits, carrot, strawberry, tomato, or pepper.

In a further preferred embodiment, the non-transgenic plant used to produce a transgenic plant of the invention produces oil, especially in the seed, which has less than 20%, less than 10% or less than 5% 18:2 fatty acids and/or which has less than 10% or less than 5% 18:3 fatty acids.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

The transgenic plants may also comprise additional transgenes involved in the production of LC-PUFAs such as, but not limited to, a $\Delta 6$ desaturase, a $\Delta 9$ elongase, a $\Delta 8$ desaturase, a $\Delta 6$ elongase, a $\Delta 5$ desaturase with activity on a 20:3 substrate, an omega-desaturase, a $\Delta 9$ elongase, a $\Delta 4$ desaturase, a $\Delta 7$ elongase and/or members of the polyketide synthase pathway. Examples of such enzymes are known in the art and include those described in WO 05/103253 (see, for example, Table 1 of WO 05/103253).

A polynucleotide of the present invention may be expressed constitutively in the transgenic plants during all stages of development. Depending on the use of the plant or plant organs, the polypeptides may be expressed in a stage-specific manner. Furthermore, the polynucleotides may be expressed tissue-specifically.

Regulatory sequences which are known or are found to cause expression of a gene encoding a polypeptide of interest in plants may be used in the present invention. The choice of the regulatory sequences used depends on the target plant and/or target organ of interest. Such regulatory sequences may be obtained from plants or plant viruses, or may be chemically synthesized. Such regulatory sequences are well known to those skilled in the art.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triosephosphate isomerase promoter, the adenine phosphoribosyltransferase promoter of *Arabidopsis*, the rice actin 1 gene promoter, the mannopine synthase and octopine synthase promoters, the Adh promoter, the sucrose synthase promoter, the R gene complex promoter, and the chlorophyll α/β binding protein gene promoter. These promoters have been used to create DNA vectors that have been expressed in plants; see, e.g., PCT publication WO 8402913. All of these promoters have been used to create various types of plant-expressible recombinant DNA vectors.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea, the chloroplast fructose-1,6-biphosphatase promoter from wheat, the nuclear photosynthetic ST-LS1 promoter from potato, the serine/threonine kinase promoter and the glucoamylase (CHS) promoter from *Arabidopsis thaliana*. Also reported to be active in photosynthetically active tissues are the ribulose-1,5-bisphosphate carboxylase promoter from eastern larch (*Larix laricina*), the promoter for the Cab gene, Cab6, from pine, the promoter for the Cab-1 gene from wheat, the promoter for the Cab-1 gene from spinach, the promoter for the Cab 1R gene from rice, the pyruvate, orthophosphate dikinase (PPDK) promoter from *Zea mays*, the promoter for the tobacco Lhcb1*2 gene, the *Arabidopsis thaliana* Suc2 sucrose-H$^{30}$ symporter promoter, and the promoter for the thylakoid membrane protein genes from spinach (PsaD, PsaF, PsaE, PC, FNR, AtpC, AtpD, Cab, RbcS).

Other promoters for the chlorophyll α/β-binding proteins may also be utilized in the present invention, such as the promoters for LhcB gene and PsbP gene from white mustard (*Sinapis alba*). A variety of plant gene promoters that are regulated in response to environmental, hormonal, chemical, and/or developmental signals, also can be used for expression of RNA-binding protein genes in plant cells, including promoters regulated by (1) heat, (2) light (e.g., pea RbcS-3A promoter, maize RbcS promoter); (3) hormones, such as abscisic acid, (4) wounding (e.g., WunI); or (5) chemicals, such as methyl jasminate, salicylic acid, steroid hormones, alcohol, Safeners (WO 9706269), or it may also be advantageous to employ (6) organ-specific promoters.

For the purpose of expression in sink tissues of the plant, such as the tuber of the potato plant, the fruit of tomato, or the seed of soybean, canola, cotton, *Zea mays*, wheat, rice, and barley, it is preferred that the promoters utilized in the present invention have relatively high expression in these specific tissues. A number of promoters for genes with tuber-specific or -enhanced expression are known, including the class I patatin promoter, the promoter for the potato tuber ADPGPP genes, both the large and small subunits, the sucrose synthase promoter, the promoter for the major tuber proteins including the 22 kD protein complexes and proteinase inhibitors, the promoter for the granule bound starch synthase gene (GBSS), and other class I and II patatins promoters. Other promoters can also be used to express a protein in specific tissues, such as seeds or fruits. The promoter for β-conglycinin or other seed-specific promoters such as the napin and phaseolin promoters, can be used. A particularly preferred promoter for *Zea mays* endosperm expression is the promoter for the glutelin gene from rice, more particularly the Osgt-1 promoter. Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadini, and the glutenins. Examples of such promoters in rice include those promoters for the ADPGPP subunits, the granule bound and other starch synthase, the branching enzymes, the debranching enzymes, sucrose synthases, and the glutelins. A particularly preferred promoter is the promoter for rice glutelin, Osgt-1 gene. Examples of such promoters for barley include those for the ADPGPP subunits, the granule bound and other starch synthase, the branching enzymes, the debranching enzymes, sucrose synthases, the hordeins, the embryo globulins, and the aleurone specific proteins.

Root specific promoters may also be used. An example of such a promoter is the promoter for the acid chitinase gene. Expression in root tissue could also be accomplished by utilizing the root specific subdomains of the CaMV 35S promoter that have been identified.

In a particularly preferred embodiment, the promoter directs expression in tissues and organs in which fatty acid and oil biosynthesis take place, particularly in seed cells such as endosperm cells and cells of the developing embryo. Promoters which are suitable are the oilseed rape napin gene promoter (U.S. Pat. No. 5,608,152), the *Vicia faba* USP promoter (Baumlein et al., 1991), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumin B4 promoter (Baumlein et al., 1992), and promoters which lead to the seed-specific expression in monocots such as maize, barley, wheat, rye, rice and the like. Notable promoters which are suitable are the barley lpt2 or lpt1 gene promoter (WO 95/15389 and WO 95/23230) or the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene, the rye secalin gene). Other promoters include those described by Broun et al. (1998) and US 20030159173.

The 5' non-translated leader sequence can be derived from the promoter selected to express the heterologous gene sequence of the polynucleotide of the present invention, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. Nos. 5,362,865 and 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265).

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

Modern *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834, 5,416,011); *Brassica* (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, Canadian Patent Application No. 2,092,588, Australian Patent Application No 61781/94, Australian Patent No 667939, U.S. Pat. No. 6,100,447, International Patent Application PCT/US97/10621, U.S. Pat. Nos. 5,589,617, 6,541,257, and other methods are set out in Patent specification WO99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts.

The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Transgenic Hon-Human Animals

A "transgenic non-human animal" refers to an animal, other than a human, that contains a gene construct ("transgene") not found in a wild-type animal of the same species or breed. A "transgene" as referred to herein has the normal meaning in the art of biotechnology and includes a genetic sequence which has been produced or altered by recombinant DNA or RNA technology and which has been introduced into an animal cell. The transgene may include genetic sequences derived from an animal cell. Typically, the transgene has been introduced into the animal by human manipulation such as, for example, by transformation but any method can be used as one of skill in the art recognizes.

Techniques for producing transgenic animals are well known in the art. A useful general textbook on this subject is Houdebine, Transgenic animals—Generation and Use (Harwood Academic, 1997).

Heterologous DNA can be introduced, for example, into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In a highly preferred method, developing embryos are infected with a retrovirus containing the desired DNA, and transgenic animals produced from the infected embryo. In a most preferred method, however, the appropriate DNAs are coinjected into the pronucleus or cytoplasm of embryos, preferably at the single cell stage, and the embryos allowed to develop into mature transgenic animals.

Another method used to produce a trans genic animal involves microinjecting a nucleic acid into pro-nuclear stage eggs by standard methods. Injected eggs are then cultured before transfer into the oviducts of pseudopregnant recipients.

Transgenic animals may also be produced by nuclear transfer technology. Using this method, fibroblasts from donor animals are stably transfected with a plasmid incorporating the coding sequences for a binding domain or binding partner of interest under the control of regulatory sequences. Stable transfectants are then fused to enucleated oocytes, cultured and transferred into female recipients.

Feedstuffs

The present invention includes compositions which can be used as feedstuffs. For purposes of the present invention, "feedstuffs" include any food or preparation for human or animal consumption (including for enteral and/or parenteral consumption) which when taken into the body (a) serve to nourish or build up tissues or supply energy; and/or (b) maintain, restore or support adequate nutritional status or metabolic function. Feedstuffs of the invention include nutritional compositions for babies and/or young children.

Feedstuffs of the invention comprise, for example, a cell of the invention, a plant of the invention, the plant part of the invention, the seed of the invention, an extract of the invention, the product of the method of the invention, the product of the fermentation process of the invention, or a composition along with a suitable carrier(s). The term "carrier" is used in its broadest sense to encompass any component which may or may not have nutritional value. As the skilled addressee will appreciate, the carrier must be suitable for use (or used in a sufficiently low concentration) in a feedstuff such that it does not have deleterious effect on an organism which consumes the feedstuff.

The feedstuff of the present invention comprises an oil, fatty acid ester, or fatty acid produced directly or indirectly by use of the methods, cells or plants disclosed herein. The composition may either be in a solid or liquid form. Additionally, the composition may include edible macronutrients, vitamins, and/or minerals in amounts desired for a particular use. The amounts of these ingredients will vary depending on whether the composition is intended for use with normal individuals or for use with individuals having specialized needs, such as individuals suffering from metabolic disorders and the like.

Examples of suitable carriers with nutritional value include, but are not limited to, macronutrients such as edible fats, carbohydrates and proteins. Examples of such edible fats include, but are not limited to, coconut oil, borne oil, fungal oil, black current oil, soy oil, and mono- and diglycerides. Examples of such carbohydrates include (but are not limited to): glucose, edible lactose, and hydrolyzed search. Additionally, examples of proteins which may be utilized in the nutritional composition of the invention include (but are not limited to) soy proteins, electrodialysed whey, electrodialysed skim milk, milk whey, or the hydrolysates of these proteins.

With respect to vitamins and minerals, the following may be added to the feedstuff compositions of the present invention: calcium, phosphorus, potassium, sodium, chloride, magnesium, manganese, iron, copper, zinc, selenium, iodine, and Vitamins A, E, D, C, and the B complex. Other such vitamins and minerals may also be added.

The components utilized in the feedstuff compositions of the present invention can be of semi-purified or purified origin. By semi-purified or purified is meant a material which has been prepared by purification of a natural material or by de novo synthesis.

A feedstuff composition of the present invention may also be added to food even when supplementation of the diet is not required. For example, the composition may be added to food of any type, including (but not limited to): margarine, modified butter, cheeses, milk, yogurt, chocolate, candy, snacks, salad oils, cooking oils, cooking fats, meats, fish and beverages.

The genus *Saccharomyces* spp is used in both brewing of beer and wine making and also as an agent in baking, particularly bread. Yeast is a major constituent of vegetable extracts. Yeast is also used as an additive in animal feed. It will be apparent that genetically engineered yeast strains can be provided which are adapted to synthesise LC-PUFA as described herein. These yeast strains can then be used in food stuffs and in wine and beer making to provide products which have enhanced fatty acid content.

Additionally, fatty acids produced in accordance with the present invention or host cells transformed to contain and express the subject genes may also be used as animal food supplements to alter an animal's tissue or milk fatty acid composition to one more desirable for human or animal consumption. Examples of such animals include sheep, cattle, horses and the like.

Furthermore, feedstuffs of the invention can be used in aquaculture to increase the levels of fatty acids in fish for human or animal consumption.

Compositions

The present invention also encompasses compositions, particularly pharmaceutical compositions, comprising one or more of the fatty acids and/or resulting oils produced using the methods of the invention.

A pharmaceutical composition may comprise one or more of the fatty acids and/or oils, in combination with a standard, well-known, non-toxic pharmaceutically-acceptable carrier, adjuvant or vehicle such as phosphate-buffered saline, water, ethanol, polyols, vegetable oils, a wetting agent or an emulsion such as a water/oil emulsion. The composition may be in either a liquid or solid form. For example, the composition may be in the form of a tablet, capsule, ingestible liquid or powder, injectible, or topical ointment or cream. Proper fluidity can be maintained, for example, by the maintenance of the required particle size in the case of dispersions and by the use of surfactants. It may also be desirable to include isotonic agents, for example, sugars, sodium chloride, and the like. Besides such inert diluents, the composition can also include adjuvants, such as wetting agents, emulsifying and suspending agents, sweetening agents, flavoring agents and perfuming agents.

Suspensions, in addition to the active compounds, may comprise suspending agents such as ethoxylated isostearyl alcohols, polyoxyethylene sorbitol and sorbitan esters, microcrystalline cellulose, aluminum metahydroxide, bentonite, agar-agar, and tragacanth or mixtures of these substances.

Solid dosage forms such as tablets and capsules can be prepared using techniques well known in the art. For example, fatty acids produced in accordance with the present invention can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant fatty acid (s).

For intravenous administration, the fatty acids produced in accordance with the present invention or derivatives thereof may be incorporated into commercial formulations.

A typical dosage of a particular fatty acid is from 0.1 mg to 20 g, taken from one to five times per day (up to 100 g daily) and is preferably in the range of from about 10 mg to about 1, 2, 5, or 10 g daily (taken in one or multiple doses). As known in the art, a minimum of about 300 mg/day of fatty acid, especially LC-PUFA, is desirable. However, it will be appreciated that any amount of fatty acid will be beneficial to the subject.

Possible routes of administration of the pharmaceutical compositions of the present invention include, for example, enteral (e.g., oral and rectal) and parenteral. For example, a liquid preparation may be administered orally or rectally. Additionally, a homogenous mixture can be completely dispersed in water, admixed under sterile conditions with physiologically acceptable diluents, preservatives, buffers or propellants to form a spray or inhalant.

The dosage of the composition to be administered to the patient may be determined by one of ordinary skill in the art and depends upon various factors such as weight of the patient, age of the patient, overall health of the patient, past history of the patient, immune status of the patient, etc.

Additionally, the compositions of the present invention may be utilized for cosmetic purposes. It may be added to pre-existing cosmetic compositions such that a mixture is formed or a fatty acid produced according to the subject invention may be used as the sole "active" ingredient in a cosmetic composition.

Production of Oils

Techniques that are routinely practiced in the art can be used to extract, process, and analyze the oils produced by cells, plants, seeds, etc of the instant invention. Typically, plant seeds are cooked, pressed, and extracted to produce crude oil, which is then degummed, refined, bleached, and deodorized. Generally, techniques for crushing seed are known in the art. For example, oilseeds can be tempered by spraying them with water to raise the moisture content to, e.g., 8.5%, and flaked using a smooth roller with a gap setting of 0.23 to 0.27 mm. Depending on the type of seed, water may not be added prior to crushing. Application of heat deactivates enzymes, facilitates further cell rupturing, coalesces the oil droplets, and agglomerates protein particles, all of which facilitate the extraction process.

The majority of the seed oil is released by passage through a screw press. Cakes expelled from the screw press are then solvent extracted, e.g., with hexane, using a heat traced column. Alternatively, crude oil produced by the pressing operation can be passed through a settling tank with a slotted wire drainage top to remove the solids that are expressed with the oil during the pressing operation. The clarified oil can be passed through a plate and frame filter to remove any remaining fine solid particles. If desired, the oil recovered from the extraction process can be combined with the clarified oil to produce a blended crude oil.

Once the solvent is stripped from the crude oil, the pressed and extracted portions are combined and subjected to normal oil processing procedures (i.e., degumming, caustic refining, bleaching, and deodorization). Degumming can be performed by addition of concentrated phosphoric acid to the crude oil to convert non-hydratable phosphatides to a hydratable form, and to chelate minor metals that are present. Gum is separated from the oil by centrifugation. The oil can be refined by addition of a sufficient amount of a sodium hydroxide solution to titrate all of the fatty acids and removing the soaps thus formed.

Deodorization can be performed by heating the oil to 260° C. under vacuum, and slowly introducing steam into the oil at a rate of about 0.1 ml/minute/100 ml of oil. After about 30 minutes of sparging, the oil is allowed to cool under vacuum. The oil is typically transferred to a glass container and flushed with argon before being stored under refrigeration. If the amount of oil is limited, the oil can be placed under vacuum, e.g., in a Parr reactor and heated to 260° C. for the same length of time that it would have been deodorized. This treatment improves the color of the oil and removes a majority of the volatile substances.

Antibodies

The invention also provides monoclonal or polyclonal antibodies to polypeptides of the invention or fragments thereof. Thus, the present invention further provides a process for the production of monoclonal or polyclonal antibodies to polypeptides of the invention.

The term "binds specifically" refers to the ability of the antibody to bind to proteins of the present invention but not other known desaturase, conjugase, epoxidase and/or hydroxylase-like polypeptides.

As used herein, the term "epitope" refers to a region of a polypeptide of the invention which is bound by the antibody. An epitope can be administered to an animal to generate antibodies against the epitope, however, antibodies of the present invention preferably specifically bind the epitope region in the context of the entire polypeptide.

If polyclonal antibodies are desired, a selected mammal (e.g., mouse, rabbit, goat, horse, etc.) is immunised with an immunogenic polypeptide such as those provided as SEQ ID NOs: 16 to 30, 73 to 78, 80 and 134. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides peptides of the invention or fragments thereof haptenised to another peptide for use as immunogens in animals.

Monoclonal antibodies directed against polypeptides of the invention can also be readily produced by one skilled in the art. The general methodology for making monoclonal antibodies by hybridomas is well known Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. Such fragments include Fir, F(ab') and F(ab)$_2$ fragments, as well as single chain antibodies (scFv). Furthermore, the antibodies and fragments thereof may be humanised antibodies, for example as described in EP-A-239400.

Antibodies of the invention may be bound to a solid support and/or packaged into kits in a suitable container along with suitable reagents, controls, instructions and the like.

In an embodiment, antibodies of the present invention are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, phypoerythrin and allophycocyanins; fluorescein and Texas red), which can be used with a fluorescence activated cell sorter; haptens; and the like. Preferably, the detectable label allows for direct measurement in a plate luminometer, e.g., biotin. Such labeled antibodies can be used in techniques known in the art to detect polypeptides of the invention.

EXAMPLES

Example 1—Identification of Desaturases in the *Tribolium castaneum* Genome

Sixty-four published full length insect desaturase protein sequences available at the end of 2005 were aligned using the Clustal X program (Thompson et al., 1997). From this sequence alignment, a highly conserved peptide sequence was selected (HNYHHAYPWDYKAAEIGMPLNSTAS LIRLCASLGWAYDLKSV (SEQ ID NO: 31)) and used to search the *Tribolium castaneum* genome using TBLASTN program (Altschul et al., 1997). From this analysis, 15 desaturase-like sequences were identified which have been termed, Tribdesat1 (coding sequence provided as SEQ ID NO:1, amino acid sequence provided as SEQ ID NO:16), Tribdesat2a (coding sequence provided as SEQ ID NO:2, amino acid sequence provided as SEQ ID NO:17), Tribdesat2b (coding sequence provided as SEQ ID NO:3, amino acid sequence provided as SEQ ID NO:18), Tribdesat2c (coding sequence provided as SEQ ID NO:4, amino acid sequence provided as SEQ ID NO:19), Tribdesat3 (coding sequence provided as SEQ ID NO:5, amino acid sequence provided as SEQ ID NO:20), Tribdesat4 (coding sequence provided as SEQ ID NO:6, amino acid sequence provided as SEQ ID NO:21), Tribdesat5 (coding sequence provided as SEQ ID NO:7, amino acid sequence provided as SEQ ID NO:22), Tribdesat6a (coding sequence provided as SEQ ID NO:8, amino acid sequence provided as SEQ ID NO:23), Tribdesat6b (coding sequence provided as SEQ ID NO:9, amino acid sequence provided as SEQ ID NO:24), Tribdesat7a (coding sequence provided as SEQ ID NO:10, amino acid sequence provided as SEQ ID NO:25), Tribdesat7b (coding sequence provided as SEQ ID NO:11, amino acid sequence provided as SEQ ID NO:26), Tribde-sat8 (coding sequence provided as SEQ ID NO:12, amino acid sequence provided as SEQ ID NO:27), Tribdesat10 (coding sequence provided as SEQ ID NO:13, amino acid sequence provided as SEQ ID NO:28), Tribdesat11 (coding sequence provided as SEQ ID NO:14, amino acid sequence provided as SEQ ID NO:29) and Tribdesat12 (coding sequence provided as SEQ ID NO:15, amino acid sequence provided as SEQ ID NO:30). The sequences listed above as Tribdesat2a, 2b, 2c, 3, 4, 5, 6a, 8, 10, 11, 12 were corrected on the basis of cloning and sequencing of the corresponding cDNAs (see Examples 2-5).

Each of the contigs was then subjected to a gene prediction program in Softberry (http://www.softberry.com/cgi-bin/programs/gfin/fgenesh). Parameters for *Drosophila, Anopheles, C. elegans* and *Brugia malaya* were tested for their ability to predict desaturase genes. For each of the gene predictions, the proteins were subjected to a BLASTP analysis against all proteins in the NCBI database to determine if they resembled desaturases. Neither *Anopheles* nor *Drosophila* parameters gave the correct prediction for desaturases except for Tribdesat10 which used *Anopheles* parameters. For some of the desaturases, parameters for predicting genes in *C. elegans* or *B. malaya* predicted genes similar to desaturases. For three of the desaturases, none of the predictions using any of the default parameters predicted desaturase genes (Tribdesat4, Tribdesat7a and Tribdesat7b).

For three of the desaturase genes (2 contigs) that could not be predicted using the gene prediction programs, the genomic regions were subjected to a BLASTX comparison with all proteins in the NCBI database. The most 5' region of the genomic fragment resembling desaturases was noted and DNA sequences upstream were translated in silico and visually examined for a methionine residue. This was taken to be the start methionine of the protein sequence. The 3' region of the genomic fragment that resembled desaturases were examined in a similar manner for a stop codon. Each of these protein sequences were visually inspected for all the conserved motifs of desaturases (Table 2). For Tribdesat4, no reasonable prediction of the N-terminus or C-terminus of the protein could be made due to incomplete sequence of the genome in these regions.

Each protein sequence was also examined for the presence of three "histidine boxes" (His boxes) which are motifs that are strongly conserved in all desaturases. The histidine residues in these boxes are thought to be involved in binding iron atoms required for desaturase activity. The amino acid positions and sequences of the His boxes in the proteins and two others from *Chauliognathus lugubris* (see Example 5) are listed in Table 3, after correction of the predicted protein sequences from analysis of the cDNA clones (Examples 2-5).

TABLE 2

Presence (✓) or absence (X) of conserved desaturase motifs in identified *Tribolium* amino acid sequences.
(Note: Motifs in the sequences may not be identical to the corresponding conserved sequence motif).

| Identified Gene | Predicted protein size (amino acids) | Conserved sequence motif | | | | | | | |
|---|---|---|---|---|---|---|---|---|---|
| | | 1 | 2 | 3 | 4 | 5 | 6 | 7 | 8 |
| Tribdesat 1 | 348 | ✓ | ✓ | ✓ | X | ✓ | ✓ | ✓ | ✓ |
| Tribdesat 2a | 320 | ✓ | ✓ | ✓ | ✓ | ✓ | ✓ | ✓ | ✓ |
| Tribdesat 2b | 297 | ✓ | ✓ | ✓ | ✓ | ✓ | ✓ | ✓ | ✓ |
| Tribdesat 2c | 321 | ✓ | ✓ | ✓ | ✓ | ✓ | ✓ | ✓ | ✓ |
| Tribdesat 3 | 286 | ✓ | X | ✓ | ✓ | ✓ | ✓ | ✓ | ✓ |
| Tribdesat 5 | 353 | ✓ | ✓ | ✓ | ✓ | ✓ | ✓ | ✓ | ✓ |

TABLE 2-continued

Presence (✓) or absence (X) of conserved desaturase motifs in identified *Tribolium* amino acid sequences. (Note: Motifs in the sequences may not be identical to the corresponding conserved sequence motif).

| Identified Gene | Predicted protein size (amino acids) | Conserved sequence motif | | | | | | | |
|---|---|---|---|---|---|---|---|---|---|
| | | 1 | 2 | 3 | 4 | 5 | 6 | 7 | 8 |
| Tribdesat 6a | 350 | ✓ | ✓ | ✓ | ✓ | ✓ | ✓ | ✓ | ✓ |
| Tribdesat 6b | 289 | ✓ | X | X | ✓ | X | X | ✓ | X |
| Tribdesat 8 | 374 | ✓ | ✓ | ✓ | ✓ | ✓ | ✓ | ✓ | ✓ |
| Tribdesat 10 | 366 | ✓ | ✓ | ✓ | ✓ | ✓ | ✓ | ✓ | ✓ |
| Tribdesat 11 | 323 | ✓ | ✓ | ✓ | ✓ | ✓ | ✓ | ✓ | ✓ |
| Tribdesat 12 | 455 | ✓ | ✓ | ✓ | ✓ | ✓ | ✓ | ✓ | ✓ |

Concensus amino acid sequences of motifs:

1, AGAHRLW; (SEQ ID NO: 104)

2, SETDAD; (SEQ ID NO: 105)

3, FFFSHVG; (SEQ ID NO: 106)

4, QKKY; (SEQ ID NO: 107)

5, NSAAH; (SEQ ID NO: 108)

6, GEGWHNYHH; (SEQ ID NO: 109)

7, PWDY; (SEQ ID NO: 110)

8, GWAY. (SEQ ID NO: 111)

TABLE 3

Amino acid location and sequences of histidine boxes in *Tribolium* and soldier beetle desaturase sequences. The number for each box corresponds to the location in the protein of the first amino acid residue of the motif.

| | First HIS box | Second HIS box | Third HIS box |
|---|---|---|---|
| Tribdesat1 | 90; HRLWtH (SEQ ID NO: 112) | 109; HRVHH (SEQ ID NO: 116) | 249; HNYHH (SEQ ID NO: 121) |
| Tribdesat2a | 60; HRLWSH (SEQ ID NO: 113) | 97; HRAHH (SEQ ID NO: 117) | 238; HNYHH |
| Tribdesat2b | 62; HRLWAH (SEQ ID NO: 114) | 99; HRIHH | 240; HNYHH |
| Tribdesat2c | 55; HRLWAH | 92; HRVHH | 233; HNYHH |
| Tribdesat3 | 65; HRLWAH | 102; HQVHH (SEQ ID NO: 118) | 243; HNYHH |
| Tribdesat4 | 96; HRLWSH | 133; HRVHH | 274; HNYHH |
| Tribdesat5 | 88; HRLWAH | 125; HRVHH | 265; HNYHH |
| Tribdesat6a | 88; HRLWAH | 125; HRVHH | 265; HNYHH |
| Tribdesat6b | 15; HRLWAH | 52; HRVHH (SEQ ID NO: 119) | 189; WISYH (SEQ ID NO: 122) |
| Tribdesat7a | 57; HRLWSH | 94; HRAHH | 234; HNYHH |
| Tribdesat8 | 93; HRLWAH | 130; HRVHH | 271; HNYHH |
| Tribdesat10 | 75; HRLWAH | 112; HRVHH | 254; HNYHH |
| Tribdesat11 | 77; HRLYSH (SEQ ID NO: 115) | 114; HRQHH (SEQ ID NO: 120) | 255; HNYHH |
| Tribdesat12 | 104; HRLWAH | 141; HRVHH | 282; HNYHH |
| CL1 (SEQ ID NO: 73) | 88; HRLWAH | 125; HRVHH | 265; HNYHH |
| CL3 (SEQ ID NO: 74) | 88; HRLWSH | 125; HRVHH | 265; HNYHH |

Example 2—Cloning of Tribdesat4

The inventors attempted to obtain Tribdesat4 using inverse PCR on cDNA as we could not predict from the genome sequence either the beginning or the end of the gene. First strand synthesis was performed by mixing 3 µl larval RNA (24 µg), 100 pmol of each of the oligonucleotide primers from Clontech, Smart N Oligo 5'AAGCAGTGG-TATCAACGCAGAGTGGCCATTACGGCCGGG-3' (SEQ ID NO: 32); and CDS/3' (5'ATTCTAGAGGCCGAGGCG-GCCGACATG-d(T)30VN) (N=A, G, C or T; V=A, G or C (SEQ ID NO: 33)). This was incubated at 72° C. for 2 min after which it was immediately cooled on ice. To the contents of the tube was added 2 µl 5× first strand buffer (Powerscript; Clontech), 1 µl DTT (20 mM), 1 µl dNTP mix (final concentration of 200 µM each dNTP) and 1 µl Powerscript reverse transcriptase (Clontech). First strand cDNA synthesis was allowed to occur at 42° C. for 1 hour, after which it was immediately cooled on ice. NaOH (1 µl, 25 mM) was added and incubated at 68° C. for 30 min. An aliquot of the first strand synthesis (6 µl) was mixed with 5 µl 10× Advantage 2 Buffer (Clontech), 1 µl 50× dNTP mix, 1 µl CDS/5 oligo (5'AAGCAGTGGTATCAACGCAGAGT; Clontech (SEQ ID NO: 34)), 1 µl CDS/3 oligo, 1 µl 50× Advantage 2 Polymerase and made to a final volume of 50 µl. The mixture then went through a temperature regime as follows: 72° C./10 min; 95° C./1 min; then 3 cycles of 95° C./15 sec, 68° C./8 min.

An aliquot (5 µl) was separated on a 1% agarose gel to ensure that amplification had occurred. The sample was then digested with SfiI for 2 hours at 50° C. and the restriction enzyme removed using the QIAgen PCR purification kit according to the manufacturer's instructions. The eluted sample was diluted for ligation to ensure intramolecular ligations rather than intermolecular ligation. Digested DNA (0.5 µg) was diluted in a ligation mixture of 500 µl and incubated overnight at 16° C. The ligation was concentrated by glycogen precipitation (150 µg glycogen, 1.4 ml ice-cold 95% ethanol at −80° C. for 2 hours) after which DNA was pelleted by centrifugation (12 000 g, 20 min). The DNA was resuspended in 10 µl sterile water. The inverse PCR reaction was performed on 1 µl of this precipitated DNA and included 5 µl 10× Advantage 2 PCR Buffer (Clontech), 10 pmol Desat4 GSP1 (5'ATTATGAGCGGATCGGCTTCCAAGTC (SEQ ID NO: 35), 10 pmol Desat4 GSP2 (5'CGAAA CAATTTGGAATTCGTTTTGGG (SEQ ID NO: 36), 200 µM each dNTP, 1 µl 50× BD Advantage 2 Polymerase and sterile water to a final volume of 50 µl. The PCR conditions were as follows: 95° C./1 min, then 30 cycles of 95° C./30 sec, 68° C./3 min, then 68° C./3 min.

An aliquot (5 µl) of the PCR was separated on a 1% agarose gel. A single band was noted and cloned into pGEM-T-Easy. The insert was sequenced and shown to contain most of the 5' end of Tribdesat4 and the entire 3' end of Tribdesat4. The existing 5' end of Tribdesat4 was then subject to BLASTN analysis against available sequences of ESTs from *T. castaneum*. One EST was identified from this analysis (Accession No. DT795463) and the rest of the 5' end was identified.

Primers were designed to the 5' and 3' end of the coding region of Tribdesat4 and used in an RT-PCR reaction to obtain full length Tribdesat4. The RT-PCR reaction consisted of 25 µl 2× Reaction mix (Invitrogen), 37 ng RNA, 1 µl Superscript II RT/Platinum Taq DNA polymerase (Invitrogen), 100 pmol of each primer and sterile water to 50 µl. The reaction conditions were as follows: 50° C./30 min, 94° C./2 min, then 35 cycles of 94° C./30 sec, 55° C./1 min, 72° C./1 min, then 72° C./5 min. An aliquot was run on a 1% agarose gel. A single band (approximately 1 kb) was obtained and cloned into pGEM T Easy. The sequence of the insert was examined and verified as the full length cDNA. SEQ ID NO: 6 shows the nucleotide sequence of the coding region of the cDNA.

Example 3—Amplification of Desaturase Sequences from Adult *Tribolium* RNA

RNA was extracted from *T. castaneum* (strain TC4) beetles using the Trizol method (Invitrogen). 100 mg of adult beetles were homogenized in 1 ml Trizol reagent and the mixture incubated for 5 minutes at 25° C., after which 200 µl chloroform was added to the sample. The mixture was shaken by hand for 15 seconds and then allowed to settle for 3 minutes at 25° C. The organic and aqueous layers were separated by centrifugation (12,000 g, 15 minutes, 4° C.). The upper aqueous layer was transferred to a fresh tube and the RNA precipitated by the addition of 500 µl isopropanol. After 10 minute incubation at 25° C., the RNA was pelleted by centrifugation at 12,000 g/10 minutes at 4° C. The RNA pellet was washed once with 75% ethanol and then air-dried for 10 minutes. The RNA was then dissolved in 30 µl of RNase-free water. There was a noticeable brown colouration to the RNA which was further purified using the RNeasy mini protocol for RNA cleanup (QIAgen), according to the manufacturer's instructions.

RT-PCR amplification reactions were carried out for 10 desaturase sequences (Tribdesat1, 2a, 2b, 3, 5, 6a, 6b, 8, 10 and 11). To each sample was added 25 µl 2× Reaction mix (Invitrogen), 37 ng RNA, 1 µl Superscript II RT/Platinum Taq DNA polymerase (Invitrogen), 100 pmol of each primer and sterile water to 50 µl. The reaction conditions were as follows: 50° C./30 min, 94° C./2 min, then 35 cycles of 94° C./30 sec, 55° C./1 min, 72° C./1 min, then 72° C./5 min (PCR conditions 55/72).

An aliquot of each sample was run on a 1% agarose gel. Those samples containing a single amplification product of about 1 kb (Tribdesat1, 3, 5, 6a, 10, 11) were purified using the QIAquick PCR purification kit (QIAgen) and cloned into pGEM T Easy (Promega). Ligation mixtures were transformed into *E. coli* DH10B using standard molecular biological techniques (Sambrook et al., 1989). The DNA sequence of clones containing inserts was examined. Comparisons of gene predictions with those of RT-PCR products obtained for Tribedesat2b, 3, 6b, 10 and 11 are shown in FIGS. 1 to 5. It was apparent that the sequences as predicted from the genome sequence were not the same as the observed cDNA sequences, in some cases this would have been due to incorrect predictions for coding sequences from the genomic sequence. In other cases, differences such as single nucleotide polymorphisms may have been due to different alleles of the genes present in populations of the insects.

RNA was also extracted from *T. castaneum* larvae using the Trizol method as above. RT-PCR reactions were carried out to amplify 6 desaturase sequences (Tribdesat2a, 2b, 2c, 6b, 8 and 12) by the method see as above. No amplification products were observed after a first round of PCR and so the reactions were subject to a second round of PCR. Amplification products of about 1 kb were observed in the Tribdesat2b, Tribdesat2c, Tribdesat12 and Tribdesat8 samples. These products were extracted from an agarose gel using the QIAquick gel extraction kit (QIAgen) and cloned into pGEM T Easy (Promega). The DNA sequences of clones containing inserts were examined. Comparisons of gene predictions with those of RT-PCR products obtained for Tribdesat2b and 6b are shown in FIGS. 1 and 3, respectively.

Example 4. Amplification of Desaturase Gene Fragments from Soldier Beetles (*Chauliognathus lugubris*)

Amplification of Internal Desaturase Fragments from Male Soldier Beetles

RNA was extracted from 100 mg of adult male *C. lugubris* beetles using the Trizol method as described above for *Tribolium*. The synthesis of cDNA was performed using the Invitrogen Superscript II and using a polyT primer (5'TTTTTTTTTTTTTTTTTT (SEQ ID NO: 81)). The polyT primer (100 pmol), RNA (2 µA) and RNase-free water to a final volume of 15.5 µl were incubated at 70° C. for 10 minutes and then chilled on ice. To this was added 10×PCR Buffer (2.5 µl), 25 mM MgCl$_2$ (2.5 µl), 10 mM dNTP mix (1 µl) and 0.1M DTT (2.5 µl). This mixture was heated to 42° C. for 1 minute after which Superscript II Reverse Transcriptase (1 µl) was added and the mixture left for 50 minutes at 42° C. Superscript II Reverse Transcriptase was inactivated at 70° C. for 15 minutes and RNA degraded with 1 µl RNaseH (2 Units, 30 minutes at 37° C.).

PCR reactions were setup containing 1 µl dNTPs (200 µM each dNTP), 5 µl 10× ThermoPol Buffer (NEB), 1.5 µl F2 (5'TTCTTCTTCKCNCAYKTHGGNTGG (SEQ ID NO: 82)), 1.5 µl R2 (5'TGRTGGTAGTTGTGVHANCCCTC (SEQ ID NO: 83)), 5 µl cDNA, 0.1 U Taq DNA Polymerase (NEB) and sterile water to 50 µl. The PCR conditions were as follows: an initial denaturation of 94° C. for 3 minutes and then 30 cycles of 94° C./15s, 48° C./30s, 72° C./2 min and then a final extension of 72° C./5 min. An aliquot was separated on a 1.5% agarose gel and a band of approximately 400 bp was visualised. The PCR reaction was purified using the QIAgen QIAquick PCR purification kit according to the manufacturer's instructions and cloned into pGEM T Easy (Promgea). Approximately 30 clones containing inserts were examined by DNA sequence analysis. A total of three unique desaturase sequences were identified corresponding to CL6 (SEQ ID NO: 75), CL7 (SEQ ID NO: 76) and CL8 (SEQ ID NO: 77).

Amplification of Internal Desaturase Fragments from Female Soldier Beetles

RNA was extracted and cDNA synthesised as described above. Two degenerate PCRs were performed on female adult RNA using the degenerate primers F2/R2 and Clu_f (5'GCNCAYMGNYTNTGGGCNCA (SEQ ID NO: 84))/Clu-r (5'AANRYRTGRTGGTAGTTGIG (SEQ ID NO: 85)) (see Table 4) by the same method as above. Amplification products of approximately 400 bp (F2/R2) and 550 bp (Clu_f/Clu_r) were visualised and cloned into pGEM T Easy. Each insert from 70 colonies from the F2/R2 transformation was amplified by PCR using the T7 (5'TAATAC-GACTCACTATAGGG (SEQ ID NO: 86)) and SP6 (5'ATT-TAGGTGACACTATAG (SEQ ID NO: 87)) primers and analysed. Since approximately 70% of the sequenced clones from male soldier beetle tissue that had sequence similarity with desaturases were CL6, the PCR products were digested with restriction enzyme RsaI to remove CL6 clones. Of the 70 PCR products obtained, only 20 were not digested with RsaI. Resultant desaturase fragments obtained were CL7, CL8 and a new unique desaturase fragment called CL9.

Sixteen further clones were obtained from another degenerate PCR reaction using female adult RNA and primers Clu_f/Clu_r, and their nucleotide sequences obtained and compared to the previous clones. One of these was designated CL1.

TABLE 4

The tissue source of RNA and degenerate primer pairs used to isolate internal desaturase fragments from *C. lugubris*.

| Tissue Source | Degenerate Primers | Internal desaturase products |
|---|---|---|
| Male adult | F2/R2 | CL6, CL7, CL8 |
| Female adult | F2/R2 | CL9 |
| Female adult | Clu_f/Clu_r | CL1 |
| Mixed male/female adult defence gland | XRF2b/Clu_r | CL3, CL5 |

Amplification of Degenerate PCR from Defence Gland Tissue

A mixed population of males and females were dissected to obtain their defence gland tissue. Initially, the heads and the elytra were removed. The remaining tissue was divided into two parts—the abdomen sample and the defence gland tissue.

RNA was extracted and cDNA synthesised as described above. Degenerate PCR was performed with three different combinations of primers. These were Clu_f/Clu_r, F2/Clu_r and XRF2b (5'TTYTTYTWYKCNCAYATGGGNTGG (SEQ ID NO: 88))/Clu_r. After analysis on a 1.5% agarose gel, a band of the expected size was observed only in the sample with the XRF2b/Clu_r combination. No amplification products were observed with either of the other two pairs even after 60 cycles of PCR. The PCR products obtained were purified using the QIAgen QIAquick PCR purification kit and cloned into pGEM-T-Easy. Eleven clones were examined by sequence analysis. New desaturase gene fragments were obtained and designated CL3 and CL5. The CL5 internal fragment appeared to contain remnants of an intron, as determined by a section that did not show close sequence similarity with desaturases and also affected the reading frame, thereby inserting a stop codon.

5' and 3' RACE to Obtain Full Length Sequence Information

Primers for 5'- and 3'-RACE (Table 5) were designed based on sequences internal to the degenerate primer binding sites for each of the clones described above.

TABLE 5

Primers (5' to 3') used for 5' and 3' RACE.

| Clone | 5'RACE primer (CLXfront) | 3'RACE primer (CLXend) |
|---|---|---|
| CL6 | CCCAGAGATATAACCGATACA (SEQ ID NO: 89) | TTATATACGCCGACCCTATTC (SEQ ID NO: 90) |
| CL7 | CCTCTCCAAGTCCGAGAGAAG (SEQ ID NO: 91) | TGGCTCATGTGCAAAAAGCAT (SEQ ID NO: 92) |
| CL1 | TTGTGCCATCCCTCACCGTTG (SEQ ID NO: 93) | TGGCTAACATCGAGACCCTG (SEQ ID NO: 94) |
| CL3 | GCCATATAGATGAGCAGCTGA (SEQ ID NO: 95) | ATGGGATGGCATTATGTGCAG (SEQ ID NO: 96) |

The Clontech Creator™ SMART™ System was used to obtain both 5' and 3' RACE products according to the manufacturer's instructions with RNA from either abdomen or defence gland tissue. Oligonucleotide primers Smart IV (5'AAGCAGTGGTATCAACGCAGAGTGGCCATTACG-GCCGGG (SEQ ID NO: 97)) and CDS III/3' (5'ATTCTA-GAGGCCGAGGCGGCCGACATG-d(T)$_{30}$N$_{31}$ $_{-1}$N; N=A, G,C or T; N$_{-1}$=A,G or C (SEQ ID NO: 98)) were used for the reverse transcription-PCR. The 5' RACE reactions used primer CDS V 5'AAGCAGTGGTATCAACGCAGAGT (SEQ ID NO: 99), and CLXfront primer. The 3' RACE reactions used primers CDS 111/3' PCR and CLXend.

Clones were screened by colony PCR for insertions. Any clones that gave a band of the expected size (~350 bp) were examined by DNA sequence analysis. The DNA sequence was initially examined for sequence similarity with desaturases. Full length sequences were compiled in silico using sequence information from internal sequence, 5'RACE and 3'RACE products and examined for an open reading frame beginning with an ATG and ending in a stop codon that when translated possessed all the motifs of desaturases (Table 2).

Example 5. Isolation of Full Length *C. lugubris* Desaturase cDNAs

Full length cDNA clones of CL1 and other desaturase-like sequences were obtained using a one-step RT-PCR kit from Invitrogen according to the manufacturer's instructions and PCR conditions 55/72 (above). The primers used were GGTACCATGCCACCCAACGCCCAC (SEQ ID NO: 100) and GAATTCTCACTTTTGTTTGTGAGT (SEQ ID NO: 101). Bands of approximately 1 kb were purified using the QIAquick PCR purification kit from QIAgen according to the manufacturer's instructions and cloned into pGEM-T-Easy. Positive clones were obtained and examined by DNA sequence analysis. After verification of sequence, the pGEM-T-Easy clones containing the desaturase cDNAs were digested with restriction enzymes to excise the inserts, separated on a 1% agarose gel and the ~1 kb fragments were excised and purified using the QIAquick gel extraction kit (QIAgen) for cloning into yeast expression vectors such as pYES2 (below).

Example 6. Isolation of Desaturase Genes from *Chauliognathus nobiliatus*

*Chauliognathus nobiliatus* (Erichson) is another species of soldier beetle, which resembles *C. lugubris* but is generally smaller in size and less prevalent in the south-east regions of Australia. These beetle species are not closely related to moths such as *Tribolium*, indeed they are widely separated within the Insectae.

RNA was extracted from *C. nobiliatus* adults using the Trizol method as above. cDNA was synthesised using SuperScript II kit from Invitrogen. Three degenerate PCRs were performed. The first used the degenerate primers F2/Clu_r, the second used the degenerate primers XRF2b/Clu_r and the third with degenerate primers Clu_f/Clu_r. An aliquot of each reaction was separated on a 1.5% agarose gel and a band was observed for the first two reactions. These were purified using the QIAquick PCR purification kit (QIAgen) and cloned into pGEM-T-Easy. A total of 12 clones from the first PCR and 14 from the second PCR were examined by DNA sequence analysis. Three unique desaturase sequences were obtained and their corresponding orthologues from *C. lugubris* as well as the signature motif as described by Knipple et al. (2002) are shown in Table 6.

TABLE 6

The internal desaturase fragments isolated from *C. nobiliatus* and their corresponding orthologues in *C. lugubris*. Also shown is the signature motif and the primers used to isolate these internal fragments.

| C. nobiliatus | C. lugubris | Signature | Primers |
|---|---|---|---|
| CN8 | CL8 | GPAE (SEQ ID NO: 123) | F2/Clu_r |
| CN7 | CL7 | NPVE (SEQ ID NO: 124) | CL7end/CL7front |
| CN1 | CL1 | YPAE (SEQ ID NO: 125) | CL1end/CL1front |
| CN9 | CL9 | SPVE (SEQ ID NO: 126) | CL9end/CL9front |

A second approach used to isolate internal desaturase fragments from *C. nobiliatus* was to use primers specific to *C. lugubris* desaturases. The cDNA synthesised as described above was used as a template for PCR with specific primers to CL6, CL7, CL9, and CL1. An aliquot of each reaction was separated on a 1.5% agarose gel and bands were observed with the CL7, CL9 and CL1-specific primers but no products were observed for either the CL6 or the CL10 primers. The CL7, CL9 and CL1 products were purified using the QIAgen QIAquick PCR purification kit and cloned into pGEM-T-Easy. Positive clones were obtained and examined by DNA sequence analysis.

Full-length cDNA sequences for the CL3 and CL1 orthologues were amplified from *C. nobiliatus* RNA using the One-step SuperScript II Reverse Transcriptase/Platinum Taq DNA Polymerase kit from Invitrogen as described in Example 5. The primers used are shown in Table 7. A clone obtained from each reaction was sequenced to confirm identity of each cDNA.

TABLE 7

Primers used to obtain full length *C. nobiliatus* orthologues of selected desaturases.

| Gene | Forward Primer (5'→3') | Reverse Primer (5'→3') |
|---|---|---|
| CL1 | GGTACCATGCCACCCAACGC CCAC (SEQ ID NO: 100) | GAATTCTCACTTTTGTTTGTGA GT (SEQ ID NO: 101) |
| CL3 | AAGCTTATGCTACCGGAGTT TTGC (SEQ ID NO: 102) | CTCCAGCTAAGACTGATTATA GGC (SEQ ID NO: 103) |

Example 7. Isolation of Desaturase Genes from cDNA Libraries

Construction of a cDNA library from *C. lugubris* abdomen tissue RNA was extracted from *C. lugubris* abdomen tissue using the method described above. A cDNA library was constructed using the Invitrogen Cloneminer kit according to the manufacturer's instructions. A fraction of the library was transformed into *E. coli* DH10B ElectroMax competent cells (Invitrogen) and transformants selected on LB agar plates containing 25 µg/ml kanamycin. Approximately 90% of the clones contained inserts with an average insert size of 1.5 kb. Desaturase clones were identified and isolated from this library by PCR methods or by hybridisation screening using probes derived from the clones described above.

PCR Method for Screening Plasmid cDNA Library

A volume of plasmid cDNA library representing approximately 50 colony forming units was seeded into 96 well plates containing 300 µB supplemented with 50 µg/ml kanamycin and grown overnight at 37° C. with shaking. 100 µl of each liquid culture from the wells across the plate were pooled into 1.5 ml tubes to yield eight "lane pools" and a plasmid extraction was performed using a QIAquick miniprep spin kit (Qiagen) according to manufacturers instructions. 10 µl of each "lane pool" elutant was mixed into a 1.5 ml tube creating a "plate pool". PCR screening was done on each "plate pool" using gene specific primers and run out on 1% TAE agarose gel to identify positive plate pool/s. Once positive plate/s were identified PCR screening was repeated on each "lane pool" corresponding to a positive "plate pool" and run out on 1% TAE agarose gel to identify positive "lane pools", and in subsequent screening rounds on single wells and individual colonies to isolate positive clones. Plasmids which contained the gene of interest were analysed by restriction enzyme digest and sequence analysis.

Screening Using Non-Radioactive Colony Hybridisation.

10-fold serial dilutions of the cDNA library were made (1-10⁶) and plated on LB agar supplemented with 500 ml kanamycin to determine the dilution which produced approximately 300-500 colonies per 82 mm petri dish. Transformed bacteria of a suitable dilution were spread on LB agar plates supplemented with 50 µg/ml kanamycin and incubated overnight at 37° C. Nylon membranes (Hybond-N+, Amersham Biosciences) were used to obtain colony lifts and treated according to standard methods for colony hybridisation. Biotin labelled DNA probes were prepared using desaturase gene fragments labelled using dNTPs plus Biotin-dATP and DNA polymerase I Klenow fragment according to NEBlot phototope kit (New England Biolabs). Probes were hybridised to the membranes overnight at temperatures of 65° C. (high stringency) or 55° C. (moderate stringency). The hybridised biotinylated DNA was detected according to the Phototope-Star detection Kit manual (New England Biolabs) following the modification for colony hybridisations detailed in Appendix C. The membrane was exposed to Hyperfilm ECL (Amersham Biosciences) for 1 minute and processed manually according to Amersham Biosciences recommendations. Positively hybridising clones were analysed by restriction enzyme digest and sequence analysis.

Example 8. Yeast Expression Vector Construction and Functional Analysis of Genes Each of the full-length desaturase genes was expressed in *Saccharomyces cerevisiae* for functional characterization using the yeast expression vectors pYES2 or pVT100-U (Vernet, T et al. 1987). Each of the genomic regions containing putative desaturase genes was examined for restriction nuclease recognition sites. Restriction enzymes were chosen that did not cut the genomic regions but would facilitate directional cloning into pYES2 or pVT100-U. Primers were designed (Table 8) to the most 5' and 3' regions of the predicted desaturase genes with restriction sites at the 5' end of each of the primers to allow directional cloning.

DNAs of the yeast vectors were prepared and digested with the corresponding restriction enzymes and then dephosphorylated using Calf Intestinal Alkaline Phosphatase (Roche). After dephosphorylation, the digested vectors were purified using the QIAquick PCR purification kit (QIAgen). Gel extracted desaturase-containing fragments were ligated with digested vector and ligations transformed into *E. coli* DH10B with transformants selected on LB agar plates with 100 μg/ml ampicillin. Clones containing inserts were confirmed by restriction enzyme analysis.

TABLE 8

Primers used for directional cloning into pYES2. Restriction sites are shown in bold face.

| Tribdesat No. | Primer | Oligonucleotide primer sequence |
|---|---|---|
| 1 | Forward | GGATCCATGGCCCCCAACAGCACA (SEQ ID NO: 37) |
| 1 | Reverse | GAATTCTTAATCTCTGCGTGTGCG (SEQ ID NO: 38) |
| 2a | Forward | GGATCCATGTCAACGCTTGAAACA (SEQ ID NO: 39) |
| 2a | Reverse | GAATTCTTATCCTCGATTTCGTTC (SEQ ID NO: 40) |
| 2b | Forward | GGATCCATGTCTAGCGAGCTAGCG (SEQ ID NO: 41) |
| 2b | Reverse | GAATTCTTAATTTTTCGCCTTACA (SEQ ID NO: 42) |
| 2c | Forward | GGATCCATGGAACGTGAAATCGCGTGG (SEQ ID NO: 43) |
| 2c | Reverse | GAATTCTTATCCTGTTTGTGAAGC (SEQ ID NO: 44) |
| 3 | Forward | GGATCCATGTTTTTACGTACAATA (SEQ ID NO: 45) |
| 3 | Reverse | GAATTCTTAATAATCACAATCCCC (SEQ ID NO: 46) |
| 4 | Forward | AAGCTTATGACGGAAGGCAGCGATGAA (SEQ ID NO: 47) |
| 4 | Reverse | GCGGCCGCTCAGTTAAAATCCTCCATTT (SEQ ID NO: 48) |
| 5 | Forward | GGATCCATGCCACCCTATGTGTCC (SEQ ID NO: 49) |
| 5 | Reverse | GCATGCTTAATTAAAATCGTCAGA (SEQ ID NO: 50) |
| 6a | Forward | GGATCCATGACACCAAATGCTTCA (SEQ ID NO: 51) |
| 6a | Reverse | GAATTCCTACGCACTCTTCCTATG (SEQ ID NO: 52) |
| 6b | Forward | GGTACCATGCTAATCTTACTTTCC (SEQ ID NO: 53) |
| 6b | Reverse | CTCGAGCTAATGAAATTTTGAAGG (SEQ ID NO: 54) |
| 7a | Forward | GGATCCATGTTTCAAACACCCATCGTCTGG (SEQ ID NO: 55) |
| 7a | Reverse | CTCGAGTTATTGCCCAGTCCTCAAAACCCGCTT (SEQ ID NO: 56) |
| 7b | Forward | GGATCCATGGTAGATTTGTTTTTG (SEQ ID NO: 57) |
| 7b | Reverse | GAATTCTTATTTTTGCAATTGTTT (SEQ ID NO: 58) |
| 8 | Forward | GGATCCATGGCTCCAAATTCGCTC (SEQ ID NO: 59) |
| 8 | Reverse | GAATTCTTACAGTTCTTTGCTACT (SEQ ID NO: 60) |
| 10 | Forward | GGATCCATGTCGGCCCAGACCATT (SEQ ID NO: 61) |
| 10 | Reverse | GAATTCTTAATCCTCCTTCCTGTT (SEQ ID NO: 62) |
| 11 | Forward | AAGCTTATGGGAGCGCTCAAACAA (SEQ ID NO: 63) |
| 11 | Reverse | GAATTCTTAACCATTTGCCGTAAC (SEQ ID NO: 64) |
| 12 | Forward | GAATTCATGGCTCCTAATTTGCTAGGA (SEQ ID NO: 65) |
| 12 | Reverse | CTCGAGTTAATCAAATTTCTCTCTACT (SEQ ID NO: 66) |

Transformation of Expression Constructs into *Saccharomyces cerevisiae*

Two *S. cerevisiae* host strains were used as recipients for pYES-derived constructs. These were S288C (genotype MATα, SUC2 gal2 mal mel flo1 flo8-1 hap1 (Mortimer and Johnston (1986)) and OLE1 (his3Δ1, leu2Δ0, ura3Δ0, YMR272c::kanMX4) which is mutant for the gene encoding Δ9-desaturase and could be used for complementation analysis. Five *S. cerevisiae* host strains were used as recipients for pVT-100 derived constructs. These were S288C, OLE1, and INVSCi (MATa, his3D1 leu2 trp1-289 ura3-52), YPH499 (MATa, ura3-52 lys2-801_amber ade2-101_ochre trp1-Δ63 his1-Δ200 leu2-M) and ELO-1 (MATa his3 Δ1 leu2Δ0 met15Δ0 ura3Δ0 ΔELO1). These strains were treated the same during transformation except that 17:1 (cis-10-heptadecenoic acid, 1 mM) and tergitol (NP-40; 1%) were added in all media in which *S. cerevisiae* OLE1 was grown and geneticin (200 μg/ml) was added to all media in which ELO-1 was grown.

For transformation, each *S. cerevisiae* strain was streaked onto YPD (20 g/l peptone, 10 g/l yeast extract, 2% glucose) and grown for several days at 30° C. Transformations were performed using the Sigma Yeast Transformation kit according to manufacturer's instructions. Transformants were selected on SCMM-U agar plates (6.7 g/l yeast nitrogen base without amino acids, 1.92 g/l yeast synthetic drop-out media supplement without uracil, 2% glucose and 2% agar) at 30° C. for up to 5 days. A number of transformants were selected for each construct and tested for the presence of plasmid DNA.

Confirmation of Transformants

To confirm the identity of the expression constructs within transformants, DNA was isolated from a loopful of growth using the Y-DER yeast DNA extraction kit from Pierce (Illinois) according to the manufacturer's instructions. The presence of the plasmid was analysed and confirmed by PCR analysis using a gene specific reverse primer and a T7 primer (vector primer). Positive bands were observed and the corresponding transformants were retained for further analysis.

Assessment of OLE1 Complementation

Fifty microlitres of OLE1 transformants grown on SCMM-U containing cis-10-heptadecenoic acid (1 mM) and 1% tergitol was pelleted by centrifugation (13,000 rpm, 3 ses) and resuspended in 50 μl YP (20 g/l peptone, 10 g/l yeast extract). The resuspended mixture was diluted 1:10 and 20 μl of each mixture was spotted onto YP containing 2% galactose plates to induce desaturase gene expression and these were incubated for 3-5 days at 30° C. The presence or absence of growth was noted. Control plates containing cis-10-heptadecenoic acid (1 mM) and 1% tergitol were also used to ensure yeast viability. The results for the OLE1 complementation tests for *Tribolium* and *Chaulioganthus* desaturases were as follows. Positive complementation was observed for Tribdesat2a, Tribdesat5, Tribdesat6a and Tribdesat11, the last one with a lag phase. Possibly weak complementation was observed for Tribdesat2b and Tribdesat8. No complementation was observed for Tribdesat1, Tribdesat2c, Tribdesat4, Tribdesat10, Tribdesat12, CL1 and CL3.

Complementation of the yeast OLE1 phenotype occurs when a heterologously expressed gene expresses a functional Δ9- or Δ11-desaturase and results in the production of palmitoleic, oleic, or cis-11-octadecanoic fatty acids. Therefore, it was concluded that Tribdesat2a, Tribdesat5, Tribdesat6a and Tribdesat11 were desaturases able to desaturate the native lipids of OLE1 yeast cells to produce one of the complementing fatty acids and therefore were likely to be Δ9 desaturases active on C16:0 or C18:0, or Δ11 desaturases active on C18:0, whereas Tribdesat1, Tribdesat2c, Tribdesat4, Tribdesat10, Tribdesat12, CL1 and CL3 were unlikely to encode one of these activities and therefore likely to encode a different desaturase.

Growth of Transformed *S. Cerevisiae* for Substrate Feeding Experiments

Yeast transformants derived from stains S288C or OLE1 were inoculated into 25 ml of synthetic minimal defined medium for yeast without Uracil (SCMM-U medium) containing 2% glucose and additionally 0.5 mM cis-11-heptadecenoic acid for the OLE1 strain. This inoculation culture was grown for 24-48 hr at 30° C. with shaking. The OD600 of the culture was determined. From this, the amount of culture necessary to obtain an OD600 of 0.4 in 50 ml of induction medium was calculated. This amount of inoculation culture was removed and the cells pelleted at 1500×g for 5 minutes at 4° C. The cells were then resuspended in 10 ml of induction medium, SCMM-U containing 2% galactose, 1% raffinose and 0.5 mM fatty acid substrate (added in ethanol/20% tergitol) and additionally 0.5 mM cis-11-heptadecenoic acid for OLE1 derived transformants. Each culture was grown for 24-48 h at 30° C. with shaking. Either 2 ml or the total culture was then used for analysis of fatty acids after harvesting cells by centrifugation, storage at −20° C. if needed.

Extraction of Lipids from Transformed *S. Cerevisiae* and Analysis

The yeast cells from fatty acid feeding experiments were washed in 1% tergitol in water and pelleted at 1500×g for 5 minutes at 4° C. Cell pellets (200-500 mg) were then resuspended in water, transferred to glass test tubes and the cells again pelleted. Water was removed from the cell pellets in a Savant SpeedVac Plus SC110A concentrator/dryer. Each pellet was used either used directly or lipids were extracted with solvent as described below.

Lipids were extracted based on a Modified Folch Method (Protocol 7, pp 22-24, Lipid Analysis, Hamilton and Hamilton, 1992). Lipids were extracted with 2 ml chloroform/methanol (2:1), and 0.5 ml of a saline solution, 0.9% w/v NaCl in water, was added. This was mixed thoroughly by vortexing. The layers were then allowed to separate; when a large amount of cell debris was present the samples were centrifuged at 2500×g for 5 minutes. The top aqueous layer was removed and discarded. The bottom solvent layer was removed to a clean glass test tube. This was then dried down under nitrogen at 30° C.

Lipids were then derivatised prior to analysis by two different methylation methods. The first was the basic methylation of incorporated fatty acids, i.e. those found in triacyl glycerides or phospholipids, not free fatty acids, based on the method of Christie (2003). The lipid sample was first dissolved in 0.5 ml hexane. Methyl acetate, 60 μl, was added, followed by 50 nl sodium methoxide at 0.5 M in methanol. The sealed test tube was then mixed thoroughly and placed in a heating block at 50° C. for 10 minutes. After being allowed to cool for 5 minutes, a drop of acetic acid was added. The sample was dried in a gentle stream of nitrogen at 30° C., dissolved in 200 μl hexane and transferred to a vial prior to GC analysis.

The second method was an acidic methylation of all free and incorporated fatty acids, based on the method of Lewis et al. (2000). A methanolic solution, 2 ml of methanol/hydrochloric acid/chloroform (10:1:1), was added to the dried yeast pellet or extracted lipid sample. The sealed test tube was mixed thoroughly and placed in a heating block at 90° C. for 60 minutes. After being allowed to cool for 10 minutes, 1 ml of 0.9% saline (NaCl in water) was added. The methylated fatty acids were then extracted with 0.3 ml hexane. The hexane layer was transferred to a vial prior to analysis.

These fatty acid methyl ester (FAME) samples were analysed by GC and GCMS. GC analysis was carried out with a Varian 3800 gas chromatograph fitted with a flame ionisation detector (FID) and a BPX70 capillary column (length 30m, i.d. 0.32 mm, film thickness 0.25 µm). Injections were made in the split mode using helium as the carrier gas and an initial column temperature of 100° C. The temperature was raised at 3° C./minute until 150° C., then raised at 5° C./minute until 170° C., held for 5 minutes, then raised at 50° C./minute until 255° C. GC/MS analysis was carried out under similar chromatography conditions but with an initial column temperature of 60° C., raised at 20° C./minute until 170° C., held for 5 minutes, then raised at 50° C./minute until 255° C. Detection was carried out using either a TEC PolarisQ Ion Trap or a Varian 1200 Single Quadrupole mass spectrometer. Mass spectra were acquired under positive electron impact in full scan mode between 50-400 amu at the rate of 2 scans per sec. The mass spectra corresponding to each peak in the chromatogram was automatically compared with spectra in the computerised NIST library. Test spectra that matched library spectra with a high degree of accuracy and eluted at the same time as an authentic standard or eluted at a plausible retention time, were tentatively identified. Confirmation of the identity of a fatty acid was achieved by the conversion of the fatty acid to its dimethyloxazoline (DMOX) derivative using the method of Yu et al. (1988) and comparison with DMOX mass spectra described in Dobson and Christie (2002) and references within.

Results of Functional Analysis in Yeast.

From the experiments carried out as described above and summarised in Table 10 (below), it was concluded as follows:

Tribdesat2a had Δ9 desaturase activity on saturated fatty acid carbon chain length from C10:0 to C16:0 when these fatty acids were fed to the yeast transformants. Activity was greatest on 14:0, but 15:0 and 16:0 were also efficient substrates. It had no detectable desaturase activity on 18:0, 20:0 or even longer saturated fatty acids in the yeast cells. The protein had a predicted size of 320 amino acids and included the 8 conserved desaturase motifs and three His boxes (Table 3). On the basis of the sequence homology with known acyl-CoA desaturases, this enzyme was presumed to be acting on the acyl-CoA substrate. This enzyme was therefore characterised as a myristoyl-CoA Δ9 desaturase.

Tribdesat2b and Tribdesat2c were closely related proteins, having 64% amino acid sequence identity based on global alignment using BLOSUM62, which catalysed production of 5-hexadecenoic and 5-octadecenoic acids from palmitic acid and stearic acid, respectively. They were therefore characterised as Δ5 desaturases acting on the saturated substrates C16:0 and C18:0. The efficiency of conversion in yeast cells of C18:0 to C18:1$^{\Delta 5}$ was more than twice as efficient as the conversion of C16:0 to C16:1$^{\Delta 5}$ (Table 9). The enzymes were able to convert at least 8.0% of the substrate to the product in each case, to at least 40% for Tribdesat2b on C18:0. The enzymes did not detectably desaturate substrates of C14 or shorter when fed to the yeast cells, including C14:0 or C14:1$^{\Delta 9}$, or the substrates of C20 or longer including C20:0 or C20:1$^{\Delta 13}$. Furthermore, the enzymes did not desaturate monounsaturated or polyunsaturated fatty acids including C16:1Δ9, C18:1Δ9, C18:2 or C18:3. The proteins included the 8 conserved desaturase motifs and three His boxes (Table 3) and showed sequence homology with known acyl-CoA desaturases. They were therefore characterised as stearoyl-CoA Δ5 desaturases. They also have palmitoyl-CoA Δ5 desaturase activity.

TABLE 9

Fatty acid composition (% total fatty acids) of yeast cells expressing Tribdesat 2b, or empty pYes vector, supplied with 0.5 mM 18:0.

| Beetle desaturase | Fatty acid composition (% total fatty acids) | | | | | | | | |
|---|---|---|---|---|---|---|---|---|---|
|  | 12:0 | 14:0 | 15:0 | 16:0 | 16:1Δ5 | 17:0 | 17:1 | 18:0 | 18:1Δ5 |
| TD2b + 18:0 | 2.4 | 0.7 | 0.5 | 24.3 | 3.2 | 0.2 | 62.4 | 3.2 | 3.0 |
| pYes empty + 18:0 | 1.6 | 0.4 | 0.4 | 22.7 | 0 | 0.4 | 65.7 | 8.9 | 0 |

Cahoon et al. (2000) isolated a gene from *Limnanthes* (meadowfoam) which encoded a Δ5 desaturase which was more active on C20:0 than C18:0 or C16:0 and is therefore was not a stearoyl-CoA Δ5 desaturase as defined herein. Sayanova et al. (2007) cloned two genes encoding Δ5 desaturases active on acyl-CoA substrates from *Anemone leveillei* seeds. The desaturase AL21 was active on both saturated and unsaturated substrates, C16:0, C18:0 and C20:2, while AL10 was active only on C20:2, n-6. However, AL21 was more active on the unsaturated substrate than the saturated substrate so it would not be considered as a stearoyl-CoA Δ5 desaturase as defined herein. The degree of identity in amino acid sequences when the proteins were compared over the entire sequences were: between AL21 and Tribdesat2b, 25%; AL21 and Tribdesat2b, 27%; AL10 and Tribdesat2b, 24%; AL10 and Trib2c, 28%. Therefore, it was concluded that there was insignificant or little homology between the plant acyl-CoA dependent desaturases and the insect ones.

Tribdesat5 and 6a showed activity in yeast cells as Δ9 desaturases that acted primarily and very efficiently on stearic acid to produce oleic acid. They also had some activity on palmitic acid to produce palmitoleic acid. The enzymes did not detectably desaturate substrates of C14 or shorter when fed to the yeast cells, including C14:0 or C14:1$^{\Delta 9}$, or the substrates of C20 or longer including C20:0. They were therefore characterised as stearoyl-CoA Δ9 desaturases.

Tribdesat8 was able to desaturate palmitic acid to produce palmitoleic acid, so it was considered to be a Δ9 desaturase. It did not have detectable desaturase activity in the yeast cells on C14 or shorter substrates, or on C18:0 or longer saturated substrates, or on monounsaturated or polyunsaturated substrates including C16:1$^{69}$, C18:1$^{\Delta 9}$, C18:2 or C18:3. It therefore appeared to be specific for palmitic acid. The protein had a predicted size of 374 amino acids and included the 8 conserved desaturase motifs and three His boxes (Table 3). On the basis of the sequence homology with known acyl-CoA desaturases, this enzyme was presumed to be acting on the acyl-CoA substrate. This enzyme was therefore characterised as a palmitoyl-CoA Δ9 desaturase.

Tribdesat10 showed Δ12 desaturase activity on palmitoleic and oleic acids resulting in C16:2$^{\Delta 9, \Delta 12}$ and C18:2$^{\Delta 9, \Delta 12}$ (LA), respectively. Conversion of oleic acid substrate (at least 30% converted) was about twice as efficient in yeast cells compared to conversion of palmitoleic acid. There was no detectable activity on C16:0, C18:0 or longer saturated substrates, or C14 or shorter substrates including C14:0$^{\Delta 9}$, so the enzyme appeared to be specific as a Δ12 desaturase acting on Δ9-mono-unsaturated substrates of C18 and C16 length joined to CoA. The protein had a predicted size of 366 amino acids and included the 8 conserved desaturase motifs and three His boxes (Table 3). On the basis of the sequence homology with known acyl-CoA desaturases, this enzyme was presumed to be acting on acyl-CoA substrates. This enzyme was therefore characterised as an oleoyl-CoA Δ2 desaturase. It also showed palmitoleoyl-CoA Δ2 desaturase activity. It was believed this is the first gene to be characterised encoding such an enzyme.

Tribdesat11 showed Δ9 desaturase activity on saturated substrates having a chain length from C14:0 to C24:0, with the greatest efficiency of conversion observed for C22:0 (known as behenic or docosanoic acid) and C24:0 (known as lignoceric or teracosanoic acid). Therefore, this enzyme was considered to be a lignoceroyl-CoA Δ9 desaturase, although it also has behenoyl-CoA Δ9 desaturase activity.

CL1 showed Δ12 desaturase activity on palmitoleic and oleic acids resulting in C16:2$^{\Delta 9, \Delta 12}$ and LA, respectively, the same spectrum of activity as Tribdesat10 although the activity was less efficient than for Tribdesat10.

CL3 showed efficient desaturation activity on C14:0 to produce C14:1$^{\Delta 9}$. The enzyme did not have detectable activity for C12:0 or C16:0 and therefore appeared to be a specific myristoyl-CoA Δ9 desaturase. It did not have activity on mono-unsaturated substrates such as C12:1 Δ5 or C20:1. On the basis of the sequence homology with known acyl-CoA desaturases, this enzyme was presumed to be acting on the acyl-CoA substrate. This enzyme was therefore characterised as a myristoyl-CoA Δ9 desaturase.

TABLE 10

| Desaturase | Substrates (n.d.—no product detected) | | | | | | | |
|---|---|---|---|---|---|---|---|---|
| | 10:0 | 12:0 | 12:1Δ5 | 14:0 | 14:1Δ9 | 15:0 | 16:0 | 16:1Δ9 |
| Tribdesat 2a | 10:1Δ9 0.5% | 12:1Δ9 1.8% | — | 14:1Δ9 48.6% | — | 15:1Δ9 28.0% | 16:1Δ9 27.8% | — |
| Tribdesat 2b | n.d. | n.d. | — | n.d. | n.d. | — | 16:1Δ5 17.0% | n.d. |
| Tribdesat 2c | n.d. | n.d. | — | n.d. | n.d. | — | 16:1Δ5 8.0% | n.d. |
| Tribdesat 4 | n.d. | n.d. | — | n.d. | n.d. | — | n.d. | n.d. |
| Tribdesat 5 | n.d. | n.d. | — | n.d. | n.d. | — | 16:1Δ9 11.8% | n.d. |
| Tribdesat 6a | n.d. | n.d. | — | n.d. | n.d. | — | 16:1Δ9 8.9% | n.d. |
| Tribdesat 8 | n.d. | n.d. | — | n.d. | n.d. | — | 16:1Δ9 5.0% | n.d. |
| Tribdesat 10 | n.d. | n.d. | — | n.d. | n.d. | — | n.d. | 16:2Δ9 Δ12 15.9% |
| Tribdesat 11 | n.d. | n.d. | — | 14:1Δ9 12.0% | — | n.d. | 16:1Δ9 8.3% | — |
| Tribdesat 12 | n.d. | n.d. | — | n.d. | n.d. | — | n.d. | n.d. |
| CL1 | n.d. | n.d. | n.d. | n.d. | n.d. | — | n.d. | 16:2Δ9 Δ12 0.1% |
| CL3 | n.d. | n.d. | n.d. | 14:1Δ9 61.2% | n.d. | — | n.d. | n.d. |

| Desaturase | Substrates (n.d.—no product detected) | | | | | | | |
|---|---|---|---|---|---|---|---|---|
| | 18:0 | 18:1Δ9 | 18:2 | 18:3 | 20:0 | 20:1Δ13 | 22:0 | 24:0 |
| Tribdesat 2a | n.d. | — | | — | n.d. | — | n.d. | n.d. |
| Tribdesat 2b | 18:1Δ5 43.3% | n.d. | n.d. | n.d. | n.d. | — | n.d. | n.d. |
| Tribdesat 2c | 18:1Δ5 19.0% | n.d. | n.d. | — | n.d. | — | n.d. | n.d. |
| Tribdesat 4 | n.d. | n.d. | n.d. | n.d. | n.d. | — | n.d. | n.d. |
| Tribdesat 5 | 18:1Δ9 88.7% | n.d. | n.d. | — | n.d. | — | n.d. | n.d. |
| Tribdesat 6a | 18:1Δ9 79.2% | n.d. | n.d. | — | — | — | n.d. | n.d. |
| Tribdesat 8 | n.d. | n.d. | n.d. | — | — | — | n.d. | n.d. |
| Tribdesat 10 | n.d. | 18:2Δ9 Δ12 30.5% | n.d. | — | n.d. | — | n.d. | n.d. |
| Tribdesat 11 | 18:1Δ9 35.6% | — | n.d. | — | 20:1Δ9 14.7% | — | 22:1Δ9 50.3% | 24:1Δ9 58.3% |
| Tribdesat 12 | n.d. | n.d. | n.d. | n.d. | n.d. | — | n.d. | n.d. |
| CL1 | n.d. | 18:2Δ9 Δ12 1.5% | n.d. | n.d. | n.d. | — | n.d. | n.d. |
| CL3 | n.d. | n.d. | — | — | n.d. | — | n.d. | n.d. |

Example 9. Cloning of Desaturase Genes into Gateway Entry Vector pENTR11

To construct the functional genes or genes to be tested in a Gateway entry vector, the pGem-T-Easy constructs containing full-length gene sequences were digested with restriction enzymes to excise the inserts. These were separated on a 1% agarose gel and the DNA of the approximately 1 kb fragments purified using the QIAquick Gel Extraction kit (Qiagen) according to the manufacturer's instructions. The Gateway entry vector pENTR 11 (Invitrogen) was prepared and digested with the required restriction enzymes and dephosphorylated using Calf Intestine Alkaline Phosphatase (Roche). Gene fragments were ligated with the vector and transformed into E. coli strain JM109. Transformants were selected on LB agar plates containing 50 µg/ml kanamycin. Clones containing inserts were confirmed by restriction enzyme and sequence analysis.

Cloning of Desaturase Genes into Gateway Destination Vectors to Create Expression Clones.

Two expression system, SF9 insect cells and *Arabidopsis*, were selected and Gateway expression vectors chosen for each. For SF9 insect cells, pDEST8 was chosen and selection for DH10Bac transformants carried out in LB supplemented with kanamycin (50 µg/ml), gentamicin (7 µg/ml) and tetracycline (10 µg/ml), Bluo-gal (100 µg/ml) and IPTG (40 µg/ml). For *Arabidopsis* transformation, binary vector pXZP391 (CSIRO Plant Industry) was chosen and selection for transformants carried out in LB supplemented with spectinomycin (50 µg/ml).

pENTR11 clones containing the gene inserts and appropriate pDEST vectors were prepared and under-went an LR recombination reaction according to manufacturers instructions (Gateway LR clonase enzyme mix, Invitrogen). The resultant recombination mixtures were transformed into E. coli strain IM109 for pXZP391 or DH10Bac (Invitrogen) for pDEST8. Transformants containing correct inserts were confirmed by restriction enzyme analysis and sequence analysis using vector specific primers.

Example 10. Recombinant Baculovirus Production of Insect Desaturases or Acetylenases The Tribdesat2b and CL3 genes were cloned into the pDest8 vector (Invitrogen), using Gateway recombination as above. Competent DH10Bac cells (Invitrogen) were transformed with the pDest8 clones by heat shock method. Transformants were selected on LB agar containing kanamycin, tetracycline and gentamycin (50 µg/mL, 10 µg/mL and 7 µg/mL respectively) and IPTG and Xgal at the appropriate concentrations, and purified by re-streaking on this medium. Once the recombination events had taken place in DH10Bac, the recombinant bacmids (now called pFastbac) were identified using M13 forward and reverse primers to colony screen the 2b and CL2 inserts in pFastbac in DH10Bac cells. Positive clones produced a band of approximately 3 kb. Clones were picked for downstream applications that did not have any evidence of empty vector contamination which could be observed as a 300 bp product.

Transformants containing pFastbac plasmids having the 2b and CL2 inserts were grown overnight in LB medium containing the antibiotics. A modified alkaline lysis plasmid isolation protocol was used according to the manufacturer's instructions in the Bac-to-Bac Expression System manual. Isolated DNA was dissolved in 40l of 1×TE buffer pH 8.0 and quantitated using the Nanodrop spectrophotometer and stored at 4° C.

Transfecting Insect Cells

Sf9 (*Spodoptera frugiperda* ovary cell line) cells were seeded in a 6 well tissue culture plate at a rate of $9 \times 10^5$ cells per well, in 2 mL of SF900II serum free medium (Invitrogen). The cells were allowed to adhere to the well surface for 2 hours at 27° C. For each transfection, 1 µg of purified bacmid DNA was diluted in 100 uL of unsupplemented Grace's Medium (Invitrogen), in polystyrene tubes. 6 µL of Cellfectin® Reagent (Invitrogen) was diluted in 100 µL of unsupplemented Grace's Medium in polystyrene tubes. The DNA and Cellfectin® Reagent were then mixed together and incubated at RT for 30 minutes. While DNA:lipid complexes were incubating, the cells were washed once with 2 mL of unsupplemented Grace's Medium and the medium was then removed. 0.8 mL of unsupplemented Grace's Medium was added to the DNA:lipid complex, mixed and then added to the washed SF9 cells. The transfection was allowed to proceed at 27° C. for 5 hours. The DNA:lipid complexes were removed from the cells and 2 mL of SF900II were added. Cells were incubated at 27° C. until signs of infection were obvious. Once the cells appeared infected, the virus was harvested by centrifuging the cell culture medium at 1 Krpm for 5 minutes at 20° C. The clarified cell culture medium was transferred to tubes and stored at 4° C. This was called P1 viral stock.

Amplifying the Baculovirus Stocks

Sf9 cells were used to seed 25 cm² flasks at a rate of $1 \times 10^6$ cells/mL in 5 mL of medium. The cells were infected with P1 viral stock at a multiplicity of infection (MOI) of 0.1 virus particles per cell, which was estimated to be $5 \times 10^6$ cells/mL. After 48 hours at 27° C., the cells were showing signs of infection and the cell culture medium was harvested as outlined above. This was called P2 viral stock. The P2 stock was then used to produce a P3 stock. 75 cm² flasks were seeded at a rate of $1 \times 10^6$ cells/mL in 15 mL SF900II medium, and infected at a MOI of 0.1 virus particles per cell, which was estimated to be $5 \times 10^6$ cells/mL. After 48 hours at 27° C., the cells were showing signs of infection and the cell culture medium was harvested as outlined above. This was called P3 viral stock.

To determine the exact titre of each P3 stock, a $TCID_{50}$ (Tissue Culture Infectious dose) was performed. A 96 well tray was seeded with $3 \times 10^3$ cells per well. Cells were incubated at 27° C. overnight. 10-fold dilutions of the virus were prepared to $10^{-8}$. 50 µL of dilutions $10^{-3}$-$10^{-8}$ were added to 8 wells each. The $TCID_{50}$ was then incubated for 7 days at 27° C. The wells were scored positive or negative for virus infection. Once the viruses were titrated, infections of SF9 cells with known multiplicity of infections (MOI) could proceed. Infested cells were removed and dried under vacuum.

Methyl esters of fatty acids of insect cells infected with the construct expressing Tribdesat2b were obtained using the direct acidic methanol reagent as previously described and analysed by GC/MS. The GC/MS trace and spectrum showed C16:1Δ5 and C18:1 Δ5 production by SF9 expressing Tribdesat2b, as compared to the SF9 control. The efficiency of conversion of C16:0 to C16:1d5 in the insect cells transduced with the construct was 16.9% and the efficiency of conversion of C18:0 to C18:1d5 was 29.7%. These data therefore confirmed the data obtained from yeast cells expressing Tribdesat2b and it was concluded that this gene encoded a Δ5-desaturase active on C16:0 and C18:0 substrates, with greater activity on the latter. It therefore almost certainly encoded a Stearoyl-CoA Δ5-desaturase, which activity has not previously been reported for a cloned gene. The other desaturases are likewise expected to show activity in insect cells.

Example 11. Expression of *Tribolium* and *Chauliognathus* Genes in Plants

The *Tribolium* Tribdesat10 and 2b genes were cloned into pENTR11 as described above and then recombined into plant expression vector pXZP391 which provides for expression of the coding region insert under the control of a seed-specific napin promoter (Fp1) isolated from *Brassica napus* (Stalberg et al., 1993). The expression plasmid was transformed into *Agrobacterium tumefaciens* AGL1, and used for plant transformation into the *Arabidopsis thaliana* fad2/fae1 double mutant which lacks Δ2-desaturase activity, by in planta method. Seeds of spray-inoculated plants were harvested 3-4 weeks later and plated onto selective media. T1 transformed plants were identified on MS media containing 40 mg/L kanamycin and 100 mg/L timentin, and transferred into pots in the glasshouse. T2 seeds from each T1 plant were analysed for fatty acid composition by gas chromatography. The data shown in FIG. 6 demonstrated the M2 desaturase activity of Tribdesat10 in *Arabidopsis*, as LA was produced from oleic acid in the fad2/fae1 mutant plant.

Expression of Transgenes in Tobacco Calli and Plants

The Tribdesat2b, CL1 and CL2 coding regions were cloned in the 'sense' orientation into the plant expression vector pVEC8 (Wang et al., 1997) under the control of the regulatory sequences CaMV 35S promoter and octopine synthase transcription termination/polyadenylation signal (Gleave, 1992), providing strong constitutive expression of the transgene in most plant tissues. The transgene was introduced into tobacco by *Agrobacterium*-mediated transformation of leaf tissue (Horsch et al., 1985) with selection of the transgenic cell lines on hygromycin-containing media. Transgenic plant cells were selected based on the resistance to hygromycin, as conferred by a hpt resistance marker gene in the pVEC8 derived vector. Transformed tobacco lines were cultured to produce either calli or regenerated to produce whole plants, depending on the phytohormone regime in the selection and growth media (Murashige and Skoog, 1962; Horsch et al., 1985). Undifferentiated transgenic tobacco calli were produced by selection on calli-inducing phytohormones (0.5 mg/L indole acetic acid (IAA) and 0.05 mg/L kinetin) and calli were maintained on agar plates. Differentiated tobacco plants were produced by first selecting transgenic material on shoot-inducing media by the addition of shoot-inducing phytohormones (100 µg/L N-6-benzyladinine (BAP) and 500 ng/L L IAA). After 3 weeks of growth on this media individual tobacco apices were cut from the leaf discs and re-plated onto root-inducing media containing root-inducing phytohormones (50 ng/L IAA). A further 3 weeks are required for the formation of roots. Transgenic material, either calli or whole plants, were selected for analysis as required.

The Tribdesat2b gene was also recombined using LR clonase into plant expression vector pXZP393 (CSIRO Plant Industry) under control of the constitutive CaMV 35S promoter. The resulting expression plasmid pXZP384 was transformed into AGL1, and used for plant transformation into tobacco leaves as described above. Fatty acid composition of transgenic tobacco leaves and seed will be analysed by GC and GC-MS to shown modification of fatty acid composition by addition of the new desaturase activity.

Example 12. Cloning of Desaturase Genes from *Acheta domesticus*

Some insects are thought to possess Δ12-desaturase activity but as yet no gene encoding such an enzyme has been isolated despite extensive effort over 20 years. The reasons for this failure were unknown until the present work. One insect known to possess Δ12-desaturase activity is *Acheta domesticus*, the common cricket. In an initial attempt to clone an *A. domesticus* Δ12-desaturase gene, a set of degenerate primers AdD12Des-F1 (5'-TTGTTCTGTGTGGGT-CAYGAYTGYGGWCA (SEQ ID NO: 127)) and AdD12Des-R1 (5'-GTGATGGGCGACGTGACYGTYKG-TRAT (SEQ ID NO: 128) were designed based on the conserved histidine Box I and histidine Box III regions of *A. thaliana* Δ12-desaturase FAD2 (P46313), *Caenorhabditis elegans* Δ12-desaturase FAT-2 (AAF63745) and Δ15-desaturase FAT-1 (L41807), corresponding to LFCVCHDCGH (amino acid residues 88-97) and ITNGHVAHH (amino acid residues 291-299) of FAT-2. However, RT-PCR reactions using *A. domesticus* fat body total RNA with this set of primers failed to amplify any specific product despite repeated attempts and varied conditions, suggesting that the *A. domesticus* gene(s) encoding Δ12-desaturase might share low homology to the plant or nematode Δ12-desaturase genes.

A different approach was considered to clone the *A. domesticus* Δ12-desaturase gene. Based on the amino acid sequence homology shared among 55 insect fatty acid acyl-CoA Δ9-, Δ10-, Δ11- and Δ4-desaturases from species including *Argyrotaenia velutinana* (AAF44709), *Bombyx mori* (BAD18122, AAF80355), *Epiphyas postvittana* (AAK94070), *Helicoverpa assult* (AAM28484, AAM28483), *H. zea* (AAF81787, AAF81788), *Musca domestica* (AAN31393), *Ostrinia furnacalis* (AAL27034, AAL32060, AAL35746), *O. nubilalis* (AAF44710, AAL35330, AAL35331), *Trichoplusia ni* (AAB92583, O44390, AAD03775) etc, degenerate primers (AdD12Des-F2 5'-TTCTTCTTCKCNCAYKTHGGNTGG (SEQ ID NO: 129) and AdD12Des-R2 5'-TGRTGGTAGTTGTGVHANC-CCTC (SEQ ID NO: 130)) were designed that targeted two conserved regions of these desaturases (FFFS/AHI/VGW (SEQ ID NO: 131) and EGY/W/FHNYHH (SEQ ID NO: 132), corresponding to amino acid residues 145-152 and 263-270 of *A. velutinana* Δ9-desaturase AAF44709) in an attempt to clone an insect Δ12-desaturase gene. Surprisingly, RT-PCR from *A. domesticus* fat body total RNA amplified a divergent 360 bp desaturase-like sequence, along with another desaturase gene fragment identical to part of the known *A. domesticus* Δ9-desaturase (AdD9Des, AF338466). Rapid amplification of cDNA ends using GeneRacer Kit (Invitrogen) and sequences internal to the 360 bp fragment resulted in a 1597 bp cDNA sequence that was designated AdD12Des (SEQ ID NO: 133) coding for a peptide of 357 amino acid residues (SEQ ID NO: 134).

The cDNA sequences of AdD9Des, AdD12Des and Tribdesat10 were each cloned in yeast expression vector pYES2 (Invitrogen), generating plasmids pXZP277, pXZP282 and pYES2-Trib10 respectively. Plasmids pYES2, pXZP277, pXZP282 and pYES2-Trib10 were transformed into *Saccharomyces cerevisiae* cell of the strain ole1 which contains a Δ9-desaturase knock-out mutation, (Stukey et al., 1990) in order to test for complementation of this mutation and therefore indicate Δ9-desaturase activity. Yeast ole1 cells needed to be supplied with an unsaturated fatty acid such as $C16:1^{\Delta 9}$ to maintain growth, unless a Δ9-desaturase is expressed within the cells, which was the basis of the complementation test. Transformants in ole1 cells were selected on drop-out media (SD-Ura) agar plate supplied with 0.5 mM $C16:1^{\Delta 9}$ and 1% NP-40. Yeast ole1 transformants carrying the above mentioned plasmids were first grown in YPD media (1% yeast extract, 2% peptone, 2% dextrose), supplied with 0.5 mM $C16:1^{\Delta 9}$ and 1% NP-40 at 30° C. until $OD_{600}$ around 1.0. The samples were then adjusted to an $OD_{600}$ of 1.0, diluted in 1:10 series and 1 μL aliquots of each dilution spotted onto YPG agar plates, which was the same as YPD media except that it contained 2% galactose instead of dextrose to induce the gene expression from the pYES2 derived vectors. The growth of cells was observed after 2 days at 30° C. Expression of *A. domesticus* Δ9-desaturase in ole1 cells clearly complemented the ole1 phenotype, while expression of *A. domesticus* AdD12Des did not complement, indicating that it was not functioning as a Δ9-desaturase in yeast cells. The ole1 cells expressing the *T. castaneum* Δ12-desaturase were shown to grow on YPG plate only in the presence of added C17:1. These data established that the cloned AdD12Des or Tribdesat10 genes did not encode another member of a Δ9-desaturase family.

These expression plasmids were also transformed into *Saccharomyces cerevisiae* S288C cells, which is a common laboratory yeast strain. Fatty acid methyl esters (FAME) extraction from yeast cells and analysis were performed as described by Zhou, et al. (2006). Expression of AdD12Des in *S. cerevisiae* produced new diene fatty acids C18:2 and C16:2 from C18:1 and C16:1, respectively, as demonstrated by gas chromatography (GC) of yeast fatty acid methyl esters (FIG. 7A) when compared to cells with pYES2 vector only (FIG. 7B), confirmed by the identical retention time and mass spectrum as the pure $C18:2^{\Delta 9,12}$ standard in the first instance. The double bond positions of the C16:2 and C18:2 products were confirmed by GC-mass spectrometry of the 4,4-dimethyloxazoline derivative (Fay and Richli, 1991) to be at the Δ9 and Δ12 positions by the gap of 12 atomic mass units between m/z 196 and 208, 236 and 248 (FIG. 2C). The production of these dienes demonstrated that AdD12Des and Tribdesat10 encoded Δ12-desaturases acting on $C16:1^{\Delta 9}$ or $C18:1^{\Delta 9}$.

When expressing in cells of yeast strain ole1, *T. castaneum* Δ12-desaturase produced C18:2 from C18:1 at conversion rate of 30.5%, and C16:2 from C16:1 at the conversion rate of 16.0% (Table 11), indicating a preference of the enzyme for the C18 substrate over the C16 substrate. There was a concomitant decrease in the level of substrate fatty acid in the cells.

TABLE 11

Fatty acid composition (% total fatty acids) of yeast ole1 cells expressing *Tribolium castaneum* desaturase Tribdesat 10 in pYES2 when fed C16:1 or C18:1 substrates, compared to an empty pYES2 vector control.

| | Fatty acid composition (% total fatty acids) | | | | | | | | | | |
|---|---|---|---|---|---|---|---|---|---|---|---|
| | 12:0 | 14:0 | 15:0 | 16:0 | 16:1 | 17:0 | 16:2 | 17:1 | 18:0 | 18:1 | 18:2 |
| pYES2 + C18:1 | 3.0 | 2.2 | 0.7 | 41.7 | 0.2 | 0.6 | 0 | 10.9 | 16.9 | 23.8 | 0 |
| Tribdesat10 + C18:1 | 3.3 | 2.3 | 1.0 | 43.2 | 0.1 | 0.8 | 0 | 8.6 | 18.0 | 15.7 | 6.9 |
| pYES2 + C16:1 | 3.9 | 2.9 | 0.7 | 42.5 | 20.6 | 0.5 | 0 | 9.1 | 19.4 | 0.4 | 0 |
| Tribdesat10 + C16:1 | 4.2 | 3.1 | 0.8 | 43.6 | 14.7 | 0.6 | 2.8 | 7.8 | 21.9 | 0.4 | 0 |

The *A. domesticus* and *T. castaneum* Δ12-desaturase protein coding regions were also cloned into a plant expression vector to generate plasmid pXZP375 and pXZP376 respectively, under control of the seed specific promoter Fp1 (Stalberg et al., 1993). These expression plasmids were introduced into tissues of an *A. thaliana* fad2/fae1 double mutant (Smith et al., 2003) to produce transformed plants via *Agrobacterium tumefaciens* as described by Zhou et al., (2006). GC analysis of seed FAMEs was essentially as described above. Shown in Table 12 as an example, six transgenic lines transformed with the AdD12Des gene encoding the *A. domesticus* Δ12-desaturase efficiently produced C18:2, with levels obtained of at least 42% of the total fatty acid in the seedoil, and at least 20% C18:3, both of which were produced in the seed from C18:1. Since the *A. thaliana* fad2/fae1 double mutant still had the wild-type Δ15-desaturase (FAD3), this enzyme was presumed to desaturate C18:2, when available, into C18:3. Therefore, the C18:3 produced in these transgenic lines was also a product of the conversion of C18:1 to C18:2 by the *A. domesticus* Δ12-desaturase, and represented *A. domesticus* Δ12-desaturase product. This result confirmed the Δ12-desaturase activity of the cloned gene, and represented the first demonstration of a recombinant insect Δ12-desaturase in transformed cells.

TABLE 12

Fatty acid composition (% total fatty acids) of transgenic *Arabidopsis* seeds expressing *A. domesticus* AdD12Des in fad2/fae1 double mutant.

| Sample | C16:0 | C16:1 | C18:0 | C18:1 | C18:2 | C18:3 | C20:0 | C20:1 |
|---|---|---|---|---|---|---|---|---|
| fad2/fae1* | 4.9 | 0.5 | 2.09 | 90.21 | 0.2 | 2.06 | 0.0 | 0.35 |
| EY1 | 6.33 | 0.0 | 2.46 | 26.61 | 40.07 | 24.53 | Trace | Trace |
| EY6 | 5.27 | | 2.48 | 85.93 | 3.74 | 2.47 | 0.11 | Trace |
| EY7 | 2.9 | 0.0 | | 44.7 | 29.1 | 23.3 | 0.0 | |
| EY13 | 2.3 | 0.0 | | 43.1 | 31.0 | 23.6 | 0.0 | |
| EY15 | 3.9 | 0.0 | | 25.4 | 46.2 | 24.6 | 0.0 | |
| EY20 | 4.16 | 0.0 | 0.05 | 55.81 | 19.20 | 21.11 | Trace | Trace |

*fad2/fae1 corresponds to the control (untransformed) plants

Phylogenetic analysis of representative acyl-CoA or acyl-lipid desaturase protein sequences showed that the amino acid sequences of AdD12Des and Tribdesat10 clustered with other acyl-CoA desaturases (right hand side of FIG. 9; FIG. 10). The accession numbers and species for insect desaturases used in the analysis were: AdD9, *Acheta domesticus* AAK25796; AdD12, *A. domesticus* SEQ ID NO: (SEQ ID NO: 135); BmD10-11, *Bombyx mori* AAF80355; BmD11, *B. mori* BAD18122; DmD9, *Drosophila melanogaster* CAB69054; MdD9, *Musca domesticus* AAN31393; OnD9, *Ostrinia nubilalis* AAF44710; OnD11, *O. nubilalis* AAL35331; OnD14, *O. nubilalis* AAL35330; PoD9, *Planotortrix octo* AAF73073; PoD10, *P. octo* AAG54077; TcD9A, *Tribolium castaneum* XP_969607; TcD9B, *T. castaneum* XP_966962; TcD12, *T. castaneum* Tribdesat10 (SEQ ID NO: 28); TnD9, *Trichoplusia ni* AAB92583; TnD11, *T. ni* 044390; other animal desaturases AcD12-15, *Acanthamoeba castellanii* ABK15557; CeD12, *Caenorhabditis elegans* AAF63745; RnD9, *Rattus norvegicus* P07308; bacterial desaturases N36D9, *Nostoc* sp. 36 CAF18423ΔNoD9, *Nostoc* sp. PCC 7120 (*Anabaena variabilis*) BAA03434; NoD9, *Nostoc* sp. PCC 7120 BAA03435; SyD9, *Synechocystis* PC 6803 BAA03982; SyD12, *Synechocystis* PC 6803 P20388; fungal desaturases LkD12, *Lachancea kluyveri* BAD08375; MaD9, *Mortierella alpina* BAA75927; YlD12, *Yarrowia lipolytica* CA181209; ScD9, *Saccharomyces cerevisiae* P21147; plant desaturases AtD9, *Arabidopsis thaliana* AAK76592; AtD12FAD2 (ER M2-desaturase), *Arabidopsis thaliana* P46313; AtD12_FAD6 (plastid Δ12-desaturase), *A. thaliana* P46312; PgD9, *Picea glauca* AAM12238). D9, D10, D11, D12, and D14 designate Δ9-, Δ10-, Δ11-, Δ12-, and D14-desaturases, respectively.

AdD12Des and Tribdesat10 showed only low identities (up to 23%) over the full-length amino acid sequences to bacterial Δ9-desaturases or plant, fungal and animal Δ12-desaturases which formed another major cluster of predominantly acyl-lipid desaturases (left hand side of FIG. 4). The low level of identity of AdD12Des and Tribdesat10 with Δ12-desaturases from other animals, plants or fungi was particularly unexpected. Instead, AdD12Des formed a discrete cluster with insect Δ9-desaturases including those of house cricket and red flour beetle suggesting its possible evolution from Δ9-desaturase genes. The extent of identity in amino acid sequence of AdD12Des to these were 65.2%, 55.2%, 55.5%, 53.5%, 53.5%, 55.3%, 59.4% and 53.6%, respectively, to insect Δ9-desaturases from *A. domesticus* AF338466, *D. melanogaster* CAB69054, *M. domesticus* AAN31393, *O. nubilalis* AAF44710, *P. octo* AAF73073, *T. castaneum* XP_969607, *T. castaneum* XP_966962 and *T. ni* AAB9258. In particularly, AdD12Des was relatively close in sequence to the Δ9-desaturase protein from the same species, sharing about 65% amino acid identity.

As Tribdesat10 appeared on a separate branch of the phylogenic tree to the other acyl CoA desaturases including *Tribolium* Δ9-desaturases to which it shared up to 48% identity, it may have evolved independently of the insect Δ9-desaturase genes. As shown by the data in FIG. 3, AdD12Des retained low levels of Δ9-desaturation activity on the medium chain saturated fatty acids, C14:0 and C15:0, when expressed in yeast. FIG. 3A shows the partial GC graph of fatty acid profile in yeast cells expressing pYES2 vector only, while 3B shows fatty acid profile in yeast cells expressing pXZP282, with extra C14:1 and C15:1 peaks. However, no detectable Δ9-desaturation activity was seen in yeast expressing Tribdesat10. These findings suggest that these two insect Δ12-desaturases independently diverged from an ancient desaturase. It was also noteworthy that the other animal M2-desaturases from *Caenorhabditis elegans* and *Acanthamoeba castellanii* were more closely related to the plant Δ12-desaturases than to insect Δ12-desaturases AdD12Des and Tribdesat10 (27.2% and 38.6% amino acid sequence identities to *Arabidopsis thaliana* Δ12-desaturase FAD2, respectively, or 11.6% and 11.1% amino acid sequence identities to *A. domesticus* AdD12Des, respectively).

To test whether the cloned *A. domesticus* Δ12-desaturase used acyl-CoA C18:1 as substrate rather than acyl-PC C18:1, the Δ12-desaturase gene from *A. domesticus* in pXZP282 was expressed in yeast S288C cells. The *Arabidopsis thaliana* Δ12-desaturase gene coding region encoding. FAD2 was also cloned into pYES2, resulted in the construct pXZP279, and expressed in S288C as a control gene, as an example of a plant Δ12-desaturase that was known to be an acyl-PC type enzyme. Cultures of the yeast transformants were incubated in the presence of $C^{14}$ labelled C18:1 ($5\times10^6$ dpm) and cells were harvested at 2, 5, and 30 minutes, and 1, 6 and 24 hours later. For optimal results, cells were lysed using glass beads followed by repeated passes through a tissue grinder. Fatty acids bound to CoA were extracted as described by Domergue et al. (2005), converted to FAMEs and separated by argentation-thin layer chromatography (TLC). Oleic acid added to the medium during induction became immediately available in the acyl-CoA, PC and TAG fractions. It was observed that *Arabidopsis* FAD2 accumulated labelled C18:2 product in the acyl-CoA fraction from minutes onwards. In contrast, conversion of labelled C18:1 to C18:2 by the cricket desaturase was observed as early as 2 minutes after addition of the substrate, indicating that this enzyme uses acyl-CoA as substrate. Therefore, AdD12Des, and presumably Tribdesat10, were of the acyl-CoA oleoyl Δ12-desaturase type, rather than acyl- PC oleoyl Δ12-desaturases. Genes encoding the former class of M2-desaturase have not previously been identified.

Cloning of the insect acyl-CoA Δ12-desaturases described herein is expected to stimulate the discovery of other novel insect polyunsaturated fatty acid desaturase genes and provide greater insight into insect fatty acid metabolism. The role of this gene in insect development and physiology can be studied in knockout mutants. Characterization of these Δ12-desaturase genes will also shed more light on the evolution of insect desaturases via ancestral genes. Finally, this will increase our understanding of sequence-substrate type relationships among fatty acid desaturases, since membrane-associated insect Δ12-desaturases are thought to use acyl-CoA substrates (Cripps, et al. 1990), while membrane-associated plant Δ12-desaturases utilize phosphatidylcholine (PC) as a substrate (Stymne and Appelqvist, 1978).

REFERENCES

Abdullah et al. (1986) Biotechnology 4:1087.
Altschul et al. (1997) Nucleic Acids Res 25: 3389-3402.
Badami and Patil (1981) Prog. Lipid Res 19: 119-153.
Baumlein et al. (1991) Mol. Gen. Genet. 225:459-467.
Baumlein et al. (1992) Plant J. 2:233-239.
Broun et al. (1998) Plant J. 13:201-210.
Cahoon et al. (2001) J Biol Chem 276:2637-2643.
Cahoon, et al. (2000) Plant Physiology 124, 243-251.
Cahoon, et al (1992) Proc Nat Acad Sci USA 89: 11184-11188.
Capecchi (1980) Cell 22:479-488.
Cheng et al. (1996) Plant Cell Rep. 15:653-657.
Christie (2003) Lipid Analysis: isolation, separation, identification and structural analysis of lipids. 3rd edition, The Oily Press, Bridgwater, UK.
Clapp (1993) Clin. Perinatol. 20:155-168.
Cripps et al. (1990) Arch Biochem Biophys, 278, 46.
Crombie et al. (1984) J Chem Soc Chem Commun 15:953-955.
Crombie et al. (1985) J Chem Soc Perkin Trans 1:2425-2434.
Cuperus and Derksen (1996) High Value-Added Applications from Vernolic Acid. p. 354-356. In: J. Janick (ed.), Progress in new crops. ASHS Press, Alexandria, Va.
Curiel et al. (1992) Hum. Gen. Ther. 3:147-154.
Domergue et al. (2005) Biochem J. 389, 483-490.
De Renobales et al. (1987) Trends in Biochemical Sciences 12, 364.
Dobson and Christie (2002) European Journal of Lipid Science and Technology, 104: 36-43.
Eglitis et al. (1988) Biotechniques 6:608-614.
Fay and Richli (1991) J. Chromatography 541, 89-98.
Fritsche et al. (1999) FEBS Letters 462:249-253.
Fujimura et al. (1985) Plant Tissue Culture Letters 2:74.
Gleave (1992). Plant Molecular Biology 20, 1203-1207.
Graham et al. (1973) Virology 54:536-539.
Grant et al. (1995). Plant Cell Rep. 15:254-258.
Gunstone et al. (1994) (Editors), The Lipid Handbook (2nd Edition). Chapman & Hall, London).
Hao et al. (2002) Insect Biochem Mol Biol 32 961-966.
Harayama (1998). Trends Biotechnol 16:76-82.
Horsch et al. (1985). Science 227, 1229-1231.
Kleiman and Spencer (1982) J Am Oil Chem Soc 59, 29-38.
Knipple et al. (2002) Genetics 162: 1737-1752.
Koziel et al. (1996) Plant Mol. Biol. 32:393-405.
Lee et al. (1998) Science 280:915-8.
Lewis et al. (2000) J Microbiol Methods 43:107-116.
Lu et al. (1993) J. Exp. Med. 178:2089-2096.
Mortimer and Johnston (1986) Genetics 113: 35-43.
Moto et al. (2004) Proc Natl Acad Sci USA 101: 8631-8636.
Murashige and Skoog (1962). Physiologia Plantarum 15, 473-477.
Murata and Wada (1995) Biochem. J. 308:1-8.
Needleman and Wunsch (1970) J. Mol. Biol. 48:443-453.
Qiu et al. (2001) Plant Physiol 125:847-855.
Rodriguez et al. (2004) Insect Biochem Mol Biol 34: 1315-1328.
Sayanova et al (2007) Plant Physiology 144: 455-467.
Serra et al. (2006) Insect Biochem Mol Biol 36:822-825.
Shanklin and Cahoon (1998) Annu. Rev. Plant Physiol. Plant Mol. Biol. 49:611-641.
Simopoulos (2000) Poultry Science 79:961-970.
Smith (1971) Prog. Chem. Fats other Lipids 11:137-177.
Smith et al. 2003. Planta 217, 507-516.
Stalberg et al. (1993) Plant Molecular Biology 23, 671-683.
Stukey et al. 1990. J Biol Chem 265, 20144-20149.
Stymne and Appelqvist (1978). Eur J Biochem 90, 223-229.
Thompson et al. (1997) Nucleic Acids Res. 25: 4876-4882.
Toriyama et al. (1986) Theor. Appl. Genet. 205:34.
Trautwein (2001) Eur. J. Lipid Sci. Technol. 103:45-55.
van de Loo et al. (1995) Proc Natl Acad Sci USA. 92:6743-7.
Vernet et al. (1987) Gene, 52: 225-233.
Wagner et al. (1992) Proc. Natl. Acad. Sci. USA 89:6099-6103.
Wang et al. (1997) The Journal of Genetics & Breeding 51: 325-334.
Whittle et al. (2005) J Biol. Chem. 280:28169-76.
Yu et al. (1988) Lipids 23: 804-810.
Zhou et al. (2006) Plant Science 170, 665-673.

The claims defining the invention are as follows:

1. A process for producing oil containing unsaturated fatty acids comprising
    i) obtaining a yeast cell, a plant or a part thereof comprising an exogenous acyl-CoA Δ12 desaturase which is capable of desaturating oleoyl-CoA and an increased level of production of $16:2^{\Delta 9,\Delta 12}$ and/or $18:2^{\Delta 9,\Delta 12}$ fatty acids relative to a corresponding yeast cell, plant or part thereof lacking the exogenous Δ12 desaturase, and
    ii) extracting oil from the cell, the plant or the part thereof.

2. The process of claim 1, wherein step ii) comprises producing crude oil by cooking, pressing and/or crushing the yeast cell, the plant or part thereof.

3. The process of claim 2 which further comprises degumming, refining, bleaching and/or deodorizing the crude oil.

4. The process of claim 1 which comprises using a solvent to extract the crude oil.

5. The process of claim 1, wherein step i) comprises obtaining a yeast cell which comprises the exogenous acyl-CoA Δ12 desaturase and the increased level of production of $16:2^{\Delta 9,\Delta 12}$ and/or $18:2^{\Delta 9,\Delta 12}$ fatty acids, and step (ii) comprises extracting oil from the yeast cell.

6. The process of claim 1, wherein the yeast cell, plant or part thereof comprises an increased level of $16:2^{\Delta 9,\Delta 12}$ and/or $18:2^{\Delta 9,\Delta 12}$ fatty acids which are esterified to CoA relative to a corresponding yeast cell, plant or part thereof lacking the Δ12 desaturase.

7. The process of claim 5, wherein step ii) comprises producing crude oil by cooking, pressing and/or crushing the yeast cell.

8. The process of claim 7 further comprises degumming, refining, bleaching and/or deodorizing the crude oil.

9. The process of claim 5 which comprises using a solvent to extract the crude oil.

10. The process of claim 5, wherein the yeast cell comprises an increased level of $16:2^{\Delta 9,\Delta 12}$ and/or $18:2^{\Delta 9,\Delta 12}$ fatty acids which are esterified to CoA relative to a corresponding yeast cell lacking the Δ12 desaturase.

11. The process of claim 1, wherein step i) comprises obtaining a plant or part thereof which comprises the exogenous acyl-CoA Δ12 desaturase and the increased level of production of $16:2^{\Delta 9,\Delta 12}$ and/or $18:2^{\Delta 9,\Delta 12}$ fatty acids, and step (ii) comprises extracting oil from the plant or part thereof.

12. The process of claim 11, wherein step ii) comprises producing crude oil by cooking, pressing and/or crushing the plant or part thereof.

13. The process of claim 12 which further comprises degumming, refining, bleaching and/or deodorizing the crude oil.

14. The process of claim 11 which comprises using a solvent to extract the crude oil.

15. The process of claim 11, wherein step (ii) comprises extracting oil from a seed of a plant.

16. The process of claim 11, wherein step (ii) comprises extracting oil from an oilseed.

17. The process of claim 11, wherein the plant or part thereof comprises an increased level of $16:2^{\Delta 9,\Delta 12}$ and/or $18:2^{\Delta 9,\Delta 12}$ fatty acids which are esterified to CoA relative to a corresponding plant or part thereof lacking the Δ12 desaturase.

* * * * *

SEQUENCE LISTING

```
<160> NUMBER OF SEQ ID NOS: 135

<210> SEQ ID NO 1
<211> LENGTH: 933
<212> TYPE: DNA
<213> ORGANISM: Tribolium castaneum

<400> SEQUENCE: 1
atggccccca acagcacagt aactaccaca ctcacagcat cagaattatc acctagagaa      60
tcaaaaatat tacctgaagt gacctatcgt acactttggg gtaatttcaa aacacccctc     120
atctggccaa acatcatcgg aataatctca gtacatgtta ttacaatcat aggattcgtc     180
```

```
acatttccgt attttcaaca caaaagcact tttgcgtggt gtaatgtaac aggttgggct    240
ggaggttttg gagtaacagc aggagcacac agactatgga ctcataaatc atacaagaac    300
agattgcgtg aatgggtcag agatcataga gtgcaccaca aatttagcga atcagatgct    360
gacccacata atgcaaatcg aggttttttt ttcgcccatg ttggatggct aatgatgcgg    420
aaacatccgg aggttttaag aaaaggaaaa tcaattgact gtagcgatct gtttgaagac    480
tcggttgttg tattttttcga aaagttcttt tggccaatga aattattttg gtgtttcatt    540
tttccaacaa tgattccgta cttttgttgg aacgaaacct tctactggtg tgtgatgagt    600
tgcatagcaa gatacgtatg tggccttaat ttcacatggt tagttaatag tgcggcccat    660
atgtttggaa acaaaccttta cgatagaaaa atccaaccag ttgaaaattt gatggtttct    720
attttggcaa tgggcgaagg ttggcacaat tatcatcata cattcccttg ggattataaa    780
gcagctgaat taggaaatta caaagttaac gctacgacct tacttttaga tttatttgcc    840
aaaataggat gggcctatga tttaaaaagt ccatcgaaac agcttataca gcaagttata    900
gaaaatcatg gggatggcac acgcagagat taa                                933

<210> SEQ ID NO 2
<211> LENGTH: 963
<212> TYPE: DNA
<213> ORGANISM: Tribolium castaneum

<400> SEQUENCE: 2
atgtcaacgc ttgaaacaca agtccaaatc gtttggcgaa acgtaatttt atttatctat     60
ttacatgtcg cagctatcta tggcctctac ttcacattta cagccgctaa atggcccaca    120
atattgttca catattttt aacaattatc tcgactcaag gcaccggagc cggtgtccat    180
cgtttgtggt cccataggtc atacaaggcc aaactacccc ttcgtatttt actctgtata    240
taccagaccc attgcctcca aaaccatatt tacgaatggg tgcgtgacca tcgtgctcat    300 cacaagtttta gtgacaccga tgcagaccca cataattcta ctcggggatt ttttttctcc    360
catatgggtt ggttactagt gcgcaaacac ccacaagtca aaattaaagg caaattgatt    420
gatttgagcg atttagaaga ggatcaagtg gtcatgtttc aaaaaaagta ctacttgatt    480
cttgccccat ttttcgcgtt tttattacca gcatgggtac catggtactt ctggggtgaa    540
gatttacatg tttcatggtg cgtggctagt atgctacggt acgctttgag tttgcacgga    600
acatggctgg ttaatagtgc tgcccatatg tggggtactc gcccatatga caggaacatt    660
aaagcgaccg aaaccaaagt cgtgtcgtac attaccaacg gggaaaggtt ccataattac    720
catcacacct ttccatggga ctataaagca gctgaacttg gtagctattg gggaaattgg    780
agtaccgcgt ttattgactt tatggctaaa attggatggg cctatgattt aaaaataata    840
ccacctgaac tggttgaaaa aagagcgaaa aggaccggtg aatgtaccca taagtttgg    900 ggttggggtg ataagacat agataaggaa gaaatcgaaa ttgttgaacg aaatcgaggg    960
taa                                                                  963

<210> SEQ ID NO 3
<211> LENGTH: 957
<212> TYPE: DNA
<213> ORGANISM: Tribolium castaneum

<400> SEQUENCE: 3
atgtctagcg agctagcgcc ccttaacatc cgaccagttt ggttaaaaat agtatatttt     60 gcg

-continued aaaacaattc tatggaccta tttattactc ctttcggcca ctcatggtat tgcagtgggt 180
gcccatagat tatgggccca tagggcttac aaagccaaac taccattgcg cctccttctg 240
gcctttgacc agactttaac attccagaaa gatatatatg attgggttcg agaccatcga 300
atccatcaca agtactctga cacagagtac gacccccata acgcaaccag agggttcttt 360
tacagccaca ttggttggct gatgattaaa aaatcggata aagttatcgc aaaagggaaa 420
gaactagact tgagtgattt ggagcaagac ccagtagtat ggtaccaaag aaagtactac 480
tggtatatgg caccgtttct cgcctttatt ttcccagcta tggtaccatg gtacttttgg 540
tcggaacagt tcaaagtctc atggtacctt tgcagtattt ttcgcttatg tgttactcta 600
catggtactt gtttggtaaa cagtgcggcc cacatttggg gctccaaacc atacgataaa 660
aatattaaac cagtggaaac gtcatgggtg gctcatatta gtcatggtga gggttggcat 720
aactaccatc atgtcttccc atgggattat aaagctgcag aattggggtc atattatggc 780
aattggaata cggcctttat tgattttatg gccaaaattg ggtgggccta tgaccttaaa 840
agcgccccat tggacatggt caaaaaaagg ggggagagga cgggcgatgg caccaaattg 900
tggggctggg ggatgagga tatggataag gaagatgtgt gtaaggcgaa aaattaa 957

<210> SEQ ID NO 4
<211> LENGTH: 966
<212> TYPE: DNA
<213> ORGANISM: Tribolium castaneum

<400> SEQUENCE: 4
atggaacgtg aaatcgcgtg gaagaaagtc tttttcttg tgtatttaca tttgggggct 60
ttgtacggct tgtacctcat cctaactgaa gcttcgtggt tgacctgctt ttggttctat 120
ttcctggtac aaatctcgac gcaaggtacc ggagcaggtg tccatcgctt atgggcacat 180
agggcctaca aggccacggt accacttcga ctcttactaa cattttacca aactttaacc 240
ttccaaaaag atatttacga ttgggtgcgc gaccatcgag tccatcacaa gtactctgac 300
acggaacccg acccacataa tgcctccaat gggttctttt acagtcacat gggttggtta 360
atgttgaaaa agacccaatg taccatcgat aagggcaaaa aattggactt gagtgacttg 420
gaagccgacc caatcgtcat gtttcagaga aagtactatt ggtacttggc accggttata 480
gctttgggaa tgcccgcctt tgtaccgtgg tacttttggg gtgagagatt tgtagtttca 540
tggtacgtct gtagcatgtt tagatactgt ctaacccttc atggtacctg tctggtaaat 600
agcgccgccc atatttacgg aaatcgtcca tatgacaaga acattttacc aacgcaaaat 660
ttgttggtct cgtacattac gaacggagaa ggcttccata attaccacca tgccttccca 720
tgggactaca aagcggccga attggggtca tattatggca attggagtac ggcatttatt 780
gattttatgg cccgaattgg atgggcatat gaccttaaaa gtgtcccatt ggcaatggtc 840
gaaaagaggg ttaaaaggac aggtgatggt acccataatg tgtggggatg gggtgacaag 900
gatttacacc cagatgacgc caaaatggtc gaaattacac acacacgagc ttcacaaaca 960
ggataa 966

<210> SEQ ID NO 5
<211> LENGTH: 909
<212> TYPE: DNA
<213> ORGANISM: Tribolium castaneum

<400> SEQUENCE: 5

```
atgttttac gtacaataac atccaaattt tattcagacc aaattgtgtg gcgtaatgtt         60
tttcttttgc tcattctcca cattatttct ctgcagggtt ggtattttgt tctgacaaca        120
acgaattggc ccacattaat ttacgggttt attttcgggg ccttgactgg ccaaggaatc       180
aaattggggg cccatcgcct gtgggcccac cgttgctaca aagcgaaact tcctctaaga       240
atatttttgt gttttttgca aactgttact ttacaaaatc ccctgtatga atgggtgagg       300
gaccatcaag tccatcacaa atataccgat accaacgcag acccacttaa tgcaaccagg       360 ggatttttt  tctcacacat gggttggttg ttggtacgta aacacccaaa tgtcattgcg       420
aaaggaaaaa cattggattt gagtgatctc gaagaagatc cggtcgttat gtttcaaaaa       480
aagtactaca aaattatagc cccggtcttg acccttgcca taccagccct aatcccatgg       540 tactttttg  gagaggattt atacttatca tgggttacga catgtgtgct tccctacttc       600
attaccctgc attccacgtg ggctgtgaac agcgtggccc atatctgggg cacaaaacca       660
tacaataaaa acattctccc cacagaaaat atcgcagtgg caatagttgc ctatggagaa       720
ggttggcata attaccatca cgttttcca tgggattata aagcagctga gttgggaaac       780
tacagaccaa atcttagtac tgcttttatt gactttatgg caaaaattgc atgggcgtat       840
gatttgaaaa gtgtctctcc tgaaatgttg agaaaacgga aatgcggac  cggggattgt       900 gattattaa                                                                 909

<210> SEQ ID NO 6
<211> LENGTH: 1071
<212> TYPE: DNA
<213> ORGANISM: Tribolium castaneum

<400> SEQUENCE: 6
atgacggaag cagcgatga atgttcaaaa ggtgcttgtt caactgctgc taaagagaca        60
tcgcgacgtc tgaacgcttt aaccaaaacc gaaattccag aaaacaaatt gaaaaagaa        120 gaattccggc caagaattcg atggcctgat ttaacagtac aagtatttat tcatgtagga       180
tgtttatatg gactgtattt gtgccttgtg tctgccagat tatacacaac acttttgca        240 ttcctaacga tatacctctc agggtttggc atcaccgcgg gtgctcatag attatggtca      300 cataqggctt acaaggccaa atggccactt aagatacttc tactcatctt atttacgatt       360
acgggtcaga ggcatgtcta cgtctgggca ttggaccatc gagttcacca caaatacagc       420
gaaaccgacg ccgatccaca taatgcgaaa cgcggttttc tgttttcaca cgtcggttgg       480
cttgttctaa cccctcatcc tgatgttgtc gaaaaacgaa aagccgtcga tatgagcgac       540
ttggaagccg atccgctcat aatgtggcac aaaaaattat atccaccact attttcctg       600 ttcgttattt ttctaccagt ttttaccccc gtgtattttt ggaacgaaac aatttggaat       660 tcgtttggg  tgaatttaa  cgccagattt tgtatcactt taaacatcgc atttttcgtg       720
aacagcgttg cgcatatgtg gggccagaaa ccttacgaca gatatataag tccagtggaa       780
aatttagcag tgtctttagc agcgttgggt gaaggttggc ataactacca tcacgtcttc       840
ccatgggatt acagaactgg agaacttgga aatagctaca cccatctac  cacgtttatt       900 gatttcttcg caaaaattgg atgggcctac gacttgaaat cgcttcgaa  ttcgatgatt       960 gcaagaagag cgaagaaaag tggcgatgga agtcacattt ggggttacgg agatgcagat      1020
atagaaaaag aagatttaga agaactgaat aaaatggagg attttaactg a              1071

<210> SEQ ID NO 7
<211> LENGTH: 1062
```

```
<212> TYPE: DNA
<213> ORGANISM: Tribolium castaneum

<400> SEQUENCE: 7
atgccaccct atgtgtccca cgttaccggc gttcttgacg aaaatgacga agaagtctct      60
accaaaaata tcctaccaga agtaacaaaa cccgaaaacc gaaaattaca actcgtttgg    120
agaaacatta tactgtttgc atacttatat ctggcatcat tctatggatt atacttgatg    180
tttacctcag ccaagttagc aacttcgatt tttgcttatt ttctctatca actgggaggt    240
ttcggaatca cggctggagc ccaccgtttg tgggcccatc gctctttcaa agccaaatgg    300
cccttgcgtc tcctccttgc cttttgcaac actttggcct tcgaggactc ggtcatcgac    360
tggtctcgag accaccgcgt ccaccacaaa ttctccgaaa ccgatgccga cccttacaat    420
gccaaacgcg gctttttttt ctcacacatc gggtggcttt tatgccgaaa caccccccaa    480
gtcaaggaaa agggcaaaca aatcgacctg tccgacttat accagaccc gattttgcgt     540
taccagaaaa aatactactt gtttgtaatg ccagttatct gttttgttct accaaccgct    600
gcaccaatgt atttctgggg cgaaagtttc aaaaatgcgt ttttgttaa tcttttaggg    660
tattgttta ctttgaattc gacgtggttg gttaattccg ctgctcattt atggggaagt     720
aaaccctatg ataagtttat taacccggcg gaaaatttcg ccgtttcggt actggcttta    780
ggcgaaggat ggcataattt tcatcatact tttccatggg attataaggc ttcagagttg    840
gggaaatata gtgtgaattt tcgtcggct tttattgatt tttttgccaa aattggatgg      900
gcttatgatt tgaaaactgt ctcggaggat tggtcaaga agagggtttt gagaactggt     960
gatgggtcgc accatgtttg gggatgggt gatatggacc aagcgttgga ggattatgaa    1020
ggggcgatta tcaagcacag aaaatctgac gattttaatt aa                      1062

<210> SEQ ID NO 8
<211> LENGTH: 1053
<212> TYPE: DNA
<213> ORGANISM: Tribolium castaneum

<400> SEQUENCE: 8
atgacaccaa atgcttcaat tccaactggt gttctccacg aaaatgacga agaagtttcc     60
aatgcaacgc ttccaccaga ggtcaacaaa ccggacgacc gcaaactgca gttagtttgg    120
aggaacatca ttttgttcgc ttatctgcat ttggccgctt tgtatggaat ctggatcatg    180
ttcacctctg caaaagtcgc aacgtctcta tttggcattc tactttacca acttggaggt    240
ttcggaataa cggctggagc tcaccgtttg tgggctcatc gttcgtacaa agccaagtgg    300
cctttacgtc taatcctcac tttctgcaac actttggcct tgaagattc cgtcatcgat    360
tggtccagag accaccgagt ccatcacaag ttctccgaaa ctgatgctga tccacataat    420
gccaaacgtg gtttcttctt ctctcacgtt ggctggcttt tgtgccgtaa acatcctcaa    480
gtaaaagaaa agggcaaaca aatcgatctc tccgacttgt acgctgatcc gattttgcga    540
ttccagaaga aatactacac cattgtaatg ccttggtta gttttgtaat gccaaccgtc    600
gtgccaatgt acctctgggg tgaaaccttc aagaacgcct ttctggtcaa tctcttcaga    660
tattgtctaa ctttgaacgc cacctggttg gtcaattccg ctgccatat gtggggagat     720
aagccctatg ataggtttat caatccagct gagaatttcg tggtttcggt tttggccttg    780
ggtgaaggtt ggcataacta ccatcatact ttcccttggg attacaaaac gtccgaattg    840
gggaaataca gtgtgaactt ctcgaccgct ttcattgatt tcttcgccaa gatcggatgg    900
```

| | |
|---|---|
| gcttatgatt tgaaaactgt tcatcggaa atgatcaaga aacgcgttac gagaactgga | 960 |
| gatggaacgc acgaaatttg gggatgtggg gataaggatc agtctcagga agactaccaa | 1020 |
| gacgcgatta tcactcatag gaagagtgcg tag | 1053 |

<210> SEQ ID NO 9
<211> LENGTH: 834
<212> TYPE: DNA
<213> ORGANISM: Tribolium castaneum

<400> SEQUENCE: 9

| | |
|---|---|
| atgctaatct tactttccac aattggagta acagccggag cacatcgatt atgggcacac | 60 |
| aattcctacc aagcaacaac ttcactaaaa atatttctta tgctttgtca aacattggct | 120 |
| ggacaaacct ccatttacaa ctgggttcgt cttcatcgcc ttcatcacaa atatttccaa | 180 |
| acagaaatgg atccatttaa ccctcaaaaa ggtttcattt attctcattt tatagcaaat | 240 |
| aatttgaaac tgagtccagc gcaagaaaaa ttgttggaag aaatcgacat gtctgattta | 300 |
| gagcaagaca aaattgtcat gtttcagaaa aagtattatt ggttccttt tgtaattgta | 360 |
| acttactttt tgccaataaa tgctcctgtg gaatattggg acgaaactat tttgaattca | 420 |
| ttcttcatac ttgggtggtt acgtttggga attagttacc atttaacttt actaattcac | 480 |
| agcgctataa atgtttttga tttaaaacaa atggacagga attcttatga cagcaatgca | 540 |
| gttttcttca taaacaagtc ttattggatt tcttatcact acatgtctcc ttgggattac | 600 |
| caaacgggtg aatatggcaa atatggaagt gattgtactt caaaatttat tcgagtgtgc | 660 |
| gctgctttgg aacttgcaac agatttgaaa acagttgata tgaaatgat tcgagaagct | 720 |
| ttgactctgt gtgttgatga agaaaaacca atagaagaat gtttgacacg gctaggaaaa | 780 |
| aaatcccatg ataaattgtt aaagcattat ctaacaccct caaaatttca ttag | 834 |

<210> SEQ ID NO 10
<211> LENGTH: 873
<212> TYPE: DNA
<213> ORGANISM: Tribolium castaneum

<400> SEQUENCE: 10

| | |
|---|---|
| atgtttcaaa cacccatcgt ctggcccaac gtcattctct tcatccttta ccatgccata | 60 |
| gcccttcaag ggtggtacta ttttataact tttcaaacga atttaagaac tatatttggg | 120 |
| gccttcttga ttttggtcct agctggacaa gggattacct ccggagtcca tcgtttatgg | 180 |
| tctcatagat catacaaagc caaactccct ctccgaattt ttctatgtct gtgtcaaact | 240 |
| ataagtttcc aaaattccat ttacgaatgg gcacgtgacc atcgtgccca tcacaagttt | 300 |
| agcgacaccg atgctgaccc acataacatt aaacgtggct ttttcttcgc ccatatgggt | 360 |
| tggttactag tacgcaaaca cccacaagtc aaaatgaagg gtcaattgat tgatttgagt | 420 |
| gatttagaaa atgatccagt ggtacgtttt cagaaaaagt actaccatgt tttagctccg | 480 |
| ctttgttgct tgtcgtacc aacaatggta ccgtggtact tctggaagga gaatttttat | 540 |
| gtttcgtttt gtgtttgtat gttgaggtat ttgataagtt tacatttttac gtggttggta | 600 |
| aacagtgcgg ctcattatg ggggtttaaa ccttacgaca ggtttattaa accatcagaa | 660 |
| aatcaaattg ttgcaaagtt aacaatgggt gaaggttggc acaattacca tcataccttc | 720 |
| ccatgggatt ataaggctgc ggaactggac agttacaatg gtaatttgag tactgccttc | 780 |
| attgatttga tggcgaagat tgggtgggcc tatgatttga aaacggtacc attggatgtg | 840 |
| atcaggaagc gggttttgag gactgggcaa taa | 873 |

```
<210> SEQ ID NO 11
<211> LENGTH: 990
<212> TYPE: DNA
<213> ORGANISM: Tribolium castaneum

<400> SEQUENCE: 11
atgagacaaa ttcaggtcag atttgaatca caaatcgggc ttctttattt aaaaactagt      60
gcatttccgc gaactatcat ttcgagaaaa aaatgttag aaattgtttg gaaaaacgtt      120
ttttccttca ttctgtacca ttatctcgcc ttccatgggc tgttttatct cgtgacagga      180
cacacccatt gggccacttt cgccttcaat ttgttttttgg cccaattgtc caatctgggt      240
accatctcag gggcccatcg tttatggacc catcgttcgt accaagccca actaccatta      300
aaacttttcc tcatgttttg taataacata agcaaccaaa actccattta tgattgggtt      360
agagaccacc gagttcacca caagtttagt gacactgatg ccgaccctca caacatcaag      420
cgtggctttt tttcgccca tatgggttgg ttaatggtta ggaagcaccc agaagttacc      480
atcaaaggac aaactttgga ttttagcgac atagatagcg acaaattaat acaattccaa      540
cgaaaatatt tcaagttttt ggcgtttttt tgctccattt tcctaccagt tgtagtacca      600
tggtactact ggggtgagaa ctggtacgtt tccttgtgta tcacttttgt gcgctatgtt      660
ggtactttgc atggtacctg gttggttaat agtgccgccc atgtctatgg tacccggcct      720
tacgacagtg acattaaacc gacggagaat ccaatcgtgg cttatattac catgggtgag      780
ggttggcata actaccatca caccttccca tgggactacc gagcttcaga atttgacagt      840
ttcaatggca atgtcaatac agtatttatc aattttatgg caaagttgg actagcccat      900 ggtttaaaaa cggcatcact tagtctgatc cagcgaaaaa aactgaaaag taccaatagt      960
actacgaata aaaaacaatt gcaaaaataa                                       990

<210> SEQ ID NO 12
<211> LENGTH: 1125
<212> TYPE: DNA
<213> ORGANISM: Tribolium castaneum

<400> SEQUENCE: 12
atggctccaa attcgctcag caaatcggaa tatttgggag aaccagtcca aattattagt      60
aaaccaaatg ttgaatacag tatagaaact caaaataaat acaatttacc tcacaataga      120
tggcaaatag tttggagaaa cgtcttaata tttgcatatc ttcattatgc agcttttac      180 ggcttatatt acatgctcac tttagctcaa tggaaaagta tcatttgggg atatgctgtt      240
atcctatttg caagtattgg agtaaccgga ggagcacata ggttatgggc ccatcgttcg      300
tataaagcaa aactcccatt acgaatttat ttagcttttt ggcagactgt tgctttacaa      360
aatcacatct atgaatgggt gcgagatcac cgagtgcacc acaaatttac agacacagat      420
gctgatcctc ataattctaa tcaaggattt tttttctcac atatggggttg gctgatgctc      480 aaaaaacaca agatgtatt tattaaaggc aaaactattg atctgagtga tgtagcagct      540
gatccagttg tccagtttca aaaaaatat tatttaatct ggctccgat tctaacgttt      600 gttttcctg caattgttcc ttggtacttc tggaacgaaa atccaatagt gtgctattat      660
tctttagcaa ttttgaggta catttttaaat cttcatgggg cttggttggt aaatagcgca      720
gctcatatct ggggctacaa accattcgat aagaacataa atgctacaga caatataagc      780
gtcgctatta tcgctttcgg tgaaggatgg cacaattacc accacgtttt tccttgggat      840
```

| | |
|---|---|
| tacaaagctg cagaattagg taactacagg atgaatttta ctacggcttt tcttgatctg | 900 |
| atggcaagaa ttggacaggc ttatgatttg aaaacagtgt ccgttgaaat gatcaacaag | 960 |
| agaaggaaaa gaactggtga tggtaccggt gtagttgatc ctttggtgga aaataaagaa | 1020 |
| gaccatcgcc atgaagacac tgtttgggga tggggtgaca agatatgaa ccaagatgaa | 1080 |
| atgaatttgg ttgaaattta taatccaagt agcaaagaac cgtaa | 1125 |

<210> SEQ ID NO 13
<211> LENGTH: 1077
<212> TYPE: DNA
<213> ORGANISM: Tribolium castaneum

<400> SEQUENCE: 13

| | |
|---|---|
| atgtcggccc agaccattac cacgacggag accacacaaa atgcccagaa accgcagcag | 60 |
| taccattgga ggatggtctg gaggaacatc atcctgtaca ttatcatgca cctcaccggc | 120 |
| ttctatggac tgtacctggc catgttctac gcccagtgga aaacagtctt ttacagttgg | 180 |
| ttccttctgg tcatagccct tcaaggagtg acagctggta gtcaccgcct ctgggccacc | 240 |
| aaggcctaca aggcgcgact cccccctccga atgcttcttt gtattttcca aaccctgtcc | 300 |
| ctccagaacc acatctacga ctgggccacg taccaccgcg tccaccacaa gttcgtcgat | 360 |
| accaacgccg acccacacaa ctcgcgccgc ggcttcttct tctcccatat gggctggttg | 420 |
| ttcatcgagc cccacaaaga cgtggaggat aaatacaagt cgatcgactt cagcgacttg | 480 |
| catgccgatt ccgtggtcat gatccagaaa aagtactacc acacgttctt tgcgccagtc | 540 |
| attgggttct acctcccggc ggcgatccca tggtacttct ggggcgagaa cttctggacc | 600 |
| gcgtttttcg ttgcgaccat gctgcggtac tgcgcctgta ccaacattac gttccttgtg | 660 |
| aacagttggg cccatatttta tgggtcccgc ccatacgaca gaacattta tcccaccgaa | 720 |
| agtgcaacga ttgcggtttt gaccggtggg gagggttggc acaactacca tcacaccttc | 780 |
| ccgtgggatt ataagaccgg ggagtttggg aagtaccgga gtaaccttac cacgggcttt | 840 |
| ttggactta tggcggccat aggctgggcc tatgacctca agaccgtgtc ggaagagatg | 900 |
| ataatgaaga gggtgctgcg cacgggtgat ggtactcgga agtttgataa gatcgataag | 960 |
| atactcaatg tggacgatga ccaccaccat gaagacatgc tctgggggtg gggggatagt | 1020 |
| gatatggcca agagggaaat gaactacgtc aaaattcaca acaggaagga ggattaa | 1077 |

<210> SEQ ID NO 14
<211> LENGTH: 1008
<212> TYPE: DNA
<213> ORGANISM: Tribolium castaneum

<400> SEQUENCE: 14

| | |
|---|---|
| atgggagcgc tcaaacaaac cgaggaggaa aaaactctac taccacaaga catcggaacc | 60 |
| gattacaccct tcaagcggaa aatcgtctgg ttcaatgcta ttggattctt catcttgcac | 120 |
| ctcttggccc tttatggcgg ctaccggctg ctgcattgcc acatcctgac gccgcttttc | 180 |
| gccctagcac tgatgttcgt ctctggcgaa ggcatcaccc tcggggccca ccgcctgtac | 240 |
| tcccacaagg ccttcaaagc gtctttcgtc gtgcgattag ctgtgataat tttgcacacc | 300 |
| atcgccggtc agaattgtct ctacatctgg gttcgcgacc accgccagca ccacaaatac | 360 |
| agcgacaccg acgccgaccc ccacaactcc aacaggggct tcttcttctc gcacatcggc | 420 |
| tggctgatga gcaggaagca ccctgctgtc atcgccaagg gcaagaccat cgacatgagc | 480 |
| gacctggaga acgactcgct cgtgatgcta cagaaagaac attacaagtt tctgtacatc | 540 |

```
attttcgcca tcgggatccc aatcgcaatc ccgatttacg gctggaacga gtctttcacc      600
aactcgctct ttatcagcta ctttggaaga tacattcttc agttacacgc cacttggctg      660
atcaacagcg ctacgcactt gtacgggacc aagccctacg acaagttcat gaatccggtg      720
gagaattatt ttatttcgat gattgccctt ggcgaaggct ggcataacta ccaccacgcc      780
tttccctcag attatcgggc ggcggagtat ggcgttagat actcgataac gacttttctg      840
atagacgctc ttgccttttt tggcctgctt tatgacttga agaggccaa ctcggagcaa      900 gtcaaaatcc gggcggtcaa aaggggat ggcagccacc cagtcttcgg gaaacagaag      960
gagatggaag ttaactttag cgataggcag gttacggcaa atggttaa                   1008

<210> SEQ ID NO 15
<211> LENGTH: 1170
<212> TYPE: DNA
<213> ORGANISM: Tribolium castaneum

<400> SEQUENCE: 15
atggctccta atttgctagg aaattcaacg ttatttctcg ctgaaacaaa ttcagccgaa       60
ccaatacaga ttattagtaa accaggactg caagatgtac taccgcaagt aaagccacaa      120
atttccagca gatcttctgt gtcccaatat agatggcaga ttgtatggag aaacgttttg      180
atatttatat acttgcacat tgctggtatt tatggattat attatgctat tgctcaagcg      240
caatggaaaa ctcttctctg gggatatttta gttattctag catcaggaat tggcgtaaca      300
gcaggagcgc acagactgtg ggcccatcgc acatacaaag ctaaacttcc attacgaatt      360
tacttagctt tttgtcaaac tgttgcttta caaaatgaca tctacgaatg ggtgcgagac      420
catcgagttc atcacaaatt cacagataca gacgctgatc ctcacaactc taatcgagga      480 ttcttttttct cacacatggg atggttattg gttaaaaaac acaaggatgt tttcgtcaag      540
ggcaaaactg tggatatgag tgatgtggaa gccgatccgg tggtacggtt tcaaagaaaa      600
tactacataa ttctaactcc aatttttaaca tttgttttttc ctgctatcgt tccttggtac      660
ttctggaacg aaactcccac tgtttgcttc tatagtgtcg ccatctttag atatattctc      720
acacttcatg ggacttggct ggtaaatagt gcagctcata tttggggcta tagaccctat      780
gacaaaaaca taaatgccac agaaaacaaa agcgtttcaa ttctcgcttt cggtgaagga      840
tggcacaact atcatcatgt cttcccttgg gattacaaag ccgcagaatt aggaaactac      900
aggatgaatt ttactacggc ttttctggat ttgatgtcaa aaattggaca ggcttatgat      960
ttgaaaaccg tgtcagttga tatgatcaat aagagaagaa agagaactgg agatggtact     1020
ggattggttg acgaggaatt gctagaaaat gaagataaac atcaccacca tcatgatgac     1080
agcatctggg gatggggtga taagatatg aaacaagatg acatggatat ggtacaagtg     1140
cataatccaa gtagagagaa atttgattaa                                       1170

<210> SEQ ID NO 16
<211> LENGTH: 310
<212> TYPE: PRT
<213> ORGANISM: Tribolium castaneum

<400> SEQUENCE: 16

Met Ala Pro Asn Ser Thr Val Thr Thr Thr Leu Thr Ala Ser Glu Leu
1               5                   10                  15

Ser Pro Arg Glu Ser Lys Ile Leu Pro Glu Val Thr Tyr Arg Thr Leu
            20                  25                  30
```

```
Trp Gly Asn Phe Lys Thr Pro Leu Ile Trp Pro Asn Ile Gly Ile
             35                  40                  45

Ile Ser Val His Val Ile Thr Ile Ile Gly Phe Val Thr Phe Pro Tyr
 50                  55                  60

Phe Gln His Lys Ser Thr Phe Ala Trp Cys Asn Val Thr Gly Trp Ala
 65                  70                  75                  80

Gly Gly Phe Gly Val Thr Ala Gly Ala His Arg Leu Trp Thr His Lys
                 85                  90                  95

Ser Tyr Lys Asn Arg Leu Arg Glu Trp Val Arg Asp His Arg Val His
            100                 105                 110

His Lys Phe Ser Glu Ser Asp Ala Asp Pro His Asn Ala Asn Arg Gly
        115                 120                 125

Phe Phe Phe Ala His Val Gly Trp Leu Met Met Arg Lys His Pro Glu
130                 135                 140

Val Leu Arg Lys Gly Lys Ser Ile Asp Cys Ser Asp Leu Phe Glu Asp
145                 150                 155                 160

Ser Val Val Val Phe Glu Lys Phe Phe Trp Pro Met Lys Leu Phe
                    165                 170                 175

Trp Cys Phe Ile Phe Pro Thr Met Ile Pro Tyr Phe Cys Trp Asn Glu
            180                 185                 190

Thr Phe Tyr Trp Cys Val Met Ser Cys Ile Ala Arg Tyr Val Cys Gly
        195                 200                 205

Leu Asn Phe Thr Trp Leu Val Asn Ser Ala Ala His Met Phe Gly Asn
    210                 215                 220

Lys Pro Tyr Asp Arg Lys Ile Gln Pro Val Glu Asn Leu Met Val Ser
225                 230                 235                 240

Ile Leu Ala Met Gly Glu Gly Trp His Asn Tyr His His Thr Phe Pro
                245                 250                 255

Trp Asp Tyr Lys Ala Ala Glu Leu Gly Asn Tyr Lys Val Asn Ala Thr
            260                 265                 270

Thr Leu Leu Leu Asp Leu Phe Ala Lys Ile Gly Trp Ala Tyr Asp Leu
        275                 280                 285

Lys Ser Pro Ser Lys Gln Leu Ile Gln Gln Val Ile Glu Asn His Gly
290                 295                 300

Asp Gly Thr Arg Arg Asp
305                 310

<210> SEQ ID NO 17
<211> LENGTH: 320
<212> TYPE: PRT
<213> ORGANISM: Tribolium castaneum

<400> SEQUENCE: 17

Met Ser Thr Leu Glu Thr Gln Val Gln Ile Val Trp Arg Asn Val Ile
 1               5                  10                  15

Leu Phe Ile Tyr Leu His Val Ala Ala Ile Tyr Gly Leu Tyr Phe Thr
                 20                  25                  30

Phe Thr Ala Ala Lys Trp Pro Thr Ile Leu Phe Thr Tyr Phe Leu Thr
             35                  40                  45

Ile Ile Ser Thr Gln Gly Thr Gly Ala Gly Val His Arg Leu Trp Ser
 50                  55                  60

His Arg Ser Tyr Lys Ala Lys Leu Pro Leu Arg Ile Leu Leu Cys Ile
 65                  70                  75                  80

Tyr Gln Thr His Cys Leu Gln Asn His Ile Tyr Glu Trp Val Arg Asp
                 85                  90                  95
```

His Arg Ala His His Lys Phe Ser Asp Thr Asp Ala Asp Pro His Asn
            100                 105                 110

Ser Thr Arg Gly Phe Phe Ser His Met Gly Trp Leu Leu Val Arg
            115                 120                 125

Lys His Pro Gln Val Lys Ile Lys Gly Lys Leu Ile Asp Leu Ser Asp
            130                 135                 140

Leu Glu Glu Asp Gln Val Val Met Phe Gln Lys Lys Tyr Tyr Leu Ile
145                 150                 155                 160

Leu Ala Pro Phe Phe Ala Phe Leu Leu Pro Ala Trp Val Pro Trp Tyr
                165                 170                 175

Phe Trp Gly Glu Asp Leu His Val Ser Trp Cys Val Ala Ser Met Leu
                180                 185                 190

Arg Tyr Ala Leu Ser Leu His Gly Thr Trp Leu Val Asn Ser Ala Ala
            195                 200                 205

His Met Trp Gly Thr Arg Pro Tyr Asp Arg Asn Ile Lys Ala Thr Glu
            210                 215                 220

Thr Lys Val Val Ser Tyr Ile Thr Asn Gly Glu Arg Phe His Asn Tyr
225                 230                 235                 240

His His Thr Phe Pro Trp Asp Tyr Lys Ala Ala Glu Leu Gly Ser Tyr
                245                 250                 255

Trp Gly Asn Trp Ser Thr Ala Phe Ile Asp Phe Met Ala Lys Ile Gly
                260                 265                 270

Trp Ala Tyr Asp Leu Lys Ile Ile Pro Pro Glu Leu Val Glu Lys Arg
            275                 280                 285

Ala Lys Arg Thr Gly Glu Cys Thr His Lys Val Trp Gly Trp Gly Asp
            290                 295                 300

Lys Asp Ile Asp Lys Glu Glu Ile Glu Ile Val Glu Arg Asn Arg Gly
305                 310                 315                 320

<210> SEQ ID NO 18
<211> LENGTH: 318
<212> TYPE: PRT
<213> ORGANISM: Tribolium castaneum

<400> SEQUENCE: 18

Met Ser Ser Glu Leu Ala Pro Leu Asn Ile Arg Pro Val Trp Leu Lys
1               5                   10                  15

Ile Val Tyr Phe Ala Tyr Leu His Tyr Gly Thr Ile Leu Gly Thr Tyr
                20                  25                  30

Tyr Leu Leu Thr Ala Ala Gln Trp Lys Thr Ile Leu Trp Thr Tyr Leu
            35                  40                  45

Leu Leu Leu Ser Ala Thr His Gly Ile Ala Val Gly Ala His Arg Leu
50                  55                  60

Trp Ala His Arg Ala Tyr Lys Ala Lys Leu Pro Leu Arg Leu Leu Leu
65                  70                  75                  80

Ala Phe Asp Gln Thr Leu Thr Phe Gln Lys Asp Ile Tyr Asp Trp Val
                85                  90                  95

Arg Asp His Arg Ile His His Lys Tyr Ser Asp Thr Glu Tyr Asp Pro
            100                 105                 110

His Asn Ala Thr Arg Gly Phe Phe Tyr Ser His Ile Gly Trp Leu Met
            115                 120                 125

Ile Lys Lys Ser Asp Lys Val Ile Ala Lys Gly Lys Glu Leu Asp Leu
            130                 135                 140

Ser Asp Leu Glu Gln Asp Pro Val Val Trp Tyr Gln Arg Lys Tyr Tyr

```
145                 150                 155                 160
Trp Tyr Met Ala Pro Phe Leu Ala Phe Ile Phe Pro Ala Met Val Pro
                165                 170                 175

Trp Tyr Phe Trp Ser Glu Gln Phe Lys Val Ser Trp Tyr Leu Cys Ser
                180                 185                 190

Ile Phe Arg Leu Cys Val Thr Leu His Gly Thr Cys Leu Val Asn Ser
                195                 200                 205

Ala Ala His Ile Trp Gly Ser Lys Pro Tyr Asp Lys Asn Ile Lys Pro
                210                 215                 220

Val Glu Thr Ser Trp Val Ala His Ile Ser His Gly Glu Gly Trp His
225                 230                 235                 240

Asn Tyr His His Val Phe Pro Trp Asp Tyr Lys Ala Ala Glu Leu Gly
                245                 250                 255

Ser Tyr Tyr Gly Asn Trp Asn Thr Ala Phe Ile Asp Phe Met Ala Lys
                260                 265                 270

Ile Gly Trp Ala Tyr Asp Leu Lys Ser Ala Pro Leu Asp Met Val Lys
                275                 280                 285

Lys Arg Gly Glu Arg Thr Gly Asp Gly Thr Lys Leu Trp Gly Trp Gly
                290                 295                 300

Asp Glu Asp Met Asp Lys Glu Asp Val Cys Lys Ala Lys Asn
305                 310                 315

<210> SEQ ID NO 19
<211> LENGTH: 321
<212> TYPE: PRT
<213> ORGANISM: Tribolium castaneum

<400> SEQUENCE: 19

Met Glu Arg Glu Ile Ala Trp Lys Lys Val Phe Phe Val Tyr Leu
1               5                   10                  15

His Leu Gly Ala Leu Tyr Gly Leu Tyr Leu Ile Leu Thr Glu Ala Ser
                20                  25                  30

Trp Leu Thr Cys Phe Trp Phe Tyr Phe Leu Val Gln Ile Ser Thr Gln
                35                  40                  45

Gly Thr Gly Ala Gly Val His Arg Leu Trp Ala His Arg Ala Tyr Lys
                50                  55                  60

Ala Thr Val Pro Leu Arg Leu Leu Leu Thr Phe Tyr Gln Thr Leu Thr
65                  70                  75                  80

Phe Gln Lys Asp Ile Tyr Asp Trp Val Arg Asp His Arg Val His His
                85                  90                  95

Lys Tyr Ser Asp Thr Glu Pro Asp Pro His Asn Ala Ser Asn Gly Phe
                100                 105                 110

Phe Tyr Ser His Met Gly Trp Leu Met Leu Lys Lys Thr Gln Cys Thr
                115                 120                 125

Ile Asp Lys Gly Lys Lys Leu Asp Leu Ser Asp Leu Glu Ala Asp Pro
                130                 135                 140

Ile Val Met Phe Gln Arg Lys Tyr Tyr Trp Tyr Leu Ala Pro Val Ile
145                 150                 155                 160

Ala Leu Gly Met Pro Ala Phe Val Pro Trp Tyr Phe Trp Gly Glu Arg
                165                 170                 175

Phe Val Val Ser Trp Tyr Val Cys Ser Met Phe Arg Tyr Cys Leu Thr
                180                 185                 190

Leu His Gly Thr Cys Leu Val Asn Ser Ala Ala His Ile Tyr Gly Asn
                195                 200                 205
```

Arg Pro Tyr Asp Lys Asn Ile Leu Pro Thr Gln Asn Leu Leu Val Ser
210                 215                 220

Tyr Ile Thr Asn Gly Glu Gly Phe His Asn Tyr His His Ala Phe Pro
225                 230                 235                 240

Trp Asp Tyr Lys Ala Ala Glu Leu Gly Ser Tyr Tyr Gly Asn Trp Ser
            245                 250                 255

Thr Ala Phe Ile Asp Phe Met Ala Arg Ile Gly Trp Ala Tyr Asp Leu
                260                 265                 270

Lys Ser Val Pro Leu Ala Met Val Glu Lys Arg Val Lys Arg Thr Gly
            275                 280                 285

Asp Gly Thr His Asn Val Trp Gly Trp Gly Asp Lys Asp Leu His Pro
290                 295                 300

Asp Asp Ala Lys Met Val Glu Ile Thr His Thr Arg Ala Ser Gln Thr
305                 310                 315                 320

Gly

<210> SEQ ID NO 20
<211> LENGTH: 302
<212> TYPE: PRT
<213> ORGANISM: Tribolium castaneum

<400> SEQUENCE: 20

Met Phe Leu Arg Thr Ile Thr Ser Lys Phe Tyr Ser Asp Gln Ile Val
1               5                   10                  15

Trp Arg Asn Val Phe Leu Leu Ile Leu His Ile Ile Ser Leu Gln
            20                  25                  30

Gly Trp Tyr Phe Val Leu Thr Thr Asn Trp Pro Thr Leu Ile Tyr
            35                  40                  45

Gly Phe Ile Phe Gly Ala Leu Thr Gly Gln Gly Ile Lys Leu Gly Ala
50                  55                  60

His Arg Leu Trp Ala His Arg Cys Tyr Lys Ala Lys Leu Pro Leu Arg
65                  70                  75                  80

Ile Phe Leu Cys Phe Leu Gln Thr Val Thr Leu Gln Asn Pro Leu Tyr
                85                  90                  95

Glu Trp Val Arg Asp His Gln Val His His Lys Tyr Thr Asp Thr Asn
            100                 105                 110

Ala Asp Pro Leu Asn Ala Thr Arg Gly Phe Phe Phe Ser His Met Gly
            115                 120                 125

Trp Leu Leu Val Arg Lys His Pro Asn Val Ile Ala Lys Gly Lys Thr
130                 135                 140

Leu Asp Leu Ser Asp Leu Glu Glu Asp Pro Val Val Met Phe Gln Lys
145                 150                 155                 160

Lys Tyr Tyr Lys Ile Ile Ala Pro Val Leu Thr Leu Ala Ile Pro Ala
                165                 170                 175

Leu Ile Pro Trp Tyr Phe Phe Gly Glu Asp Leu Tyr Leu Ser Trp Val
            180                 185                 190

Thr Thr Cys Val Leu Pro Tyr Phe Ile Thr Leu His Ser Thr Trp Ala
            195                 200                 205

Val Asn Ser Val Ala His Ile Trp Gly Thr Lys Pro Tyr Asn Lys Asn
210                 215                 220

Ile Leu Pro Thr Glu Asn Ile Ala Val Ala Ile Val Ala Tyr Gly Glu
225                 230                 235                 240

Gly Trp His Asn Tyr His His Val Phe Pro Trp Asp Tyr Lys Ala Ala
            245                 250                 255

```
Glu Leu Gly Asn Tyr Arg Pro Asn Leu Ser Thr Ala Phe Ile Asp Phe
                260                 265                 270

Met Ala Lys Ile Ala Trp Ala Tyr Asp Leu Lys Ser Val Ser Pro Glu
            275                 280                 285

Met Leu Arg Lys Arg Lys Met Arg Thr Gly Asp Cys Asp Tyr
            290                 295                 300

<210> SEQ ID NO 21
<211> LENGTH: 356
<212> TYPE: PRT
<213> ORGANISM: Tribolium castaneum

<400> SEQUENCE: 21

Met Thr Glu Gly Ser Asp Glu Cys Ser Lys Gly Ala Cys Ser Thr Ala
1               5                   10                  15

Ala Lys Glu Thr Ser Arg Arg Leu Asn Ala Leu Thr Lys Thr Glu Ile
            20                  25                  30

Pro Glu Asn Lys Leu Lys Lys Glu Glu Phe Arg Pro Arg Ile Arg Trp
        35                  40                  45

Pro Asp Leu Thr Val Gln Val Phe Ile His Val Gly Cys Leu Tyr Gly
    50                  55                  60

Leu Tyr Leu Cys Leu Val Ser Ala Arg Leu Tyr Thr Thr Leu Phe Ala
65                  70                  75                  80

Phe Leu Thr Ile Tyr Leu Ser Gly Phe Gly Ile Thr Ala Gly Ala His
                85                  90                  95

Arg Leu Trp Ser His Arg Ala Tyr Lys Ala Lys Trp Pro Leu Lys Ile
            100                 105                 110

Leu Leu Leu Ile Leu Phe Thr Ile Thr Gly Gln Arg His Val Tyr Val
        115                 120                 125

Trp Ala Leu Asp His Arg Val His His Lys Tyr Ser Glu Thr Asp Ala
    130                 135                 140

Asp Pro His Asn Ala Lys Arg Gly Phe Leu Phe Ser His Val Gly Trp
145                 150                 155                 160

Leu Val Leu Thr Pro His Pro Asp Val Val Glu Lys Arg Lys Ala Val
                165                 170                 175

Asp Met Ser Asp Leu Glu Ala Asp Pro Leu Ile Met Trp His Lys Lys
            180                 185                 190

Leu Tyr Pro Pro Leu Phe Phe Leu Phe Val Ile Phe Leu Pro Val Phe
        195                 200                 205

Thr Pro Val Tyr Phe Trp Asn Glu Thr Ile Trp Asn Ser Phe Trp Val
    210                 215                 220

Asn Phe Asn Ala Arg Phe Cys Ile Thr Leu Asn Ile Ala Phe Phe Val
225                 230                 235                 240

Asn Ser Val Ala His Met Trp Gly Gln Lys Pro Tyr Asp Arg Tyr Ile
                245                 250                 255

Ser Pro Val Glu Asn Leu Ala Val Ser Leu Ala Ala Leu Gly Glu Gly
            260                 265                 270

Trp His Asn Tyr His His Val Phe Pro Trp Asp Tyr Arg Thr Gly Glu
        275                 280                 285

Leu Gly Asn Ser Tyr Asn Pro Ser Thr Thr Phe Ile Asp Phe Phe Ala
    290                 295                 300

Lys Ile Gly Trp Ala Tyr Asp Leu Lys Phe Ala Ser Asn Ser Met Ile
305                 310                 315                 320

Ala Arg Arg Ala Lys Lys Ser Gly Asp Gly Ser His Ile Trp Gly Tyr
                325                 330                 335
```

Gly Asp Ala Asp Ile Glu Lys Glu Asp Leu Glu Glu Leu Asn Lys Met
            340                 345                 350
Glu Asp Phe Asn
        355

<210> SEQ ID NO 22
<211> LENGTH: 353
<212> TYPE: PRT
<213> ORGANISM: Tribolium castaneum

<400> SEQUENCE: 22

Met Pro Pro Tyr Val Ser His Val Thr Gly Val Leu Asp Glu Asn Asp
1               5                   10                  15

Glu Glu Val Ser Thr Lys Asn Ile Leu Pro Glu Val Thr Lys Pro Glu
            20                  25                  30

Asn Arg Lys Leu Gln Leu Val Trp Arg Asn Ile Ile Leu Phe Ala Tyr
        35                  40                  45

Leu Tyr Leu Ala Ser Phe Tyr Gly Leu Tyr Leu Met Phe Thr Ser Ala
    50                  55                  60

Lys Leu Ala Thr Ser Ile Phe Ala Tyr Phe Leu Tyr Gln Leu Gly Gly
65                  70                  75                  80

Phe Gly Ile Thr Ala Gly Ala His Arg Leu Trp Ala His Arg Ser Phe
                85                  90                  95

Lys Ala Lys Trp Pro Leu Arg Leu Leu Leu Ala Phe Cys Asn Thr Leu
            100                 105                 110

Ala Phe Glu Asp Ser Val Ile Asp Trp Ser Arg Asp His Arg Val His
        115                 120                 125

His Lys Phe Ser Glu Thr Asp Ala Asp Pro Tyr Asn Ala Lys Arg Gly
    130                 135                 140

Phe Phe Phe Ser His Ile Gly Trp Leu Leu Cys Arg Lys His Pro Gln
145                 150                 155                 160

Val Lys Glu Lys Gly Lys Gln Ile Asp Leu Ser Asp Leu Tyr Gln Asp
                165                 170                 175

Pro Ile Leu Arg Tyr Gln Lys Lys Tyr Tyr Leu Phe Val Met Pro Val
            180                 185                 190

Ile Cys Phe Val Leu Pro Thr Ala Ala Pro Met Tyr Phe Trp Gly Glu
        195                 200                 205

Ser Phe Lys Asn Ala Phe Phe Val Asn Leu Phe Arg Tyr Cys Phe Thr
    210                 215                 220

Leu Asn Ser Thr Trp Leu Val Asn Ser Ala Ala His Leu Trp Gly Ser
225                 230                 235                 240

Lys Pro Tyr Asp Lys Phe Ile Asn Pro Ala Glu Asn Phe Ala Val Ser
                245                 250                 255

Val Leu Ala Leu Gly Glu Gly Trp His Asn Phe His His Thr Phe Pro
            260                 265                 270

Trp Asp Tyr Lys Ala Ser Glu Leu Gly Lys Tyr Ser Val Asn Phe Ser
        275                 280                 285

Ser Ala Phe Ile Asp Phe Phe Ala Lys Ile Gly Trp Ala Tyr Asp Leu
    290                 295                 300

Lys Thr Val Ser Glu Asp Leu Val Lys Lys Arg Val Leu Arg Thr Gly
305                 310                 315                 320

Asp Gly Ser His His Val Trp Gly Trp Gly Asp Met Asp Gln Ala Leu
                325                 330                 335

Glu Asp Tyr Glu Gly Ala Ile Ile Lys His Arg Lys Ser Asp Asp Phe

| | | | 340 | | | 345 | | | 350 | | |

Asn

<210> SEQ ID NO 23
<211> LENGTH: 350
<212> TYPE: PRT
<213> ORGANISM: Tribolium castaneum

<400> SEQUENCE: 23

| Met | Thr | Pro | Asn | Ala | Ser | Ile | Pro | Thr | Gly | Val | Leu | His | Glu | Asn | Asp |
|---|---|---|---|---|---|---|---|---|---|---|---|---|---|---|---|
| 1 | | | | 5 | | | | | 10 | | | | | 15 | |
| Glu | Glu | Val | Ser | Asn | Ala | Thr | Leu | Pro | Pro | Glu | Val | Asn | Lys | Pro | Asp |
| | | | 20 | | | | | 25 | | | | | 30 | | |
| Asp | Arg | Lys | Leu | Gln | Leu | Val | Trp | Arg | Asn | Ile | Ile | Leu | Phe | Ala | Tyr |
| | | 35 | | | | | 40 | | | | | 45 | | | |
| Leu | His | Leu | Ala | Ala | Leu | Tyr | Gly | Ile | Trp | Ile | Met | Phe | Thr | Ser | Ala |
| | 50 | | | | | 55 | | | | | 60 | | | | |
| Lys | Val | Ala | Thr | Ser | Leu | Phe | Gly | Ile | Leu | Leu | Tyr | Gln | Leu | Gly | Gly |
| 65 | | | | | 70 | | | | | 75 | | | | | 80 |
| Phe | Gly | Ile | Thr | Ala | Gly | Ala | His | Arg | Leu | Trp | Ala | His | Arg | Ser | Tyr |
| | | | | 85 | | | | | 90 | | | | | 95 | |
| Lys | Ala | Lys | Trp | Pro | Leu | Arg | Leu | Ile | Leu | Thr | Phe | Cys | Asn | Thr | Leu |
| | | | 100 | | | | | 105 | | | | | 110 | | |
| Ala | Phe | Glu | Asp | Ser | Val | Ile | Asp | Trp | Ser | Arg | Asp | His | Arg | Val | His |
| | | | | 115 | | | | | 120 | | | | | 125 | |
| His | Lys | Phe | Ser | Glu | Thr | Asp | Ala | Asp | Pro | His | Asn | Ala | Lys | Arg | Gly |
| | 130 | | | | | 135 | | | | | 140 | | | | |
| Phe | Phe | Phe | Ser | His | Val | Gly | Trp | Leu | Leu | Cys | Arg | Lys | His | Pro | Gln |
| 145 | | | | | 150 | | | | | 155 | | | | | 160 |
| Val | Lys | Glu | Lys | Gly | Lys | Gln | Ile | Asp | Leu | Ser | Asp | Leu | Tyr | Ala | Asp |
| | | | | 165 | | | | | 170 | | | | | 175 | |
| Pro | Ile | Leu | Arg | Phe | Gln | Lys | Lys | Tyr | Tyr | Thr | Ile | Val | Met | Pro | Leu |
| | | | 180 | | | | | 185 | | | | | 190 | | |
| Val | Ser | Phe | Val | Met | Pro | Thr | Val | Val | Pro | Met | Tyr | Leu | Trp | Gly | Glu |
| | | | | 195 | | | | | 200 | | | | | 205 | |
| Thr | Phe | Lys | Asn | Ala | Phe | Leu | Val | Asn | Leu | Phe | Arg | Tyr | Cys | Leu | Thr |
| | 210 | | | | | 215 | | | | | 220 | | | | |
| Leu | Asn | Ala | Thr | Trp | Leu | Val | Asn | Ser | Ala | Ala | His | Met | Trp | Gly | Asp |
| 225 | | | | | 230 | | | | | 235 | | | | | 240 |
| Lys | Pro | Tyr | Asp | Arg | Phe | Ile | Asn | Pro | Ala | Glu | Asn | Phe | Val | Val | Ser |
| | | | | 245 | | | | | 250 | | | | | 255 | |
| Val | Leu | Ala | Leu | Gly | Glu | Gly | Trp | His | Asn | Tyr | His | His | Thr | Phe | Pro |
| | | | 260 | | | | | 265 | | | | | 270 | | |
| Trp | Asp | Tyr | Lys | Thr | Ser | Glu | Leu | Gly | Lys | Tyr | Ser | Val | Asn | Phe | Ser |
| | | 275 | | | | | 280 | | | | | 285 | | | |
| Thr | Ala | Phe | Ile | Asp | Phe | Ala | Lys | Ile | Gly | Trp | Ala | Tyr | Asp | Leu |
| | 290 | | | | | 295 | | | | | 300 | | | | |
| Lys | Thr | Val | Ser | Ser | Glu | Met | Ile | Lys | Lys | Arg | Val | Thr | Arg | Thr | Gly |
| 305 | | | | | 310 | | | | | 315 | | | | | 320 |
| Asp | Gly | Thr | His | Glu | Ile | Trp | Gly | Trp | Gly | Asp | Lys | Asp | Gln | Ser | Gln |
| | | | | 325 | | | | | 330 | | | | | 335 | |
| Glu | Asp | Tyr | Gln | Asp | Ala | Ile | Ile | Thr | His | Arg | Lys | Ser | Ala | | |
| | | | 340 | | | | | 345 | | | | | 350 | | |

```
<210> SEQ ID NO 24
<211> LENGTH: 277
<212> TYPE: PRT
<213> ORGANISM: Tribolium castaneum

<400> SEQUENCE: 24

Met Leu Ile Leu Leu Ser Thr Ile Gly Val Thr Ala Gly Ala His Arg
1               5                   10                  15

Leu Trp Ala His Asn Ser Tyr Gln Ala Thr Thr Ser Leu Lys Ile Phe
            20                  25                  30

Leu Met Leu Cys Gln Thr Leu Ala Gly Gln Thr Ser Ile Tyr Asn Trp
        35                  40                  45

Val Arg Leu His Arg Leu His His Lys Tyr Phe Gln Thr Glu Met Asp
    50                  55                  60

Pro Phe Asn Pro Gln Lys Gly Phe Ile Tyr Ser His Phe Ile Ala Asn
65                  70                  75                  80

Asn Leu Lys Leu Ser Pro Ala Gln Glu Lys Leu Leu Glu Glu Ile Asp
                85                  90                  95

Met Ser Asp Leu Glu Gln Asp Lys Ile Val Met Phe Gln Lys Lys Tyr
            100                 105                 110

Tyr Trp Phe Leu Phe Val Ile Val Thr Leu Leu Leu Pro Ile Asn Ala
        115                 120                 125

Pro Val Glu Tyr Trp Asp Glu Thr Ile Leu Asn Ser Phe Phe Ile Leu
    130                 135                 140

Gly Trp Leu Arg Leu Gly Ile Ser Tyr His Leu Thr Leu Leu Ile His
145                 150                 155                 160

Ser Ala Ile Asn Val Phe Asp Leu Lys Gln Met Asp Arg Asn Ser Tyr
                165                 170                 175

Asp Ser Asn Ala Val Phe Phe Ile Asn Lys Ser Tyr Trp Ile Ser Tyr
            180                 185                 190

His Tyr Met Ser Pro Trp Asp Tyr Gln Thr Gly Glu Tyr Gly Lys Tyr
        195                 200                 205

Gly Ser Asp Cys Thr Ser Lys Phe Ile Arg Val Cys Ala Ala Leu Glu
    210                 215                 220

Leu Ala Thr Asp Leu Lys Thr Val Asp Ser Glu Met Ile Arg Glu Ala
225                 230                 235                 240

Leu Thr Leu Cys Val Asp Glu Lys Lys Pro Ile Glu Glu Cys Leu Thr
                245                 250                 255

Arg Leu Gly Lys Lys Ser His Asp Lys Leu Leu Lys His Tyr Leu Thr
            260                 265                 270

Pro Ser Lys Phe His
        275

<210> SEQ ID NO 25
<211> LENGTH: 290
<212> TYPE: PRT
<213> ORGANISM: Tribolium castaneum

<400> SEQUENCE: 25

Met Phe Gln Thr Pro Ile Val Trp Pro Asn Val Ile Leu Phe Ile Leu
1               5                   10                  15

Tyr His Ala Ile Ala Leu Gln Gly Trp Tyr Tyr Phe Ile Thr Phe Gln
            20                  25                  30

Thr Asn Leu Arg Thr Ile Phe Trp Ala Phe Leu Ile Leu Val Leu Ala
        35                  40                  45

Gly Gln Gly Ile Thr Ser Gly Val His Arg Leu Trp Ser His Arg Ser
```

```
            50                  55                  60
Tyr Lys Ala Lys Leu Pro Leu Arg Ile Phe Leu Cys Leu Cys Gln Thr
 65                  70                  75                  80

Ile Ser Phe Gln Asn Ser Ile Tyr Glu Trp Ala Arg Asp His Arg Ala
                 85                  90                  95

His His Lys Phe Ser Asp Thr Asp Ala Asp Pro His Asn Ile Lys Arg
            100                 105                 110

Gly Phe Phe Ala His Met Gly Trp Leu Leu Val Arg Lys His Pro
            115                 120                 125

Gln Val Lys Met Lys Gly Gln Leu Ile Asp Leu Ser Asp Leu Glu Asn
            130                 135                 140

Asp Pro Val Val Arg Phe Gln Lys Lys Tyr Tyr His Val Leu Ala Pro
145                 150                 155                 160

Leu Cys Cys Phe Val Val Pro Thr Met Val Pro Trp Tyr Phe Trp Lys
                165                 170                 175

Glu Asn Phe Tyr Val Ser Phe Cys Val Cys Met Leu Arg Tyr Leu Ile
                180                 185                 190

Ser Leu His Phe Thr Trp Leu Val Asn Ser Ala Ala His Leu Trp Gly
                195                 200                 205

Phe Lys Pro Tyr Asp Arg Phe Ile Lys Pro Ser Glu Asn Gln Ile Val
210                 215                 220

Ala Lys Leu Thr Met Gly Glu Gly Trp His Asn Tyr His His Thr Phe
225                 230                 235                 240

Pro Trp Asp Tyr Lys Ala Ala Glu Leu Asp Ser Tyr Asn Gly Asn Leu
                245                 250                 255

Ser Thr Ala Phe Ile Asp Leu Met Ala Lys Ile Gly Trp Ala Tyr Asp
                260                 265                 270

Leu Lys Thr Val Pro Leu Asp Val Ile Arg Lys Arg Val Leu Arg Thr
                275                 280                 285

Gly Gln
    290

<210> SEQ ID NO 26
<211> LENGTH: 329
<212> TYPE: PRT
<213> ORGANISM: Tribolium castaneum

<400> SEQUENCE: 26

Met Arg Gln Ile Gln Val Arg Phe Glu Ser Gln Ile Gly Leu Leu Tyr
  1               5                  10                  15

Leu Lys Thr Ser Ala Phe Pro Arg Thr Ile Ile Ser Arg Lys Lys Met
                 20                  25                  30

Leu Glu Ile Val Trp Lys Asn Val Phe Ser Phe Ile Leu Tyr His Tyr
             35                  40                  45

Leu Ala Phe His Gly Leu Phe Tyr Leu Val Thr Gly His Thr His Trp
 50                  55                  60

Ala Thr Phe Ala Phe Asn Leu Phe Leu Ala Gln Leu Ser Asn Leu Gly
 65                  70                  75                  80

Thr Ile Ser Gly Ala His Arg Leu Trp Thr His Arg Ser Tyr Gln Ala
                 85                  90                  95

Gln Leu Pro Leu Lys Leu Phe Leu Met Phe Cys Asn Asn Ile Ser Asn
            100                 105                 110

Gln Asn Ser Ile Tyr Asp Trp Val Arg Asp His Arg Val His His Lys
            115                 120                 125
```

```
Phe Ser Asp Thr Asp Ala Asp Pro His Asn Ile Lys Arg Gly Phe Phe
    130                 135                 140

Phe Ala His Met Gly Trp Leu Met Val Arg Lys His Pro Glu Val Thr
145                 150                 155                 160

Ile Lys Gly Gln Thr Leu Asp Phe Ser Asp Ile Asp Ser Asp Lys Leu
                165                 170                 175

Ile Gln Phe Gln Arg Lys Tyr Phe Lys Phe Leu Ala Phe Phe Cys Ser
            180                 185                 190

Ile Phe Leu Pro Val Val Pro Trp Tyr Tyr Trp Gly Glu Asn Trp
            195                 200                 205

Tyr Val Ser Leu Cys Ile Thr Phe Val Arg Tyr Val Gly Thr Leu His
    210                 215                 220

Gly Thr Trp Leu Val Asn Ser Ala Ala His Val Tyr Gly Thr Arg Pro
225                 230                 235                 240

Tyr Asp Ser Asp Ile Lys Pro Thr Glu Asn Pro Ile Val Ala Tyr Ile
                245                 250                 255

Thr Met Gly Glu Gly Trp His Asn Tyr His His Thr Phe Pro Trp Asp
            260                 265                 270

Tyr Arg Ala Ser Glu Phe Asp Ser Phe Asn Gly Asn Val Asn Thr Val
    275                 280                 285

Phe Ile Asn Phe Met Ala Lys Val Gly Leu Ala His Gly Leu Lys Thr
290                 295                 300

Ala Ser Leu Ser Leu Ile Gln Arg Lys Lys Leu Lys Ser Thr Asn Ser
305                 310                 315                 320

Thr Thr Asn Lys Lys Gln Leu Gln Lys
                325

<210> SEQ ID NO 27
<211> LENGTH: 374
<212> TYPE: PRT
<213> ORGANISM: Tribolium castaneum

<400> SEQUENCE: 27

Met Ala Pro Asn Ser Leu Ser Lys Ser Glu Tyr Leu Gly Glu Pro Val
1               5                   10                  15

Gln Ile Ile Ser Lys Pro Asn Val Glu Tyr Ser Ile Glu Thr Gln Asn
                20                  25                  30

Lys Tyr Asn Leu Pro His Asn Arg Trp Gln Ile Val Trp Arg Asn Val
            35                  40                  45

Leu Ile Phe Ala Tyr Leu His Tyr Ala Ala Phe Tyr Gly Leu Tyr Tyr
    50                  55                  60

Met Leu Thr Leu Ala Gln Trp Lys Ser Ile Ile Trp Gly Tyr Ala Val
65                  70                  75                  80

Ile Leu Phe Ala Ser Ile Gly Val Thr Gly Gly Ala His Arg Leu Trp
                85                  90                  95

Ala His Arg Ser Tyr Lys Ala Lys Leu Pro Leu Arg Ile Tyr Leu Ala
            100                 105                 110

Phe Trp Gln Thr Val Ala Leu Gln Asn His Ile Tyr Glu Trp Val Arg
    115                 120                 125

Asp His Arg Val His His Lys Phe Thr Asp Thr Asp Ala Asp Pro His
    130                 135                 140

Asn Ser Asn Gln Gly Phe Phe Ser His Met Gly Trp Leu Met Leu
145                 150                 155                 160

Lys Lys His Lys Asp Val Phe Ile Lys Gly Lys Thr Ile Asp Leu Ser
                165                 170                 175
```

Asp Val Ala Ala Asp Pro Val Val Gln Phe Gln Lys Lys Tyr Tyr Leu
            180                 185                 190

Ile Leu Ala Pro Ile Leu Thr Phe Val Phe Pro Ala Ile Val Pro Trp
            195                 200                 205

Tyr Phe Trp Asn Glu Asn Pro Ile Val Cys Tyr Tyr Ser Leu Ala Ile
            210                 215                 220

Leu Arg Tyr Ile Leu Asn Leu His Gly Ala Trp Leu Val Asn Ser Ala
225                 230                 235                 240

Ala His Ile Trp Gly Tyr Lys Pro Phe Asp Lys Asn Ile Asn Ala Thr
            245                 250                 255

Asp Asn Ile Ser Val Ala Ile Ile Ala Phe Gly Glu Gly Trp His Asn
            260                 265                 270

Tyr His His Val Phe Pro Trp Asp Tyr Lys Ala Ala Glu Leu Gly Asn
            275                 280                 285

Tyr Arg Met Asn Phe Thr Thr Ala Phe Leu Asp Leu Met Ala Arg Ile
            290                 295                 300

Gly Gln Ala Tyr Asp Leu Lys Thr Val Ser Val Glu Met Ile Asn Lys
305                 310                 315                 320

Arg Arg Lys Arg Thr Gly Asp Gly Thr Gly Val Val Asp Pro Leu Val
            325                 330                 335

Glu Asn Lys Glu Asp His Arg His Glu Asp Thr Val Trp Gly Trp Gly
            340                 345                 350

Asp Lys Asp Met Asn Gln Asp Glu Met Asn Leu Val Glu Ile Tyr Asn
            355                 360                 365

Pro Ser Ser Lys Glu Pro
            370

<210> SEQ ID NO 28
<211> LENGTH: 358
<212> TYPE: PRT
<213> ORGANISM: Tribolium castaneum

<400> SEQUENCE: 28

Met Ser Ala Gln Thr Ile Thr Thr Thr Glu Thr Thr Gln Asn Ala Gln
1               5                   10                  15

Lys Pro Gln Gln Tyr His Trp Arg Met Val Trp Arg Asn Ile Ile Leu
            20                  25                  30

Tyr Ile Ile Met His Leu Thr Gly Phe Tyr Gly Leu Tyr Leu Ala Met
            35                  40                  45

Phe Tyr Ala Gln Trp Lys Thr Val Phe Tyr Ser Trp Phe Leu Leu Val
            50                  55                  60

Ile Ala Leu Gln Gly Val Thr Ala Gly Ser His Arg Leu Trp Ala His
65                  70                  75                  80

Lys Ala Tyr Lys Ala Arg Leu Pro Leu Arg Met Leu Leu Cys Ile Phe
            85                  90                  95

Gln Thr Leu Ser Leu Gln Asn His Ile Tyr Asp Trp Ala Thr Tyr His
            100                 105                 110

Arg Val His His Lys Phe Val Asp Thr Asn Ala Asp Pro His Asn Ser
            115                 120                 125

Arg Arg Gly Phe Phe Ser His Met Gly Trp Leu Phe Ile Glu Pro
            130                 135                 140

His Lys Asp Val Glu Asp Lys Tyr Lys Ser Ile Asp Phe Ser Asp Leu
145                 150                 155                 160

His Ala Asp Ser Val Val Met Ile Gln Lys Lys Tyr Tyr His Thr Phe

```
                165                 170                 175
Phe Ala Pro Val Ile Gly Phe Tyr Leu Pro Ala Ala Ile Pro Trp Tyr
                    180                 185                 190

Phe Trp Gly Glu Asn Phe Trp Thr Ala Phe Phe Val Ala Thr Met Leu
            195                 200                 205

Arg Tyr Cys Ala Cys Thr Asn Ile Thr Phe Leu Val Asn Ser Trp Ala
        210                 215                 220

His Ile Tyr Gly Ser Arg Pro Tyr Asp Lys Asn Ile Tyr Pro Thr Glu
225                 230                 235                 240

Ser Ala Thr Ile Ala Val Leu Thr Gly Gly Glu Gly Trp His Asn Tyr
                245                 250                 255

His His Thr Phe Pro Trp Asp Tyr Lys Thr Gly Glu Phe Gly Lys Tyr
            260                 265                 270

Arg Ser Asn Leu Thr Thr Gly Phe Leu Asp Phe Met Ala Ala Ile Gly
        275                 280                 285

Trp Ala Tyr Asp Leu Lys Thr Val Ser Glu Glu Met Ile Met Lys Arg
    290                 295                 300

Val Leu Arg Thr Gly Asp Gly Thr Arg Lys Phe Asp Lys Ile Asp Lys
305                 310                 315                 320

Ile Leu Asn Val Asp Asp Asp His His His Glu Asp Met Leu Trp Gly
                325                 330                 335

Trp Gly Asp Ser Asp Met Ala Lys Glu Glu Met Asn Tyr Val Lys Ile
            340                 345                 350

His Asn Arg Lys Glu Asp
            355

<210> SEQ ID NO 29
<211> LENGTH: 335
<212> TYPE: PRT
<213> ORGANISM: Tribolium castaneum

<400> SEQUENCE: 29

Met Gly Ala Leu Lys Gln Thr Glu Glu Lys Thr Leu Leu Pro Gln
1               5                   10                  15

Asp Ile Gly Thr Asp Tyr Thr Phe Lys Arg Lys Ile Val Trp Phe Asn
                20                  25                  30

Ala Ile Gly Phe Phe Ile Leu His Leu Leu Ala Leu Tyr Gly Gly Tyr
            35                  40                  45

Arg Leu Leu His Cys His Ile Leu Thr Pro Leu Phe Ala Leu Ala Leu
    50                  55                  60

Met Phe Val Ser Gly Glu Gly Ile Thr Leu Gly Ala His Arg Leu Tyr
65                  70                  75                  80

Ser His Lys Ala Phe Lys Ala Ser Phe Val Val Arg Leu Ala Val Ile
                85                  90                  95

Ile Leu His Thr Ile Ala Gly Gln Asn Cys Leu Tyr Ile Trp Val Arg
            100                 105                 110

Asp His Arg Gln His His Lys Tyr Ser Asp Thr Asp Ala Asp Pro His
        115                 120                 125

Asn Ser Asn Arg Gly Phe Phe Phe Ser His Ile Gly Trp Leu Met Ser
    130                 135                 140

Arg Lys His Pro Ala Val Ile Ala Lys Gly Lys Thr Ile Asp Met Ser
145                 150                 155                 160

Asp Leu Glu Asn Asp Ser Leu Val Met Leu Gln Lys Glu His Tyr Lys
                165                 170                 175
```

```
Phe Leu Tyr Ile Ile Phe Ala Ile Gly Ile Pro Ala Ile Pro Ile
                180                 185                 190

Tyr Gly Trp Asn Glu Ser Phe Thr Asn Ser Leu Phe Ile Ser Tyr Phe
            195                 200                 205

Gly Arg Tyr Ile Leu Gln Leu His Ala Thr Trp Leu Ile Asn Ser Ala
        210                 215                 220

Thr His Leu Tyr Gly Thr Lys Pro Tyr Asp Lys Phe Met Asn Pro Val
225                 230                 235                 240

Glu Asn Tyr Phe Ile Ser Met Ile Ala Leu Gly Glu Gly Trp His Asn
                245                 250                 255

Tyr His His Ala Phe Pro Ser Asp Tyr Arg Ala Ala Glu Tyr Gly Val
            260                 265                 270

Arg Tyr Ser Ile Thr Thr Phe Leu Ile Asp Ala Leu Ala Phe Phe Gly
        275                 280                 285

Leu Leu Tyr Asp Leu Lys Glu Ala Asn Ser Glu Gln Val Lys Ile Arg
290                 295                 300

Ala Val Lys Lys Gly Asp Gly Ser His Pro Val Phe Gly Lys Gln Lys
305                 310                 315                 320

Glu Met Glu Val Asn Phe Ser Asp Arg Gln Val Thr Ala Asn Gly
                325                 330                 335

<210> SEQ ID NO 30
<211> LENGTH: 389
<212> TYPE: PRT
<213> ORGANISM: Tribolium castaneum

<400> SEQUENCE: 30

Met Ala Pro Asn Leu Leu Gly Asn Ser Thr Leu Phe Leu Ala Glu Thr
1               5                   10                  15

Asn Ser Ala Glu Pro Ile Gln Ile Ile Ser Lys Pro Gly Leu Gln Asp
                20                  25                  30

Val Leu Pro Gln Val Lys Pro Gln Ile Ser Ser Arg Ser Ser Val Ser
            35                  40                  45

Gln Tyr Arg Trp Gln Ile Val Trp Arg Asn Val Leu Ile Phe Ile Tyr
        50                  55                  60

Leu His Ile Ala Gly Ile Tyr Gly Leu Tyr Tyr Ala Ile Ala Gln Ala
65                  70                  75                  80

Gln Trp Lys Thr Leu Leu Trp Gly Tyr Leu Val Ile Leu Ala Ser Gly
                85                  90                  95

Ile Gly Val Thr Ala Gly Ala His Arg Leu Trp Ala His Arg Thr Tyr
            100                 105                 110

Lys Ala Lys Leu Pro Leu Arg Ile Tyr Leu Ala Phe Cys Gln Thr Val
        115                 120                 125

Ala Leu Gln Asn Asp Ile Tyr Glu Trp Val Arg Asp His Arg Val His
130                 135                 140

His Lys Phe Thr Asp Thr Asp Ala Asp Pro His Asn Ser Asn Arg Gly
                150                 155                 160
    145

Phe Phe Phe Ser His Met Gly Trp Leu Leu Val Lys Lys His Lys Asp
                165                 170                 175

Val Phe Val Lys Gly Lys Thr Val Asp Met Ser Asp Val Glu Ala Asp
            180                 185                 190

Pro Val Val Arg Phe Gln Arg Lys Tyr Tyr Ile Ile Leu Thr Pro Ile
        195                 200                 205

Leu Thr Phe Val Phe Pro Ala Ile Val Pro Trp Tyr Phe Trp Asn Glu
210                 215                 220
```

```
Thr Pro Thr Val Cys Phe Tyr Ser Val Ala Ile Phe Arg Tyr Ile Leu
225                 230                 235                 240

Thr Leu His Gly Thr Trp Leu Val Asn Ser Ala Ala His Ile Trp Gly
            245                 250                 255

Tyr Arg Pro Tyr Asp Lys Asn Ile Asn Ala Thr Glu Asn Lys Ser Val
        260                 265                 270

Ser Ile Leu Ala Phe Gly Glu Gly Trp His Asn Tyr His His Val Phe
    275                 280                 285

Pro Trp Asp Tyr Lys Ala Ala Glu Leu Gly Asn Tyr Arg Met Asn Phe
290                 295                 300

Thr Thr Ala Phe Leu Asp Leu Met Ser Lys Ile Gly Gln Ala Tyr Asp
305                 310                 315                 320

Leu Lys Thr Val Ser Val Asp Met Ile Asn Lys Arg Arg Lys Arg Thr
                325                 330                 335

Gly Asp Gly Thr Gly Leu Val Asp Glu Glu Leu Leu Glu Asn Glu Asp
            340                 345                 350

Lys His His His His Asp Asp Ser Ile Trp Gly Trp Gly Asp Lys
            355                 360                 365

Asp Met Lys Gln Asp Asp Met Asp Met Val Gln Val His Asn Pro Ser
    370                 375                 380

Arg Glu Lys Phe Asp
385

<210> SEQ ID NO 31
<211> LENGTH: 42
<212> TYPE: PRT
<213> ORGANISM: Tribolium castaneum

<400> SEQUENCE: 31

His Asn Tyr His His Ala Tyr Pro Trp Asp Tyr Lys Ala Ala Glu Ile
1               5                   10                  15

Gly Met Pro Leu Asn Ser Thr Ala Ser Leu Ile Arg Leu Cys Ala Ser
            20                  25                  30

Leu Gly Trp Ala Tyr Asp Leu Lys Ser Val
        35                  40

<210> SEQ ID NO 32
<211> LENGTH: 39
<212> TYPE: DNA
<213> ORGANISM: Artificial
<220> FEATURE:
<223> OTHER INFORMATION: Oligonucleotide

<400> SEQUENCE: 32
aagcagtggt atcaacgcag agtggccatt acggccggg                            39

<210> SEQ ID NO 33
<211> LENGTH: 59
<212> TYPE: DNA
<213> ORGANISM: Artificial
<220> FEATURE:
<223> OTHER INFORMATION: Oligonucleotide
<220> FEATURE:
<221> NAME/KEY: -d(T)
<222> LOCATION: (28)..(28)
<220> FEATURE:
<221> NAME/KEY: misc_feature
<222> LOCATION: (29)..(58)
<223> OTHER INFORMATION: v = A, G or C
<220> FEATURE:
<221> NAME/KEY: misc_feature
```

```
<222> LOCATION: (59)..(59)
<223> OTHER INFORMATION: n = A, G, C or T

<400> SEQUENCE: 33
attctagagg ccgaggcggc cgacatgtvv vvvvvvvvv vvvvvvvvv vvvvvvvn        59

<210> SEQ ID NO 34
<211> LENGTH: 23
<212> TYPE: DNA
<213> ORGANISM: Artificial
<220> FEATURE:
<223> OTHER INFORMATION: Oligonucleotide

<400> SEQUENCE: 34
aagcagtggt atcaacgcag agt                                           23

<210> SEQ ID NO 35
<211> LENGTH: 26
<212> TYPE: DNA
<213> ORGANISM: Artificial
<220> FEATURE:
<223> OTHER INFORMATION: Oligonucleotide

<400> SEQUENCE: 35
attatgagcg gatcggcttc caagtc                                        26

<210> SEQ ID NO 36
<211> LENGTH: 26
<212> TYPE: DNA
<213> ORGANISM: Artificial
<220> FEATURE:
<223> OTHER INFORMATION: Oligonucleotide

<400> SEQUENCE: 36
cgaaacaatt tggaattcgt tttggg                                        26

<210> SEQ ID NO 37
<211> LENGTH: 24
<212> TYPE: DNA
<213> ORGANISM: Artificial
<220> FEATURE:
<223> OTHER INFORMATION: Oligonucleotide

<400> SEQUENCE: 37
ggatccatgg cccccaacag caca                                          24

<210> SEQ ID NO 38
<211> LENGTH: 24
<212> TYPE: DNA
<213> ORGANISM: Artificial
<220> FEATURE:
<223> OTHER INFORMATION: Oligonucleotide

<400> SEQUENCE: 38
gaattcttaa tctctgcgtg tgcg                                          24

<210> SEQ ID NO 39
<211> LENGTH: 24
<212> TYPE: DNA
<213> ORGANISM: Artificial
<220> FEATURE:
<223> OTHER INFORMATION: Oligonucleotide

<400> SEQUENCE: 39
ggatccatgt caacgcttga aaca                                          24
```

<210> SEQ ID NO 40
<211> LENGTH: 24
<212> TYPE: DNA
<213> ORGANISM: Artificial
<220> FEATURE:
<223> OTHER INFORMATION: Oligonucleotide

<400> SEQUENCE: 40
gaattcttat cctcgatttc gttc                                              24

<210> SEQ ID NO 41
<211> LENGTH: 24
<212> TYPE: DNA
<213> ORGANISM: Artificial
<220> FEATURE:
<223> OTHER INFORMATION: Oligonucleotide

<400> SEQUENCE: 41
ggatccatgt ctagcgagct agcg                                              24

<210> SEQ ID NO 42
<211> LENGTH: 24
<212> TYPE: DNA
<213> ORGANISM: Artificial
<220> FEATURE:
<223> OTHER INFORMATION: Oligonucleotide

<400> SEQUENCE: 42
gaattcttaa tttttcgcct taca                                              24

<210> SEQ ID NO 43
<211> LENGTH: 27
<212> TYPE: DNA
<213> ORGANISM: Artificial
<220> FEATURE:
<223> OTHER INFORMATION: Oligonucleotide

<400> SEQUENCE: 43
ggatccatgg aacgtgaaat cgcgtgg                                           27

<210> SEQ ID NO 44
<211> LENGTH: 24
<212> TYPE: DNA
<213> ORGANISM: Artificial
<220> FEATURE:
<223> OTHER INFORMATION: Oligonucleotide

<400> SEQUENCE: 44
gaattcttat cctgtttgtg aagc                                              24

<210> SEQ ID NO 45
<211> LENGTH: 24
<212> TYPE: DNA
<213> ORGANISM: Artificial
<220> FEATURE:
<223> OTHER INFORMATION: Oligonucleotide

<400> SEQUENCE: 45
ggatccatgt ttttacgtac aata                                              24

<210> SEQ ID NO 46
<211> LENGTH: 24
<212> TYPE: DNA
<213> ORGANISM: Artificial
<220> FEATURE:
<223> OTHER INFORMATION: Oligonucleotide

```
<400> SEQUENCE: 46
gaattcttaa taatcacaat cccc                                          24

<210> SEQ ID NO 47
<211> LENGTH: 27
<212> TYPE: DNA
<213> ORGANISM: Artificial
<220> FEATURE:
<223> OTHER INFORMATION: Oligonucleotide

<400> SEQUENCE: 47
aagcttatga cggaaggcag cgatgaa                                       27

<210> SEQ ID NO 48
<211> LENGTH: 29
<212> TYPE: DNA
<213> ORGANISM: Artificial
<220> FEATURE:
<223> OTHER INFORMATION: Oligonucleotide

<400> SEQUENCE: 48
gcggccgctc agttaaaatc ctccatttt                                     29

<210> SEQ ID NO 49
<211> LENGTH: 24
<212> TYPE: DNA
<213> ORGANISM: Artificial
<220> FEATURE:
<223> OTHER INFORMATION: Oligonucleotide

<400> SEQUENCE: 49
ggatccatgc caccctatgt gtcc                                          24

<210> SEQ ID NO 50
<211> LENGTH: 24
<212> TYPE: DNA
<213> ORGANISM: Artificial
<220> FEATURE:
<223> OTHER INFORMATION: Oligonucleotide

<400> SEQUENCE: 50
gcatgcttaa ttaaaatcgt caga                                          24

<210> SEQ ID NO 51
<211> LENGTH: 24
<212> TYPE: DNA
<213> ORGANISM: Artificial
<220> FEATURE:
<223> OTHER INFORMATION: Oligonucleotide

<400> SEQUENCE: 51
ggatccatga caccaaatgc ttca                                          24

<210> SEQ ID NO 52
<211> LENGTH: 24
<212> TYPE: DNA
<213> ORGANISM: Artificial
<220> FEATURE:
<223> OTHER INFORMATION: Oligonucleotide

<400> SEQUENCE: 52
gaattcctac gcactcttcc tatg                                          24

<210> SEQ ID NO 53
```

```
<211> LENGTH: 24
<212> TYPE: DNA
<213> ORGANISM: Artificial
<220> FEATURE:
<223> OTHER INFORMATION: Oligonucleotide

<400> SEQUENCE: 53
ggtaccatgc taatcttact ttcc                                              24

<210> SEQ ID NO 54
<211> LENGTH: 24
<212> TYPE: DNA
<213> ORGANISM: Artificial
<220> FEATURE:
<223> OTHER INFORMATION: Oligonucleotide

<400> SEQUENCE: 54
ctcgagctaa tgaaattttg aagg                                              24

<210> SEQ ID NO 55
<211> LENGTH: 30
<212> TYPE: DNA
<213> ORGANISM: Artificial
<220> FEATURE:
<223> OTHER INFORMATION: Oligonucleotide

<400> SEQUENCE: 55
ggatccatgt ttcaaacacc catcgtctgg                                        30

<210> SEQ ID NO 56
<211> LENGTH: 33
<212> TYPE: DNA
<213> ORGANISM: Artificial
<220> FEATURE:
<223> OTHER INFORMATION: Oligonucleotide

<400> SEQUENCE: 56
ctcgagttat tgcccagtcc tcaaaacccg ctt                                    33

<210> SEQ ID NO 57
<211> LENGTH: 24
<212> TYPE: DNA
<213> ORGANISM: Artificial
<220> FEATURE:
<223> OTHER INFORMATION: Oligonucleotide

<400> SEQUENCE: 57
ggatccatgg tagatttgtt tttg                                              24

<210> SEQ ID NO 58
<211> LENGTH: 24
<212> TYPE: DNA
<213> ORGANISM: Artificial
<220> FEATURE:
<223> OTHER INFORMATION: Oligonucleotide

<400> SEQUENCE: 58
gaattcttat ttttgcaatt gttt                                              24

<210> SEQ ID NO 59
<211> LENGTH: 24
<212> TYPE: DNA
<213> ORGANISM: Artificial
<220> FEATURE:
<223> OTHER INFORMATION: Oligonucleotide

<400> SEQUENCE: 59
```
ggatccatgg ctccaaattc gctc	24

<210> SEQ ID NO 60
<211> LENGTH: 24
<212> TYPE: DNA
<213> ORGANISM: Artificial
<220> FEATURE:
<223> OTHER INFORMATION: Oligonucleotide

<400> SEQUENCE: 60
gaattcttac agttctttgc tact	24

<210> SEQ ID NO 61
<211> LENGTH: 24
<212> TYPE: DNA
<213> ORGANISM: Artificial
<220> FEATURE:
<223> OTHER INFORMATION: Oligonucleotide

<400> SEQUENCE: 61
ggatccatgt cggcccagac catt	24

<210> SEQ ID NO 62
<211> LENGTH: 24
<212> TYPE: DNA
<213> ORGANISM: Artificial
<220> FEATURE:
<223> OTHER INFORMATION: Oligonucleotide

<400> SEQUENCE: 62
gaattcttaa tcctccttcc tgtt	24

<210> SEQ ID NO 63
<211> LENGTH: 24
<212> TYPE: DNA
<213> ORGANISM: Artificial
<220> FEATURE:
<223> OTHER INFORMATION: Oligonucleotide

<400> SEQUENCE: 63
aagcttatgg gagcgctcaa acaa	24

<210> SEQ ID NO 64
<211> LENGTH: 24
<212> TYPE: DNA
<213> ORGANISM: Artificial
<220> FEATURE:
<223> OTHER INFORMATION: Oligonucleotide

<400> SEQUENCE: 64
gaattcttaa ccatttgccg taac	24

<210> SEQ ID NO 65
<211> LENGTH: 27
<212> TYPE: DNA
<213> ORGANISM: Artificial
<220> FEATURE:
<223> OTHER INFORMATION: Oligonucleotide

<400> SEQUENCE: 65
gaattcatgg ctcctaattt gctagga	27

<210> SEQ ID NO 66
<211> LENGTH: 27
<212> TYPE: DNA

<213> ORGANISM: Artificial
<220> FEATURE:
<223> OTHER INFORMATION: Oligonucleotide

<400> SEQUENCE: 66
ctcgagttaa tcaaatttct ctctact                                              27

<210> SEQ ID NO 67
<211> LENGTH: 1050
<212> TYPE: DNA
<213> ORGANISM: Chauliognathus lugubris

<400> SEQUENCE: 67
atgccaccca acgcccacga cagtaccggg gttatgtttg aggatgatag cgaagtatcg     60
cctcagcaga tcgaagatgt tctcaaatta tccaagaacc gagatcttcc tttggtttgg    120
agagatgtga tcaagtttgt ggttcttcac gtgatcggat tctacggctt ctatcttatg    180
ttcacatccg ctagcatctg gacgtctgtc ttagtgttcg tgaattatca tcttggaatc    240
ttgggaatca ccgccggcgc gcacaggttg tgggcccaca atcgtacaa ggcgaggtgg     300
cccctaaagc tcttcctggc ttacatcgag accctggcct tccagtttga catcatcttc    360
tgggccaagt accatcgcgt gcaccacaag tacagtgaaa ccgacgccga tcctcacaac    420
gccaagcgcg gtttcttctt ctctcacatg ggttggacca tgtgcgaaaa gaaccctgaa    480
tttgagacca gatgcaatga ggtcgatctc tctgacttat acgccgatcc catcgtgcgc    540
taccaagaaa aatactacta ccaactcttg gtcctcatct tcttcgtaat tcccacttgc    600
atgcccatgt atctctggaa cgaatccttt gaaaacgcct tctgcatcaa tctaacccgc    660
taccttatca gtcttcactg cacctggcta gtaaactctg ccgctcactt ctacggaaac    720
aagccatacg acaggtcttt gtatcccgcc gaaaacatgc tggtaactgt cttggtcaac    780
ggtgagggat ggcacaacta ccaccacacc ttcccatggg actacaaggc gtccgagttg    840
ggtctctggg ccaccaacac gactgcaggt ttcatcgaca tcatggccaa gatgggcctt    900
gcttacgatc tcaagtctgt gtctcccgac atggtcaagc gacgcgtcaa gaggaccggt    960
gatggctccc acaacatctg gggatggggc gacaaggatc tgactgaaga ggagaggcaa   1020
tgcgccgtca ttactcacaa acaaaagtga                                    1050

<210> SEQ ID NO 68
<211> LENGTH: 1050
<212> TYPE: DNA
<213> ORGANISM: Chauliognathus lugubris

<400> SEQUENCE: 68
atggcaccaa acagcaacga tgctaccgga gttttgcagg aaaccgacga cgacgtatcg     60
tctaatcaag tttttacagca aattacaaaa tcggagaagt caaaattgat aattgtttgg    120
tctaatgtaa tgtattttgt aatactacac gtgggagcgt tgtacggtct gtggttgtta    180
ttaacttcgg ctcaaatatg gacatgtctt tgggttttg cgatgtacga gtttggtgaa     240
atttgtatca cagcaggagt tcacagattg tggtcacatc gctcgtacaa agcaaagtgg    300
ccgttaaggc tgtttcatac aatgggtcaa actctagctt ttcaggatgc agtggttgat    360
tgggccagag atcacagggt tcatcataag tacagcgaaa cggacgcaga tcctcataac    420
gccaaacgtg gttttttctt ttctcacatg ggatggctta tgtgcagaaa aagtaaacaa    480
gtgaaagaaa aaggaaaaga gccagacatc tctgatttat acgcggatcc tattttacgt    540
taccaaaaaa agtattacat gctatttatg ccgctgatgt gtttcgcgtt tcctacggtc    600

```
gtaccacttt attttttggaa tgaatcgctt aaaactgcat tctttgttaa catatttaga    660
tacatattta gtttgcatgc tacctggttg gtaaactcag ctgctcatct atatggcgaa    720
aagccgtaca acaagcatat aaatcctgct gaaaacttgg ccgtttctct catagtaaac    780
ggagaaagat ggcacaatta tcaccacaca tttccgtggg attataaagc gggcgaattt    840
ggaagatacg gaacaaactt gactacagtt ttcataaacg cgatggctaa aattggtctg    900
gcatacgatc ttaaattcgt tccagaagat gtggtaaaaa gacgcgtaca taaaaccgga    960
gacggcagtc acgctgtttg gggttgggga gacaaagatc aaacagtaga agaaattagt    1020
aaaactattg tagcctataa tcagtcttag                                     1050

<210> SEQ ID NO 69
<211> LENGTH: 375
<212> TYPE: DNA
<213> ORGANISM: Chauliognathus lugubris

<400> SEQUENCE: 69
ttcttcttcg ctcatgtagg ttggttactt tgccggaagc atccagacgt tcgcaccaaa    60
ggaaaaggaa tcgatctgtc agatttatac gccgaccca ttctcagata ccaaaagaaa    120
tactatcatt atttgatgat tccactttgt tttattttac caactatggt tcccatgtac    180
tattggaacg aaacttttaa aaacgcattc tgcgtaaatc tccttcgata cacttttacg    240
cttaacgcaa tttggttgat caactcgatc gctcatttgt acggtcacaa accgtacgat    300
agaaatatca atccggccga gagcttgagt gtatcggtta tatctctggg agagggctac    360
cacaactacc accaa                                                     375

<210> SEQ ID NO 70
<211> LENGTH: 460
<212> TYPE: DNA
<213> ORGANISM: Chauliognathus lugubris

<400> SEQUENCE: 70
ttcttcttct tactcacatg taggtatggc tcatgtgcaa aaagcatccg ctagtaatca    60
gcaagggaaa aggaatagac atgtcggaca tcaatgccga ctatatggtc atgctgcaaa    120
agagattcta caagactttt tatatgatat ttgccatcgg cgttccggtg ttcgtgccag    180
tctatttttg aacgaaagc ctctggaatt cgttcttcac ggcctacatg gctcgcacct    240
ttattaccct aaatttgact tggatggtta acagctgggc tcacttttc ggaacgagac    300 ctttcgacac acgactgaaa cccgtagaaa gtgtcctggt tcttctctc ggacttggag    360 agggctgcca caactaccaa tcgaattccc gcggccgctc atggcgtgcc gggagcatgc    420
gacgtttggt cccattttttt ccatatagtg aatcatataa                         460

<210> SEQ ID NO 71
<211> LENGTH: 378
<212> TYPE: DNA
<213> ORGANISM: Chauliognathus lugubris

<400> SEQUENCE: 71
ttcttcttct ctcaggtcgg gtggttgatg atgaagaaac atccggaggt gtacagacga    60
ggccaggagg tcgacatgag cgacgtcctg gcggatcccg tagtgcaatt tcatcaaaag    120
tacttcattc ctctgaagct aattcttgga ttcgtcattc cttcgatcat tccgcctctt    180
ctttggaatg aagattggat gtggtccatc ctgttggcgt gcgtcggacg ttacgtcttg    240
```

-continued

```
tctctcaact ttacatggtt ggtgaacagc gccgctcaca tctggggata tagaccatat      300
gacaagaaga taggaccggc cgaaaataaa tacgtgtctg tgttagcgat gggcgagggc      360
tagcacaact accaccaa                                                    378
```

<210> SEQ ID NO 72
<211> LENGTH: 378
<212> TYPE: DNA
<213> ORGANISM: Chauliognathus lugubris

<400> SEQUENCE: 72

```
ttcttcttcg cgcacttcgg gtggctggtg ctgacgccgc accccgatgt cgtcaccaag       60
agggcggccg ttgacatgag cgacctagaa gaggacgcca tagttatgtg cacaagaag      120 tactacccac tcctattcgc cctgctgtgc atcggtcttc ccgtgggaat acccgtatac     180
ttttggaacg aaacgctctg gaacgcattc tggacttgct tcaacacgcg cttctgcgcg     240
acgctaaaca tcgccttttg cgtcaacagt ctggcgcata tgtggggcca aaagccctac     300
gataggaaca tcagtccggt ggaaaatttg gccgtgtcca tggcagctct tggcgagggt     360
taccacaact accatcaa                                                    378
```

<210> SEQ ID NO 73
<211> LENGTH: 349
<212> TYPE: PRT
<213> ORGANISM: Chauliognathus lugubris

<400> SEQUENCE: 73

```
Met Pro Pro Asn Ala His Asp Ser Thr Gly Val Met Phe Glu Asp Asp
1               5                   10                  15

Ser Glu Val Ser Pro Gln Gln Ile Glu Asp Val Leu Lys Leu Ser Lys
            20                  25                  30

Asn Arg Asp Leu Pro Leu Val Trp Arg Asp Val Ile Lys Phe Val Val
        35                  40                  45

Leu His Val Ile Gly Phe Tyr Gly Phe Tyr Leu Met Phe Thr Ser Ala
    50                  55                  60

Ser Ile Trp Thr Ser Val Leu Val Phe Val Asn Tyr His Leu Gly Ile
65                  70                  75                  80

Leu Gly Ile Thr Ala Gly Ala His Arg Leu Trp Ala His Lys Ser Tyr
                85                  90                  95

Lys Ala Arg Trp Pro Leu Lys Leu Phe Leu Ala Tyr Ile Glu Thr Leu
            100                 105                 110

Ala Phe Gln Phe Asp Ile Ile Phe Trp Ala Lys Tyr His Arg Val His
        115                 120                 125

His Lys Tyr Ser Glu Thr Asp Ala Asp Pro His Asn Ala Lys Arg Gly
    130                 135                 140

Phe Phe Phe Ser His Met Gly Trp Thr Met Cys Glu Lys Asn Pro Glu
145                 150                 155                 160

Phe Glu Thr Arg Cys Asn Glu Val Asp Leu Ser Asp Leu Tyr Ala Asp
                165                 170                 175

Pro Ile Val Arg Tyr Gln Glu Lys Tyr Tyr Gln Leu Leu Val Leu
            180                 185                 190

Ile Phe Val Ile Pro Thr Cys Met Pro Met Tyr Leu Trp Asn Glu
        195                 200                 205

Ser Phe Glu Asn Ala Phe Cys Ile Asn Leu Thr Arg Tyr Leu Ile Ser
    210                 215                 220

Leu His Cys Thr Trp Leu Val Asn Ser Ala Ala His Phe Tyr Gly Asn
```

```
            225                 230                 235                 240
Lys Pro Tyr Asp Arg Ser Leu Tyr Pro Ala Glu Asn Met Leu Val Thr
                245                 250                 255
Val Leu Val Asn Gly Glu Gly Trp His Asn Tyr His His Thr Phe Pro
                260                 265                 270
Trp Asp Tyr Lys Ala Ser Glu Leu Gly Leu Trp Ala Thr Asn Thr Thr
                275                 280                 285
Ala Gly Phe Ile Asp Ile Met Ala Lys Met Gly Leu Ala Tyr Asp Leu
                290                 295                 300
Lys Ser Val Ser Pro Asp Met Val Lys Arg Val Lys Arg Thr Gly
305                 310                 315                 320
Asp Gly Ser His Asn Ile Trp Gly Trp Gly Asp Lys Asp Leu Thr Glu
                325                 330                 335
Glu Glu Arg Gln Cys Ala Val Ile Thr His Lys Gln Lys
                340                 345

<210> SEQ ID NO 74
<211> LENGTH: 349
<212> TYPE: PRT
<213> ORGANISM: Chauliognathus lugubris

<400> SEQUENCE: 74

Met Ala Pro Asn Ser Asn Asp Ala Thr Gly Val Leu Gln Glu Thr Asp
1               5                   10                  15
Asp Asp Val Ser Ser Asn Gln Val Leu Gln Ile Thr Lys Ser Glu
                20                  25                  30
Lys Ser Lys Leu Ile Ile Val Trp Ser Asn Val Met Tyr Phe Val Ile
                35                  40                  45
Leu His Val Gly Ala Leu Tyr Gly Leu Trp Leu Leu Thr Ser Ala
                50                  55                  60
Gln Ile Trp Thr Cys Leu Trp Val Phe Ala Met Tyr Glu Phe Gly Glu
65                  70                  75                  80
Ile Cys Ile Thr Ala Gly Val His Arg Leu Trp Ser His Arg Ser Tyr
                85                  90                  95
Lys Ala Lys Trp Pro Leu Arg Leu Phe His Thr Met Gly Gln Thr Leu
                100                 105                 110
Ala Phe Gln Asp Ala Val Val Asp Trp Ala Arg Asp His Arg Val His
                115                 120                 125
His Lys Tyr Ser Glu Thr Asp Ala Asp Pro His Asn Ala Lys Arg Gly
                130                 135                 140
Phe Phe Phe Ser His Met Gly Trp Leu Met Cys Arg Lys Ser Lys Gln
145                 150                 155                 160
Val Lys Glu Lys Gly Lys Glu Pro Asp Ile Ser Asp Leu Tyr Ala Asp
                165                 170                 175
Pro Ile Leu Arg Tyr Gln Lys Lys Tyr Tyr Met Leu Phe Met Pro Leu
                180                 185                 190
Met Cys Phe Ala Phe Pro Thr Val Pro Leu Tyr Phe Trp Asn Glu
                195                 200                 205
Ser Leu Lys Thr Ala Phe Phe Val Asn Ile Phe Arg Tyr Ile Phe Ser
                210                 215                 220
Leu His Ala Thr Trp Leu Val Asn Ser Ala Ala His Leu Tyr Gly Glu
225                 230                 235                 240
Lys Pro Tyr Asn Lys His Ile Asn Pro Ala Glu Asn Leu Ala Val Ser
                245                 250                 255
```

```
Leu Ile Val Asn Gly Glu Arg Trp His Asn Tyr His Thr Phe Pro
            260                 265                 270

Trp Asp Tyr Lys Ala Gly Glu Phe Gly Arg Tyr Gly Thr Asn Leu Thr
275                 280                 285

Thr Val Phe Ile Asn Ala Met Ala Lys Ile Gly Leu Ala Tyr Asp Leu
        290                 295                 300

Lys Phe Val Pro Glu Asp Val Val Lys Arg Val His Lys Thr Gly
305                 310                 315                 320

Asp Gly Ser His Ala Val Trp Gly Trp Gly Asp Lys Asp Gln Thr Val
            325                 330                 335

Glu Glu Ile Ser Lys Thr Ile Val Ala Tyr Asn Gln Ser
            340                 345
```

<210> SEQ ID NO 75
<211> LENGTH: 125
<212> TYPE: PRT
<213> ORGANISM: Chauliognathus lugubris

<400> SEQUENCE: 75

```
Phe Phe Phe Ala His Val Gly Trp Leu Leu Cys Arg Lys His Pro Asp
1               5                   10                  15

Val Arg Thr Lys Gly Lys Gly Ile Asp Leu Ser Asp Leu Tyr Ala Asp
            20                  25                  30

Pro Ile Leu Arg Tyr Gln Lys Lys Tyr Tyr His Tyr Leu Met Ile Pro
        35                  40                  45

Leu Cys Phe Ile Leu Pro Thr Met Val Pro Met Tyr Tyr Trp Asn Glu
    50                  55                  60

Thr Phe Lys Asn Ala Phe Cys Val Asn Leu Leu Arg Tyr Thr Phe Thr
65                  70                  75                  80

Leu Asn Ala Ile Trp Leu Ile Asn Ser Ile Ala His Leu Tyr Gly His
                85                  90                  95

Lys Pro Tyr Asp Arg Asn Ile Asn Pro Ala Glu Ser Leu Ser Val Ser
            100                 105                 110

Val Ile Ser Leu Gly Glu Gly Tyr His Asn Tyr His Gln
        115                 120                 125
```

<210> SEQ ID NO 76
<211> LENGTH: 124
<212> TYPE: PRT
<213> ORGANISM: Chauliognathus lugubris

<400> SEQUENCE: 76

```
Phe Phe Phe Ser His Ile Gly Trp Leu Met Cys Lys Lys His Pro Leu
1               5                   10                  15

Val Ile Ser Lys Gly Lys Gly Ile Asp Met Ser Asp Ile Asn Ala Asp
            20                  25                  30

Tyr Met Val Met Leu Gln Lys Arg Phe Tyr Lys Thr Phe Tyr Met Ile
        35                  40                  45

Phe Ala Ile Gly Ile Pro Val Phe Val Pro Val Tyr Phe Trp Asn Glu
    50                  55                  60

Ser Leu Trp Asn Ser Phe Phe Thr Ala Tyr Met Ala Arg Thr Phe Ile
65                  70                  75                  80

Thr Leu Asn Leu Thr Trp Met Val Asn Ser Trp Ala His Phe Phe Gly
                85                  90                  95

Thr Arg Pro Phe Asp Thr Arg Leu Lys Pro Val Glu Ser Val Leu Val
            100                 105                 110
```

```
Ser Ser Leu Gly Leu Gly Glu Gly Tyr His Asn Tyr
        115                 120
```

<210> SEQ ID NO 77
<211> LENGTH: 118
<212> TYPE: PRT
<213> ORGANISM: Chauliognathus lugubris

<400> SEQUENCE: 77

```
Phe Phe Phe Ala His Val Gly Trp Leu Met Met Lys Lys His Pro Glu
1               5                   10                  15

Val Tyr Arg Arg Gly Gln Glu Val Asp Met Ser Asp Val Leu Ala Asp
            20                  25                  30

Pro Val Val Gln Phe His Gln Lys Tyr Phe Ile Pro Leu Lys Leu Ile
        35                  40                  45

Leu Gly Phe Val Ile Pro Ser Ile Ile Pro Pro Leu Leu Trp Asn Glu
    50                  55                  60

Asp Trp Met Trp Ser Ile Leu Leu Ala Cys Val Gly Arg Tyr Val Leu
65                  70                  75                  80

Ser Leu Asn Phe Thr Trp Leu Val Asn Ser Ala Ala His Ile Trp Gly
                85                  90                  95

Tyr Arg Pro Tyr Asp Lys Lys Ile Gly Pro Ala Glu Asn Lys Tyr Val
            100                 105                 110

Ser Val Leu Ala Met Gly
        115
```

<210> SEQ ID NO 78
<211> LENGTH: 126
<212> TYPE: PRT
<213> ORGANISM: Chauliognathus lugubris

<400> SEQUENCE: 78

```
Phe Phe Phe Ala His Phe Gly Trp Leu Val Leu Thr Pro His Pro Asp
1               5                   10                  15

Val Val Thr Lys Arg Ala Ala Val Asp Met Ser Asp Leu Glu Glu Asp
            20                  25                  30

Ala Ile Val Met Trp His Lys Lys Tyr Tyr Pro Leu Leu Phe Ala Leu
        35                  40                  45

Leu Cys Ile Gly Leu Pro Val Gly Ile Pro Val Tyr Phe Trp Asn Glu
    50                  55                  60

Thr Leu Trp Asn Ala Phe Trp Thr Cys Phe Asn Thr Arg Phe Cys Ala
65                  70                  75                  80

Thr Leu Asn Ile Ala Phe Cys Val Asn Ser Leu Ala His Met Trp Gly
                85                  90                  95

Gln Lys Pro Tyr Asp Arg Asn Ile Ser Pro Val Glu Asn Leu Ala Val
            100                 105                 110

Ser Met Ala Ala Leu Gly Glu Gly Tyr His Asn Tyr His Gln
        115                 120                 125
```

<210> SEQ ID NO 79
<211> LENGTH: 1050
<212> TYPE: DNA
<213> ORGANISM: Chauliognathus nobiliatus

<400> SEQUENCE: 79

```
atgccaccca acgcccacga cagcactggg gttatgtttg aggatgatgc cgaggtatcg      60
cctcagcaga tcgaagatgt cctcaaatta tcccataacc gagatcttcc tttggtatgg    120
```

-continued

```
agagatgtga tcaagtttgt ggttcttcac gtgatcggtc tctacggctt ctatcttatg    180
ttcacttccg ctagtatctg gacatcggtt ttagtgttcg tgaattacca tcttggtatc    240
ttgggaatca ccgccggcgc gcacagattg tgggcccaca atcgtacaa ggcgagatgg     300 cccctaaaac tcttcctggc ttacatcgaa accctggcct tccagttcga catcatcttc    360
tgggccaagt accatcgcgt gcatcacaaa tacagcgaaa ccgacgccga ccctcacaat    420
gccaagcgcg gattcttctt ctctcacatg ggttggacca tgtgcgaaaa gaaccccgaa    480
ttcgagacca gatgcaagga ggtcgatctt tccgacttgt acgccgatcc catcgtgcgc    540
taccaagaaa aatactacta ccaactcctg gtattcatct tcttcgtaat tcccacttgc    600
atgcccatgt acctctggaa cgaatctttc gaaaacgcct tctgcatcaa tctaacccgc    660
taccttatca gtcttcactg cacctggcta gtaaactccg ccgcccactt ctacggaaac    720
aagccttacg ataggtcttt gtatcccgcc gaaaacatgc tggtaactgt cttggtcaac    780
ggcgagggat ggcacaacta ccaccacacc ttcccatggg actacaaggc gtccgagctt    840
ggtctctggg csaccaacac caccgcaggt ttcatcgaca tcatggccaa gatgggtctt    900
gcgtacgatc tcaagtctgt atctcccgat atggtcaagc gacgtgtcaa gaggaccggt    960
gacggcaccc acaacgtctg gggatggggc gacaaggacc tgaccgaaga ggagaggcaa    1020
tgcgccgtca ttactcacaa acaaaagtga                                     1050
```

<210> SEQ ID NO 80
<211> LENGTH: 349
<212> TYPE: PRT
<213> ORGANISM: Chauliognathus nobiliatus
<220> FEATURE:
<221> NAME/KEY: misc_feature
<222> LOCATION: (284)..(284)
<223> OTHER INFORMATION: Xaa can be any naturally occurring amino acid

<400> SEQUENCE: 80

```
Met Pro Pro Asn Ala His Asp Ser Thr Gly Val Met Phe Glu Asp Asp
1               5                   10                  15

Ala Glu Val Ser Pro Gln Gln Ile Glu Asp Val Leu Lys Leu Ser His
            20                  25                  30

Asn Arg Asp Leu Pro Leu Val Trp Arg Asp Val Ile Lys Phe Val Val
        35                  40                  45

Leu His Val Ile Gly Leu Tyr Gly Phe Tyr Leu Met Phe Thr Ser Ala
    50                  55                  60

Ser Ile Trp Thr Ser Val Leu Val Phe Val Asn Tyr His Leu Gly Ile
65                  70                  75                  80

Leu Gly Ile Thr Ala Gly Ala His Arg Leu Trp Ala His Lys Ser Tyr
                85                  90                  95

Lys Ala Arg Trp Pro Leu Lys Leu Phe Leu Ala Tyr Ile Glu Thr Leu
            100                 105                 110

Ala Phe Gln Phe Asp Ile Ile Phe Trp Ala Lys Tyr His Arg Val His
        115                 120                 125

His Lys Tyr Ser Glu Thr Asp Ala Asp Pro His Asn Ala Lys Arg Gly
    130                 135                 140

Phe Phe Phe Ser His Met Gly Trp Thr Met Cys Glu Lys Asn Pro Glu
145                 150                 155                 160

Phe Glu Thr Arg Cys Lys Glu Val Asp Leu Ser Asp Leu Tyr Ala Asp
                165                 170                 175

Pro Ile Val Arg Tyr Gln Glu Lys Tyr Tyr Tyr Gln Leu Leu Val Phe
            180                 185                 190
```

Ile Phe Phe Val Ile Pro Thr Cys Met Pro Met Tyr Leu Trp Asn Glu
    195                 200                 205

Ser Phe Glu Asn Ala Phe Cys Ile Asn Leu Thr Arg Tyr Leu Ile Ser
    210                 215                 220

Leu His Cys Thr Trp Leu Val Asn Ser Ala Ala His Phe Tyr Gly Asn
225                 230                 235                 240

Lys Pro Tyr Asp Arg Ser Leu Tyr Pro Ala Glu Asn Met Leu Val Thr
                245                 250                 255

Val Leu Val Asn Gly Glu Gly Trp His Asn Tyr His His Thr Phe Pro
            260                 265                 270

Trp Asp Tyr Lys Ala Ser Glu Leu Gly Leu Trp Xaa Thr Asn Thr Thr
                275                 280                 285

Ala Gly Phe Ile Asp Ile Met Ala Lys Met Gly Leu Ala Tyr Asp Leu
            290                 295                 300

Lys Ser Val Ser Pro Asp Met Val Lys Arg Arg Val Lys Arg Thr Gly
305                 310                 315                 320

Asp Gly Thr His Asn Val Trp Gly Trp Gly Asp Lys Asp Leu Thr Glu
                325                 330                 335

Glu Glu Arg Gln Cys Ala Val Ile Thr His Lys Gln Lys
            340                 345

<210> SEQ ID NO 81
<211> LENGTH: 18
<212> TYPE: DNA
<213> ORGANISM: Artificial
<220> FEATURE:
<223> OTHER INFORMATION: Oligonucleotide

<400> SEQUENCE: 81
tttttttttt tttttttt                                                        18

<210> SEQ ID NO 82
<211> LENGTH: 24
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 82
ttcttcttck cncaykthgg ntgg                                                 24

<210> SEQ ID NO 83
<211> LENGTH: 23
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (18)..(18)
<223> OTHER INFORMATION: n is a, c, g, or t

<400> SEQUENCE: 83
tgrtggtagt tgtgvhancc ctc                                                  23

<210> SEQ ID NO 84
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 84 gncaymgny tntgggcnca                                              20

<210> SEQ ID NO 85
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (19)..(19)
<223> OTHER INFORMATION: n = Inosine

<400> SEQUENCE: 85
aanryrtgrt ggtagttgng                                             20

<210> SEQ ID NO 86
<211> LENGTH: 20
<212> TYPE: DNA
<213> ORGANISM: Artificial
<220> FEATURE:
<223> OTHER INFORMATION: Olignonucleotide

<400> SEQUENCE: 86
taatacgact cactataggg                                             20

<210> SEQ ID NO 87
<211> LENGTH: 18
<212> TYPE: DNA
<213> ORGANISM: Artificial
<220> FEATURE:
<223> OTHER INFORMATION: Oligonucleotide

<400> SEQUENCE: 87
atttaggtga cactatag                                               18

<210> SEQ ID NO 88
<211> LENGTH: 24
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 88
ttyttytwyk cncayatggg ntgg                                          24

<210> SEQ ID NO 89
<211> LENGTH: 21
<212> TYPE: DNA
<213> ORGANISM: Artificial
<220> FEATURE:
<223> OTHER INFORMATION: Oligonucleotide

<400> SEQUENCE: 89
cccagagata taaccgatac a                                             21

<210> SEQ ID NO 90
<211> LENGTH: 21
<212> TYPE: DNA
<213> ORGANISM: Artificial
<220> FEATURE:
<223> OTHER INFORMATION: Oligonucleotide

<400> SEQUENCE: 90
ttatatacgc cgaccctatt c                                             21

<210> SEQ ID NO 91
<211> LENGTH: 21
<212> TYPE: DNA
<213> ORGANISM: Artificial
<220> FEATURE:
<223> OTHER INFORMATION: Oligonucleotide

<400> SEQUENCE: 91
cctctccaag tccgagagaa g                                             21

<210> SEQ ID NO 92
<211> LENGTH: 21
<212> TYPE: DNA
<213> ORGANISM: Artificial
<220> FEATURE:
<223> OTHER INFORMATION: Oligonucleotide

<400> SEQUENCE: 92
tggctcatgt gcaaaaagca t                                             21

<210> SEQ ID NO 93
<211> LENGTH: 21
<212> TYPE: DNA
<213> ORGANISM: Artificial
<220> FEATURE:
<223> OTHER INFORMATION: Oligonucleotide

<400> SEQUENCE: 93
ttgtgccatc cctcaccgtt g                                             21

<210> SEQ ID NO 94
<211> LENGTH: 20
<212> TYPE: DNA
<213> ORGANISM: Artificial
<220> FEATURE:

```
<223> OTHER INFORMATION: Oligonucleotide

<400> SEQUENCE: 94
tggctaacat cgagaccctg                                              20

<210> SEQ ID NO 95
<211> LENGTH: 21
<212> TYPE: DNA
<213> ORGANISM: Artificial
<220> FEATURE:
<223> OTHER INFORMATION: Oligonucleotide

<400> SEQUENCE: 95
gccatataga tgagcagctg a                                            21

<210> SEQ ID NO 96
<211> LENGTH: 21
<212> TYPE: DNA
<213> ORGANISM: Artificial
<220> FEATURE:
<223> OTHER INFORMATION: Oligonucleotide

<400> SEQUENCE: 96
atgggatggc attatgtgca g                                            21

<210> SEQ ID NO 97
<211> LENGTH: 39
<212> TYPE: DNA
<213> ORGANISM: Artificial
<220> FEATURE:
<223> OTHER INFORMATION: Oligonucleotide

<400> SEQUENCE: 97
aagcagtggt atcaacgcag agtggccatt acggccggg                         39

<210> SEQ ID NO 98
<211> LENGTH: 59
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (58)..(58)
<223> OTHER INFORMATION: n = A, G, C, or T
<220> FEATURE:
<221> NAME/KEY: misc_feature
<222> LOCATION: (59)..(59)
<223> OTHER INFORMATION: n = A, G, or C

<400> SEQUENCE: 98
attctagagg ccgaggcggc cgacatgttt tttttttttt tttttttttt tttttttnn   59

<210> SEQ ID NO 99
<211> LENGTH: 23
<212> TYPE: DNA
<213> ORGANISM: Artificial
<220> FEATURE:
<223> OTHER INFORMATION: Oligonucleotide

<400> SEQUENCE: 99
aagcagtggt atcaacgcag agt                                          23

<210> SEQ ID NO 100
<211> LENGTH: 24
<212> TYPE: DNA
<213> ORGANISM: Artificial
```

```
<220> FEATURE:
<223> OTHER INFORMATION: Oligonucleotide

<400> SEQUENCE: 100
ggtaccatgc cacccaacgc ccac                                              24

<210> SEQ ID NO 101
<211> LENGTH: 24
<212> TYPE: DNA
<213> ORGANISM: Artificial
<220> FEATURE:
<223> OTHER INFORMATION: Oligonucleotide

<400> SEQUENCE: 101
gaattctcac ttttgtttgt gagt                                              24

<210> SEQ ID NO 102
<211> LENGTH: 24
<212> TYPE: DNA
<213> ORGANISM: Artificial
<220> FEATURE:
<223> OTHER INFORMATION: Oligonucleotide

<400> SEQUENCE: 102
aagcttatgc taccggagtt ttgc                                              24

<210> SEQ ID NO 103
<211> LENGTH: 24
<212> TYPE: DNA
<213> ORGANISM: Artificial
<220> FEATURE:
<223> OTHER INFORMATION: Oligonucleotide

<400> SEQUENCE: 103
ctccagctaa gactgattat aggc                                              24

<210> SEQ ID NO 104
<211> LENGTH: 7
<212> TYPE: PRT
<213> ORGANISM: artificial
<220> FEATURE:
<223> OTHER INFORMATION: Consensus sequence

<400> SEQUENCE: 104

Ala Gly Ala His Arg Leu Trp
1               5

<210> SEQ ID NO 105
<211> LENGTH: 6
<212> TYPE: PRT
<213> ORGANISM: Artificial
<220> FEATURE:
<223> OTHER INFORMATION: Consensus sequence

<400> SEQUENCE: 105

Ser Glu Thr Asp Ala Asp
1               5

<210> SEQ ID NO 106
<211> LENGTH: 7
<212> TYPE: PRT
<213> ORGANISM: Artificial
<220> FEATURE:
<223> OTHER INFORMATION: Consensus sequence

<400> SEQUENCE: 106
```

```
Phe Phe Phe Ser His Val Gly
1               5

<210> SEQ ID NO 107
<211> LENGTH: 4
<212> TYPE: PRT
<213> ORGANISM: Artificial
<220> FEATURE:
<223> OTHER INFORMATION: Consensus sequence

<400> SEQUENCE: 107

Gln Lys Lys Tyr
1

<210> SEQ ID NO 108
<211> LENGTH: 5
<212> TYPE: PRT
<213> ORGANISM: Artificial
<220> FEATURE:
<223> OTHER INFORMATION: Consensus sequence

<400> SEQUENCE: 108

Asn Ser Ala Ala His
1               5

<210> SEQ ID NO 109
<211> LENGTH: 9
<212> TYPE: PRT
<213> ORGANISM: Artificial
<220> FEATURE:
<223> OTHER INFORMATION: Consensus sequence

<400> SEQUENCE: 109

Gly Glu Gly Trp His Asn Tyr His His
1               5

<210> SEQ ID NO 110
<211> LENGTH: 4
<212> TYPE: PRT
<213> ORGANISM: Artificial
<220> FEATURE:
<223> OTHER INFORMATION: Consensus sequence

<400> SEQUENCE: 110

Pro Trp Asp Tyr
1

<210> SEQ ID NO 111
<211> LENGTH: 4
<212> TYPE: PRT
<213> ORGANISM: Artificial
<220> FEATURE:
<223> OTHER INFORMATION: Consensus sequence

<400> SEQUENCE: 111

Gly Trp Ala Tyr
1

<210> SEQ ID NO 112
<211> LENGTH: 6
<212> TYPE: PRT
<213> ORGANISM: Artificial
<220> FEATURE:
<223> OTHER INFORMATION: Histidine box

<400> SEQUENCE: 112

His Arg Leu Trp Thr His
```

```
1               5

<210> SEQ ID NO 113
<211> LENGTH: 6
<212> TYPE: PRT
<213> ORGANISM: Artificial
<220> FEATURE:
<223> OTHER INFORMATION: Histidine box

<400> SEQUENCE: 113

His Arg Leu Trp Ser His
1               5

<210> SEQ ID NO 114
<211> LENGTH: 6
<212> TYPE: PRT
<213> ORGANISM: Artificial
<220> FEATURE:
<223> OTHER INFORMATION: Histidine box

<400> SEQUENCE: 114

His Arg Leu Trp Ala His
1               5

<210> SEQ ID NO 115
<211> LENGTH: 6
<212> TYPE: PRT
<213> ORGANISM: Artificial
<220> FEATURE:
<223> OTHER INFORMATION: Histidine box

<400> SEQUENCE: 115

His Arg Leu Tyr Ser His
1               5

<210> SEQ ID NO 116
<211> LENGTH: 5
<212> TYPE: PRT
<213> ORGANISM: Artificial
<220> FEATURE:
<223> OTHER INFORMATION: Histidine box

<400> SEQUENCE: 116

His Arg Val His His
1               5

<210> SEQ ID NO 117
<211> LENGTH: 5
<212> TYPE: PRT
<213> ORGANISM: Artificial
<220> FEATURE:
<223> OTHER INFORMATION: Histidine box

<400> SEQUENCE: 117

His Arg Ala His His
1               5

<210> SEQ ID NO 118
<211> LENGTH: 5
<212> TYPE: PRT
<213> ORGANISM: Artificial
<220> FEATURE:
<223> OTHER INFORMATION: Histidine box

<400> SEQUENCE: 118

His Gln Val His His
1               5
```

```
<210> SEQ ID NO 119
<211> LENGTH: 5
<212> TYPE: PRT
<213> ORGANISM: Artificial
<220> FEATURE:
<223> OTHER INFORMATION: Histidine box

<400> SEQUENCE: 119

His Arg Leu His His
1               5

<210> SEQ ID NO 120
<211> LENGTH: 5
<212> TYPE: PRT
<213> ORGANISM: Artificial
<220> FEATURE:
<223> OTHER INFORMATION: Histidine box

<400> SEQUENCE: 120

His Arg Gln His His
1               5

<210> SEQ ID NO 121
<211> LENGTH: 5
<212> TYPE: PRT
<213> ORGANISM: Artificial
<220> FEATURE:
<223> OTHER INFORMATION: Histidine box

<400> SEQUENCE: 121

His Asn Tyr His His
1               5

<210> SEQ ID NO 122
<211> LENGTH: 5
<212> TYPE: PRT
<213> ORGANISM: Artificial
<220> FEATURE:
<223> OTHER INFORMATION: Histidine box

<400> SEQUENCE: 122

Trp Ile Ser Tyr His
1               5

<210> SEQ ID NO 123
<211> LENGTH: 4
<212> TYPE: PRT
<213> ORGANISM: Artificial
<220> FEATURE:
<223> OTHER INFORMATION: Signature sequence

<400> SEQUENCE: 123

Gly Pro Ala Glu
1

<210> SEQ ID NO 124
<211> LENGTH: 4
<212> TYPE: PRT
<213> ORGANISM: Artificial
<220> FEATURE:
<223> OTHER INFORMATION: Signature sequence

<400> SEQUENCE: 124

Asn Pro Val Glu
1
```

<210> SEQ ID NO 125
<211> LENGTH: 4
<212> TYPE: PRT
<213> ORGANISM: Artificial
<220> FEATURE:
<223> OTHER INFORMATION: Signature sequence

<400> SEQUENCE: 125

Tyr Pro Ala Glu
1

<210> SEQ ID NO 126
<211> LENGTH: 4
<212> TYPE: PRT
<213> ORGANISM: Artificial
<220> FEATURE:
<223> OTHER INFORMATION: Signature sequence

<400> SEQUENCE: 126

Ser Pro Val Glu
1

<210> SEQ ID NO 127
<211> LENGTH: 29
<212> TYPE: DNA
<213> ORGANISM: Artificial
<220> FEATURE:
<223> OTHER INFORMATION: Oligonucleotide

<400> SEQUENCE: 127
ttgttctgtg tgggtcayga ytgyggwca                                          29

<210> SEQ ID NO 128
<211> LENGTH: 27
<212> TYPE: DNA
<213> ORGANISM: Artificial
<220> FEATURE:
<223> OTHER INFORMATION: Oligonucleotide

<400> SEQUENCE: 128
gtgatgggcg acgtgacygt ykgtrat                                            27

<210> SEQ ID NO 129
<211> LENGTH: 24
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 129
ttcttcttck cncaykthgg ntgg                                               24

<210> SEQ ID NO 130
<211> LENGTH: 23
<212> TYPE: DNA
<213> ORGANISM: Artificial
<220> FEATURE:
<223> OTHER INFORMATION: Oligonucleotide
<220> FEATURE:
<221> NAME/KEY: misc_feature

```
<222> LOCATION: (18)..(18)
<223> OTHER INFORMATION: n is a, c, g, or t

<400> SEQUENCE: 130
tgrtggtagt tgtgvhancc ctc                                              23

<210> SEQ ID NO 131
<211> LENGTH: 9
<212> TYPE: PRT
<213> ORGANISM: Artificial
<220> FEATURE:
<223> OTHER INFORMATION: Conserved region
<220> FEATURE:
<221> NAME/KEY: misc_feature
<222> LOCATION: (4)..(4)
<223> OTHER INFORMATION: Xaa = S or A
<220> FEATURE:
<221> NAME/KEY: misc_feature
<222> LOCATION: (6)..(6)
<223> OTHER INFORMATION: Xaa = I or V

<400> SEQUENCE: 131

Phe Phe Phe Xaa His Xaa Val Gly Trp
1               5

<210> SEQ ID NO 132
<211> LENGTH: 8
<212> TYPE: PRT
<213> ORGANISM: Artificial
<220> FEATURE:
<223> OTHER INFORMATION: Conserved region
<220> FEATURE:
<221> NAME/KEY: misc_feature
<222> LOCATION: (3)..(3)
<223> OTHER INFORMATION: Xaa = Y or W or F

<400> SEQUENCE: 132

Glu Gly Xaa His Asn Tyr His His
1               5

<210> SEQ ID NO 133
<211> LENGTH: 1074
<212> TYPE: DNA
<213> ORGANISM: Acheta domesticus

<400> SEQUENCE: 133
atggatctca acgaggaaag tgcgcccagc ggagtcctat cgaagaaga gtggctgag        60 caggaagcca agatggcgaa cggaggaccg aagaagggca agaaacttga agaaccctac     120
cggctcgaaa ttgtatggtt caatgtccta tggtttgtcc ttcttcatgc tggtgctttg     180
tacggtgtat atctcatctt tgcatctgcc aagatctaca caacattata tggcttcttg     240
ctgtgcgaat tgtcgctgct gagcatcacg gcgggcgtgc accgcctgtg ggctcatcgc     300
gcctacaagg ccaagtggcc cctgcgcctc accctcatgg tcctcaacct gctggcgtac     360
cagaactcca tctacgagtg ggcgcgcgac cacagggtgc accacaagtt cagcgagacc     420
aacgccgacc ccgtgaacgc caagcgcggc ttcttcttct cgcacgtggg ctggctgctg     480
tgccgcaagc acccggaggt ccgcgccaag ggcggccgca tcgacctcag cgacctggag     540
cgcgacccca tcgtcatgtt ccagaagagg cattattaca aattggtgcc attcgtttcc     600
tttgtgattc caaccctcat tcctatgtat ttctggggag agacgctatc taattcttgg     660
tatgtgtcga ctatgttccg ttattgcctc tctctcaact taacatggct ggtcaacagt     720
gcggctcaca tgtggggcaa caagcctac gacaagaaca tcaatcctgt tgaaaacctt     780
```

```
gctgtcgcca tcggaagctt gggtgaggga tggcataact tccaccacgt tttcccctgg    840
gactacaaga catcagaact cggcaactac agcctcaatt tcacaaacgc cttcatcgac    900
ctggctgtcc tactagggtt ggcatacgac ctcaagaccg tcccagtttc tatgatcaag    960
actcgcgtag gcgcaccgg tgatggcagc cacgatgtgt ggggctgggg ggacaaagat   1020
cttccgaaag aactcgcaga tcaaactatg atcgaaaata ggaaaacaga atag         1074
```

<210> SEQ ID NO 134
<211> LENGTH: 357
<212> TYPE: PRT
<213> ORGANISM: Acheta domesticus

<400> SEQUENCE: 134

```
Met Asp Leu Asn Glu Glu Ser Ala Pro Ser Gly Val Leu Phe Glu Glu
1               5                   10                  15

Asp Val Ala Glu Gln Glu Ala Lys Met Ala Asn Gly Gly Pro Lys Lys
            20                  25                  30

Gly Lys Lys Leu Glu Glu Pro Tyr Arg Leu Glu Ile Val Trp Phe Asn
        35                  40                  45

Val Leu Trp Phe Val Leu Leu His Ala Gly Ala Leu Tyr Gly Val Tyr
50                  55                  60

Leu Ile Phe Ala Ser Ala Lys Ile Tyr Thr Thr Leu Tyr Gly Phe Leu
65                  70                  75                  80

Leu Cys Glu Leu Ser Leu Leu Ser Ile Thr Ala Gly Val His Arg Leu
                85                  90                  95

Trp Ala His Arg Ala Tyr Lys Ala Lys Trp Pro Leu Arg Leu Thr Leu
            100                 105                 110

Met Val Leu Asn Leu Leu Ala Tyr Gln Asn Ser Ile Tyr Glu Trp Ala
        115                 120                 125

Arg Asp His Arg Val His His Lys Phe Ser Glu Thr Asn Ala Asp Pro
    130                 135                 140

Val Asn Ala Lys Arg Gly Phe Phe Phe Ser His Val Gly Trp Leu Leu
145                 150                 155                 160

Cys Arg Lys His Pro Glu Val Arg Ala Lys Gly Gly Arg Ile Asp Leu
                165                 170                 175

Ser Asp Leu Glu Arg Asp Pro Ile Val Met Phe Gln Lys Arg His Tyr
            180                 185                 190

Tyr Lys Leu Val Pro Phe Val Ser Phe Val Ile Pro Thr Leu Ile Pro
        195                 200                 205

Met Tyr Phe Trp Gly Glu Thr Leu Ser Asn Ser Trp Tyr Val Ser Thr
    210                 215                 220

Met Phe Arg Tyr Cys Leu Ser Leu Asn Leu Thr Trp Leu Val Asn Ser
225                 230                 235                 240

Ala Ala His Met Trp Gly Asn Lys Pro Tyr Asp Lys Asn Ile Asn Pro
                245                 250                 255

Val Glu Asn Leu Ala Val Ala Ile Gly Ser Leu Gly Glu Gly Trp His
            260                 265                 270

Asn Phe His His Val Phe Pro Trp Asp Tyr Lys Thr Ser Glu Leu Gly
        275                 280                 285

Asn Tyr Ser Leu Asn Phe Thr Asn Ala Phe Ile Asp Leu Ala Val Leu
    290                 295                 300

Leu Gly Leu Ala Tyr Asp Leu Lys Thr Val Pro Val Ser Met Ile Lys
305                 310                 315                 320

Thr Arg Val Gly Arg Thr Gly Asp Gly Ser His Asp Val Trp Gly Trp
```

```
                        325                 330                 335
Gly Asp Lys Asp Leu Pro Lys Glu Leu Ala Asp Gln Thr Met Ile Glu
                340                 345                 350

Asn Arg Lys Thr Glu
        355

<210> SEQ ID NO 135
<211> LENGTH: 383
<212> TYPE: PRT
<213> ORGANISM: Arabidopsis thaliana

<400> SEQUENCE: 135

Met Gly Ala Gly Gly Arg Met Pro Val Pro Thr Ser Ser Lys Lys Ser
1               5                   10                  15

Glu Thr Asp Thr Thr Lys Arg Val Pro Cys Glu Lys Pro Pro Phe Ser
                20                  25                  30

Val Gly Asp Leu Lys Lys Ala Ile Pro Pro His Cys Phe Lys Arg Ser
            35                  40                  45

Ile Pro Arg Ser Phe Ser Tyr Leu Ile Ser Asp Ile Ile Ala Ser
    50                  55                  60

Cys Phe Tyr Tyr Val Ala Thr Asn Tyr Phe Ser Leu Leu Pro Gln Pro
65                  70                  75                  80

Leu Ser Tyr Leu Ala Trp Pro Leu Tyr Trp Ala Cys Gln Gly Cys Val
                85                  90                  95

Leu Thr Gly Ile Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
    290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335
```

-continued

```
Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
        355                 360                 365

Arg Glu Gly Asp Lys Lys Gly Val Tyr Trp Tyr Asn Asn Lys Leu
    370                 375                 380
```